US012469580B2

(12) United States Patent
Collins et al.

(10) Patent No.: US 12,469,580 B2
(45) Date of Patent: Nov. 11, 2025

(54) IN SILICO DISCOVERY OF EFFECTIVE ANTIMICROBIALS

(71) Applicants: MASSACHUSETTS INSTITUTE OF TECHOLOGY, Cambridge, MA (US); THE BROAD INSTITUTE, INC., Cambridge, MA (US)

(72) Inventors: James Collins, Cambridge, MA (US); Regina Barzilay, Cambridge, MA (US); Jonathan Stokes, Cambridge, MA (US); Ian Andrews, Cambridge, MA (US); Daniel Collins, Cambridge, MA (US)

(73) Assignees: MASSACHUSETTS INSTITUTE OF TECHOLOGY, Cambridge, MA (US); THE BROAD INSTITUTE, INC., Cambridge, MA (US)

( * ) Notice: Subject to any disclaimer, the term of this patent is extended or adjusted under 35 U.S.C. 154(b) by 798 days.

(21) Appl. No.: 17/641,704

(22) PCT Filed: Sep. 9, 2020

(86) PCT No.: PCT/US2020/049830

§ 371 (c)(1),
(2) Date: Mar. 9, 2022

(87) PCT Pub. No.: WO2021/050473

PCT Pub. Date: Mar. 18, 2021

(65) Prior Publication Data

US 2022/0310198 A1 Sep. 29, 2022

Related U.S. Application Data

(60) Provisional application No. 62/971,801, filed on Feb. 7, 2020, provisional application No. 62/898,363, filed on Sep. 10, 2019.

(51) Int. Cl.

| | |
|---|---|
| ***G16B 15/30*** | (2019.01) |
| ***A61K 31/433*** | (2006.01) |
| ***A61K 31/655*** | (2006.01) |
| ***A61P 31/04*** | (2006.01) |
| ***G06N 3/126*** | (2023.01) |
| ***G16B 5/20*** | (2019.01) |
| ***G16B 35/20*** | (2019.01) |
| ***G16B 40/20*** | (2019.01) |

(52) U.S. Cl.

CPC ............ *G16B 15/30* (2019.02); *A61K 31/433* (2013.01); *A61K 31/655* (2013.01); *A61P 31/04* (2018.01); *G06N 3/126* (2013.01); *G16B 5/20* (2019.02); *G16B 35/20* (2019.02); *G16B 40/20* (2019.02)

(58) Field of Classification Search

CPC ........................................................ A61P 31/04

See application file for complete search history.

(56) References Cited

U.S. PATENT DOCUMENTS

2012/0095064 A1 4/2012 Ballell Pages et al.

FOREIGN PATENT DOCUMENTS

| | | | |
|---|---|---|---|
| WO | 1998/027092 | A1 | 6/1998 |
| WO | 2008/118626 | A1 | 10/2008 |
| WO | 2018/220365 | A1 | 12/2018 |

OTHER PUBLICATIONS

Barot et al. Design, synthesis and antimicrobial activities of some novel, 1,3,4-thiadiazole, 1,2,4-triazole-5-thione and 1,3-thiazolan-4-one derivatives of benzimidazole. Oct. 8, 2013.

International Search Report and Written Opinion in corresponding PCT application No. PCT/US2020/049830 dated Feb. 9, 2021.

*Primary Examiner* — Golam M Shameem

(74) *Attorney, Agent, or Firm* — Day Pitney LLP; Christopher R. Cowles; Richard B. Emmons

(57) ABSTRACT

The present disclosure relates to antimicrobial compositions, particularly to antibiotic compositions; to methods for identification of antimicrobial compositions involving in silico prediction of antimicrobial activity; and to use of antimicrobial compositions and methods.

20 Claims, 170 Drawing Sheets

Specification includes a Sequence Listing.

| | EC | SA | KP | AB | PA |
|---|---|---|---|---|---|
| 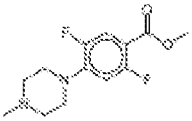 | | | | 128 | |
| 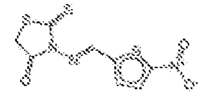 | 32 | 8 | | 32 | |
| 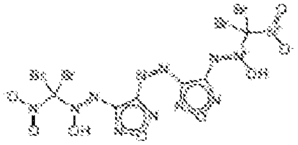 | 4 | 2 | 4 | 4 | 4 |
|  | | 32 | | | |
| 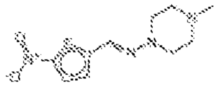 | 32 | 32 | 32 | 16 | |
| 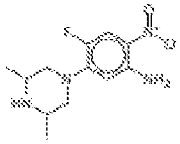 | 128 | | 128 | 64 | |
| 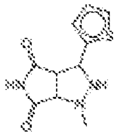 | | | | 128 | |
| 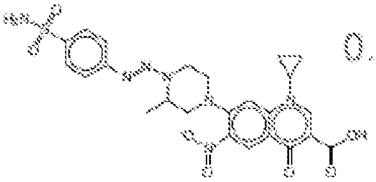 | 0.01 | 0.25 | 4 | 0.25 | 0.06 |
FIG. 6D

| | EC | SA | KP | AB | PA |
|---|---|---|---|---|---|
| 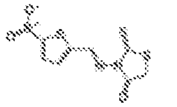 | 32 | 8 | | 32 | |
| 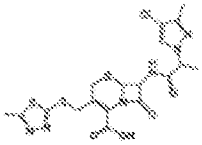 | 32 | 16 | | 128 | |
| 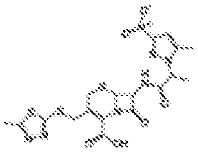 | 32 | 16 | | | |
| 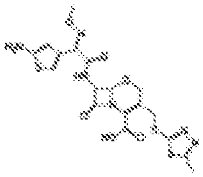 | 8 | 16 | 32 | 16 | 32 |
| 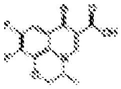 | 1 | 2 | 128 | 0.5 | 64 |
| 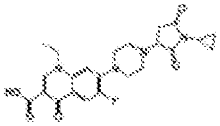 | 4 | 1 | | 32 | 16 |
| 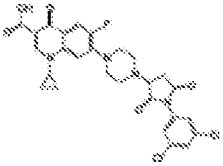 | 1 | 0.5 | | 8 | 8 |
FIG. 12G
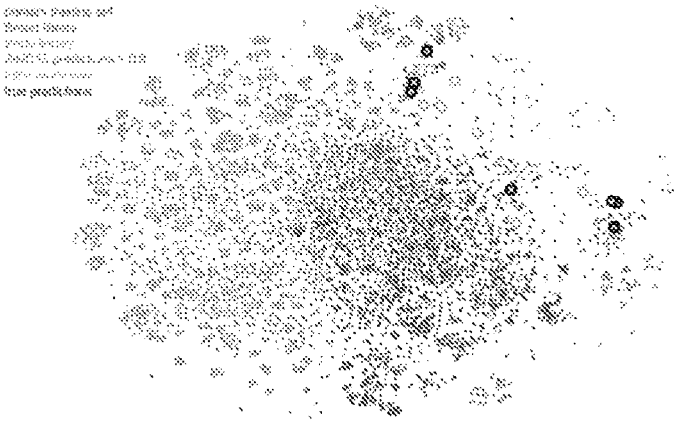
FIG. 12H

| Broad ID | Compound Name | SMILES String | Prediction Score | Clinical Toxicity (low=less Tox) |
|---|---|---|---|---|
| BRD-A20839672-003-01-5 | cefmenoxime | CO\N=C(\C(=O)NC1C2SCC(CSc3nnnn3C)=C(N2C1=O)C(O)=O)c1csc(N)n1 | 0.9672 | 0.001422 |
| BRD-A61633223-001-02-8 | ulifloxacin | CC1Sc2c(C(O)=O)c(=O)c3cc(F)c(cc3n12)N1CCNCC1 | 0.957037 | 0.958267 |
| BRD-K02275692-300-02-6 | cefotiam | CN(C)CCn1nnnc1SCC1=C(N2[C@H](SC1)[C@H](NC(=O)Cc1csc(N)n1)C2=O)C(O)=O | 0.952527 | 0.229829 |
| BRD-K96734425-304-01-7 | ceftriaxone | CO\N=C(/C(=O)N[C@H]1[C@H]2SCC(CSc3nc(=O)c(O)nn3C)=C(N2C1=O)C(O)=O)c1csc(N)n1 | 0.94216 | 0.011146 |
| BRD-A47790386-001-03-6 | balofloxacin | CNC1CCCN(C1)c1c(F)cc2c(c1OC)n(cc(C(O)=O)c2=O)C1CC1 | 0.931109 | 0.927147 |
| BRD-K77073709-435-01-2 | cefminox | CO[C@]1(NC(=O)CSC[C@@H](N)C(O)=O)[C@H]2SCC(CSc3nnnn3C)=C(N2C1=O)C(O)=O | 0.931014 | 0.281643 |
| BRD-K45916615-066-02-5 | danofloxacin | CN1C[C@@H]2C[C@H]1CN2c1cc2n(cc(C(O)=O)c(=O)c2cc1F)C1CC1 | 0.928767 | 0.998927 |
| BRD-K10196357-003-02-0 | besifloxacin | N[C@@H]1CCCCN(C1)c1c(F)cc2c(c1Cl)n(cc(C(O)=O)c2=O)C1CC1 | 0.9287 | 0.95083 |
| BRD-K99750640-236-19-5 | cefazolin | Cc1nnc(SCC2=C(N3[C@H](SC2)[C@H](NC(=O)Cn2cnnn2)C3=O)C(O)=O)s1 | 0.927871 | 0.002623 |
| BRD-K22641081-304-01-8 | cefodizime | CO\N=C(/C(=O)N[C@H]1[C@H]2SCC(CSc3nc(C)c(CC(O)=O)s3)=C(N2C1=O)C(O)=O)c1csc(N)n1 | 0.92321 | 0.001982 |
| BRD-K00494077-066-01-9 | trovafloxacin | N[C@H]1[C@@H]2CN(C[C@H]12)c1nc2n(cc(C(O)=O)c(=O)c2cc1F)-c1ccc(F)cc1F | 0.921312 | 0.975778 |
| BRD-K56542719-065-01-4 | cefpirome | CO\N=C(\C(=O)N[C@H]1[C@H]2SCC(C[n+]3cccc4CCCc34)=C(N2C1=O)C(O)=O)c1csc(N)n1 | 0.916152 | 7.92E-06 |

FIG. 13

| | | | | |
|---|---|---|---|---|
| BRD-A76661185-300-01-6 | cefotiam-cilexetil | CC(OC(=O)OC1CCCCC1)OC(=O)C1=C(CSc2nnnn2CCN(C)C)CSC2C(NC(=O)Cc3csc(N)n3)C(=O)N12 | 0.915957 | 0.007503 |
| BRD-K10836013-001-01-3 | sitafloxacin | N[C@@H]1CN(CC11CC1)c1c(F)cc2c(c1Cl)n(cc(C(O)=O)c2=O)[C@@H]1C[C@@H]1F | 0.908552 | 0.967324 |
| BRD-K04301924-236-01-6 | ceftizoxim | CO\N=C(/C(=O)N[C@H]1[C@H]2SCC=C(N2C1=O)C(O)=O)c1csc(N)n1 | 0.897801 | 0.060884 |
| BRD-K48470486-236-12-4 | cefmetazole | CO[C@]1(NC(=O)CSCC#N)[C@H]2SCC(CSc3nnnn3C)=C(N2C1=O)C(O)=O | 0.896626 | 0.001164 |
| BRD-K72339976-065-02-1 | cefoselis | CO\N=C(/C(=O)N[C@H]1[C@H]2SCC(Cn3ccc(=N)n3CCO)=C(N2C1=O)C(O)=O)c1csc(N)n1 | 0.881417 | 0.005438 |
| BRD-K78364995-236-16-7 | cefotaxime | CO\N=C(/C(=O)N[C@H]1[C@H]2SCC(COC(C)=O)=C(N2C1=O)C(O)=O)c1csc(N)n1 | 0.875134 | 0.025665 |
| BRD-K57502136-345-03-4 | ceftazidime | CC(C)(O\N=C(\C(=O)N[C@H]1[C@H]2SCC(C[n+]3ccccc3)=C(N2C1=O)C(O)=O)c1csc(N)n1)C(O)=O | 0.865381 | 3.29E-05 |
| BRD-K27798832-001-01-5 | cefetamet | CO\N=C(/C(=O)N[C@H]1[C@H]2SCC(C)=C(N2C1=O)C(O)=O)c1csc(N)n1 | 0.861591 | 0.027228 |
| BRD-K27130738-236-15-8 | cefamandole | Cn1nnnc1SCC1=C(N2[C@H](SC1)[C@H](NC(=O)[C@H](O)c1ccccc1)C2=O)C(O)=O | 0.851349 | 0.004676 |
| BRD-K02733959-236-07-7 | cefuroxime | CO\N=C(/C(=O)N[C@H]1[C@H]2SCC(COC(N)=O)=C(N2C1=O)C(O)=O)c1ccco1 | 0.847685 | 0.005419 |
| BRD-K61443650-236-13-1 | thiomersal | CC[Hg]Sc1ccccc1C(O)=O | 0.814054 | 0.000258 |
| BRD-K70976396-236-25-2 | cefoxitin | CO[C@]1(NC(=O)Cc2cccs2)[C@H]2SCC(COC(N)=O)=C(N2C1=O)C(O)=O | 0.804871 | 0.081745 |
| BRD-K34058848-304-01-5 | cefonicid | O[C@@H](C(=O)N[C@H]1[C@H]2SCC(CSc3nnnn3CS(O)(=O)=O)=C(N2C1=O)C(O)=O)c1ccccc1 | 0.798953 | 0.042414 |
| BRD-K17903788-236-03-5 | cefamandole-nafate | Cn1nnnc1SCC1=C(N2[C@H](SC1)[C@H](NC(=O)[C@H](OC=O)c1ccccc1)C2=O)C(O)=O | 0.786564 | 0.00967 |
| BRD-K21372554-003-02-5 | cefetamet-pivoxil | CO\N=C(/C(=O)N[C@H]1[C@H]2SCC(C)=C(N2C1=O)C(=O)OCOC(=O)C(C)(C)C)c1csc(N)n1 | 0.774125 | 0.000661 |
| BRD-K98384930-003-01-5 | finafloxacin | OC(=O)c1cn(C2CC2)c2c(C#N)c(N3C[C@@H]4NCCO[C@H]4C3)c(F)cc2c1=O | 0.771686 | 0.988549 |

FIG. 13 (Continued)

| | | | | |
|---|---|---|---|---|
| BRD-A08899266-304-05-0 | moxalactam | CO[C@]1(NC(=O)C(C(O)=O)c2ccc(O)cc2)[C@H]2OCC(CSc3nnnn3C)=C(N2C1=O)C(O)=O | 0.769149 | 0.01443 |
| BRD-K46970505-003-01-9 | cefozopran | CO\N=C(/C(=O)N[C@H]1[C@H]2SCC(C[n+]3ccn4ccccc34)=C(N2C1=O)C(O)=O)c1nsc(N)n1 | 0.760973 | 7.01E-06 |
| BRD-K57284066-001-01-6 | Ro-9187 | Nc1ccn([C@@H]2O[C@@](CO)(N=[N+]=[N-])[C@@H](O)[C@@H]2O)c(=O)n1 | 0.757486 | 1.16E-07 |
| BRD-K28442028-001-01-3 | R-1479 | Nc1ccn([C@@H]2O[C@@](CO)(N=[N+]=[N-])[C@@H](O)[C@H]2O)c(=O)n1 | 0.757082 | 1.29E-07 |
| BRD-A44936478-001-01-1 | cephalosporin-c-zn | CC(=O)OCC1=C2N3C(SC1)[C@H](NC(=O)CCCC(N)C(=O)O[Zn]OC2=O)C3=O | 0.745065 | 0.050624 |
| BRD-K73394555-237-01-1 | oxolinic-acid | CCn1cc(C(O)=O)c(=O)c2cc3OCOc3cc12 | 0.735233 | 0.064816 |
| BRD-K71026158-304-01-0 | carumonam | NC(=O)OC[C@@H]1[C@H](NC(=O)C(=N/OCC(O)=O)\c2csc(N)n2)C(=O)N1S(O)(=O)=O | 0.725698 | 0.060892 |
| BRD-A99949740-236-04-6 | piperacillin | CCN1CCN(C(=O)NC(C(=O)N[C@H]2[C@H]3SC(C)(C)[C@@H](N3C2=O)C(O)=O)c2ccccc2)C(=O)C1=O | 0.711954 | 0.014909 |
| BRD-A42083487-001-01-3 | bleomycin | C[C@@H](O)[C@@H](NC(=O)[C@H](C)[C@@H](O)[C@H](C)NC(=O)[C@@H](NC(=O)c1nc(nc(N)c1C)[C@H](CC(N)=O)NC[C@@H](N)C(N)=O)C(O[C@H]1O[C@H](CO)[C@H](O)[C@@H](O)[C@H]1O[C@H]1O[C@H](CO)[C@@H](O)[C@H](OC(N)=O)[C@@H]1O)c1c[nH]cn1)C(=O)NCCc1nc(cs1)-c1nc(cs1)C(=O)NCCC[S+](C)C | 0.682685 | 0.010557 |
| BRD-K37252028-349-01-8 | ceftaroline-fosamil | CCO\N=C(\C(=O)N[C@H]1[C@H]2SCC(Sc3nc(cs3)-c3cc[n+](C)cc3)=C(N2C1=O)C(O)=O)c1nsc(NP(O)(O)=O)n1 | 0.675396 | 0.001544 |
| BRD-A94813917-001-01-0 | bleomycetin | C[C@@H](O)[C@H](NC(=O)[C@@H](C)[C@H](O)[C@@H](C)NC(=O)C(NC(=O)c1nc(nc(N)c1C)[C@H](CC(N)=O)NC[C@H](N)C(N)=O)[C@@H](O[C@H]1O[C@H](CO)[C@H](O)[C@@H](O)[C@H]1O[C@H]1O[C@H](CO)[C@@H](O)[C@@H](OC(N)=O)[C@@H]1O)c1c[nH]c | 0.670675 | 0.136128 |

FIG. 13 (Continued)

| | | | | |
|---|---|---|---|---|
| | | n1)C(=O)NCCc1nc(cs1)-c1nc(cs1)C(=O)NCCCNCCCCN | | |
| BRD-K65377893-001-07-4 | 7-aminocephalosporanic-acid | CC(=O)OCC1=C(N2[C@H](SC1)[C@H](N)C2=O)C(O)=O | 0.666072 | 0.965656 |
| BRD-A71407503-001-02-6 | inimur | CSCC1CN(\N=C\c2ccc(o2)[N+]([O-])=O)C(=O)O1 | 0.662373 | 1.97E-06 |
| BRD-K23677682-003-01-2 | voreloxin | CN[C@H]1CN(C[C@@H]1OC)c1ccc2c(n1)n(cc(C(O)=O)c2=O)-c1nccs1 | 0.646374 | 0.968997 |
| BRD-A36456202-001-01-3 | colistin-b-sulfate | CC(C)CCCCC(=O)NC(CCN)C(=O)NC(C(C)O)C(=O)NC(CCN)C(=O)NC1CCNC(=O)C(NC(=O)C(CCN)NC(=O)C(CCN)NC(=O)[C@H](CC(C)C)NC(=O)[C@@H](CC(C)C)NC(=O)C(CCN)NC1=O)C(C)O | 0.620286 | 0.251098 |
| BRD-K47976015-001-01-2 | balapiravir | CC(C)C(=O)OC[C@]1(O[C@H]([C@H](OC(=O)C(C)C)[C@@H]1OC(=O)C(C)C)n1ccc(N)nc1=O)N=[N+]=[N-] | 0.618948 | 9.48E-06 |
| BRD-A49622760-001-01-9 | faropenem | CC(O)C1C2SC(C3CCCO3)=C(N2C1=O)C(O)=O | 0.618812 | 0.001248 |
| BRD-A44942307-405-01-9 | colistimethate | CCC(C)CCCCC(=O)N[C@@H](CCN)C(=O)N[C@@H]([C@@H](C)O)C(=O)N[C@@H](CCN)C(=O)N[C@H]1CCNC(=O)C(NC(=O)[C@H](CCN)NC(=O)[C@H](CCN)NC(=O)[C@H](CC(C)C)NC(=O)[C@@H](CC(C)C)NC(=O)[C@H](CCN)NC1=O)[C@@H](C)O | 0.611832 | 0.353319 |
| BRD-K23200955-002-02-3 | imipenem | C[C@@H](O)[C@@H]1[C@H]2CC(SCCNC=N)=C(N2C1=O)C(O)=O | 0.608859 | 0.001988 |
| BRD-A07600638-060-04-5 | meclocycline-sulfosalicylate | CN(C)[C@H]1[C@@H]2[C@@H](O)[C@H]3C(C(=O)c4c(O)ccc(Cl)c4C3=C)C(=O)[C@]2(O)C(=O)C(C(N)=O)C1=O | 0.588053 | 0.287366 |
| BRD-A18924964-065-02-3 | colistin | CCC(C)CCCC(=O)N[C@@H](CCN)C(=O)N[C@@H]([C@@H](C)O)C(=O)N[C@@H](CCN)C(=O)N[C@H]1CCNC(=O)[C@@H](NC(=O)[C@H](CCN)NC(=O)[C@H](CCN)NC(=O)[C@H] | 0.583388 | 0.34216 |

FIG. 13 (Continued)

| | | | | |
|---|---|---|---|---|
| | | (CC(C)C)NC(=O)[C@@H](CC(C)C)NC(=O)[C@H](CCN)NC1=O)[C@@H](C)O | | |
| BRD-K59045783-001-01-1 | faropenem-medoxomil | C[C@@H](O)[C@@H]1[C@H]2SC([C@H]3CCCO3)=C(N2C1=O)C(=O)OCc1oc(=O)oc1C | 0.565004 | 0.000441 |
| BRD-K28210218-236-08-1 | cephalothin | CC(=O)OCC1=C(N2[C@H](SC1)[C@H](NC(=O)Cc1cccs1)C2=O)C(O)=O | 0.564703 | 0.076239 |
| BRD-A34145622-003-25-1 | demeclocycline | CN(C)[C@H]1[C@@H]2C[C@@H]3[C@H](O)c4c(Cl)ccc(O)c4C(=O)C3C(=O)[C@]2(O)C(=O)C(C(N)=O)C1=O | 0.563861 | 0.489343 |
| BRD-K32533226-001-01-3 | AGN-195183 | CC1(C)CCC(C)(C)c2c(Cl)c(O)c(cc12)C(=O)Nc1cc(F)c(C(O)=O)c(F)c1 | 0.552245 | 0.010053 |
| BRD-K45319714-002-01-9 | doripenem | C[C@@H](O)[C@@H]1[C@H]2[C@@H](C)C(S[C@@H]3CN[C@H](CNS(N)(=O)=O)C3)=C(N2C1=O)C(O)=O | 0.551649 | 0.014885 |
| BRD-A00100033-001-08-9 | nifurtimox | CC1CS(=O)(=O)CCN1N=Cc1ccc(o1)[N+]([O-])=O | 0.537445 | 1.64E-05 |
| BRD-K18157228-001-01-7 | fdcyd | Nc1nc(=O)n(cc1F)[C@H]1C[C@H](O)[C@@H](CO)O1 | 0.523781 | 0.197285 |
| BRD-A25492003-003-14-1 | chlortetracycline | CN(C)[C@H]1[C@@H]2C[C@H]3C(C(=O)c4c(O)ccc(Cl)c4[C@@]3(C)O)C(=O)[C@]2(O)C(=O)C(C(N)=O)C1=O | 0.498914 | 0.374111 |
| BRD-K83146339-001-05-7 | strontium-ranelate | O=C1CN(CC(=O)O[Sr]O1)c1sc2c(CC(=O)O[Sr]OC2=O)c1C#N | 0.488415 | 0.051415 |
| BRD-K32256160-001-01-9 | solithromycin | CC[C@H]1OC(=O)[C@@](C)(F)C(=O)[C@H](C)[C@@H](O[C@@H]2O[C@H](C)C[C@@H]([C@H]2O)N(C)C)[C@@](C)(C[C@@H](C)C(=O)[C@H](C)[C@H]2N(CCCCn3cc(nn3)-c3cccc(N)c3)C(=O)O[C@]12C)OC | 0.473244 | 0.134997 |
| BRD-K76819217-001-01-4 | cabotegravir | C[C@H]1CO[C@@H]2Cn3cc(C(=O)NCc4ccc(F)cc4F)c(=O)c(O)c3C(=O)N12 | 0.469964 | 0.065372 |
| BRD-K36386086-001-01-1 | dolutegravir | C[C@H]1CCO[C@H]2Cn3cc(C(=O)NCc4ccc(F)cc4F)c(=O)c(O)c3C(=O)N12 | 0.46829 | 0.102365 |
| BRD-K54472332-001-03-4 | elvitegravir | COc1cc2n(cc(C(O)=O)c(=O)c2cc1Cc1cccc(Cl)c1F)[C@H](CO)C(C)C | 0.457042 | 0.005634 |

FIG. 13 (Continued)

| | | | | |
|---|---|---|---|---|
| BRD-K83988098-001-02-0 | alvespimycin | CO[C@H]1C[C@H](C)CC2=C(NCCN(C)C)C(=O)C=C(NC(=O)\C(C)=C\C=C/[C@H](OC)[C@@H](OC(N)=O)\C(C)=C\[C@H](C)[C@H]1O)C2=O | 0.434449 | 0.026376 |
| BRD-K27871792-236-01-0 | flucloxacillin | Cc1onc(c1C(=O)N[C@H]1[C@H]2SC(C)(C)[C@@H](N2C1=O)C(O)=O)-c1c(F)cccc1Cl | 0.421634 | 0.006533 |
| BRD-K68544925-001-01-1 | avatrombopag | OC(=O)C1CCN(CC1)c1ncc(cc1Cl)C(=O)Nc1nc(-c2cc(Cl)cs2)c(s1)N1CCN(CC1)C1CCCCC1 | 0.412199 | 0.993454 |
| BRD-K74759733-065-01-4 | isepamicin | CN[C@@H]1[C@@H](O)[C@@H](O[C@H]2[C@@H](C[C@H](N)[C@@H](O[C@H]3O[C@H](CN)[C@@H](O)[C@H](O)[C@H]3O)[C@@H]2O)NC(=O)[C@@H](O)CN)OC[C@]1(C)O | 0.406064 | 0.996819 |
| BRD-K97840621-001-01-5 | API-1 | NC(=O)c1cn([C@@H]2O[C@H](CO)[C@@H](O)[C@H]2O)c2ncnc(N)c2c1=O | 0.396363 | 0.257284 |
| BRD-K13169950-001-14-4 | NSC-3852 | Oc1ccc([N+][O-])c2cccnc12 | 0.38406 | 6.52E-11 |
| BRD-K11576103-003-01-1 | benzyldimethyl octylammonium | CCCCCCCC[N+](C)(C)Cc1ccccc1 | 0.381267 | 1.73E-09 |
| BRD-K90177246-001-05-5 | tetroquinone | OC1C(=O)C(=O)C(O)C(=O)C1=O | 0.380798 | 0.674753 |
| BRD-A04915500-002-01-3 | loracarbef | N[C@@H](C(=O)NC1C2CCC(Cl)=C(N2C1=O)C(O)=O)c1ccccc1 | 0.380187 | 0.97567 |
| BRD-M28128163-003-01-7 | doxycycline-hyclate | CCO.C[C@@H]1[C@H]2[C@H](O)[C@H]3[C@H](N(C)C)C(=O)C(C(N)=O)C(=O)[C@@]3(O)C(=O)C2C(=O)c2c(O)cccc12.C[C@@H]1[C@H]2[C@H](O)[C@H]3[C@H](N(C)C)C(=O)C(C(N)=O)C(=O)[C@@]3(O)C(=O)C2C(=O)c2c(O)cccc12 | 0.378874 | 0.08591 |
| BRD-K31144453-001-02-2 | AC-261066 | CCCCOCCOc1nc(sc1C)-c1ccc(C(O)=O)c(F)c1 | 0.376118 | 0.012828 |
| BRD-K15514357-001-05-6 | cefalonium | NC(=O)c1cc[n+](CC2=C(N3[C@H](SC2)[C@H](NC(=O)Cc2cccs2)C3=O)C(O)=O)cc1 | 0.372798 | 1.49E-05 |
| BRD-K33622447-066-01-9 | abemaciclib | CCN1CCN(Cc2ccc(Nc3ncc(F)c(n3)-c3cc(F)c4nc(C)n(C(C)C)c4c3)nc2)CC1 | 0.372567 | 0.950358 |

FIG. 13 (Continued)

| | | | | |
|---|---|---|---|---|
| BRD-A41063939-001-01-0 | nisin | CCC(C)C(N)C(=O)N\C(=C/C)C(=O)NC1CSCC(NC(=O)C(CC(C)C)NC(=O)C(=C)NC(=O)C(NC1=O)C(C)CC)C(=O)NC1C(C)SCC(NC(=O)CNC(=O)C2CCCN2C1=O)C(=O)NC(CCCCN)C(=O)NC1C(C)SCC(NC(=O)CNC(=O)C(CCSC)NC(=O)C(CC(C)C)NC(=O)C(C)NC(=O)CNC1=O)C(=O)NC(CC(N)=O)C(=O)NC(CCSC)C(=O)NC(CCCCN)C(=O)NC1C(C)SCC2NC(=O)C(NC(=O)C(C)NC1=O)C(C)SCC(NC(=O)C(Cc1c[nH]cn1)NC2=O)C(=O)NC(CO)C(=O)NC(C(C)CC)C(=O)NC(Cc1c[nH]cn1)C(=O)NC(C(C)C)C(=O)NC(=C)C(=O)NC(CCCCN)C(O)=O | 0.372298 | 0.083874 |
| BRD-A96510685-213-03-7 | piroctone-olamine | CC(Cc1cc(C)cc(=O)n1O)CC(C)(C)C | 0.368635 | 0.015488 |
| BRD-A56621826-001-02-1 | oxytetracycline | CN(C)[C@H]1[C@@H]2[C@@H](O)[C@H]3C(C(=O)c4c(O)cccc4C3(C)O)C(=O)[C@]2(O)C(=O)C(C(N)=O)C1=O | 0.367559 | 0.165845 |
| BRD-K30930903-001-01-3 | WIN-18446 | ClC(Cl)C(=O)NCCCCCCCCNC(=O)C(Cl)Cl | 0.366441 | 0.001761 |
| BRD-K77038618-356-01-3 | garenoxacin | C[C@H]1NCc2cc(ccc12)-c1ccc2c(c1OC(F)F)n(cc(C(O)=O)c2=O)C1CC1 | 0.365771 | 0.958475 |
| BRD-K16136380-001-02-5 | pyrithione-zinc | O1[n+]2ccccc2S[Zn]11O[n+]2ccccc2S1 | 0.364747 | 2.61E-07 |
| BRD-M10279501-065-05-9 | gentamycin | CN[C@@H]1[C@@H](O)[C@@H](O[C@H]2[C@H](N)C[C@H](N)[C@@H](O[C@H]3O[C@H](CN)CC[C@H]3N)[C@@H]2O)OC[C@]1(C)O.CN[C@@H]1[C@@H](O)[C@@H](O[C@H]2[C@H](N)C[C@H](N)[C@@H](O[C@H]3O[C@@H](CC[C@H]3N)[C@@H](C)N)[C@@H]2O)OC[C@]1(C)O.CN[C@H](C)[C@@H]1CC[C@@H](N)[C@@H](O[C@@H]2[C@@H](N)C[C@@H](N)[C@H](O[C@H]3OC[C@](C)(O)[C@H](NC)[C@H]3O)[C@H]2O)O1 | 0.355342 | 0.999988 |
| BRD-K48988407-001-01-2 | cytochlor | Nc1nc(=O)n(cc1Cl)[C@H]1C[C@@H](O)[C@@H](CO)O1 | 0.347386 | 0.220412 |

FIG. 13 (Continued)

| | | | | |
|---|---|---|---|---|
| BRD-K79254416-001-21-8 | decitabine | Nc1ncn([C@H]2C[C@H](O)[C@@H](CO)O2)c(=O)n1 | 0.346336 | 0.291253 |
| BRD-K82823076-001-02-6 | Ro-15-4513 | CCOC(=O)c1ncn-2c1CN(C)C(=O)c1cc(ccc-21)N=[N+]=[N-] | 0.344653 | 6.28E-07 |
| BRD-K17555800-001-01-9 | talmapimod | C[C@H]1CN([C@H](C)CN1Cc1ccc(F)cc1)C(=O)c1cc2c(cn(C)c2cc1Cl)C(=O)C(=O)N(C)C | 0.344507 | 0.758747 |
| BRD-A40472231-304-02-5 | ertapenem | C[C@@H](O)C1[C@H]2[C@@H](C)C(S[C@@H]3CN[C@@H](C3)C(=O)Nc3cccc(c3)C(O)=O)=C(N2C1=O)C(O)=O | 0.340127 | 0.131861 |
| BRD-K44731351-001-01-6 | AL-8697 | Cc1c(F)cc(cc1-c1c(F)cn2c(nnc2c1F)C(C)(C)C)C(=O)NC1CC1 | 0.337061 | 0.014781 |
| BRD-K32730239-001-02-8 | SU3327 | Nc1nnc(Sc2ncc(s2)[N+]([O-])=O)s1 | 0.331535 | 3.01E-06 |
| BRD-A72591750-066-01-1 | omadacycline | CN(C)[C@H]1[C@@H]2C[C@@H]3Cc4c(cc(CNCC(C)(C)C)c(O)c4C(=O)C3C(=O)[C@]2(O)C(=O)C(C(N)=O)C1=O)N(C)C | 0.326923 | 0.996938 |
| BRD-K26824830-001-03-8 | azomycin-(2-nitroimidazole) | [O-][N+](=O)c1ncc[nH]1 | 0.325204 | 4.25E-10 |
| BRD-K04254814-001-01-8 | sulfanilate-zinc | Nc1ccc(cc1)S(=O)(=O)O[Zn]OS(=O)(=O)c1ccc(N)cc1 | 0.319806 | 0.026383 |
| BRD-K37379014-001-02-0 | filanesib | CON(C)C(=O)N1N=C(S[C@@]1(CCCN)c1ccccc1)c1cc(F)ccc1F | 0.313928 | 0.423489 |
| BRD-K34437622-001-08-0 | 5-FP | Oc1ncc(F)cn1 | 0.312077 | 0.0408 |
| BRD-K66213167-001-01-2 | RX-3117 | Nc1ccn([C@H]2[C@H](O)[C@H](O)C(CO)=C2F)c(=O)n1 | 0.311773 | 0.307731 |
| BRD-K32007074-001-01-1 | enocitabine | CCCCCCCCCCCCCCCCCCCCCC(=O)Nc1ccn([C@@H]2O[C@H](CO)[C@@H](O)[C@@H]2O)c(=O)n1 | 0.308728 | 0.042065 |
| BRD-K03083257-001-01-6 | 1-octacosanol | CCCCCCCCCCCCCCCCCCCCCCCCCCCO | 0.307259 | 0.000386 |
| BRD-K68928792-001-02-4 | aldoxorubicin | COc1cccc2C(=O)c3c(O)c4C[C@](O)(C[C@H](O[C@H]5C[C@H](N)[C@H](O)[C@H](C)O5)c4c(O)c3C(=O)c12)C(\CO)=N\NC(=O)CCCCCN1C(=O)C=CC1=O | 0.306254 | 0.538452 |

FIG. 13 (Continued)

| | | | | |
|---|---|---|---|---|
| BRD-K03128512-001-02-8 | MK-2048 | CCN1C[C@H](C)n2c(c(O)c3c2c(nn(Cc2ccc(F)c(Cl)c2)c3=O)C(=O)NC)C1=O | 0.304334 | 0.006607 |
| BRD-K37602296-001-01-6 | NS-309 | ON=C1C(=O)Nc2c1ccc(Cl)c2Cl | 0.300315 | 0.010308 |
| BRD-K38913877-300-01-9 | azimilide | CN1CCN(CCCCN2C(=O)CN(\N=C\c3ccc(o3)-c3ccc(Cl)cc3)C2=O)CC1 | 0.294804 | 0.979066 |
| BRD-K65904673-001-01-4 | tandospirone | O=C1[C@H]2[C@@H]3CC[C@@H](C3)[C@H]2C(=O)N1CCCCN1CCN(CC1)c1ncccn1 | 0.293774 | 0.990471 |
| BRD-K57243773-001-02-4 | FRAX486 | CCn1c2nc(Nc3ccc(N4CCNCC4)c(F)c3)ncc2cc(-c2ccc(Cl)cc2Cl)c1=O | 0.293541 | 0.693213 |
| BRD-K53195974-001-01-9 | sipatrigine | CN1CCN(CC1)c1ncc(c(N)n1)-c1cc(Cl)cc(Cl)c1Cl | 0.291254 | 0 |
| BRD-K19412342-001-02-4 | valspodar | C\C=C\C[C@@H](C)C(=O)[C@@H]1N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@@H](NC(=O)[C@H](CC(C)C)N(C)C(=O)CN(C)C(=O)[C@@H](NC1=O)C(C)C)C(C)C | 0.290568 | 0 |
| BRD-K05717154-001-01-1 | orphanin-fq | CC(C)C[C@H](NC(=O)[C@H](CCCCN)NC(=O)[C@H](CCCNC(N)=N)NC(=O)[C@H](C)NC(=O)[C@H](CO)NC(=O)[C@H](CCCCN)NC(=O)[C@H](CCCNC(N)=N)NC(=O)[C@H](C)NC(=O)CNC(=O)[C@@H](NC(=O)[C@H](Cc1ccccc1)NC(=O)CNC(=O)CNC(=O)[C@@H](N)Cc1ccccc1)[C@@H](C)O)C(=O)N[C@@H](C)C(=O)N[C@@H](CC(N)=O)C(=O)N[C@@H](CCC(N)=O)C(O)=O | 0.290271 | 0 |
| BRD-K25209357-236-01-2 | chloramphenicol-sodium-succinate | O[C@@H]([C@@H](COC(=O)CCC(O)=O)NC(=O)C(Cl)Cl)c1ccc(cc1)[N+]([O-])=O | 0.289176 | 0 |
| BRD-K18552138-001-01-8 | micronomicin | CNC[C@@H]1CC[C@@H](N)[C@@H](O[C@@H]2[C@@H](N)C[C@@H](N)[C@H](O[C@H]3OC[C@](C)(O)[C@H](NC)[C@H]3O)[C@H]2O)O1 | 0.282506 | 0 |

FIG. 13 (Continued)

| | | | | |
|---|---|---|---|---|
| BRD-K03907181-236-07-6 | cefsulodin | NC(=O)c1cc[n+](CC2=C(N3[C@H](SC2)[C@H](NC(=O)[C@@H](c2ccccc2)S(O)(=O)=O)C3=O)C(O)=O)cc1 | 0.272708 | 0 |
| BRD-K13044802-213-20-7 | ciclopirox | Cc1cc(C2CCCCC2)n(O)c(=O)c1 | 0.271333 | 0 |
| BRD-K38332599-001-01-3 | uprosertib | Cn1ncc(Cl)c1-c1cc(oc1Cl)C(=O)N[C@H](CN)Cc1ccc(F)c(F)c1 | 0.271027 | 0 |
| BRD-K69877120-001-01-7 | CYM-50260 | FCc1ccc(OCCOc2ccc(Cl)cc2Cl)c(Cl)n1 | 0.266257 | 0 |
| BRD-A56754222-001-01-2 | gepon | CC(C)[C@@H](NC(=O)C(NC(=O)[C@@H](CCC(O)=O)NC(=O)[C@H](CCCNC(N)=N)NC(=O)C(CCCNC(N)=N)NC(=O)C(CCCCN)NC(=O)[C@@H](CCCCN)NC(=O)C(CCC(O)=O)NC(=O)[C@H](N)C(C)O)C(C)O)C(=O)N[C@H](CCC(O)=O)C(=O)NC(CCCNC(N)=N)C(=O)N[C@@H](CCC(O)=O)C(=O)NC(CCCCN)C(=O)N[C@@H](CCC(O)=O)C(O)=O | 0.26488 | 0 |
| BRD-K49880111-236-10-0 | cephapirin | CC(=O)OCC1=C(N2[C@H](SC1)[C@H](NC(=O)CSc1ccncc1)C2=O)C(O)=O | 0.263508 | 0 |
| BRD-A80321291-001-03-2 | biapenem | C[C@@H](O)[C@@H]1[C@H]2[C@@H](C)C(SC3Cn4cnc[n+]4C3)=C(N2C1=O)C(O)=O | 0.262096 | 0 |
| BRD-A49035384-003-27-1 | methacycline | CN(C)[C@H]1[C@@H]2[C@@H](O)[C@H]3C(C(=O)c4c(O)cccc4C3=C)C(=O)[C@]2(O)C(=O)C(C(N)=O)C1=O | 0.26057 | 0 |
| BRD-K49793107-402-02-6 | caspofungin-acetate | CC[C@@H](C)C[C@@H](C)CCCCCCCCC(=O)N[C@H]1C[C@@H](O)[C@@H](NCCN)NC(=O)[C@@H]2[C@@H](O)CCN2C(=O)[C@@H](NC(=O)[C@@H](NC(=O)[C@@H]2C[C@@H](O)CN2C(=O)[C@@H](NC1=O)[C@@H](C)O)[C@H](O)[C@@H](O)c1ccc(O)cc1)[C@H](O)CCN | 0.259045 | 0 |
| BRD-A31685486-402-02-7 | caspofungin | CCC(C)CC(C)CCCCCCCCC(=O)N[C@H]1C[C@@H](O)[C@@H](NCCN)NC(=O)[C@@H]2[C@@H](O)CCN2C(=O)[C@@H](NC(=O)[C@@H](NC(=O)[C@@H]2C[C@@H](O)CN2C(=O | 0.257998 | 0 |

FIG. 13 (Continued)

| | | | | |
|---|---|---|---|---|
| | | )[C@@H](NC1=O)[C@@H](C)O)[C@@H](O)[C@H](O)c1ccc(O)cc1)[C@H](O)CCN | | |
| BRD-A10991937-001-01-1 | FCE-22250 | COC1\C=C\OC2(C)Oc3c(C2=O)c2c(O)c(\C=N\N=C\N4CCCCC4)c(NC(=O)\C(C)=C/C=C/C(C)C(O)C(C)C(O)C(C)C(OC(C)=O)C1C)c(O)c2c(O)c3C | 0.257811 | 0 |
| BRD-A34462049-001-08-5 | tigecycline | CN(C)[C@H]1[C@@H]2C[C@@H]3Cc4c(cc(NC(=O)CNC(C)(C)C)c(O)c4C(=O)C3C(=O)[C@]2(O)C(=O)C(C(N)=O)C1=O)N(C)C | 0.257128 | 0 |
| BRD-A08545410-003-07-8 | doxycycline | C[C@@H]1[C@H]2[C@H](O)[C@H]3[C@H](N(C)C)C(=O)C(C(N)=O)C(=O)[C@@]3(O)C(=O)C2C(=O)c2c(O)cccc12 | 0.254539 | 0 |
| BRD-K99383816-001-02-7 | ftorafur | Fc1cn([C@H]2CCCO2)c(=O)[nH]c1=O | 0.253469 | 0 |
| BRD-A27828834-237-04-4 | hetacillin | CC1(C)S[C@@H]2C(N3C(=O)[C@H](NC3(C)C)c3ccccc3)C(=O)N2[C@H]1C(O)=O | 0.252075 | 0 |
| BRD-K30563334-001-02-9 | rifabutin | CO[C@H]1\C=C\O[C@@]2(C)Oc3c(C2=O)c2c(c(O)c3C)c(O)c(NC(=O)\C(C)=C\C=C\[C@H](C)[C@H](O)[C@@H](C)[C@@H](O)[C@@H](C)[C@H](OC(C)=O)[C@@H]1C)c1=NC3(CCN(CC(C)C)CC3)N=c21 | 0.250347 | 0 |
| BRD-A04203391-001-08-3 | piricapiron | CC1(C)C2CCC1(C)C(=O)N(CCCCN1CCN(CC1)c1ccccn1)C2=O | 0.249636 | 0 |
| BRD-K38512030-001-01-7 | rifamycin | CO[C@H]1\C=C\O[C@@]2(C)Oc3c(C2=O)c2c(O)cc(NC(=O)\C(C)=C/C=C/[C@H](C)[C@H](O)[C@@H](C)[C@@H](O)[C@@H](C)[C@H](OC(C)=O)[C@@H]1C)c(O)c2c(O)c3C | 0.249018 | 0 |
| BRD-K97714174-001-01-3 | P22077 | CC(=O)c1cc(c(Sc2ccc(F)cc2F)s1)[N+]([O-])=O | 0.245387 | 0 |
| BRD-K66192203-001-02-2 | opicapone | Cc1c(Cl)c(C)[n+]([O-])c(Cl)c1-c1noc(n1)-c1cc(O)c(O)c(c1)[N+]([O-])=O | 0.24448 | 0 |
| BRD-K76315403-015-02-5 | cetrorelix | CC(C)C[C@H](NC(=O)[C@@H](CCCNC(N)=O)NC(=O)[C@H](Cc1ccc(O)cc1)NC(=O)[C@H](CO)NC(=O)[C@@H](Cc1cccnc1)NC(=O)[C@@H](Cc1ccc(Cl)cc1)NC(=O)[C@@H](Cc1ccc2ccc | 0.240648 | 0 |

FIG. 13 (Continued)

| | | | | |
|---|---|---|---|---|
| | | cc2c1)NC(C)=O)C(=O)N[C@@H](CCCNC(N)=N)C(=O)N1CCC[C@H]1C(=O)N[C@H](C)C(N)=O | | |
| BRD-K51313569-003-03-3 | palbociclib | CC(=O)c1c(C)c2cnc(Nc3ccc(cn3)N3CCNCC3)nc2n(C2CCCC2)c1=O | 0.24026 | 0 |
| BRD-A42383464-001-06-3 | actinomycin-d | CC(C)C1NC(=O)C(NC(=O)c2ccc(C)c3oc4c(C)c(=O)c(N)c(C(=O)NC5C(C)OC(=O)C(C(C)C)N(C)C(=O)CN(C)C(=O)C6CCCN6C(=O)C(NC5=O)C(C)C)c4nc23)C(C)OC(=O)C(C(C)C)N(C)C(=O)CN(C)C(=O)C2CCCN2C1=O | 0.238502 | 0 |
| BRD-K05673000-323-12-7 | dicloxacillin | Cc1onc(c1C(=O)N[C@H]1[C@H]2SC(C)(C)[C@@H](N2C1=O)C(O)=O)-c1c(Cl)cccc1Cl | 0.236853 | 0 |
| BRD-K70578146-001-06-7 | dactinomycin | CC(C)[C@H]1NC(=O)[C@@H](NC(=O)c2ccc(C)c3oc4c(C)c(=O)c(N)c(C(=O)N[C@H]5[C@@H](C)OC(=O)[C@H](C(C)C)N(C)C(=O)CN(C)C(=O)[C@@H]6CCCN6C(=O)[C@H](NC5=O)C(C)C)c4nc23)[C@@H](C)OC(=O)[C@H](C(C)C)N(C)C(=O)CN(C)C(=O)[C@@H]2CCCN2C1=O | 0.234624 | 0 |
| BRD-K18948558-001-01-9 | clevudine | Cc1cn([C@H]2O[C@@H](CO)[C@H](O)[C@@H]2F)c(=O)[nH]c1=O | 0.233112 | 0 |
| BRD-K47554101-001-01-2 | eperezolid | CC(=O)NC[C@H]1CN(C(=O)O1)c1ccc(N2CCN(CC2)C(=O)CO)c(F)c1 | 0.231113 | 0 |
| BRD-M97302542-001-04-4 | dichloroacetate | [Na].OC(=O)C(Cl)Cl | 0.230659 | 0 |
| BRD-K87948281-001-01-9 | F-11440 | Cn1c(=O)cnn(CCCCN2CCN(CC2)c2ncccn2)c1=O | 0.22627 | 0 |
| BRD-K64716392-001-03-9 | nedocromil | CCCc1c2oc(cc(=O)c2cc2c1n(CC)c(cc2=O)C(O)=O)C(O)=O | 0.225004 | 0 |
| BRD-K00354853-001-01-2 | RO-3 | COc1cc(Cc2cnc(N)nc2N)c(cc1OC)C(C)C | 0.224644 | 0 |
| BRD-K12539416-001-01-4 | sulbutiamine | CC(C)C(=O)OCC\C(SS\C(CCOC(=O)C(C)C)=C(/C)N(Cc1cnc(C)nc1N)C=O)=C(\C)N(Cc1cnc(C)nc1N)C=O | 0.224477 | 0 |
| BRD-K92150287-066-01-2 | exatecan-mesylate | CC[C@@]1(O)C(=O)OCc2c1cc1-c3nc4cc(F)c(C)c5CC[C@H](N)c(c3Cn1c2=O)c45 | 0.223315 | 0 |

FIG. 13 (Continued)

| | | | | |
|---|---|---|---|---|
| BRD-K92428232-001-10-6 | GSK461364 | C[C@@H](Oc1cc(sc1C(N)=O)-n1cnc2ccc(CN3CCN(C)CC3)cc12)c1ccccc1C(F)(F)F | 0.222333 | 0 |
| BRD-K13277760-001-01-2 | rifamycin-sv | CO[C@H]1C=CO[C@@]2(C)Oc3c(C2=O)c2c(O)cc(NC(=O)\C(C)=C/C=C\[C@@H](C)[C@@H](O)[C@@H](C)[C@H](O)[C@H](C)[C@H]([C@H]1C)C(=O)OC)c(O)c2c(O)c3C | 0.221913 | 0 |
| BRD-K43570081-001-04-0 | geldanamycin | CO[C@H]1C[C@H](C)CC2=C(OC)C(=O)C=C(NC(=O)\C(C)=C\C=C\[C@H](OC)[C@@H](OC(N)=O)\C(C)=C\[C@H](C)[C@H]1O)C2=O | 0.221648 | 0 |
| BRD-A79643124-001-01-9 | flosequinan | Cn1cc(S(C)=O)c(=O)c2ccc(F)cc12 | 0.215392 | 0 |
| BRD-A34788695-003-12-8 | tetracycline | CN(C)[C@H]1[C@@H]2C[C@H]3C(C(=O)c4c(O)cccc4[C@@]3(C)O)C(=O)[C@]2(O)C(=O)C(C(N)=O)C1=O | 0.215227 | 0 |
| BRD-K97833335-001-08-2 | 2,4-dinitrochlorobenzene | [O-][N+](=O)c1ccc(Cl)c(c1)[N+]([O-])=O | 0.214785 | 0 |
| BRD-K44974079-001-01-3 | ticagrelor | CCCSc1nc(N[C@@H]2C[C@@H]2c2ccc(F)c(F)c2)c2nnn([C@@H]3C[C@H](OCCO)[C@H](O)[C@H]3O)c2n1 | 0.214363 | 0 |
| BRD-A69651145-003-09-8 | minocycline | CN(C)[C@H]1[C@@H]2C[C@@H]3Cc4c(ccc(O)c4C(=O)C3C(=O)[C@]2(O)C(=O)C(C(N)=O)C1=O)N(C)C | 0.213665 | 0 |
| BRD-K38564664-001-01-1 | rolziracetam | O=C1CCC2CCC(=O)N12 | 0.213539 | 0 |
| BRD-K81405859-300-02-2 | JTE-607 | CCOC(=O)[C@H](Cc1ccccc1)NC(=O)c1cc(Cl)c(OCCN2CCN(C)CC2)c(Cl)c1O | 0.209832 | 0 |
| BRD-K97428065-001-01-2 | netupitant | CN(C(=O)C(C)(C)c1cc(cc(c1)C(F)(F)F)C(F)(F)F)c1cnc(cc1-c1ccccc1C)N1CCN(C)CC1 | 0.208396 | 0 |
| BRD-A81370665-001-03-6 | BI-D1870 | CC(C)CCN1C(C)C(=O)N(C)c2cnc(Nc3cc(F)c(O)c(F)c3)nc12 | 0.207704 | 0 |
| BRD-A46717658-236-02-5 | azlocillin | CC1(C)SC2C(NC(=O)[C@H](NC(=O)N3CCNC3=O)c3ccccc3)C(=O)N2C1C(O)=O | 0.206316 | 0 |

FIG. 13 (Continued)

| | | | | |
|---|---|---|---|---|
| BRD-K31086665-005-04-6 | NH125 | CCCCCCCCCCCCCCCC[n+]1ccn(Cc2ccccc2)c1C | 0.20237 | 0 |
| BRD-K23106423-001-01-0 | substance-p | CSCC[C@H](NC(=O)[C@H](CC(C)C)NC(=O)CNC(=O)[C@H](Cc1ccccc1)NC(=O)[C@H](Cc1ccccc1)NC(=O)[C@H](CCC(N)=O)NC(=O)[C@H](CCC(N)=O)NC(=O)[C@@H]1CCCN1C(=O)[C@H](CCCCN)NC(=O)[C@@H]1CCCN1C(=O)[C@@H](N)CCCNC(N)=N)C(N)=O | 0.200636 | 0 |
| BRD-K46843573-001-01-9 | zotarolimus | CO[C@@H]1C[C@H](C[C@@H](C)[C@@H]2CC(=O)[C@H](C)\C=C(C)\[C@@H](O)[C@@H](OC)C(=O)[C@H](C)C[C@H](C)\C=C\C=C\C=C(C)\[C@H](C[C@@H]3CC[C@@H](C)[C@@](O)(O3)C(=O)C(=O)N3CCCC[C@H]3C(=O)O2)OC)CC[C@@H]1n1cnnn1 | 0.200598 | 0 |

FIG. 13 (Continued)

| SMILES String | ZINC Index | Prediction Score |
|---|---|---|
| NC12C3C4C1C1C2C3C41N | ZINC000005133023 | 0.999938667 |
| N1NP2NNP1NN2 | ZINC000263621387 | 0.995923662 |
| CCCCCCCCCCCCCn1cc(C(=O)O)c(=O)c2cc(F)c(N3CCNCC3)c(F)c21 | ZINC000097944972 | 0.992849535 |
| O=C(O)c1cn2c3c(cc(F)c(F)c3OCC2)c1=O | ZINC000146710018 | 0.992194173 |
| O/N=C1\N[C@H]2NCCN[C@H]2N\C1=N/O | ZINC000022865640 | 0.992158172 |
| CN1CCN(c2cc(F)c(C(=O)O)cc2F)CC1 | ZINC000098210484 | 0.989393172 |
| C[C@H]1COc2c(N3CCN(C)CC3)c(F)cc3c(=O)c(C(=O)N[C@H]4SC(=O)NC4=O)cn1c32 | ZINC001148155066 | 0.989257887 |
| CC(=O)N1C2C3N(C(C)=O)[C@H]4N[C@H]1[C@@H](N[C@H]4N3C(C)=O)N2C(C)=O | ZINC000169457956 | 0.989006802 |
| O/N=C1\N[C@@H]2NCCN[C@H]2N\C1=N/O | ZINC000022865638 | 0.988666186 |
| O/N=C1\N[C@H]2NCCN[C@@H]2N\C1=N/O | ZINC000022865647 | 0.98866618 |
| CO/N=C(\C(=O)N[C@H]1C(=O)N2C(C(=O)O)=CCS[C@@H]12)c1csc(N)n1 | ZINC000003830478 | 0.988517621 |
| CN1CCN(c2c(F)cc(C(=O)O)c(F)c2F)CC1 | ZINC000098210481 | 0.988381821 |
| C[C@@H]1COc2c(N3CCN(C)CC3)c(F)cc3c(=O)c(C(=O)N[C@H]4SC(=O)NC4=O)cn1c32 | ZINC001148155067 | 0.987329844 |
| C[C]1COc2c(F)c(F)cc3c(=O)c(C(=O)O)cn1c32 | ZINC001560405337 | 0.987231618 |

FIG. 14

| | | |
|---|---|---|
| C[C@H]1COc2c(F)c(F)cc3c(=O)c(C(=O)O)cn1c32 | ZINC000000057096 | 0.987121335 |
| C[C@H]1COc2c(N3CCN(C)CC3)c(F)cc3c(=O)c(C(=O)N[C@@H]4SC(=O)NC4=O)cn1c32 | ZINC001148155068 | 0.986908647 |
| C[C@H]1COc2c(N3CCN(C)CC3)c(F)cc3c(=O)c(C(=O)n4c(N)csc4=N)cn1c32 | ZINC001148156838 | 0.986669132 |
| CO/N=C(\C(=O)N[C@H]1C(=O)N2C(C(=O)O)=CCS[C@H]12)c1csc(N)n1 | ZINC000001530594 | 0.986548293 |
| COCC1=C(C(=O)O)N2C(=O)[C@@H](NC(=O)/C(=N\OC)c3csc(N)n3)[C@H]2SC1 | ZINC000003830453 | 0.985835081 |
| CO/N=C(/C(=O)N[C@H]1C(=O)N2C(C(=O)O)=C(CSc3nnc(C)s3)CS[C@@H]12)c1csc(N)n1 | ZINC000004109048 | 0.985117623 |
| CO/N=C(\C(=O)N[C@H]1C(=O)N2C(C(=O)O)=C(C[N+]3(C)CCCC3)CS[C@@H]12)c1csc(N)n1 | ZINC000008582322 | 0.984606066 |
| C[C@@H]1COc2c(N3CCN(C)CC3)c(F)cc3c(=O)c(C(=O)n4c(N)csc4=N)cn1c32 | ZINC001148156836 | 0.984488067 |
| C[C@@H]1COc2c(N3CCN(C)CC3)c(F)cc3c(=O)c(C(=O)N[C@@H]4SC(=O)NC4=O)cn1c32 | ZINC001148155065 | 0.984170145 |
| O=C1C(N2CC2)=C(N2CC2)C(=O)C(N2CC2)=C1N1CC1 | ZINC000049877717 | 0.983924422 |
| COCC1=C(C(=O)O)N2C(=O)[C@@H](NC(=O)/C(=N/OC)c3csc(N)n3)[C@H]2SC1 | ZINC000038321403 | 0.983802453 |
| Nc1nc(-n2cc(C(=O)O)c(=O)c3cc(F)c(NC[C@@H](O)COC4CN(c5c(F)cc6c(=O)c(C(=O)O)cn(-c7nc(N)c(F)cc7F)c6c5Cl)C4)c(Cl)c32)c(F)cc1F | ZINC000167293190 | 0.983788905 |
| CO/N=C(\C(=O)N[C@H]1C(=O)N2C(C(=O)O)=C(CSc3nnnn3C)CS[C@@H]12)c1csc(N)n1 | ZINC000003830416 | 0.983714405 |

FIG. 14 (Continued)

| | | |
|---|---|---|
| CC(=O)N1C2C3N(C(C)=O)[C@@H]4N[C@H]1[C@@H](N[C@H]4N3C(C)=O)N2C(C)=O | ZINC000033692493 | 0.983623058 |
| Nc1nc(-n2cc(C(=O)O)c(=O)c3cc(F)c(NC[C@H](O)COC4CN(c5c(F)cc6c(=O)c(C(=O)O)cn(-c7nc(N)c(F)cc7F)c6c5Cl)C4)c(Cl)c32)c(F)cc1F | ZINC000167293302 | 0.983247107 |
| CO/N=C(/C(=O)N[C@H]1C(=O)N2C(C(=O)O)=C(CSc3nnc(C)s3)CS[C@H]12)c1csc(N)n1 | ZINC000004109046 | 0.983075052 |
| CO/N=C(/C(=O)N[C@H]1C(=O)N2C(C(=O)O)=C(C[N+]3(C)CCCC3)CS[C@@H]12)c1csc(N)n1 | ZINC000009230258 | 0.982798028 |
| C[C@@H]1COc2c(F)c(F)cc3c(=O)c(C(=O)O)cn1c32 | ZINC000000057097 | 0.982360741 |
| CO/N=C(\C(=O)N[C@H]1C(=O)N2C(C(=O)O)=C(C[N+]3(C)CCCC3)CS[C@H]12)c1csc(N)n1 | ZINC000008582321 | 0.982121953 |
| CO/N=C(/C(=O)N[C@H]1C(=O)N2C(C(=O)O)=C(CSc3nnnn3C)CS[C@@H]12)c1csc(N)n1 | ZINC000011616517 | 0.981920066 |
| C[C@H]1COc2c(N3CCN(C)CC3)c(F)cc3c2n1cc(C(=O)NC(=N)SCCN)c3=O | ZINC001148156901 | 0.981878924 |
| C[C@H]1COc2c(N3CCN(C)CC3)c(F)cc3c(=O)c(C(=O)n4cc(F)c(O)nc4=N)cn1c32 | ZINC001148153929 | 0.981826201 |
| CO/N=C(\C(=O)N[C@H]1C(=O)N2C(C(=O)O)=C(CSc3nnnn3C)CS[C@H]12)c1csc(N)n1 | ZINC000003830415 | 0.981301928 |
| C[C@H]1COc2c(N3CCN(C)CC3)c(F)cc3c(=O)c(C(=O)Nc4c(N)c(=O)c4=O)cn1c32 | ZINC001148155979 | 0.980918702 |
| CO/N=C(/C(=O)N[C@H]1C(=O)N2C(C(=O)O)=C(C[N+]3(C)CCCC3)CS[C@H]12)c1csc(N)n1 | ZINC000021999743 | 0.980134004 |

FIG. 14 (Continued)

| | | |
|---|---|---|
| CO/N=C(\C(=O)N[C@H]1C(=O)N2C(C(=O)O)=C(CSc3nc(=O)c(O)nn3C)CS[C@@H]12)c1csc(N)n1 | ZINC000028467868 | 0.97967768 |
| CO/N=C(/C(=O)N[C@H]1C(=O)N2C(C(=O)O)=C(CSc3nnnn3C)CS[C@H]12)c1csc(N)n1 | ZINC000026892366 | 0.979359913 |
| C[C@@H]1COc2c(N3CCN(C)CC3)c(F)cc3c(=O)c(C(=O)n4cc(F)c(O)nc4=N)cn1c32 | ZINC001148153928 | 0.979008028 |
| C[C@H]1COc2c(N3CCN(C)CC3)c(F)cc3c(=O)c(C(=O)N[C@@H](CO)C(N)=O)cn1c32 | ZINC001148163802 | 0.979007661 |
| CO/N=C(\C(=O)N[C@@H]1C(=O)N2C(C(=O)N[C@H]3SC(=O)NC3=O)=CCS[C@H]12)c1csc(N)n1 | ZINC001185592135 | 0.978558823 |
| CO/N=C(\C(=O)N[C@@H]1C(=O)N2C(C(=O)O)=CCS[C@@H]12)c1csc(N)n1 | ZINC000003830479 | 0.978524035 |
| CCn1cc(C(=O)O)c(=O)c2cc(F)c(N3CCN([C@H]4CC(=O)N(C5CC5)C4=O)CC3)cc21 | ZINC000025059144 | 0.978382105 |
| CN1CCN(c2c(=O)c(=O)c2N2CCN(C)CC2)CC1 | ZINC000101688175 | 0.978258508 |
| CCn1cc(C(=O)O)c(=O)c2c(F)ccc(F)c21 | ZINC000062624998 | 0.978163502 |
| CO/N=C(\C(=O)N[C@H]1C(=O)N2C(C(=O)O)=C(CSc3nc(C)c(C(=O)O)s3)CC[C@@H]12)c1csc(N)n1 | ZINC000100030372 | 0.978119013 |
| CO/N=C(\C(=O)N[C@H]1C(=O)N2C(C(=O)O)=C(CSc3[nH]c(=O)c(O)n[n+]3C)CS[C@@H]12)c1csc(N)n1 | ZINC000409412963 | 0.97801635 |
| O=C(O)c1cn(C2CC2)c2cc(N3CCN([C@H]4CC(=O)N(c5cc(Cl)cc(Cl)c5)C4=O)CC3)c(F)cc2c1=O | ZINC000102923413 | 0.977939057 |
| C[C@@H]1COc2c(N3CCN(C)CC3)c(F)cc3c2n1cc(C(=O)NC(=N)SCCN)c3=O | ZINC001148156895 | 0.977903554 |
| C[C@H]1COc2c(N3CCN(C)CC3)c(F)cc3c2n1cc(C(=O)n1c(Cl)ncc(N)c1=N)c3=O | ZINC001148156368 | 0.977872974 |

FIG. 14 (Continued)

| | | |
|---|---|---|
| C[C@@H]1COc2c(F)c(F)cc3c(=O)c(C(=O)N4CN[C@H](N)[C@H]5NCN[C@H]54)cn1c32 | ZINC001152661908 | 0.977850181 |
| C=C1c2c(Cl)ccc(O)c2C(O)=C2C(=O)[C@]3(O)C(=O)/C(=C(/N)O)C(=O)[C@@H](N(C)C)[C@@H]3[C@@H](O)[C@H]12 | ZINC000060298588 | 0.977633175 |
| CO/N=C(/C(=O)N[C@H]1C(=O)N2C(C(=O)O)=C(CSc3nc(=O)c(O)nn3C)CS[C@@H]12)c1csc(N)n1 | ZINC000033185495 | 0.977565622 |
| CO/N=C(\C(=O)N[C@H]1C(=O)N2C(C(=O)O)=C(CSc3nc(=O)c(=O)[nH]n3C)CS[C@H]12)c1csc(N)n1 | ZINC000003977804 | 0.977487716 |
| CO/N=C(\C(=O)N[C@@H]1C(=O)N2C(C(=O)O)=C(C[N+]3(C)CCCC3)CS[C@@H]12)c1csc(N)n1 | ZINC000008035460 | 0.9773846 |
| C[C@H]1COc2c(N3CCN(C)CC3)c(F)cc3c(=O)c(C(=O)ON4C(=O)CCC4=O)cn1c32 | ZINC000138786489 | 0.977143291 |
| CO/N=C(/C(=O)N[C@@H]1C(=O)N2C(C(=O)O)=C(CSc3nnc(C)s3)CS[C@@H]12)c1csc(N)n1 | ZINC000004109044 | 0.976674965 |
| CO/N=C(\C(=O)N[C@H]1C(=O)N2C(C(=O)O)=C(CSc3nc(C)c(C(=O)O)s3)CC[C@H]12)c1csc(N)n1 | ZINC000100030376 | 0.97656576 |
| CNc1nnc(SCC2=C(C(=O)O)N3C(=O)[C@@H](NC(=O)/C(=N/OC)c4csc(N)c4)[C@H]3SC2)s1 | ZINC000006878964 | 0.97621685 |
| CC(=O)N1C2C3N(C(C)=O)[C@@H]4N[C@@H]1[C@@H](N[C@H]4N3C(C)=O)N2C(C)=O | ZINC000101421827 | 0.97604723 |
| CN(C)[C@@H]1C(=O)[C@@H](C(N)=O)C(=O)[C@@]2(O)C(=O)[C@H]3C(=O)c4c(O)cccc4[C@@](C)(O)[C@H]3[C@H](O)[C@@H]12 | ZINC000101163284 | 0.976016775 |
| C[C@@H]1COc2c(N3CCN(C)CC3)c(F)cc3c(=O)c(C(=O)Nc4c(N)c(=O)c4=O)cn1c32 | ZINC001148155982 | 0.976002488 |

FIG. 14 (Continued)

| | | |
|---|---|---|
| C[C@H]1COc2c(N3CCN(C)CC3)c(F)cc3c2n1cc(C(=O)n1cc(N)c(O)nc1=N)c3=O | ZINC001148164204 | 0.975933596 |
| C[C@H]1COc2c(N3CCN(C)CC3)c(F)cc3c(=O)c(C(=O)N[C@H](CO)C(N)=O)cn1c32 | ZINC001148163803 | 0.975920469 |
| O=C(O)c1cn(C2CC2)c2cc(N3CCN([C@@H]4CC(=O)N(c5cc(Cl)cc(Cl)c5)C4=O)CC3)c(F)cc2c1=O | ZINC000102923414 | 0.975721759 |
| CO[C@@]1(NC(=O)C2SC(=C(C(N)=O)C(=O)O)S2)C(=O)N2C(C(=O)O)=C(CSc3nnnn3C)CS[C@H]21 | ZINC000003830442 | 0.975676125 |
| CC(=O)N1C2C3N(C(C)=O)[C@@H]4N[C@H]1[C@H](N[C@H]4N3C(C)=O)N2C(C)=O | ZINC000101421822 | 0.975482899 |
| CCn1cc(C(=O)O)c(=O)c2cc(F)c(N3CCN([C@@H]4CC(=O)N(C5CC5)C4=O)CC3)cc21 | ZINC000071796197 | 0.975391698 |
| CO/N=C(\C(=O)N[C@@H]1C(=O)N2C(C(=O)N[C@@H]3C[C@H]3F)=CCS[C@H]12)c1csc(N)n1 | ZINC001185591037 | 0.975350127 |
| C[C@H]1COc2c(N3CCN(C)CC3)c(F)cc3c(=O)c(C(=O)N(C)[C@@H]4[C@H]5CNC[C@H]54)cn1c32 | ZINC001161220333 | 0.975290784 |
| CO/N=C(/C(=O)N[C@@H]1C(=O)N2C(C(=O)O)=C(C[N+]3(C)CCCC3)CS[C@@H]12)c1csc(N)n1 | ZINC000003871925 | 0.975144503 |
| C[C@H]1COc2c(N3CCN(C)CC3)c(F)cc3c(=O)c(C(=O)N[C@H]4CCC(=O)NC4=O)cn1c32 | ZINC001148155082 | 0.975049827 |
| C[C@H]1COc2c(N3CCN(C)CC3)c(F)cc3c(=O)c(C(=O)N[C@@H]4CNC[C@H]4O)cn1c32 | ZINC001219714768 | 0.975044486 |
| CO/N=C(\C(=O)N[C@H]1C(=O)N2C(C(=O)O)=C(CSc3[nH]c(=O)c(O)n[n+]3C)CS[C@H]12)c1csc(N)n1 | ZINC000409412961 | 0.974993792 |

FIG. 14 (Continued)

| | | |
|---|---|---|
| CCn1cc(C(=O)O)c(=O)c2cc(F)c(F)cc21 | ZINC000000307134 | 0.974882334 |
| C[C@H]1COc2c(N3CCN(C)CC3)c(F)cc3c2n1cc(C(=O)N(CCCCN)C(=N)N)c3=O | ZINC001148157388 | 0.974787706 |
| CO/N=C(/C(=O)N[C@H]1C(=O)N2C(C(=O)O)=C(CSc3nc(=O)c(O)nn3C)CS[C@H]12)c1csc(N)n1 | ZINC000038147281 | 0.974671444 |
| C[C@@H]1COc2c(N3CCN(C)CC3)c(F)cc3c2n1cc(C(=O)n1c(Cl)ncc(N)c1=N)c3=O | ZINC001148156366 | 0.973874968 |
| C[C@@H]1COc2c(F)c(F)cc3c(=O)c(C(=O)N4CN[C@H](N)[C@@H]5NCN[C@H]54)cn1c32 | ZINC001152661909 | 0.973847032 |
| C[C@@H]1COc2c(F)c(F)cc3c(=O)c(C(=O)N4CN[C@H](N)[C@H]5NCN[C@@H]54)cn1c32 | ZINC001152661906 | 0.973808026 |
| C[C@@H]1COc2c(N3CCN(C)CC3)c(F)cc3c(=O)c(C(=O)N[C@@H](CO)C(N)=O)cn1c32 | ZINC001148163800 | 0.9737746 |
| CO/N=C(\C(=O)N[C@@H]1C(=O)N2C(C(=O)n3c(N)csc3=N)=CCS[C@H]12)c1csc(N)n1 | ZINC001185591169 | 0.9737293 |
| CO/N=C(/C(=O)N[C@H]1C(=O)N2C(C(=O)O)=C(CSc3nnc(C)s3)CS[C@@H]12)c1csc(N)c1 | ZINC000111069331 | 0.973697221 |
| C[C@H]1COc2c(N3CCN(C)CC3)c(F)cc3c2n1cc(C(=O)N[C@@H](C#N)C(N)=O)c3=O | ZINC001148162289 | 0.973500919 |
| CO/N=C(\C(=O)N[C@@H]1C(=O)N2C(C(=O)O)=CCS[C@H]12)c1csc(N)n1 | ZINC000003830477 | 0.973492661 |
| C1CCC(N2N[C@H]2[C@H]2NN2C2CCCCC2)CC1 | ZINC000019169129 | 0.973159 |
| CO/N=C(\C(=O)N[C@@H]1C(=O)N2C3=C(COC3=O)CS[C@H]12)c1csc(N)n1 | ZINC000039390677 | 0.973106936 |
| Cn1/c(=N/C(=N)NC(=N)N)n(/C(N)=N/C(=N)N)/c(=N/C(=N)NC(=N)N)n1C | ZINC000016363555 | 0.973060659 |

FIG. 14 (Continued)

| | | |
|---|---|---|
| CO/N=C(/C(=O)N[C@H]1C(=O)N2C(C(=O)O)=C(CSc3nnnn3C)CS[C@@H]12)c1cnc(N)s1 | ZINC000022001540 | 0.972783756 |
| CO/N=C(/C(=O)N[C@@H]1C(=O)N2C(C(=O)O)=C(CSc3nnc(C)s3)CS[C@H]12)c1csc(N)n1 | ZINC000004109042 | 0.972617751 |
| CO/N=C(\C(=O)N[C@@H]1C(=O)N2C(C(=O)N[C@@H]3SC(=O)NC3=O)=CCS[C@H]12)c1csc(N)n1 | ZINC001185592137 | 0.972541174 |
| CO/N=C(\C(=O)N[C@@H]1C(=O)N2C(C(=O)O)=C(C[N+]3(C)CCCC3)CS[C@H]12)c1csc(N)n1 | ZINC000003871923 | 0.97253533 |
| CNc1nnc(SCC2=C(C(=O)O)N3C(=O)[C@@H](NC(=O)/C(=N/OC)c4csc(N)c4)[C@@H]3SC2)s1 | ZINC000006878966 | 0.972526559 |
| CO/N=C(\C(=O)N[C@@H]1C(=O)N2C(C(=O)NC=N)=CCS[C@H]12)c1csc(N)n1 | ZINC001185592437 | 0.972502661 |
| N[C@@H]1NCN(C(=O)/C=C/c2cc(F)c(F)cc2F)[C@H]2NCN[C@H]21 | ZINC001179888657 | 0.972248569 |
| CC[C@H](C)[C@@H](CO)NC(=O)c1cn2c3c(cc(F)c(N4CCN(C)CC4)c3OC[C@H]2C)c1=O | ZINC001148155333 | 0.972227734 |
| CO[C@@]1(NC(=O)C2SC(=C(C(N)=O)C(=O)O)S2)C(=O)N2C(C(=O)O)=C(CSc3nnnn3C)CS[C@@H]21 | ZINC000003830441 | 0.972067875 |
| C[C@H]1CN(C(=O)c2cn3c4c(cc(F)c(N5CCN(C)CC5)c4OC[C@@H]3C)c2=O)C[C@H](C)N1 | ZINC001161231033 | 0.972055647 |
| C[C@@H]1COc2c(N3CCN(C)CC3)c(F)cc3c(=O)c(C(=O)N4C[C@H](C)N[C@@H](C)C4)cn1c32 | ZINC001161231032 | 0.972055641 |
| C[C@H]1COc2c(N3CCN(C)CC3)c(F)cc3c(=O)c(C(=O)N[C@@H]4CCC(=O)NC4=O)cn1c32 | ZINC001148155081 | 0.97189559 |

FIG. 14 (Continued)

| | | |
|---|---|---|
| CN(C)[C@@H]1C(=O)[C@H](C(N)=O)C(=O)[C@@]2(O)C(=O)[C@H]3C(=O)c4c(O)cccc4[C@@](C)(O)[C@H]3[C@H](O)[C@@H]12 | ZINC000101163281 | 0.971743098 |
| C[C@H]1COc2c(N3CCN(C)CC3)c(F)cc3c2n1cc(C(=O)N[C@H](C#N)C(N)=O)c3=O | ZINC001148162290 | 0.97167345 |
| CN(C)[C@@H]1C(=O)[C@@H](C(N)=O)C(=O)[C@@]2(O)C(=O)[C@@H]3C(=O)c4c(O)cccc4[C@@](C)(O)[C@H]3[C@H](O)[C@@H]12 | ZINC000101163282 | 0.971667385 |
| C[C@H]1COc2c(N3CCN(C)CC3)c(F)cc3c2n1cc(C(=O)n1c(=N)ccc(F)c1N)c3=O | ZINC001148155698 | 0.97159816 |
| C[C@@H]1COc2c(N3CCN(C)CC3)c(F)cc3c2n1cc(C(=O)n1cc(N)c(O)nc1=N)c3=O | ZINC001148164198 | 0.971524456 |
| COC(=O)c1cc(F)c(N2CCN(C)CC2)cc1F | ZINC000098210492 | 0.97141532 |
| COC(=O)[C@@H](NC(=O)c1cn2c3c(cc(F)c(N4CCN(C)CC4)c3OC[C@H]2C)c1=O)[C@@H](C)O | ZINC001148156921 | 0.971414512 |
| C[C@H]1COc2c(N3CCN(C)CC3)c(F)cc3c2n1cc(C(=O)n1cc(CN)cnc1=N)c3=O | ZINC001148163239 | 0.971300951 |
| CO/N=C(\C(=O)N[C@@H]1C(=O)N2C(C(=O)NC(=N)c3nccs3)=CCS[C@H]12)c1csc(N)n1 | ZINC001185592099 | 0.971010178 |
| CO/N=C(\C(=O)N[C@@H]1C(=O)N2C(C(=O)O)=C(CSc3nnnn3C)CS[C@@H]12)c1csc(N)n1 | ZINC000004676376 | 0.970921463 |
| CCOC(=O)c1c2c(sc1NC(=S)N1CCN(c3c(F)cc4c(=O)c(C(=O)O)cn(C5CC5)c4c3OC)C[C@@H]1C)CCCC2 | ZINC000098008256 | 0.970871383 |
| CO/N=C(\C(=O)N[C@@H]1C(=O)N2C(C(=O)O)=C(CS)CS[C@H]12)c1csc(N)n1 | ZINC000003918086 | 0.970853129 |
| CCOC(=O)c1c2c(sc1NC(=S)N1CCN(c3c(F)cc4c(=O)c(C(=O)O)cn(C5CC5)c4c3OC)C[C@H]1C)CCCC2 | ZINC000098008257 | 0.970783263 |

FIG. 14 (Continued)

| | | |
|---|---|---|
| CO/N=C(\C(=O)N[C@@H]1C(=O)N2C(C(=O)O)=C(CSc3cnns3)CS[C@H]12)c1csc(N)n1 | ZINC000004215275 | 0.970544204 |
| C[C@H]1COc2c(N3CCN(C)CC3)c(F)cc3c(=O)c(C(=O)N4CCNC[C@H]4C#N)cn1c32 | ZINC001148157676 | 0.970543545 |
| CO/N=C(\C(=O)N[C@@H]1C(=O)N2C(C(=O)O)=C(CSc3nc(C)c(C(=O)O)s3)CC[C@@H]12)c1csc(N)n1 | ZINC000100030361 | 0.970502496 |
| CCOC(=O)c1cn2c3c(cc(F)c(F)c3OCC2)c1=O | ZINC000039383796 | 0.970448107 |
| C[C@H]1COc2c(N3CCN(C)CC3)c(F)cc3c(=O)c(C(=O)NC(=N)c4ncc[nH]4)cn1c32 | ZINC001148155108 | 0.970364797 |
| CCOc1c(=O)c(=O)c1N1CCN(c2c(=O)c(=O)c2OCC)CC1 | ZINC000003126200 | 0.970157245 |
| C=C1c2c(Cl)ccc(O)c2C(O)=C2C(=O)[C@]3(O)C(O)=C(C(N)=O)C(=O)[C@@H](N(C)C)[C@@H]3[C@@H](O)[C@@H]12 | ZINC000102739374 | 0.970115197 |
| CO/N=C(/C(=O)N[C@@H]1C(=O)N2C(C(=O)O)=C(C[N+]3(C)CCCC3)CS[C@H]12)c1csc(N)n1 | ZINC000003871924 | 0.970035458 |
| C[C@@H]1COc2c(N3CCN(C)CC3)c(F)cc3c(=O)c(C(=O)N(C)[C@@H]4[C@H]5CNC[C@H]54)cn1c32 | ZINC001161220335 | 0.969714171 |
| COc1c(N2CCN(/C(S)=N\c3ccc(F)cc3)[C@@H](C)C2)c(F)cc2c(=O)c(C(=O)O)cn(C3CC3)c21 | ZINC000008672665 | 0.969406965 |
| C[C@@H]1COc2c(N3CCN(C)CC3)c(F)cc3c(=O)c(C(=O)N[C@H](CO)C(N)=O)cn1c32 | ZINC001148163801 | 0.969360372 |
| CO/N=C(/C(=O)N[C@H]1C(=O)N2C(C(=O)O)=C(CSc3nnc(C)s3)CS[C@H]12)c1csc(N)c1 | ZINC000003097992 | 0.969177428 |

FIG. 14 (Continued)

| | | |
|---|---|---|
| C[C@@H]1COc2c(N3CCN(C)CC3)c(F)cc3c(=O)c(C(=O)N[C@@H]4CNC[C@H]4O)cn1c32 | ZINC001219714767 | 0.969169527 |
| CO/N=C(/C(=O)N[C@H]1C(=O)N2C(C(=O)O)=C(Cn3nnc(C)n3)CS[C@@H]12)c1csc(N)n1 | ZINC000136464202 | 0.969153091 |
| CCCC[C@H](NC(=O)c1cn2c3c(cc(F)c(N4CCN(C)CC4)c3OC[C@H]2C)c1=O)C(N)=O | ZINC001148162434 | 0.968953735 |
| C[C@H]1COc2c(N3CCN(C)CC3)c(F)cc3c(=O)c(C(=O)N[C@@H](CN)C(C)(C)C)cn1c32 | ZINC001220859648 | 0.968926454 |
| C[C@@H]1COc2c(N3CCN(C)CC3)c(F)cc3c2n1cc(C(=O)N(CCCCN)C(=N)N)c3=O | ZINC001148157389 | 0.968804917 |
| C[C@@H]1COc2c(N3CCN(C)CC3)c(F)cc3c(=O)c(C(=O)N[C@H]4CCC(=O)NC4=O)cn1c32 | ZINC001148155084 | 0.968798122 |
| CO/N=C(/C(=O)N[C@H]1C(=O)N2C(C(=O)O)=C(CSc3nnnn3C)CS[C@H]12)c1cnc(N)s1 | ZINC000022001548 | 0.968791914 |
| N=c1scc(N)n1-c1c(F)cc(F)c(O)c1F | ZINC001176663924 | 0.968604979 |
| COCC1=C(C(=O)O)N2C(=O)[C@H](NC(=O)/C(=N\OC)c3csc(N)n3)[C@@H]2SC1 | ZINC000015848221 | 0.968594465 |
| CO/N=C(/C(=O)N[C@@H]1C(=O)N2C(C(=O)O)=C(CSc3nnnn3C)CS[C@@H]12)c1csc(N)n1 | ZINC000003830414 | 0.968550482 |
| CN(C)[C@H]1C(=O)C(C(N)=O)=C(O)[C@@]2(O)C(=O)C3=C(O)c4c(O)cccc4[C@@](C)(O)[C@H]3[C@H](O)[C@@H]12 | ZINC000199067817 | 0.968420076 |
| COc1c(N2CCN(/C(S)=N\c3ccc(F)cc3)[C@H](C)C2)c(F)cc2c(=O)c(C(=O)O)cn(C3CC3)c21 | ZINC000008672663 | 0.968329185 |

FIG. 14 (Continued)

| | | |
|---|---|---|
| CO/N=C(\C(=O)N[C@@H]1C(=O)N2C(C(=O)O)=C(CSc3nc(C)c(C(=O)O)s3)CC[C@H]12)c1csc(N)n1 | ZINC000100030364 | 0.968292063 |
| C[C@@H]1COc2c(F)c(F)cc3c(=O)c(C(=O)N4CN[C@H](N)[C@@H]5NCN[C@@H]54)cn1c32 | ZINC001152661907 | 0.968167502 |
| C[C@@H]1COc2c(N3CCN(C)CC3)c(F)cc3c2n1cc(C(=O)N[C@@H](C#N)C(N)=O)c3=O | ZINC001148162287 | 0.967813849 |
| CO/N=C(/C(=O)N[C@@H]1C(=O)N2C(C(=O)O)=C(CS)CS[C@H]12)c1csc(N)n1 | ZINC000022056129 | 0.967731002 |
| CO/N=C(\C(=O)N[C@H]1C(=O)N2C(C(=O)O)=C(CSC(=O)c3ccco3)CS[C@@H]12)c1csc(N)n1 | ZINC000011616463 | 0.967631501 |
| CO/N=C(\C(=O)N[C@H]1C(=O)N2C(C(=O)O)=C(COC(C)=O)CS[C@@H]12)c1csc(N)n1 | ZINC000004517167 | 0.967577401 |
| Cc1nnc(SCC2=C(C(=O)O)N3C(=O)[C@@H](NC(=O)c4cc(F)c(F)cc4Cl)[C@H]3SC2)s1 | ZINC000017356890 | 0.967374748 |
| C[C@H]1COc2c(N3CCN(C)CC3)c(F)cc3c(=O)c(C(=O)N4C[C@@H](F)C[C@H]4C#N)cn1c32 | ZINC001148157097 | 0.967138207 |
| N[C@@H]1NCN(C(=O)/C=C/c2cc(F)c(F)cc2F)[C@H]2NCN[C@@H]21 | ZINC001179888658 | 0.967010084 |
| N[C@@H]1NCN(C(=O)/C=C/c2cc(F)c(F)cc2F)[C@@H]2NCN[C@H]21 | ZINC001179888659 | 0.966884971 |
| C[C@H]1COc2c(N3CCN(C)CC3)c(F)cc3c(=O)c(C(=O)N4CCNCC(F)(F)C4)cn1c32 | ZINC001148154743 | 0.966664609 |
| C[C@@H]1COc2c(N3CCN(C)CC3)c(F)cc3c2n1cc(C(=O)n1cc(CN)cnc1=N)c3=O | ZINC001148163238 | 0.966663882 |
| COc1c(N2CCN(C(=S)NC(=O)c3ccco3)[C@@H](C)C2)c(F)cc2c(=O)c(C(=O)O)cn(C3CC3)c21 | ZINC000097954914 | 0.966497383 |

FIG. 14 (Continued)

| | | |
|---|---|---|
| CN(C)[C@@H]1C(=O)[C@H](C(N)=O)C(=O)[C@@]2(O)C(=O)[C@@H]3C(=O)c4c(O)cccc4[C@@](C)(O)[C@H]3[C@H](O)[C@@H]12 | ZINC000101163279 | 0.966487825 |
| C[C@H]1COc2c(N3CCN(C)CC3)c(F)cc3c(=O)c(C(=O)N(c4ncccn4)C4CNC4)cn1c32 | ZINC001148157342 | 0.966371188 |
| C[C@H]1COc2c(N3CCN(C)CC3)c(F)cc3c(=O)c(C(=O)N[C@@H]4CNCC[C@H]4F)cn1c32 | ZINC001221367780 | 0.966273719 |
| N[C@@H]1NCN(c2c(F)nc(F)nc2Cl)[C@H]2NCN[C@H]21 | ZINC001162446441 | 0.966124138 |
| C[C@H]1COc2c(N3CCN(C)CC3)c(F)cc3c(=O)c(C(=O)N4CCNC[C@@H]4C#N)cn1c32 | ZINC001148157665 | 0.966093048 |
| COc1c(N2CCN(C(=S)NC(=O)c3ccco3)[C@H](C)C2)c(F)cc2c(=O)c(C(=O)O)cn(C3CC3)c21 | ZINC000097954913 | 0.965908703 |
| C[C@@H]1COc2c(N3CCN(C)CC3)c(F)cc3c2n1cc(C(=O)N[C@H](C#N)C(N)=O)c3=O | ZINC001148162288 | 0.965750867 |
| C=C1c2cccc(O)c2C(=O)[C@@]2(F)C(=O)[C@]3(O)C(=O)C(C(N)=O)=C(O)[C@@H](N(C)C)[C@@H]3[C@@H](O)[C@@H]12 | ZINC000071769472 | 0.965738237 |
| COC(=O)c1cc(F)c(N2CCN(C)CC2)c(F)c1F | ZINC000097463429 | 0.965644917 |
| C[C@@H]1COc2c(N3CCN(C)CC3)c(F)cc3c2n1cc(C(=O)n1c(=N)ccc(F)c1N)c3=O | ZINC001148155695 | 0.965607542 |
| CC[C@H](C)[C@@H](CO)NC(=O)c1cn2c3c(cc(F)c(N4CCN(C)CC4)c3OC[C@@H]2C)c1=O | ZINC001148155334 | 0.965474188 |
| CO/N=C(\C(=O)N[C@@H]1C(=O)N2C(C(=O)NCCN)=CCS[C@H]12)c1csc(N)n1 | ZINC001219870507 | 0.965458649 |
| CO/N=C(\C(=O)N[C@@H]1C(=O)N2C(C(=O)O)=C(CSc3nc(=O)c(O)nn3C)CS[C@@H]12)c1csc(N)n1 | ZINC000028467872 | 0.965243605 |

FIG. 14 (Continued)

| | | |
|---|---|---|
| COCC1=C(C(=O)O)N2C(=O)[C@H](NC(=O)/C(=N/OC)c3csc(N)n3)[C@@H]2SC1 | ZINC000031274350 | 0.96519703 |
| C[C@H]1COc2c(N3CCN(C)CC3)c(F)cc3c(=O)c(C(=O)N[C@H]4CNC(=O)C4(C)C)cn1c32 | ZINC001148163070 | 0.965195528 |
| C[C@@H]1COc2c(N3CCN(C)CC3)c(F)cc3c(=O)c(C(=O)NC(=N)c4ncc[nH]4)cn1c32 | ZINC001148155107 | 0.965171695 |
| C[C@H]1c2cccc(O)c2C(=O)[C@H]2C(=O)[C@]3(O)C(=O)[C@@H](C(N)=O)C(=O)[C@@H](N(C)C)[C@@H]3[C@@H](O)[C@H]12 | ZINC000104215570 | 0.965161788 |
| CO/N=C(\C(=O)N[C@@H]1C(=O)N2C(C(=O)O)=C(CSc3nnnn3C)CS[C@H]12)c1csc(N)n1 | ZINC000003830413 | 0.965135205 |
| CO/N=C(\C(=O)N[C@@H]1C(=O)N2C(C(=O)N3C[C@H](C)N[C@@H](C)C3)=CCS[C@H]12)c1csc(N)n1 | ZINC001161231051 | 0.965011081 |
| COC(=O)[C@@H](C)NC(=S)N1CCN(c2c(F)cc3c(=O)c(C(=O)O)cn(C4CC4)c3c2OC)C[C@H]1C | ZINC000245245592 | 0.964909586 |
| C[C@H]1COc2c(N3CCN(C)CC3)c(F)cc3c2n1cc(C(=O)n1cnc(CN)cc1=N)c3=O | ZINC001148156518 | 0.964897597 |
| CC1CCN(c2c(F)c3sc4nc5cc(F)c(F)cc5n4c(=O)c3c(N3CCC(C)CC3)c2F)CC1 | ZINC000012417814 | 0.964565051 |
| COC(=O)C1=C(NC(=S)N2CCN(c3c(F)cc4c(=O)c(C(=O)O)cn(C5CC5)c4c3OC)C[C@H]2C)S[C@H]2CCCCC[C@@H]12 | ZINC000150387425 | 0.964463624 |
| C=CC1=C(C(=O)O)N2C(=O)[C@@H](NC(=O)/C(=N\O)c3csc(N)n3)[C@H]2SC1 | ZINC000003927198 | 0.96442762 |
| CO/N=C(/C(=O)N[C@H]1C(=O)N2C(C(=O)O)=C(CSc3nnnn3C)CS[C@@H]12)c1csc(N)c1 | ZINC000013563724 | 0.964393604 |
| C=C1c2c(Cl)ccc(O)c2C(O)=C2C(=O)[C@]3(O)C(O)=C(C(N)=O)C(=O)[C@@H](N(C)C)[C@@H]3[C@@H](O)[C@H]12 | ZINC000004149268 | 0.964377481 |

FIG. 14 (Continued)

| | | |
|---|---|---|
| CO/N=C(/C(=O)N[C@H]1C(=O)N2C(C(=O)O)=C(CSC(=O)c3ccco3)CS[C@@H]12)c1csc(N)n1 | ZINC000011616464 | 0.964377159 |
| COC(=O)[C@@H](C)NC(=S)N1CCN(c2c(F)cc3c(=O)c(C(=O)O)cn(C4CC4)c3c2OC)C[C@@H]1C | ZINC000013655682 | 0.96425947 |
| C[C@@H]1COc2c(N3CCN(C)CC3)c(F)cc3c(=O)c(C(=O)N(C)C4[C@@H]5CNC[C@@H]45)cn1c32 | ZINC001161220332 | 0.964240736 |
| C[C@@H]1COc2c(N3CCN(C)CC3)c(F)cc3c(=O)c(C(=O)N(C)C4[C@H]5CNC[C@H]45)cn1c32 | ZINC001161220334 | 0.96424073 |
| COC(=O)C1=C(NC(=S)N2CCN(c3c(F)cc4c(=O)c(C(=O)O)cn(C5CC5)c4c3OC)C[C@@H]2C)S[C@H]2CCCCC[C@@H]12 | ZINC000150387426 | 0.964047581 |
| CO/N=C(/C(=O)N[C@H]1C(=O)N2C(C(=O)O)=C(COC(C)=O)CS[C@@H]12)c1csc(N)n1 | ZINC000003830440 | 0.964045653 |
| C[C@@H]1COc2c(N3CCN(C)CC3)c(F)cc3c(=O)c(C(=O)N4CCNC[C@H]4C#N)cn1c32 | ZINC001148157670 | 0.963949391 |
| CO[C@@H]1CN(C(=O)c2cn3c4c(cc(F)c(N5CCN(C)CC5)c4OC[C@H]3C)c2=O)C[C@@H]1N | ZINC001161493262 | 0.963920182 |
| C=C1c2cccc(O)c2C(O)=C2C(=O)[C@]3(O)C(=O)/C(=C(/N)O)C(=O)[C@@H](N(C)C)[C@H]3[C@@H](O)[C@H]12 | ZINC000100374513 | 0.963785681 |
| COC(=O)[C@@H](NC(=O)c1cn2c3c(cc(F)c(N4CCN(C)CC4)c3OC[C@@H]2C)c1=O)[C@@H](C)O | ZINC001148156918 | 0.963691774 |
| COC(=O)[C@H](C)NC(=S)N1CCN(c2c(F)cc3c(=O)c(C(=O)O)cn(C4CC4)c3c2OC)C[C@H]1C | ZINC000009273940 | 0.963654715 |

FIG. 14 (Continued)

| | | |
|---|---|---|
| CO/N=C(/C(=O)N[C@H]1C(=O)N2C(C(=O)O)=C(CSc3nc(C)c(CC(=O)O)s3)CS[C@@H]12)c1csc(N)n1 | ZINC000011616586 | 0.963632655 |
| CCOC(=O)[C@@H](C#N)NC(=O)c1cn2c3c(cc(F)c(N4CCN(C)CC4)c3OC[C@H]2C)c1=O | ZINC001148163813 | 0.96356585 |
| C[C@@H]1COc2c(N3CCN(C)CC3)c(F)cc3c(=O)c(C(=O)N[C@@H]4CCC(=O)NC4=O)cn1c32 | ZINC001148155083 | 0.963513976 |
| COC(=O)c1c2c(sc1NC(=S)N1CCN(c3cc4c(cc3F)c(=O)c(C(=O)O)cn4C3CC3)CC1)CCCCC2 | ZINC000098007370 | 0.963293797 |
| CO/N=C(\C(=O)N[C@H]1C(=O)N2C(C(=O)O)=C(CSC(=O)c3ccco3)CS[C@H]12)c1csc(N)n1 | ZINC000001999440 | 0.963049582 |
| COC(=O)[C@H](C)NC(=S)N1CCN(c2c(F)cc3c(=O)c(C(=O)O)cn(C4CC4)c3c2OC)C[C@@H]1C | ZINC000009273941 | 0.96289278 |
| CO/N=C(/C(=O)N[C@@H]1C(=O)N2C(C(=O)O)=C(CSc3nnnn3C)CS[C@H]12)c1csc(N)n1 | ZINC000003871927 | 0.962592861 |
| CO/N=C(/C(=O)N[C@@H]1C(=O)N2C(C(=O)O)=C(CSc3nc(=O)c(O)nn3C)CS[C@@H]12)c1csc(N)n1 | ZINC000033185497 | 0.962347105 |
| O=c1ccn(C2CC2)c2cc(N3CCNCC3)c(F)cc12 | ZINC000022055476 | 0.962014607 |
| CO/N=C(\C(=O)N[C@H]1C(=O)N2C(C(=O)O)=C(COC(C)=O)CS[C@H]12)c1csc(N)n1 | ZINC000005223879 | 0.961968994 |
| C[C@@H]1COc2c(N3CCN(C)CC3)c(F)cc3c(=O)c(C(=O)N[C@@H](CN)C(C)(C)C)cn1c32 | ZINC001220859647 | 0.961759251 |
| COc1c(N2CCN(C(=S)Nc3ccccc3F)[C@@H](C)C2)c(F)cc2c(=O)c(C(=O)O)cn(C3CC3)c21 | ZINC000038139186 | 0.961712 |

FIG. 14 (Continued)

| | | |
|---|---|---|
| COC(=O)C1=C(NC(=S)N2CCN(c3c(F)cc4c(=O)c(C(=O)O)cn(C5CC5)c4c3OC)C[C@@H]2C)S[C@H]2CCCCC[C@H]12 | ZINC000150629982 | 0.961595726 |
| COc1c(N2CCN(C(=S)Nc3ccccc3F)[C@H](C)C2)c(F)cc2c(=O)c(C(=O)O)cn(C3CC3)c21 | ZINC000038139185 | 0.96159485 |
| C[C@H]1c2cccc(O)c2C(O)=C2C(=O)[C@]3(O)C(=O)/C(=C(/N)O)C(=O)[C@@H](N(C)C)[C@@H]3[C@@H](O)[C@@H]21 | ZINC000100056779 | 0.961379623 |
| C[C@H]1COc2c(N3CCN(C)CC3)c(F)cc3c2n1cc(C(=O)n1ccc(CN)cc1=N)c3=O | ZINC001148154680 | 0.96125088 |
| O=C(O)c1cn(C2CC2)c2cc(N3CCN(C(=S)NC(=O)c4ccc(Cl)cc4Cl)CC3)c(F)cc2c1=O | ZINC000100166381 | 0.960475335 |
| CN(C)[C@@H]1C(=O)C(C(N)=O)=C(O)[C@@]2(O)C(=O)C3=C(O)c4c(O)cccc4[C@@](C)(O)[C@H]3[C@H](O)[C@@H]12 | ZINC000100303028 | 0.960276568 |
| CCCC[C@H](NC(=O)c1cn2c3c(cc(F)c(N4CCN(C)CC4)c3OC[C@@H]2C)c1=O)C(N)=O | ZINC001148162435 | 0.960218218 |
| C[C@@H]1COc2c(N3CCN(C)CC3)c(F)cc3c(=O)c(C(=O)N(c4ncccn4)C4CNC4)cn1c32 | ZINC001148157343 | 0.960041988 |
| CN(C)[C@@H]1C(=O)[C@H](C(N)=O)C(=O)[C@@]2(O)C(=O)[C@H]3C(=O)c4c(O)ccc(Cl)c4[C@@](C)(O)[C@H]3C[C@@H]12 | ZINC000101843563 | 0.960035715 |
| CCn1cc(C(=O)N2CN[C@H](N)[C@H]3NCN[C@H]32)c(=O)c2cc(F)c(Cl)cc21 | ZINC001151284562 | 0.959878099 |
| C[C@H]1COc2c(N3CCN(C)CC3)c(F)cc3c(=O)c(C(=O)N(C)CC4(C)COC4)cn1c32 | ZINC001148155780 | 0.959672588 |
| N[C@@H]1NCN(C(=O)/C=C/c2cc(F)c(F)cc2F)[C@@H]2NCN[C@@H]21 | ZINC001179888656 | 0.959661323 |
| C[C@H]1c2cccc(O)c2C(=O)[C@@H]2C(=O)[C@]3(O)C(=O)[C@@H](C(N)=O)C(=O)[C@@H](N(C)C)[C@@H]3[C@@H](O)[C@H]12 | ZINC000169296420 | 0.959640899 |

FIG. 14 (Continued)

| | | |
|---|---|---|
| Cc1nnc(SCC2=C(C(=O)O)N3C(=O)[C@@H](NC(=O)c4cc(F)c(F)cc4Cl)[C@@H]3SC2)s1 | ZINC000017356887 | 0.95961889 |
| CO/N=C(/C(=O)N[C@H]1C(=O)N2C(C(=O)O)=C(CSC(=O)c3ccco3)CS[C@H]12)c1csc(N)n1 | ZINC000001999439 | 0.959574556 |
| N[C@@H]1NCN(c2cc(Cl)ncc2F)[C@H]2NCN[C@H]21 | ZINC001162440410 | 0.959558505 |
| CC(C)C[C@H](CO)NC(=O)c1cn2c3c(cc(F)c(N4CCN(C)CC4)c3OC[C@H]2C)c1=O | ZINC001148157976 | 0.95952993 |
| CO/N=C(\C(=O)N[C@@H]1C(=O)N2C(C(=O)N[C@@H](C)CN(C)C)=CCS[C@H]12)c1csc(N)n1 | ZINC001185591617 | 0.95939934 |
| O=c1c(=O)c2c1NCCN2 | ZINC000020357616 | 0.959380552 |
| N[C@H]1C(=O)N2C(C(=O)O)=C(Cl)CS[C@@H]12 | ZINC000002003375 | 0.959218389 |
| CO/N=C(\C(=O)N[C@@H]1C(=O)N2C(C(=O)N[C@H](C)CN(C)C)=CCS[C@H]12)c1csc(N)n1 | ZINC001185591621 | 0.959175071 |
| C[C@H]1c2cccc(O)c2C(=O)[C@H]2C(=O)[C@]3(O)C(=O)[C@H](C(N)=O)C(=O)[C@@H](N(C)C)[C@@H]3[C@@H](O)[C@H]12 | ZINC000104215576 | 0.959162909 |
| CO/N=C(/C(=O)N[C@@H]1C(=O)N2C(C(=O)O)=C(CSc3nc(=O)c(=O)[nH]n3C)CS[C@H]12)c1csc(N)n1 | ZINC000008584434 | 0.959153992 |
| CCOC(=O)[C@H](C#N)NC(=O)c1cn2c3c(cc(F)c(N4CCN(C)CC4)c3OC[C@H]2C)c1=O | ZINC001148163814 | 0.95909352 |
| C=C1c2c(Cl)ccc(O)c2C(O)=C2C(=O)[C@]3(O)C(O)=C(C(N)=O)C(=O)[C@H](N(C)C)[C@@H]3[C@@H](O)[C@@H]12 | ZINC000009231954 | 0.959080178 |
| CO/N=C(\C(=O)N[C@@H]1C(=O)N2C(C(=O)O)=C(CSc3nc(=O)c(O)nn3C)CS[C@H]12)c1csc(N)n1 | ZINC000028467879 | 0.959027842 |

FIG. 14 (Continued)

| | | |
|---|---|---|
| C=C1c2cccc(O)c2C(=O)[C@@]2(F)C(=O)[C@]3(O)C(=O)C(C(N)=O)=C(O)[C@@H](N(C)C)[C@@H]3[C@@H](O)[C@H]12 | ZINC000071769471 | 0.959011725 |
| CO/N=C(/C(=O)N[C@H]1C(=O)N2C(C(=O)O)=C(CSc3nc(C)c(CC(=O)O)s3)CS[C@H]12)c1csc(N)n1 | ZINC000100045075 | 0.958897182 |
| C[C@H]1COc2c(N3CCN(C)CC3)c(F)cc3c(=O)c(C(=O)N[C@H]4C=CS(=O)(=O)C4)cn1c32 | ZINC001148155756 | 0.95878889 |
| C=CC1=C(C(=O)O)N2C(=O)[C@@H](NC(=O)/C(=N\O)c3csc(N)n3)[C@@H]2SC1 | ZINC000008584438 | 0.958731523 |
| COCC1=C(C(=O)O)N2C(=O)[C@@H](NC(=O)C(=NOC)c3csc(N)n3)[C@H]2SC1 | ZINC000299888774 | 0.958730349 |
| C[C@@H]1COc2c(N3CCN(C)CC3)c(F)cc3c(=O)c(C(=O)N[C@H]4C[C@@H](O)C4(C)C)cn1c32 | ZINC001148163726 | 0.958668491 |
| C[C@@H]1COc2c(N3CCN(C)CC3)c(F)cc3c(=O)c(C(=O)N4CCNCC(F)(F)C4)cn1c32 | ZINC001148154744 | 0.958653733 |
| CCOC(=O)c1cn(C2CC2)c2cc(N3CCN(C(=S)NCCN)CC3)c(F)cc2c1=O | ZINC001239455176 | 0.958645174 |
| CN(C)[C@@H]1C(O)=C(C(N)=O)C(=O)[C@@]2(O)C(=O)C3=C(O)c4c(O)cccc4[C@@](C)(O)[C@H]3[C@H](O)[C@@H]12 | ZINC000100026355 | 0.958506542 |
| C=C1c2cccc(O)c2C(O)=C2C(=O)[C@]3(O)C(=O)/C(=C(/N)O)C(=O)[C@@H](N(C)C)[C@@H]3[C@@H](O)[C@H]12 | ZINC000100017626 | 0.958431041 |
| N[C@@H]1NCN(c2c(F)nc(F)nc2Cl)[C@H]2NCN[C@@H]21 | ZINC001162446440 | 0.958263147 |
| C[C@H]1COc2c(N3CCN(C)CC3)c(F)cc3c(=O)c(C(=O)N4C[C@@H](N)CC(F)(F)C4)cn1c32 | ZINC001160972517 | 0.958186331 |
| CO/N=C(/C(=O)N[C@H]1C(=O)N2C(C(=O)O)=C(COC(C)=O)CS[C@H]12)c1csc(N)n1 | ZINC000003830439 | 0.958148229 |

FIG. 14 (Continued)

| | | |
|---|---|---|
| CO/N=C(\C(=O)N[C@@H]1C(=O)N2C(C(=O)O)=C(CSc3[nH]c(=O)c(O)n[n+]3C)CS[C@@H]12)c1csc(N)n1 | ZINC000409412962 | 0.958146724 |
| C[C@H]1COc2c(N3CCN(C)CC3)c(F)cc3c(=O)c(C(=O)NCCc4cnc(N)s4)cn1c32 | ZINC001220704578 | 0.958133742 |
| C=CC1=C(C(=O)O)N2C(=O)[C@@H](NC(=O)/C(=N/O)c3csc(N)n3)[C@H]2SC1 | ZINC000013119676 | 0.958081651 |
| CO/N=C(/C(=O)N[C@H]1C(=O)N2C(C(=O)O)=C(CSc3nnnn3C)CS[C@H]12)c1csc(N)c1 | ZINC000013563730 | 0.958064252 |
| CO/N=C(\C(=O)N[C@@H]1C(=O)N2C(C(=O)N[C@@H](C#N)C(N)=O)=CCS[C@H]12)c1csc(N)n1 | ZINC001185592416 | 0.957938132 |
| C[C@H]1COc2c(N3CCN(C)CC3)c(F)cc3c(=O)c(C(=O)N[C@@H]4CNC(=O)C4(C)C)cn1c32 | ZINC001148163071 | 0.957812807 |
| C[C@H]1COc2c(N3CCN(C)CC3)c(F)cc3c(=O)c(C(=O)N[C@@H]4C[C@H](CO)[C@@H](O)[C@H]4O)cn1c32 | ZINC001148157847 | 0.957802492 |
| C[C@@H]1COc2c(N3CCN(C)CC3)c(F)cc3c2n1cc(C(=O)n1cnc(CN)cc1=N)c3=O | ZINC001148156515 | 0.957765937 |
| COC(=O)C1=C(NC(=S)N2CCN(c3c(F)cc4c(=O)c(C(=O)O)cn(C5CC5)c4c3OC)C[C@@H]2C)S[C@@H]2CCCCC[C@@H]12 | ZINC000217725627 | 0.957671809 |
| CN(C)[C@@H]1C(=O)/C(=C(\N)O)C(=O)[C@]2(O)C(=O)[C-]3C(=O)c4c(O)cccc4[C@](C)(O)[C@@H]3[C@@H](O)[C@@H]12 | ZINC000255974500 | 0.95758388 |
| CC[C@@H](CO)NC(=O)C1=CCS[C@@H]2[C@H](NC(=O)/C(=N\OC)c3csc(N)n3)C(=O)N12 | ZINC001221377535 | 0.957548517 |
| CNCCNC(=O)C1=CCS[C@@H]2[C@H](NC(=O)/C(=N\OC)c3csc(N)n3)C(=O)N12 | ZINC001220056131 | 0.957509091 |
| C[C@@H]1COc2c(N3CCN(C)CC3)c(F)cc3c(=O)c(C(=O)N4CCNC[C@@H]4C#N)cn1c32 | ZINC001148157658 | 0.957374737 |

FIG. 14 (Continued)

| | | |
|---|---|---|
| C[C@@H]1COc2c(N3CCN(C)CC3)c(F)cc3c(=O)c(C(=O)N4C[C@@H](F)C[C@H]4C#N)cn1c32 | ZINC001148157096 | 0.957361695 |
| C[C@@H]1CCc2cc(F)cc3c(=O)c(C(=O)N4CN[C@H](N)[C@H]5NCN[C@H]54)cn1c23 | ZINC001150153530 | 0.957345226 |
| C[C@@H]1COc2c(N3CCN(C)CC3)c(F)cc3c(=O)c(C(=O)N[C@@H]4CNCC[C@H]4F)cn1c32 | ZINC001221367822 | 0.957134891 |
| CN(C)[C@@H]1C(=O)[C@H](C(N)=O)C(=O)[C@@]2(O)C(=O)[C@H]3C(=O)c4c(O)ccc(Cl)c4[C@@](C)(O)[C@@H]3C[C@@H]12 | ZINC000169687156 | 0.957112435 |
| C[C@@H]1COc2c(N3CCN(C)CC3)c(F)cc3c(=O)c(C(=O)N[C@H]4CNC(=O)C4(C)C)cn1c32 | ZINC001148163069 | 0.957030347 |
| COc1c(N2CCN(C(=S)N[C@H]3C[C@H]4C=C[C@H]3C4)[C@@H](C)C2)c(F)cc2c(=O)c(C(=O)O)cn(C3CC3)c21 | ZINC000253387445 | 0.957007799 |
| C[C@H]1COc2c(N3CCN(C)CC3)c(F)cc3c(=O)c(C(=O)N[C@H]4CCCN(C)C4)cn1c32 | ZINC001148157855 | 0.956945556 |
| C[C@H]1COc2c(N3CCN(C)CC3)c(F)cc3c(=O)c(C(=O)N[C@@H](CO)C(C)(C)C)cn1c32 | ZINC001148157331 | 0.95680331 |
| COc1c(N2CCN(C(=S)N[C@H]3C[C@H]4C=C[C@H]3C4)[C@H](C)C2)c(F)cc2c(=O)c(C(=O)O)cn(C3CC3)c21 | ZINC000253387444 | 0.95675604 |
| C[C@H]1COc2c(N3CCN(C)CC3)c(F)cc3c(=O)c(C(=O)NCCn4ccnn4)cn1c32 | ZINC001148154497 | 0.956321397 |
| CO/N=C(\C(=O)N[C@@H]1C(=O)N2C(C(=O)N[C@H]3CCC(=O)NC3=O)=CCS[C@H]12)c1csc(N)n1 | ZINC001185591309 | 0.956278467 |
| COc1cc(F)c(-n2c(N)csc2=N)cc1F | ZINC001174923742 | 0.95619278 |

FIG. 14 (Continued)

| | | |
|---|---|---|
| CO/N=C(\C(=O)N[C@@H]1C(=O)N2C(C(=O)NCC(F)F)=CCS[C@H]12)c1csc(N)n1 | ZINC001185590075 | 0.956154978 |
| C=C1c2cccc(O)c2C(=O)[C@]2(F)C(=O)[C@]3(O)C(=O)C(C(N)=O)=C(O)[C@@H](N(C)C)[C@@H]3[C@@H](O)[C@@H]12 | ZINC000071769470 | 0.95602532 |
| CC(C)C[C@H](NC(=O)c1cn2c3c(cc(F)c(N4CCN(C)CC4)c3OC[C@H]2C)c1=O)C(=O)NO | ZINC001148162450 | 0.955749145 |
| CCOC(=O)[C@@H](C#N)NC(=O)c1cn2c3c(cc(F)c(N4CCN(C)CC4)c3OC[C@@H]2C)c1=O | ZINC001148163816 | 0.95545136 |
| CO/N=C(\C(=O)N[C@@H]1C(=O)N2C(C(=O)N3CCN[C@H](C)C3)=CCS[C@H]12)c1csc(N)n1 | ZINC001161016923 | 0.955117995 |
| C[C@H]1COc2c(N3CCN(C)CC3)c(F)cc3c(=O)c(C(=O)NCS(=O)(=O)O)cn1c32 | ZINC001148164372 | 0.954990217 |
| CN1N=C(O)C(=O)N[C@H]1SCC1=C(C(=O)O)N2C(=O)[C@H](NC(=O)/C(=N/O)c3csc(N)n3)[C@@H]2SC1 | ZINC000100040492 | 0.954934898 |
| CO/N=C(\C(=O)N[C@@H]1C(=O)N2C(C(=O)N[C@H](C#N)C(N)=O)=CCS[C@H]12)c1csc(N)n1 | ZINC001185592409 | 0.954875419 |
| C[C@H]1COc2c(N3CCN(C)CC3)c(F)cc3c(=O)c(C(=O)N[C@@H](C4CCC4)C4CNC4)cn1c32 | ZINC001221413128 | 0.954643318 |
| CO/N=C(\C(=O)N[C@@H]1C(=O)N2C(C(=O)N[C@@H]3CONC3=O)=CCS[C@H]12)c1csc(N)n1 | ZINC001185591060 | 0.954352057 |
| C[C@H]1COc2c(N3CCN(C)CC3)c(F)cc3c(=O)c(C(=O)NCCN4CCNCC4=O)cn1c32 | ZINC001220875246 | 0.953997633 |
| CC[C@H](CO)NC(=O)C1=CCS[C@@H]2[C@H](NC(=O)/C(=N\OC)c3csc(N)n3)C(=O)N12 | ZINC001221377536 | 0.953972411 |

FIG. 14 (Continued)

| | | |
|---|---|---|
| CO/N=C(\C(=O)N[C@@H]1C(=O)N2C(C(=O)N3CCNC[C@H]3C#N)=CCS[C@H]12)c1csc(N)n1 | ZINC001185590022 | 0.953959599 |
| C[C@H]1COc2c(N3CCN(C)CC3)c(F)cc3c(=O)c(C(=O)N4CC(=O)N(C5CC5)C(=O)C4)cn1c32 | ZINC001148157844 | 0.953892529 |
| C[C@H]1COc2c(N3CCN(C)CC3)c(F)cc3c(=O)c(C(=O)N4CC(C)(N(C)C)C4)cn1c32 | ZINC001148154341 | 0.953789306 |
| CO/N=C(\C(=O)N[C@@H]1C(=O)N2C(C(=O)NC3CN(C)C3)=CCS[C@H]12)c1csc(N)n1 | ZINC001185592230 | 0.953745687 |
| B1=B\B=B/B=B\B=B/B=B\B=B/1 | ZINC000261364492 | 0.953640233 |
| CCn1cc(C(=O)N2CN[C@H](N)[C@H]3NCN[C@@H]32)c(=O)c2cc(F)c(Cl)cc21 | ZINC001151284563 | 0.953609115 |
| O/N=C1\N[C@@H](O)[C@H](O)N\C1=N/O | ZINC000005510605 | 0.953537351 |
| O/N=C1\N[C@H](O)[C@@H](O)N\C1=N/O | ZINC000009307721 | 0.953537345 |
| COC(=O)C1=C(NC(=S)N2CCN(c3c(F)cc4c(=O)c(C(=O)O)cn(C5CC5)c4c3OC)C[C@@H]2C)S[C@@H]2CCCCC[C@H]12 | ZINC000253387780 | 0.953476936 |
| Cc1ncc(CN)c(=N)n1C(=O)c1cn2c3c(cc(F)c(N4CCN(C)CC4)c3OC[C@H]2C)c1=O | ZINC001148153972 | 0.953429633 |
| C[C@@H]1CN(c2c(F)c(F)nc(F)c2F)C[C@H](C)N1 | ZINC000858632796 | 0.953370461 |
| C[C@@H]1COc2c(N3CCN(C)CC3)c(F)cc3c2n1cc(C(=O)n1ccc(CN)cc1=N)c3=O | ZINC001148154682 | 0.953250104 |
| C[C@H]1COc2c(N3CCN(C)CC3)c(F)cc3c(=O)c(C(=O)N[C@@H]4CCOC[C@@H]4F)cn1c32 | ZINC001148163026 | 0.953247297 |
| CO[C@]1(NC(=O)C2SC(=C(C(N)=O)C(=O)O)S2)C(=O)N2C(C(=O)O)=C(CSc3nnnn3C)CS[C@H]21 | ZINC000003830444 | 0.953194845 |

FIG. 14 (Continued)

| | | |
|---|---|---|
| CO/N=C(\C(=O)N[C@H]1C(=O)N2C(C(=O)O)=C(C[n+]3ccn4ncccc43)CS[C@@H]12)c1nsc(N)n1 | ZINC000011615945 | 0.952981186 |
| CCn1cc(C(=O)N2CN[C@H](N)[C@@H]3NCN[C@H]32)c(=O)c2cc(F)c(Cl)cc21 | ZINC001151284560 | 0.952925837 |
| C[C@H]1COc2c(N3CCN(C)CC3)c(F)cc3c(=O)c(C(=O)N[C@H]4COCC[C@@H]4O)cn1c32 | ZINC001148157851 | 0.952861243 |
| C[C@@H]1COc2c(N3CCN(C)CC3)c(F)cc3c(=O)c(C(=O)N[C@H]4C[C@H](O)C4(C)C)cn1c32 | ZINC001148163723 | 0.95281316 |
| C1CCC(N2N[C@@H]2[C@H]2NN2C2CCCCC2)CC1 | ZINC000239297081 | 0.952765101 |
| C1CCC(N2N[C@H]2[C@@H]2NN2C2CCCCC2)CC1 | ZINC000019169126 | 0.952765095 |
| N[C@@H]1NCN(c2c(F)nc(F)nc2Cl)[C@@H]2NCN[C@H]21 | ZINC001162446443 | 0.952712807 |
| CC[C@H](C)[C@@H](CO)NC(=O)C1=CCS[C@@H]2[C@H](NC(=O)/C(=N\OC)c3csc(N)n3)C(=O)N12 | ZINC001185591008 | 0.952670813 |
| Cn1nnnc1SCC1=C(C(=O)O)N2C(=O)[C@@H](NC(=O)c3cc(F)c(F)cc3Cl)[C@H]2SC1 | ZINC000009944315 | 0.95264627 |
| C[C@H]1COc2c(N3CCN(C)CC3)c(F)cc3c(=O)c(C(=O)N4C[C@H](N)CC(F)(F)C4)cn1c32 | ZINC001160972523 | 0.952620655 |
| C[C@@H]1c2cccc(O)c2C(O)=C2C(=O)[C@]3(O)C(=O)/C(=C(/N)O)C(=O)[C@H](N(C)C)[C@@H]3[C@@H](O)[C@H]21 | ZINC000256003949 | 0.952568913 |
| C[C@H]1c2cccc(O)c2C(=O)[C@@H]2C(=O)[C@]3(O)C(=O)[C@H](C(N)=O)C(=O)[C@@H](N(C)C)[C@@H]3[C@@H](O)[C@H]12 | ZINC000169688935 | 0.952484608 |
| C[C@@H]1COc2c(N3CCN(C)CC3)c(F)cc3c(=O)c(C(=O)N[C@H]4CS(=O)(=O)C[C@H]4O)cn1c32 | ZINC000888104978 | 0.952361339 |

FIG. 14 (Continued)

| | | |
|---|---|---|
| CO[C@@H]1CN(C(=O)c2cn3c4c(cc(F)c(N5CCN(C)CC5)c4OC[C@@H]3C)c2=O)C[C@@H]1N | ZINC001161493261 | 0.952006692 |
| N[C@@H]1NCN(c2nc(Cl)ncc2F)[C@H]2NCN[C@H]21 | ZINC001162436492 | 0.951994583 |
| C=CC1=C(C(=O)O)N2C(=O)[C@@H](NC(=O)/C(=N/O)c3csc(N)n3)[C@@H]2SC1 | ZINC000014768522 | 0.951941586 |
| C[C@@H]1COc2c(N3CCN(C)CC3)c(F)cc3c(=O)c(C(=O)N[C@H]4[C@H]5C=C[C@@H](C5)[C@H]4C(N)=O)cn1c32 | ZINC001148162464 | 0.951844016 |
| C[C@H]1COc2c(N3CCN(C)CC3)c(F)cc3c(=O)c(C(=O)N[C@H](C4CCC4)C4CNC4)cn1c32 | ZINC001221413142 | 0.951737568 |
| C[C@H]1COc2c(N3CCN(C)CC3)c(F)cc3c(=O)c(C(=O)N4CCNC(=O)[C@@H]4C)cn1c32 | ZINC001148155764 | 0.95166468 |
| CO/N=C(\C(=O)N[C@@H]1C(=O)N2C(C(=O)N[C@H]3CCNC3)=CCS[C@H]12)c1csc(N)n1 | ZINC001185591328 | 0.951368478 |
| C=C1c2c(Cl)ccc(O)c2C(O)=C2C(=O)[C@]3(O)C(O)=C(C(N)=O)C(=O)[C@H](N(C)C)[C@@H]3[C@@H](O)[C@H]12 | ZINC000521205741 | 0.951348037 |
| C[C@@H]1COc2c(N3CCN(C)CC3)c(F)cc3c(=O)c(C(=O)N[C@@H]4C[C@@H](O)C4(C)C)cn1c32 | ZINC001148163725 | 0.951138321 |
| C[C@@H]1CCc2cc(F)cc3c(=O)c(C(=O)N4CN[C@H](N)[C@@H]5NCN[C@H]54)cn1c23 | ZINC001150153532 | 0.951000905 |
| CN(C)[C@@H]1C(=O)/C(=C(\N)O)C(=O)[C@]2(O)C(=O)[C-]3C(=O)c4c(O)cccc4[C@](C)(O)[C@@H]3[C@@H](O)[C@H]12 | ZINC000255974503 | 0.950928974 |
| CO/N=C(\C(=O)N[C@@H]1C(=O)N2C(C(=O)N[C@@H]3CCC(=O)NC3=O)=CCS[C@H]12)c1csc(N)n1 | ZINC001185591310 | 0.950908574 |

FIG. 14 (Continued)

| | | |
|---|---|---|
| CNc1nnc(SCC2=C(C(=O)O)N3C(=O)[C@H](NC(=O)/C(=N/OC)c4csc(N)c4)[C@H]3SC2)s1 | ZINC000003097993 | 0.9508223 |
| CO/N=C(\C(=O)N[C@@H]1C(=O)N2C(C(=O)NCC(C)(C)CN(C)C)=CCS[C@H]12)c1csc(N)n1 | ZINC001185590978 | 0.950792834 |
| CO/N=C(\C(=O)N[C@H]1C(=O)N2C(C(=O)O)=C(Cn3ccc(=N)n3CCO)CS[C@@H]12)c1csc(N)n1 | ZINC000011616736 | 0.950745791 |
| CO/N=C(\C(=O)N[C@@H]1C(=O)N2C(C(=O)N[C@@H](CN)C(C)(C)C)=CCS[C@H]12)c1csc(N)n1 | ZINC001220859775 | 0.950538436 |
| COc1c(N2CCN(C(=S)N[C@@H]3C[C@H]4C=C[C@H]3C4)[C@@H](C)C2)c(F)cc2c(=O)c(C(=O)O)cn(C3CC3)c21 | ZINC000100212099 | 0.950463012 |
| COc1c(N2CCN(C(=S)N[C@@H]3C[C@H]4C=C[C@H]3C4)[C@H](C)C2)c(F)cc2c(=O)c(C(=O)O)cn(C3CC3)c21 | ZINC000100212096 | 0.950436512 |
| C[C@H]1COc2c(N3CCN(C)CC3)c(F)cc3c(=O)c(C(=O)NCC(C)(C)C(N)=O)cn1c32 | ZINC001148156415 | 0.950396237 |
| C=C1c2cccc(O)c2C(O)=C2C(=O)[C@]3(O)C(=O)/C(=C(/N)O)C(=O)[C@H](N(C)C)[C@@H]3[C@@H](O)[C@@H]12 | ZINC000255974306 | 0.950358358 |
| C[C@@H]1CCc2cc(F)cc3c(=O)c(C(=O)N4CN[C@H](N)[C@H]5NCN[C@@H]54)cn1c23 | ZINC001150153531 | 0.950347728 |
| C=C1c2c(Cl)ccc(O)c2C(=O)C2=C(O)[C@]3(O)C(=O)C(C(N)=O)=C(O)[C@@H](N(C)C)[C@@H]3[C@@H](O)[C@@H]12 | ZINC000037868226 | 0.950295013 |
| N[C@@H]1NCN(c2cc(Cl)ncc2F)[C@H]2NCN[C@@H]21 | ZINC001162440411 | 0.950226167 |
| CN(C)[C@@H]1C(=O)[C@H](C(N)=O)C(=O)[C@@]2(O)C(=O)[C@@H]3C(=O)c4c(O)ccc(Cl)c4[C@@](C)(O)[C@H]3C[C@@H]12 | ZINC000101843559 | 0.950221765 |

FIG. 14 (Continued)

| | | |
|---|---|---|
| CC[C@H](COC)NC(=O)C1=CCS[C@@H]2[C@H](NC(=O)/C(=N\OC)c3csc(N)n3)C(=O)N12 | ZINC001185592210 | 0.949988183 |
| C[C@H]1COc2c(N3CCN(C)CC3)c(F)cc3c(=O)c(C(=O)N(C)c4nccnc4N)cn1c32 | ZINC001148154845 | 0.949986792 |
| CN(C)[C@@H]1C(=O)/C(=C(\N)O)C(=O)[C@]2(O)C(=O)[C-]3C(=O)c4c(O)cccc4[C@](C)(O)[C@@H]3[C@H](O)[C@@H]12 | ZINC000255974501 | 0.949952519 |
| C[C@H]1COc2c(N3CCN(C)CC3)c(F)cc3c(=O)c(C(=O)N(C)Cc4ncccn4)cn1c32 | ZINC001148156339 | 0.949814284 |
| C=C1c2c(Cl)ccc(O)c2C(O)=C2C(=O)[C@]3(O)C(O)=C(C(N)=O)C(=O)[C@H](N(C)C)[C@@H]3[C@H](O)[C@@H]12 | ZINC000078832372 | 0.949615785 |
| C[C@H]1NC(=S)N(c2cc(F)c(F)cc2F)C1=O | ZINC000171770184 | 0.949532571 |
| CO/N=C(\C(=O)N[C@@H]1C(=O)N2C(C(=O)N[C@H](C(=O)OC)[C@@H](C)O)=CCS[C@H]12)c1csc(N)n1 | ZINC001185592169 | 0.949459624 |
| CCOC(=O)[C@H](C#N)NC(=O)c1cn2c3c(cc(F)c(N4CCN(C)CC4)c3OC[C@@H]2C)c1=O | ZINC001148163815 | 0.949412039 |
| C[C@H]1COc2c(N3CCN(C)CC3)c(F)cc3c(=O)c(C(=O)NCCC[C@H]4C=NNC4=O)cn1c32 | ZINC001148157631 | 0.949304241 |
| C[C@@H]1COc2c(N3CCN(C)CC3)c(F)cc3c(=O)c(C(=O)N(C)CC4(C)COC4)cn1c32 | ZINC001148155781 | 0.949255714 |
| CCCC[C@H](NC(=O)C1=CCS[C@@H]2[C@H](NC(=O)/C(=N\OC)c3csc(N)n3)C(=O)N12)C(N)=O | ZINC001185592083 | 0.949171752 |
| N/C(=N\O)c1cn(C2CC2)c(=O)[nH]c1=O | ZINC000062710772 | 0.948734578 |
| CO/N=C(\C(=O)N[C@@H]1C(=O)N2C(C(=O)NC#N)=CCS[C@H]12)c1csc(N)n1 | ZINC001185591278 | 0.948728439 |

FIG. 14 (Continued)

| | | |
|---|---|---|
| C[C@H]1[C@@H](NC(=O)/C(=N/OC(C)(C)C(=O)O)c2csc(N)n2)C(=O)N1S(=O)(=O)O | ZINC000016958002 | 0.948712879 |
| CC(C)[C@@](C)(NC(=O)c1cn2c3c(cc(F)c(N4CCN(C)CC4)c3OC[C@H]2C)c1=O)C(N)=O | ZINC001148155362 | 0.948600224 |
| CO/N=C(\C(=O)N[C@@H]1C(=O)N2C(C(=O)N3CCN(C)CC3)=CCS[C@H]12)c1csc(N)n1 | ZINC001185590948 | 0.948331752 |
| CCOC(=O)CC(=N)NC(=O)c1cn2c3c(cc(F)c(N4CCN(C)CC4)c3OC[C@H]2C)c1=O | ZINC001148157694 | 0.948258859 |
| CC(C)C[C@H](CO)NC(=O)c1cn2c3c(cc(F)c(N4CCN(C)CC4)c3OC[C@@H]2C)c1=O | ZINC001148157977 | 0.948213774 |
| C[C@H]1COc2c(N3CCN(C)CC3)c(F)cc3c(=O)c(C(=O)N[C@H]4CCC[C@H]4CO)cn1c32 | ZINC001148163274 | 0.948115692 |
| C=C1c2cccc(O)c2C(=O)[C@]2(F)C(=O)[C@]3(O)C(=O)C(C(N)=O)=C(O)[C@@H](N(C)C)[C@@H]3[C@@H](O)[C@H]12 | ZINC000071769469 | 0.94796291 |
| C[C@@H]1c2cccc(O)c2C(O)=C2C(=O)[C@]3(O)C(=O)[C@H](C(N)=O)C(=O)[C@H](N(C)C)[C@@H]3[C@@H](O)[C@H]21 | ZINC000253388143 | 0.947489983 |
| CN(C)[C@@H]1C(=O)[C@H](C(N)=O)C(=O)[C@@]2(O)C(=O)[C@@H]3C(=O)c4c(O)ccc(Cl)c4[C@@](C)(O)[C@@H]3C[C@@H]12 | ZINC000169687154 | 0.947243294 |
| Nc1nc(/C(=C/CC(=O)O)C(=O)N[C@H]2C(=O)N3C(C(=O)O)=CCS[C@@H]23)cs1 | ZINC000004097461 | 0.947147012 |
| CO/N=C(/C(=O)N[C@H]1C(=O)N2C(C(=O)O)=C(Cn3ccc(=N)n3CCO)CS[C@@H]12)c1csc(N)n1 | ZINC000011616737 | 0.947120762 |
| C[C@@H]1c2cccc(O)c2C(O)=C2C(=O)[C@]3(O)C(=O)/C(=C(/N)O)C(=O)[C@H](N(C)C)[C@@H]3[C@@H](O)[C@@H]21 | ZINC000256003950 | 0.947118574 |

FIG. 14 (Continued)

| | | |
|---|---|---|
| C[C@@H]1C[C@@H](CNC(=O)c2cn3c4c(cc(F)c(N5CCN(C)CC5)c4OC[C@H]3C)c2=O)CN1 | ZINC001219684529 | 0.947111139 |
| N[C@H]1C(=O)N2C(C(=O)O)=C(Cl)CS[C@H]12 | ZINC000002003376 | 0.946898907 |
| CN(C)[C@@H]1C(=O)/C(=C(\N)O)C(=O)[C@]2(O)C(=O)C3=C(O)c4c(O)ccc(Cl)c4[C@H](O)[C@H]3C[C@@H]12 | ZINC000137643649 | 0.946808362 |
| CO/N=C(/C(=O)N[C@@H]1C(=O)N2C(C(=O)O)=C(/C=C/c3scnc3C)CS[C@H]12)c1csc(N)n1 | ZINC000034306485 | 0.94676739 |
| C[C@@H]1COc2c(N3CCN(C)CC3)c(F)cc3c(=O)c(C(=O)N[C@@H]4CNC(=O)C4(C)C)cn1c32 | ZINC001148163068 | 0.946734756 |
| CN1N=C(O)C(=O)N[C@@H]1SCC1=C(C(=O)O)N2C(=O)[C@H](NC(=O)/C(=N/O)c3csc(N)n3)[C@@H]2SC1 | ZINC000100040495 | 0.946296173 |
| CN(C)CCn1nnnc1SCC1=C(C(=O)O)N2C(=O)[C@@H](NC(=O)Cc3csc(N)n3)[C@H]2SC1 | ZINC000003830445 | 0.946163255 |
| C[C@H]1COc2c(N3CCN(C)CC3)c(F)cc3c(=O)c(C(=O)N=c4nc[nH]n5cccc45)cn1c32 | ZINC001148156804 | 0.946056879 |
| CSCC[C@H](NC(=O)c1cn2c3c(cc(F)c(N4CCN(C)CC4)c3OC[C@H]2C)c1=O)C(N)=O | ZINC001148162783 | 0.946046013 |
| O=C1CSC(=S)N1N1C(=O)[C@H]2[C@@H](C1=O)C1C=CC2[C@H]2C(=O)N(N3C(=O)CSC3=S)C(=O)[C@H]21 | ZINC000036416650 | 0.945828032 |
| N[C@@H]1NCN(c2cc(Cl)ncc2F)[C@@H]2NCN[C@H]21 | ZINC001162440408 | 0.945686394 |
| CO/N=C(/C(=O)N[C@@H]1C(=O)N2C(C(=O)O)=C(CSc3nnnn3C)CS[C@@H]12)c1cnc(N)s1 | ZINC000022001545 | 0.945399308 |

FIG. 14 (Continued)

| | | |
|---|---|---|
| COc1c(N2CCN(C(=S)N[C@@H]3C[C@H]4C=C[C@@H]3C4)[C@@H](C)C2)c(F)cc2c(=O)c(C(=O)O)cn(C3CC3)c21 | ZINC000217438116 | 0.945368686 |
| C[C@@H]1c2cccc(O)c2C(O)=C2C(=O)[C@]3(O)C(=O)/C(=C(/N)O)C(=O)[C@H](N(C)C)[C@@H]3[C@H](O)[C@H]21 | ZINC000139457027 | 0.945120201 |
| CC(C)(O/N=C(/C(=O)N[C@H]1C(=O)N2C(C(=O)O)=C(C[n+]3ccccc3)CS[C@@H]12)c1csc(N)n1)C(=O)O | ZINC000003830470 | 0.945119339 |
| C[C@H]1COc2c(N3CCN(C)CC3)c(F)cc3c2n1cc(C(=O)n1ccc(=N)c(N)c1)c3=O | ZINC001218694479 | 0.945108432 |
| COC(=O)[C@@H]1C[C@@H](NC(=O)c2cn3c4c(cc(F)c(N5CCN(C)CC5)c4OC[C@H]3C)c2=O)CN1 | ZINC001219967823 | 0.945029804 |
| CO/N=C(\C(=O)N[C@@H]1C(=O)N2C(C(=O)NCCN(C)C)=CCS[C@H]12)c1csc(N)n1 | ZINC001185591819 | 0.945004624 |
| CO/N=C(\C(=O)N[C@@H]1C(=O)N2C(C(=O)N3CC(C)(N)C3)=CCS[C@H]12)c1csc(N)n1 | ZINC001157650707 | 0.944984999 |
| C[C@H]1COc2c(N3CCN(C)CC3)c(F)cc3c(=O)c(C(=O)NC[C@@H](F)C(C)(C)O)cn1c32 | ZINC001148163250 | 0.944889089 |
| CC(C)C[C@H](NC(=O)c1cn2c3c(cc(F)c(N4CCN(C)CC4)c3OC[C@@H]2C)c1=O)C(=O)NO | ZINC001148162451 | 0.944885495 |
| COc1c(N2CCN(C(=S)N[C@@H]3C[C@H]4C=C[C@@H]3C4)[C@H](C)C2)c(F)cc2c(=O)c(C(=O)O)cn(C3CC3)c21 | ZINC000217438036 | 0.944772196 |
| CO/N=C(\C(=O)N[C@@H]1C(=O)N2C(C(=O)N3CCNC[C@@H]3C#N)=CCS[C@H]12)c1csc(N)n1 | ZINC001185590020 | 0.944750872 |
| CCn1cc(C(=O)N2CN[C@H](N)[C@@H]3NCN[C@@H]32)c(=O)c2cc(F)c(Cl)cc21 | ZINC001151284561 | 0.944621897 |

FIG. 14 (Continued)

| | | |
|---|---|---|
| CN(C)[C@@H]1C(=O)C(C(N)=O)=C(O)[C@]2(O)C(=O)C3=C(O)c4c(O)cccc4[C@](C)(O)[C@@H]3[C@@H](O)[C@@H]12 | ZINC000257084918 | 0.944416142 |
| CO/N=C(\C(=O)N[C@@H]1C(=O)N2C(C(=O)NC3(CN)COC3)=CCS[C@H]12)c1csc(N)n1 | ZINC001185591229 | 0.944343621 |
| C[C@@H]1[C@@H](NC(=O)/C(=N/OC(C)(C)C(=O)O)c2csc(N)n2)C(=O)N1S(=O)(=O)O | ZINC000017214369 | 0.944309044 |
| C[C@@H]1COc2c(N3CCN(C)CC3)c(F)cc3c(=O)c(C(=O)N[C@@H]4C[C@H](CO)[C@@H](O)[C@H]4O)cn1c32 | ZINC001148157846 | 0.944281459 |
| COc1c(N2CCN(C(=S)Nc3ccccc3)[C@@H](C)C2)c(F)cc2c(=O)c(C(=O)O)cn(C3CC3)c21 | ZINC000009210710 | 0.944278717 |
| COC(=O)[C@H](CCCN)NC(=O)c1cn2c3c(cc(F)c(N4CCN(C)CC4)c3OC[C@H]2C)c1=O | ZINC001221190198 | 0.944093278 |
| CN(C)[C@@H]1C(O)=C(C(N)=O)C(=O)[C@@]2(O)C(O)=C3C(=O)c4c(O)cccc4[C@@](C)(O)[C@H]3[C@@H](O)[C@@H]12 | ZINC000035947017 | 0.944060466 |
| O=C1N[C@H]2N[C@H]3NC(=O)N[C@H]3N[C@H]2N1 | ZINC000022942306 | 0.944052818 |
| C[C@H]1COc2c(N3CCN(C)CC3)c(F)cc3c(=O)c(C(=O)NCCC[C@@H]4C=NNC4=O)cn1c32 | ZINC001148157633 | 0.944040048 |
| C[C@@H]1COc2c(N3CCN(C)CC3)c(F)cc3c(=O)c(C(=O)N[C@@H](C4CCC4)C4CNC4)cn1c32 | ZINC001221413138 | 0.943976519 |
| CN(C)[C@@H]1C(=O)/C(=C(\N)O)C(=O)[C@]2(O)C(=O)C3=C(O)c4c(O)ccc(Cl)c4[C@H](O)[C@@H]3C[C@@H]12 | ZINC000255977795 | 0.943907878 |
| COc1c(F)c(F)cc2c(=O)[nH]c(=O)n(C3CC3)c21 | ZINC000044126785 | 0.943886659 |

FIG. 14 (Continued)

| | | |
|---|---|---|
| C[C@@H]1COc2c(N3CCN(C)CC3)c(F)cc3c(=O)c(C(=O)N4CC(=O)N(C5CC5)C(=O)C4)cn1c32 | ZINC001148157845 | 0.943854252 |
| CO/N=C(\C(=O)N[C@@H]1C(=O)N2C(C(=O)NCC(C)(C)CC3CC3)=CCS[C@H]12)c1csc(N)n1 | ZINC001185591318 | 0.943832555 |
| COc1c(N2CCN(C(=S)Nc3ccccc3)[C@H](C)C2)c(F)cc2c(=O)c(C(=O)O)cn(C3CC3)c21 | ZINC000009210709 | 0.943762842 |
| N=c1c(N)cnc(Cl)n1-c1c(F)cc(F)c(O)c1F | ZINC001176663722 | 0.943663231 |
| CN(C)[C@@H]1C(=O)/C(=C(\N)O)C(=O)[C@]2(O)C(=O)C3=C(O)c4c(O)ccc(Cl)c4[C@H](O)[C@H]3C[C@H]12 | ZINC000137644074 | 0.943661135 |
| C[C@H]1COc2c(N3CCN(C)CC3)c(F)cc3c(=O)c(C(=O)N4CC(=O)N(C)C[C@@H]4C)cn1c32 | ZINC001148157318 | 0.943659261 |
| C[C@H]1COc2c(N3CCN(C)CC3)c(F)cc3c(=O)c(C(=O)N[C@H]4CCCN(C)C4=O)cn1c32 | ZINC001148163255 | 0.943560296 |
| C[C@@H]1COc2c(N3CCN(C)CC3)c(F)cc3c(=O)c(C(=O)NCCn4ccnn4)cn1c32 | ZINC001148154500 | 0.943535563 |
| C[C@@H]1COc2c(N3CCN(C)CC3)c(F)cc3c(=O)c(C(=O)N[C@H]4C=CS(=O)(=O)C4)cn1c32 | ZINC001148155757 | 0.943517694 |
| CO/N=C(\C(=O)N[C@@H]1C(=O)N2C(C(=O)N(C)[C@@H]3[C@H]4CNC[C@H]43)=CCS[C@H]12)c1csc(N)n1 | ZINC001161222319 | 0.943465459 |
| C[C@@H]1COc2c(N3CCN(C)CC3)c(F)cc3c(=O)c(C(=O)NCCc4cnc(N)s4)cn1c32 | ZINC001220704577 | 0.94340319 |
| C[C@@H]1COc2c(N3CCN(C)CC3)c(F)cc3c(=O)c(C(=O)N[C@H]4CS(=O)(=O)C[C@@H]4O)cn1c32 | ZINC000888104975 | 0.943369293 |

FIG. 14 (Continued)

| | | |
|---|---|---|
| CO/N=C(\C(=O)N[C@H]1C(=O)N2C(C(=O)O)=C(Cn3ccc(=N)n3CCO)CS[C@H]12)c1csc(N)n1 | ZINC000001851185 | 0.943090662 |
| C[C@@H]1COc2c(N3CCN(C)CC3)c(F)cc3c(=O)c(C(=O)N[C@@H](CO)C(C)(C)C)cn1c32 | ZINC001148157330 | 0.943080407 |
| CC(C)(O/N=C(\C(=O)N[C@H]1C(=O)N2C(C(=O)O)=C(C[n+]3ccccc3)CS[C@@H]12)c1csc(N)n1)C(=O)O | ZINC000008582317 | 0.943037349 |
| CO/N=C(/C(=O)N[C@@H]1C(=O)N2C(C(=O)O)=C(CSc3nnc(C)s3)CS[C@@H]12)c1csc(N)c1 | ZINC000101645993 | 0.942981082 |
| CO/N=C(/C(=O)N[C@@H]1C(=O)N2C(C(=O)O)=C(CSc3nc(C)c(CC(=O)O)s3)CS[C@@H]12)c1csc(N)n1 | ZINC000003830422 | 0.942798904 |
| C[C@@H]1c2cccc(O)c2C(O)=C2C(=O)[C@]3(O)C(=O)/C(=C(\N)O)C(=O)[C@H](N(C)C)[C@@H]3[C@@H](O)[C@H]21 | ZINC000239322021 | 0.942750204 |
| CCN(C(=O)c1cn2c3c(cc(F)c(N4CCN(C)CC4)c3OC[C@H]2C)c1=O)C1CN(C)C1 | ZINC001148154691 | 0.94266209 |
| CO/N=C(\C(=O)N[C@@H]1C(=O)N2C(C(=O)N3C[C@@H](F)[C@@H](N)C3)=CCS[C@H]12)c1csc(N)n1 | ZINC001157545044 | 0.942573035 |
| C[C@@H]1COc2c(N3CCN(C)CC3)c(F)cc3c(=O)c(C(=O)N[C@@H]4C[C@H](O)C4(C)C)cn1c32 | ZINC001148163728 | 0.942481759 |
| CO/N=C(\C(=O)N[C@@H]1C(=O)N2C(C(=O)N3C[C@@H](N)C[C@H]3C)=CCS[C@H]12)c1csc(N)n1 | ZINC001161530322 | 0.942477053 |
| Cc1ncc(CN)c(=N)n1C(=O)c1cn2c3c(cc(F)c(N4CCN(C)CC4)c3OC[C@@H]2C)c1=O | ZINC001148153973 | 0.942376634 |
| C[C@@H]1COc2c(N3CCN(C)CC3)c(F)cc3c(=O)c(C(=O)N[C@H]4CCCN(C)C4)cn1c32 | ZINC001148157854 | 0.942361352 |

FIG. 14 (Continued)

| | | |
|---|---|---|
| C=C1c2cccc(O)c2C(O)=C2C(=O)[C@]3(O)C(=O)/C(=C(/N)O)C(=O)[C@H](N(C)C)[C@@H]3[C@@H](O)[C@H]12 | ZINC000255974307 | 0.942350844 |
| CCCCCCCCCCCNC(=O)c1cn(CC)c2cc(N3CCN(C)CC3)c(F)cc2c1=O | ZINC000097949656 | 0.942307997 |
| CC(C)[C@](C)(NC(=O)c1cn2c3c(cc(F)c(N4CCN(C)CC4)c3OC[C@H]2C)c1=O)C(N)=O | ZINC001148155364 | 0.942276597 |
| NC(=O)OC[C@H]1[C@@H](NC(=O)/C(=N\OCC(=O)O)c2csc(N)n2)C(=O)N1S(=O)(=O)O | ZINC000003871892 | 0.942093694 |
| CCCNC(=O)C1=CCS[C@@H]2[C@H](NC(=O)/C(=N\OC)c3csc(N)n3)C(=O)N12 | ZINC001220234407 | 0.942039794 |
| C[C@@H]1c2cccc(O)c2C(O)=C2C(=O)[C@]3(O)C(=O)[C@H](C(N)=O)C(=O)[C@H](N(C)C)[C@@H]3[C@@H](O)[C@@H]21 | ZINC000253388145 | 0.942023814 |
| CC(=O)N/C(=C\c1cc(F)ccc1F)C(=O)N1CN[C@H](N)[C@@H]2NCN[C@H]21 | ZINC001185743136 | 0.941987705 |
| COC(CN(C)C(=O)c1cn2c3c(cc(F)c(N4CCN(C)CC4)c3OC[C@H]2C)c1=O)OC | ZINC001148153903 | 0.941906747 |
| CN(C)[C@@H]1C(=O)/C(=C(\N)O)C(=O)[C@]2(O)C(=O)[C-]3C(=O)c4c(O)cccc4[C@](C)(O)[C@@H]3[C@H](O)[C@H]12 | ZINC000255974502 | 0.941902596 |
| CO/N=C(\C(=O)N[C@@H]1C(=O)N2C(C(=O)N3C[C@H](C)N(C)C[C@H]3C)=CCS[C@H]12)c1csc(N)n1 | ZINC001185591204 | 0.941876075 |
| COc1c(F)ccc2c(=O)c(C(=O)N3CN[C@H](N)[C@H]4NCN[C@H]43)cn(C3CC3)c21 | ZINC001154388539 | 0.941466463 |
| C[C@@H]1CCc2cc(F)cc3c(=O)c(C(=O)N4CN[C@H](N)[C@@H]5NCN[C@@H]54)cn1c23 | ZINC001150153529 | 0.941450384 |
| CC/C=C(/C(=O)N[C@H]1C(=O)N2C(C(=O)O)=C(COC(N)=O)CS[C@@H]12)c1csc(N)n1 | ZINC000038339224 | 0.941415739 |

FIG. 14 (Continued)

| | | |
|---|---|---|
| CO/N=C(/C(=O)N[C@@H]1C(=O)N2C(C(=O)O)=CCS[C@H]12)c1cnc(N)s1 | ZINC000008740416 | 0.941371039 |
| Cn1nnnc1SCC1=C(C(=O)O)N2C(=O)[C@@H](NC(=O)c3cc(F)c(F)cc3Cl)[C@@H]2SC1 | ZINC000009944316 | 0.941329587 |
| CN(C)[C@@H]1C(=O)/C(=C(\N)O)C(=O)[C@]2(O)C(=O)C3=C(O)c4c(O)ccc(Cl)c4[C@](C)(O)[C@H]3C[C@@H]12 | ZINC000149193683 | 0.941199231 |
| C[C@H]1COc2c(N3CCN(C)CC3)c(F)cc3c(=O)c(C(=O)N4CCN(C)C(=O)C4)cn1c32 | ZINC001148155951 | 0.941131884 |
| CO/N=C(\C(=O)N[C@@H]1C(=O)N2C(C(=O)NC3=CCOC3=O)=CCS[C@H]12)c1csc(N)n1 | ZINC001185592149 | 0.941090646 |
| C[C@H]1COc2c(N3CCN(C)CC3)c(F)cc3c(=O)c(C(=O)N4CCN(CCF)CC4)cn1c32 | ZINC001148156182 | 0.940830851 |
| C[C@@H]1COc2c(N3CCN(C)CC3)c(F)cc3c(=O)c(C(=O)N[C@H](C4CCC4)C4CNC4)cn1c32 | ZINC001221413135 | 0.940799159 |
| CCn1cc(C(=O)O)c(=O)c2cc(F)c(N3CCN(C(=O)c4cn(CC)c5cc(N6CCN(C(=O)c7ccc(C)cc7)CC6)c(F)cc5c4=O)CC3)cc21 | ZINC000150426006 | 0.940792465 |
| C[C@@H]1c2cccc(O)c2C(O)=C2C(=O)[C@]3(O)C(=O)[C@H](C(N)=O)C(=O)[C@H](N(C)C)[C@@H]3[C@H](O)[C@H]21 | ZINC000253388144 | 0.940688014 |
| C=C1c2c(Cl)ccc(O)c2C(=O)C2=C(O)[C@]3(O)C(=O)C(C(N)=O)=C(O)[C@@H](N(C)C)[C@@H]3[C@@H](O)[C@H]12 | ZINC000084402690 | 0.94067764 |
| C[C@@H]1COc2c(N3CCN(C)CC3)c(F)cc3c(=O)c(C(=O)N4C[C@@H](N)CC(F)(F)C4)cn1c32 | ZINC001160972520 | 0.940662399 |
| CCCCCCCCCCCCCCCC(=O)N1CCN(c2cc3c(cc2F)c(=O)c(C(=O)O)cn3CC)CC1 | ZINC000299738155 | 0.940567973 |
| N[C@@H]1NCN(c2nc(Cl)ncc2F)[C@H]2NCN[C@@H]21 | ZINC001162436489 | 0.940531465 |

FIG. 14 (Continued)

| | | |
|---|---|---|
| C[C@H]1c2cccc(O)c2C(O)=C2C(=O)[C@]3(O)C(O)=C(C(N)=O)C(=O)[C@@H](N(C)C)[C@@H]3[C@@H](O)[C@@H]21 | ZINC000100302137 | 0.940442073 |
| COc1c(N2CCN(C(=S)NCc3ccccc3)[C@@H](C)C2)c(F)cc2c(=O)c(C(=O)O)cn(C3CC3)c21 | ZINC000009307878 | 0.940432274 |
| CO/N=C(\C(=O)N[C@@H]1C(=O)N2C(C(=O)NCC(N)=O)=CCS[C@H]12)c1csc(N)n1 | ZINC001185589755 | 0.94039818 |
| CCOC(=O)c1cn(C2CC2)c2cc(N3CCN(C[C@H]4COCCN4)CC3)c(F)cc2c1=O | ZINC001236433400 | 0.940230757 |
| CNc1nnc(SCC2=C(C(=O)O)N3C(=O)[C@H](NC(=O)/C(=N/OC)c4csc(N)c4)[C@@H]3SC2)s1 | ZINC000100529337 | 0.940176976 |
| CN(C)[C@@H]1C(=O)/C(=C(\N)O)C(=O)[C@]2(O)C(=O)C3=C(O)c4c(O)ccc(Cl)c4[C@H](O)[C@@H]3C[C@H]12 | ZINC000255977796 | 0.93999286 |
| CO/N=C(\C(=O)N[C@@H]1C(=O)N2C(C(=O)N[C@H]3C[C@@H](O)C3(C)C)=CCS[C@H]12)c1csc(N)n1 | ZINC001185592435 | 0.939967141 |
| C[C@@H]1COc2c(N3CCN(C)CC3)c(F)cc3c(=O)c(C(=O)NCCN4CCNCC4=O)cn1c32 | ZINC001220875247 | 0.939964157 |
| CCOC(=O)[C@@H](C#N)NC(=O)C1=CCS[C@@H]2[C@H](NC(=O)/C(=N\OC)c3csc(N)n3)C(=O)N12 | ZINC001185591784 | 0.939954299 |
| N[C@@H]1NCN(c2c(F)nc(F)nc2Cl)[C@@H]2NCN[C@@H]21 | ZINC001162446435 | 0.9398146 |
| C[C@H]1COc2c(N3CCN(C)CC3)c(F)cc3c(=O)c(C(=O)N4CCN[C@H](C#N)C4)cn1c32 | ZINC001160652571 | 0.939715245 |
| C[C@@H]1COc2c(N3CCN(C)CC3)c(F)cc3c(=O)c(C(=O)NCS(=O)(=O)O)cn1c32 | ZINC001148164371 | 0.939709643 |

FIG. 14 (Continued)

| | | |
|---|---|---|
| C[C@H]1COc2c(N3CCN(C)CC3)c(F)cc3c(=O)c(C(=O)N[C@H]4CO[C@@H]5CNC[C@H]45)cn1c32 | ZINC001219856579 | 0.939688978 |
| C[C@H]1COc2c(N3CCN(C)CC3)c(F)cc3c(=O)c(C(=O)NCC4(N)CCCC4)cn1c32 | ZINC001220496928 | 0.939681563 |
| COc1c(N2CCN(C(=S)NCc3ccccc3)[C@H](C)C2)c(F)cc2c(=O)c(C(=O)O)cn(C3CC3)c21 | ZINC000009307877 | 0.939673677 |
| C[C@H]1COc2c(N3CCN(C)CC3)c(F)cc3c(=O)c(C(=O)Nc4cnc(O)nc4N)cn1c32 | ZINC001148156944 | 0.939525208 |
| C[C@H]1COc2c(N3CCN(C)CC3)c(F)cc3c(=O)c(C(=O)NCCc4nncs4)cn1c32 | ZINC001148164284 | 0.939476392 |
| CCOC(=O)c1cn(-c2nc(-c3ccc(Cl)c(Cl)c3)cs2)c2c(F)c(N3CCCC3)c(F)cc2c1=O | ZINC000002049996 | 0.939454499 |
| Cc1cc(NC(=O)c2cn3c4c(cc(F)c(N5CCN(C)CC5)c4OC[C@H]3C)c2=O)n(N)c(=O)c1 | ZINC001148162792 | 0.939161134 |
| C[C@@H]1COc2c(N3CCN(C)CC3)c(F)cc3c(=O)c(C(=O)N[C@H]4[C@H]5C=C[C@@H](C5)[C@@H]4C(N)=O)cn1c32 | ZINC001148162465 | 0.939153397 |
| COC(CCCNC(=O)c1cn2c3c(cc(F)c(N4CCN(C)CC4)c3OC[C@H]2C)c1=O)OC | ZINC001148162629 | 0.939012599 |
| C[C@@H]1COc2c(N3CCN(C)CC3)c(F)cc3c(=O)c(C(=O)N[C@@H]4CS(=O)(=O)C[C@H]4O)cn1c32 | ZINC000888104967 | 0.938860998 |
| C[C@H]1COc2c(N3CCN(C)CC3)c(F)cc3c(=O)c(C(=O)N[C@@H]4C=CS(=O)(=O)C4)cn1c32 | ZINC001148155758 | 0.938806877 |
| C=C1c2c(Cl)ccc(O)c2C(O)=C2C(=O)[C@]3(O)C(O)=C(C(N)=O)C(=O)[C@H](N(C)C)[C@@H]3[C@H](O)[C@H]12 | ZINC000199169700 | 0.938787037 |
| C[C@@H]1COc2c(N3CCN(C)CC3)c(F)cc3c(=O)c(C(=O)N(C)Cc4ncccn4)cn1c32 | ZINC001148156343 | 0.938589853 |
| C[C@H]1COc2c(F)c(F)cc3c(=O)c(C(=O)N[C@@H](CO)C(N)=O)cn1c32 | ZINC001152654515 | 0.93857986 |

FIG. 14 (Continued)

| | | |
|---|---|---|
| CO/N=C(\C(=O)N[C@@H]1C(=O)N2C(C(=O)O)=C(CSC(=O)c3ccco3)CS[C@@H]12)c1csc(N)n1 | ZINC000011616465 | 0.938449374 |
| C=C1c2cccc(O)c2C(O)=C2C(=O)[C@]3(O)C(=O)/C(=C(/N)O)C(=O)[C@H](N(C)C)[C@@H]3[C@H](O)[C@@H]12 | ZINC000255974305 | 0.938375372 |
| C[C@@H]1c2cccc(O)c2C(O)=C2C(=O)[C@]3(O)C(=O)/C(=C(/N)O)C(=O)[C@H](N(C)C)[C@@H]3[C@H](O)[C@@H]21 | ZINC000139456775 | 0.938196212 |
| Cc1nnc(SCC2=C(C(=O)O)N3C(=O)[C@@H](NC(=O)Cn4nc(C(F)F)c(Cl)c4C4CC4)[C@H]3SC2)s1 | ZINC000002798380 | 0.938186181 |
| C[C@H]1COc2c(N3CCN(C)CC3)c(F)cc3c(=O)c(C(=O)NCc4cccnn4)cn1c32 | ZINC001148155391 | 0.938137773 |
| CN(C)[C@@H]1C(=O)C(C(N)=O)=C(O)[C@@]2(O)C(=O)C3=C(O)c4c(O)ccc(Cl)c4[C@@](C)(O)[C@H]3C[C@@H]12 | ZINC000100302624 | 0.93810837 |
| CCC(CO)(CO)NC(=O)c1cn2c3c(cc(F)c(N4CCN(C)CC4)c3OC[C@H]2C)c1=O | ZINC001148155983 | 0.938095191 |
| C[C@H]1COc2c(N3CCN(C)CC3)c(F)cc3c(=O)c(C(=O)NC[C@@H]4CCN(C)C4)cn1c32 | ZINC001148163754 | 0.938046274 |
| CO/N=C(\C(=O)N[C@@H]1C(=O)N2C(C(=O)N3C[C@@H](F)C[C@H]3C#N)=CCS[C@H]12)c1csc(N)n1 | ZINC001185591303 | 0.93803511 |
| Nc1nc(/C(=C/CC(=O)O)C(=O)N[C@H]2C(=O)N3C(C(=O)O)=CCS[C@H]23)cs1 | ZINC000001530999 | 0.937956578 |
| CO/N=C(/C(=O)N[C@H]1C(=O)N2C(C(=O)O)=C(CSC(=O)c3ccco3)CS[C@@H]12)c1nc(N)cs1 | ZINC000584578375 | 0.937908652 |
| CN(C)[C@@H]1C(=O)/C(=C(\N)O)C(=O)[C@]2(O)C(=O)C3=C(O)c4c(O)ccc(Cl)c4[C@](C)(O)[C@@H]3C[C@@H]12 | ZINC000256073697 | 0.937898064 |

FIG. 14 (Continued)

| | | |
|---|---|---|
| CO[C@@H]1COCC[C@H]1NC(=O)c1cn2c3c(cc(F)c(N4CCN(C)CC4)c3OC[C@H]2C)c1=O | ZINC001148158023 | 0.937882477 |
| CN(C)[C@@H]1C(O)=C(C(N)=O)C(=O)[C@@]2(O)C(=O)C3=C(O)c4c(O)ccc(Cl)c4[C@@](C)(O)[C@H]3C[C@@H]12 | ZINC000100154659 | 0.937853551 |
| CO/N=C(\C(=O)N[C@@H]1C(=O)N2C(C(=O)N3CCNC3)=CCS[C@H]12)c1csc(N)n1 | ZINC001161418858 | 0.937841409 |
| COc1c(N2C[C@H]3CCCN[C@H]3C2)c(F)cc2c(=O)c(C(=O)OS(=O)(=O)O)cn(C3CC3)c21 | ZINC000044021607 | 0.93784036 |
| CCOC(=O)[C@@](NC(=O)CC(C)C)(N1CCN(c2cc3c(cc2F)c(=O)c(C(=O)O)cn3C2CC2)CC1)C(F)(F)F | ZINC000004047813 | 0.937790287 |
| COC(=O)[C@H](C)N(C)C(=O)c1cn2c3c(cc(F)c(N4CCN(C)CC4)c3OC[C@H]2C)c1=O | ZINC001148153923 | 0.9377832 |
| Nc1nc(/C(=C\CC(=O)O)C(=O)N[C@H]2C(=O)N3C(C(=O)O)=CCS[C@@H]23)cs1 | ZINC000031261238 | 0.937452504 |
| CN(C)[C@@H]1C(=O)[C@@H](C(N)=O)C(=O)[C@@]2(O)C(=O)[C@H]3C(=O)c4c(O)cccc4[C@@](C)(O)[C@H]3C[C@@H]12 | ZINC000169686736 | 0.93744359 |
| CCOC(=O)c1cn(C2CC2)c2cc(N3CCN([C@H]4CN[C@@H](C(=O)OC)C4)CC3)c(F)cc2c1=O | ZINC001246943459 | 0.937386873 |
| CN(C)[C@@H]1C(=O)/C(=C(\N)O)C(=O)[C@@]2(O)C(=O)C3=C(O)c4c(O)cccc4[C@@](C)(O)[C@H]3C[C@@H]12 | ZINC000102229720 | 0.937353837 |
| CN(C)[C@@H]1C(O)=C(C(N)=O)C(=O)[C@@]2(O)C(O)=C3C(=O)c4c(O)cccc4[C@](C)(O)[C@H]3[C@@H](O)[C@@H]12 | ZINC000035947015 | 0.937348956 |
| CO[C@]1(NC(=O)C2SC(=C(C(N)=O)C(=O)O)S2)C(=O)[C@H]2C(C(=O)O)=C(CSc3nnnn3C)CS[C@H]21 | ZINC000584578711 | 0.937328655 |

FIG. 14 (Continued)

| | | |
|---|---|---|
| CCCCCCCCCCCCCC(=O)N1CCN(c2cc3c(cc2F)c(=O)c(C(=O)O)cn3CC)CC1 | ZINC000097951366 | 0.937287682 |
| CN(C)[C@@H]1C(=O)/C(=C(\N)O)C(=O)[C@]2(O)C(=O)C3=C(O)c4c(O)ccc(Cl)c4[C@](C)(O)[C@H]3C[C@H]12 | ZINC000103618312 | 0.937235156 |
| C[C@H]1[C@H](NC(=O)/C(=N\OC(C)(C)C(=O)O)c2csc(N)n2)C(=O)N1S(=O)(=O)O | ZINC000003830264 | 0.937201658 |
| CN(C)CCn1nnnc1SCC1=C(C(=O)O)N2C(=O)[C@@H](NC(=O)Cc3csc(N)n3)[C@@H]2SC1 | ZINC000003830446 | 0.937047163 |
| CO/N=C(\C(=O)N[C@@H]1C(=O)N2C(C(=O)N3C[C@@H](C)C[C@H]3CF)=CCS[C@H]12)c1csc(N)n1 | ZINC001185590993 | 0.937044531 |
| CC[C@@H](C)C[C@H](C)NC(=O)C1=CCS[C@@H]2[C@H](NC(=O)/C(=N\OC)c3csc(N)n3)C(=O)N12 | ZINC001185591030 | 0.937019822 |
| C[C@@H]1COc2c(N3CCN(C)CC3)c(F)cc3c(=O)c(C(=O)N[C@@H]4[C@H]5C=C[C@@H](C5)[C@H]4C(N)=O)cn1c32 | ZINC001148162467 | 0.936987182 |
| C[C@H]1COc2c(N3CCN(C)CC3)c(F)cc3c(=O)c(C(=O)NC4(CO)CCN(C)CC4)cn1c32 | ZINC001148162390 | 0.93683897 |
| CC(C)(O/N=C(/C(=O)N[C@H]1C(=O)N2C(C(=O)O)=C(C[n+]3ccccc3)CS[C@H]12)c1csc(N)n1)C(=O)O | ZINC000001530591 | 0.936831126 |
| C[C@H]1c2cccc(O)c2C(O)=C2C(=O)[C@]3(O)C(=O)C(C(N)=O)=C(O)[C@@H](N(C)C)[C@@H]3[C@@H](O)[C@@H]21 | ZINC000109562088 | 0.93682954 |
| CO/N=C(\C(=O)N[C@H]1C(=O)N2C(C(=O)OCOC(=O)C(C)(C)C)=C(/C=C\c3scnc3C)CS[C@@H]12)c1csc(N)n1 | ZINC000008584443 | 0.936761078 |
| C[C@@H]1c2cccc(O)c2C(O)=C2C(=O)[C@]3(O)C(=O)/C(=C(\N)O)C(=O)[C@H](N(C)C)[C@@H]3[C@@H](O)[C@@H]21 | ZINC000106046010 | 0.936564445 |

FIG. 14 (Continued)

| | | |
|---|---|---|
| CCn1cc(C(=O)O)c(=O)c2cc(F)c(N3CCN([C@H]4CC(=O)N(c5cnccn5)C4=O)CC3)cc21 | ZINC000517414973 | 0.936518323 |
| Cc1nnc(CNC(=O)c2cn3c4c(cc(F)c(N5CCN(C)CC5)c4OC[C@H]3C)c2=O)o1 | ZINC001148163047 | 0.936410487 |
| CCN=c1ncc(N)cn1C(=O)c1cn2c3c(cc(F)c(N4CCN(C)CC4)c3OC[C@H]2C)c1=O | ZINC001148157383 | 0.936367437 |
| CO/N=C(\C(=O)N[C@@H]1C(=O)N2C(C(=O)O)=C(CSc3nc(C)c(CC(=O)O)s3)CS[C@H]12)c1csc(N)n1 | ZINC000003830421 | 0.936097252 |
| C[C@H]1C[C@@H](CO)N(C(=O)c2cn3c4c(cc(F)c(N5CCN(C)CC5)c4OC[C@H]3C)c2=O)C1 | ZINC001148157367 | 0.936081234 |
| N[C@@H]1NCN(c2nc(Cl)ncc2F)[C@@H]2NCN[C@H]21 | ZINC001162436490 | 0.936056188 |
| CCOC(=O)CC(=N)NC(=O)c1cn2c3c(cc(F)c(N4CCN(C)CC4)c3OC[C@@H]2C)c1=O | ZINC001148157701 | 0.935940823 |
| COC[C@H]1C(=O)N[C@@H](c2cc(F)c(F)cc2F)N1C | ZINC000334874615 | 0.935895741 |
| CO/N=C(\C(=O)N[C@@H]1C(=O)N2C(C(=O)N[C@@H](C#N)CC(C)C)=CCS[C@H]12)c1csc(N)n1 | ZINC001185590992 | 0.935719705 |
| CO/N=C(\C(=O)N[C@@H]1C(=O)N2C(C(=O)O)=C(CSc3nc(C)c(CC(=O)O)s3)CC[C@H]12)c1csc(N)n1 | ZINC000585091604 | 0.935538042 |
| N[C@@H]1NCN(c2nc(Cl)ccc2F)[C@H]2NCN[C@H]21 | ZINC001162435511 | 0.935509017 |
| C[C@H]1COc2c(N3CCN(C)CC3)c(F)cc3c(=O)c(C(=O)Nc4cccnc4CN)cn1c32 | ZINC001148162789 | 0.93544786 |
| CCOC(=O)C1(NC(=O)c2cn3c4c(cc(F)c(N5CCN(C)CC5)c4OC[C@H]3C)c2=O)CNC1 | ZINC001220853346 | 0.935394138 |
| O=C1C=C(N2CC2)C(=O)C(N2CC2)=C1N1CC1 | ZINC000008214696 | 0.935390526 |

FIG. 14 (Continued)

| | | |
|---|---|---|
| CCCCCCCCCCCCC(=O)N1CCN(c2cc3c(cc2F)c(=O)c(C(=O)O)cn3CC)CC1 | ZINC000097951396 | 0.935341772 |
| CO/N=C(\C(=O)N[C@@H]1C(=O)N2C(C(=O)N(C)C3[C@@H]4CNC[C@@H]34)=CCS[C@H]12)c1csc(N)n1 | ZINC001161222321 | 0.93522988 |
| CO/N=C(\C(=O)N[C@@H]1C(=O)N2C(C(=O)N(C)C3[C@H]4CNC[C@H]34)=CCS[C@H]12)c1csc(N)n1 | ZINC001161222320 | 0.935229877 |
| C[C@@H]1COc2c(N3CCN(C)CC3)c(F)cc3c(=O)c(C(=O)N=c4nc[nH]n5cccc45)cn1c32 | ZINC001148156807 | 0.935229391 |
| CCOC(=O)c1cn(C2CC2)c2cc(N3CCN(C[C@@H]4COCCN4)CC3)c(F)cc2c1=O | ZINC001236433404 | 0.9350353 |
| C=C1c2cccc(O)c2C(O)=C2C(=O)[C@]3(O)C(O)=C(C(N)=O)C(=O)[C@@H](N(C)C)[C@@H]3[C@@H](O)[C@H]12 | ZINC000004019716 | 0.935034174 |
| C[C@H]1c2ccc(N)c(O)c2C(=O)C2=C(O)[C@]3(O)C(=O)C(C(N)=O)=C(O)[C@@H](N(C)C)[C@H]3[C@@H](O)[C@H]21 | ZINC000095616383 | 0.935030752 |
| C[C@@H]1COc2c(N3CCN(C)CC3)c(F)cc3c(=O)c(C(=O)N(C)c4nccnc4N)cn1c32 | ZINC001148154840 | 0.935014743 |
| C[C@@H]1COc2c(N3CCN(C)CC3)c(F)cc3c(=O)c(C(=O)N4CC(C)(N(C)C)C4)cn1c32 | ZINC001148154342 | 0.934911206 |
| CO/N=C(\C(=O)N[C@@H]1C(=O)N2C(C(=O)N3CC(N(C)C)C3)=CCS[C@H]12)c1csc(N)n1 | ZINC001185590417 | 0.934842879 |
| C[C@@H]1COc2c(N3CCN(C)CC3)c(F)cc3c(=O)c(C(=O)NCC(C)(C)C(N)=O)cn1c32 | ZINC001148156414 | 0.934839958 |
| CN(C)[C@@H]1C(=O)C(C(N)=O)=C(O)[C@]2(O)C(=O)C3=C(O)c4c(O)cccc4[C@](C)(O)[C@@H]3[C@H](O)[C@@H]12 | ZINC000257084916 | 0.934646991 |

FIG. 14 (Continued)

| | | |
|---|---|---|
| CO/N=C(\C(=O)N[C@@H]1C(=O)N2C(C(=O)N[C@@H](CO)CC(C)C)=CCS[C@H]12)c1csc(N)n1 | ZINC001185590492 | 0.934627071 |
| CCOC(=O)c1cn(C2CC2)c2cc(N3CCN([C@H]4CN[C@H](C(=O)OC)C4)CC3)c(F)cc2c1=O | ZINC001246943460 | 0.934536883 |
| O=C1CSC(=S)N1/N=C/c1ccc([N+](=O)[O-])s1 | ZINC000001735150 | 0.93448709 |
| C[C@@H]1COc2c(N3CCN(C)CC3)c(F)cc3c(=O)c(C(=O)N4CCNC(=O)[C@H]4C)cn1c32 | ZINC001148155767 | 0.934448302 |
| CN(C)[C@@H]1C(=O)C(C(N)=O)=C(O)[C@]2(O)C(=O)C3=C(O)c4c(O)cccc4[C@](C)(O)[C@@H]3[C@@H](O)[C@H]12 | ZINC000200193470 | 0.934419397 |
| CO/N=C(/C(=O)N[C@@H]1C(=O)N2C(C(=O)O)=C(CSC(=O)c3ccco3)CS[C@@H]12)c1csc(N)n1 | ZINC000011616466 | 0.934234881 |
| CO/N=C(\C(=O)N[C@@H]1C(=O)N2C(C(=O)N[C@@H](C)C(C)C)=CCS[C@H]12)c1csc(N)n1 | ZINC001185590089 | 0.934142402 |
| C[C@@H]1c2cccc(O)c2C(O)=C2C(=O)[C@]3(O)C(=O)[C@H](C(N)=O)C(=O)[C@H](N(C)C)[C@@H]3[C@H](O)[C@@H]21 | ZINC000253388142 | 0.934110877 |
| CC(C)(O/N=C(\C(=O)N[C@H]1C(=O)N2C(C(=O)O)=C(C[n+]3ccccc3)CS[C@H]12)c1csc(N)n1)C(=O)O | ZINC000008582316 | 0.934090587 |
| CO/N=C(/C(=O)N[C@@H]1C(=O)N2C(C(=O)O)=C(CSc3nnnn3C)CS[C@H]12)c1cnc(N)s1 | ZINC000022001553 | 0.933741385 |
| CC[C@@H](C)C[C@@H](C)NC(=O)C1=CCS[C@@H]2[C@H](NC(=O)/C(=N\OC)c3csc(N)n3)C(=O)N12 | ZINC001185591027 | 0.933681488 |
| CO/N=C(\C(=O)N[C@@H]1C(=O)N2C(C(=O)NCCCCN)=CCS[C@H]12)c1csc(N)n1 | ZINC001221348071 | 0.933655673 |

FIG. 14 (Continued)

| | | |
|---|---|---|
| CO/N=C(\C(=O)N[C@@H]1C(=O)N2C(C(=O)N[C@H](C)c3ccno3)=CCS[C@H]12)c1csc(N)n1 | ZINC001185592350 | 0.933583978 |
| CC[C@H](C)C[C@H](C)NC(=O)C1=CCS[C@@H]2[C@H](NC(=O)/C(=N\OC)c3csc(N)n3)C(=O)N12 | ZINC001185591028 | 0.933579001 |
| O=C1CSC(=S)N1N1C(=O)[C@H]2[C@@H](C1=O)[C@@H]1C=C[C@H]2[C@@H]2C(=O)N(N3C(=O)CSC3=S)C(=O)[C@H]21 | ZINC000245285084 | 0.933503504 |
| O=C1CSC(=S)N1N1C(=O)[C@H]2[C@H](C1=O)[C@H]1C=C[C@@H]2[C@H]2C(=O)N(N3C(=O)CSC3=S)C(=O)[C@H]21 | ZINC000245285085 | 0.933503504 |
| CO/N=C(\C(=O)N[C@@H]1C(=O)N2C(C(=O)NCC(C)(F)F)=CCS[C@H]12)c1csc(N)n1 | ZINC001185590377 | 0.93332873 |
| COc1c(F)ccc2c(=O)c(C(=O)N3CN[C@H](N)[C@@H]4NCN[C@H]43)cn(C3CC3)c21 | ZINC001154388542 | 0.933286145 |
| C[C@@H]1COc2c(N3CCN(C)CC3)c(F)cc3c(=O)c(C(=O)N[C@@H]4CCOC[C@@H]4F)cn1c32 | ZINC001148163027 | 0.933221328 |
| C[C@@H]1c2cccc(O)c2C(O)=C2C(=O)[C@]3(O)C(=O)/C(=C(\N)O)C(=O)[C@H](N(C)C)[C@@H]3[C@H](O)[C@H]21 | ZINC000138347755 | 0.933177531 |
| CCCCCCCCCCCC(=O)N1CCN(c2cc3c(cc2F)c(=O)c(C(=O)O)cn3CC)CC1 | ZINC000097951386 | 0.933146659 |
| COc1c(F)ccc2c(=O)c(C(=O)N3CN[C@H](N)[C@H]4NCN[C@@H]43)cn(C3CC3)c21 | ZINC001154388541 | 0.933136278 |
| CCn1cc(Cl)c(C(=O)N[C@H]2C(=O)N3C(C(=O)O)=C(CSc4nnc(C)s4)CS[C@@H]23)n1 | ZINC000002747828 | 0.93312062 |
| CO/N=C(\C(=O)N[C@@H]1C(=O)N2C(C(=O)N3C[C@@H](OC)[C@@H](N)C3)=CCS[C@H]12)c1csc(N)n1 | ZINC001161493563 | 0.93303766 |

FIG. 14 (Continued)

| | | |
|---|---|---|
| CN(C)[C@@H]1C(O)=C(C(N)=O)C(=O)[C@@]2(O)C(O)=C3C(=O)c4c(O)cccc4[C@@](C)(O)[C@H]3[C@H](O)[C@@H]12 | ZINC000095626782 | 0.933014944 |
| CO/N=C(\C(=O)N[C@@H]1C(=O)N2C(C(=O)N[C@H]3C[C@H](O)C3(C)C)=CCS[C@H]12)c1csc(N)n1 | ZINC001185592430 | 0.93301414 |
| CO/N=C(/C(=O)N[C@@H]1C(=O)N2C(C(=O)O)=C([C@@H]3CCCO3)CS[C@H]12)c1csc(N)n1 | ZINC000034326129 | 0.932983837 |
| CN(C)[C@@H]1C(=O)/C(=C(\N)O)C(=O)[C@]2(O)C(=O)C3=C(O)c4c(O)ccc(Cl)c4[C@](C)(O)[C@@H]3C[C@H]12 | ZINC000137350593 | 0.932925597 |
| N=c1scc(N)n1-c1c(F)cc(C(=O)O)cc1F | ZINC001215608450 | 0.932769051 |
| C[C@@H]1COc2c(N3CCN(C)CC3)c(F)cc3c(=O)c(C(=O)N4CCNC(=O)[C@@H]4C)cn1c32 | ZINC001148155765 | 0.932732183 |
| C[C@@H]1C(=O)NCCN1C(=O)c1cn2c3c(cc(F)c(N4CCN(C)CC4)c3OC[C@@H]2C)c1=O | ZINC001148155766 | 0.932732177 |
| CO/N=C(/C(=O)N[C@@H]1C(=O)N2C(C(=O)O)=C(CSc3nc(C)c(CC(=O)O)s3)CS[C@H]12)c1csc(N)n1 | ZINC000003871933 | 0.932693335 |
| Cc1nnc(SCC2=C(C(=O)O)N3C(=O)[C@@H](NC(=O)c4ccc(COc5c(F)c(F)cc(F)c5F)o4)[C@H]3SC2)s1 | ZINC000150385909 | 0.932635832 |
| CC(C)[C@@](C)(NC(=O)c1cn2c3c(cc(F)c(N4CCN(C)CC4)c3OC[C@@H]2C)c1=O)C(N)=O | ZINC001148155363 | 0.93263272 |
| COC(=O)[C@H](CS)NC(=O)c1cn2c3c(cc(F)c(N4CCN(C)CC4)c3OC[C@H]2C)c1=O | ZINC001148157999 | 0.932434562 |
| CN(C)[C@@H]1C(O)=C(C(N)=O)C(=O)[C@@]2(O)C(=O)C3=C(O)c4c(O)ccc(Cl)c4[C@@](C)(O)[C@@H]3C[C@@H]12 | ZINC000100154662 | 0.932393754 |

FIG. 14 (Continued)

| | | |
|---|---|---|
| CO/N=C(\C(=O)N[C@@H]1C(=O)N2C(C(=O)NCCCCCN(C)C)=CCS[C@H]12)c1csc(N)n1 | ZINC001185592338 | 0.932164595 |
| CO/N=C(\C(=O)N[C@@H]1C(=O)N2C(C(=O)O)=C(COC(C)=O)CS[C@@H]12)c1csc(N)n1 | ZINC000005223872 | 0.932017696 |
| CO[C@@]12C(COC(=N)O)=C3C(=C([O])C(C)=C(N)C3=O)N1C[C@@H]1N[C@@H]12 | ZINC001560410897 | 0.93190707 |
| CO/N=C(\C(=O)N[C@@H]1C(=O)N2C(C(=O)N[C@@H]3CCCC[C@H]3F)=CCS[C@H]12)c1csc(N)n1 | ZINC001185590352 | 0.931832948 |
| O=C1N[C@@H](CF)C(=O)N1[C@H]1COc2cc(F)cc(F)c21 | ZINC000672813400 | 0.931769252 |
| CO/N=C(\C(=O)N[C@@H]1C(=O)N2C(C(=O)O)=C(Cn3nnc(C)n3)CS[C@H]12)c1csc(N)n1 | ZINC000004215263 | 0.931743318 |
| CO/N=C(\C(=O)N[C@@H]1C(=O)N2C(C(=O)N[C@H]3CNC(=O)C3(C)C)=CCS[C@H]12)c1csc(N)n1 | ZINC001185591020 | 0.931508151 |
| CO/N=C(\C(=O)N[C@@H]1C(=O)N2C(C(=O)N[C@@H]3C[C@@H](O)C3(C)C)=CCS[C@H]12)c1csc(N)n1 | ZINC001185592428 | 0.931444937 |
| C[C@H]1COc2c(N3CCN(C)CC3)c(F)cc3c(=O)c(C(=O)NC4=CC(=O)NCC4)cn1c32 | ZINC001221316929 | 0.931441563 |
| C[C@H]1COc2c(N3CCN(C)CC3)c(F)cc3c(=O)c(C(=O)NC[C@H]4CNC(=O)C4)cn1c32 | ZINC001148155477 | 0.931432825 |
| CO/N=C(\C(=O)N[C@@H]1C(=O)N2C(C(=O)N[C@H](C)C(C)C)=CCS[C@H]12)c1csc(N)n1 | ZINC001185590298 | 0.931324571 |
| C[C@@H]1COc2c(N3CCN(C)CC3)c(F)cc3c(=O)c(C(=O)NCCC[C@H]4C=NNC4=O)cn1c32 | ZINC001148157630 | 0.931156209 |

FIG. 14 (Continued)

| | | |
|---|---|---|
| CO/N=C(\C(=O)N[C@H]1C(=O)N2C(C(=O)O)=C(C[n+]3cccc4c3CCC4)CS[C@@H]12)c1csc(N)n1 | ZINC000025991369 | 0.931039512 |
| C[C@@H]1COc2c(N3CCN(C)CC3)c(F)cc3c(=O)c(C(=O)N[C@H]4COCC[C@@H]4O)cn1c32 | ZINC001148157850 | 0.931020504 |
| C[C@H]1COc2c(N3CCN(C)CC3)c(F)cc3c(=O)c(C(=O)N4CC5CC4(CN)C5)cn1c32 | ZINC001158191637 | 0.930921051 |
| C=C1c2cccc(O)c2C(O)=C2C(=O)[C@]3(O)C(O)=C(C(N)=O)C(=O)[C@@H](N(C)C)[C@H]3[C@H](O)[C@H]12 | ZINC000004574572 | 0.930916005 |
| C[C@@H]1COc2c(N3CCN(C)CC3)c(F)cc3c(=O)c(C(=O)N4C[C@H](N)CC(F)(F)C4)cn1c32 | ZINC001160972526 | 0.930890679 |
| C[C@@H]1CCN(C(=O)c2cn3c4c(cc(F)c(N5CCN(C)CC5)c4OC[C@H]3C)c2=O)C[C@@H]1N | ZINC001157810429 | 0.930858958 |
| C[C@H]1COc2c(N3CCN(C)CC3)c(F)cc3c(=O)c(C(=O)NC[C@@H]4C[C@H](F)CN4)cn1c32 | ZINC001219639418 | 0.93076826 |
| O=C1S/C(=N\C2CCCCC2)N(C2CCCCC2)/C1=C1\C(=O)S/C(=N\C2CCCCC2)N1C1CCCCC1 | ZINC000104270988 | 0.930668497 |
| CCOC(=O)[C@H](C#N)NC(=O)C1=CCS[C@@H]2[C@H](NC(=O)/C(=N\OC)c3csc(N)n3)C(=O)N12 | ZINC001185591781 | 0.930203846 |
| C[C@@H]1[C@H](NC(=O)/C(=N/OC(C)(C)C(=O)O)c2csc(N)n2)C(=O)N1S(=O)(=O)O | ZINC000003830263 | 0.93016749 |
| CC[C@H](C)C[C@@H](C)NC(=O)C1=CCS[C@@H]2[C@H](NC(=O)/C(=N\OC)c3csc(N)n3)C(=O)N12 | ZINC001185591029 | 0.930118591 |
| C[C@H]1COc2c(N3CCN(C)CC3)c(F)cc3c(=O)c(C(=O)Nc4cnn(C5CNC5)c4)cn1c32 | ZINC001218641407 | 0.930056801 |

FIG. 14 (Continued)

| | | |
|---|---|---|
| C[C@@H]1[C@H](NC(=O)/C(=N\OC(C)(C)C(=O)O)c2csc(N)n2)C(=O)N1S(=O)(=O)O | ZINC000015848211 | 0.930033275 |
| CO/N=C(\C(=O)N[C@@H]1C(=O)N2C(C(=O)N(C)C3CC(C)C3)=CCS[C@H]12)c1csc(N)n1 | ZINC001185591660 | 0.930020636 |
| N[C@@H]1NCN(c2cc(Cl)ncc2F)[C@@H]2NCN[C@@H]21 | ZINC001162440409 | 0.930015421 |
| CO/N=C(\C(=O)N[C@@H]1C(=O)N2C(C(=O)N[C@H](C#N)CC(C)C)=CCS[C@H]12)c1csc(N)n1 | ZINC001185590995 | 0.929978338 |
| C[C@H]1COc2c(N3CCN(C)CC3)c(F)cc3c(=O)c(C(=O)N(C)CC(=O)N(C)C)cn1c32 | ZINC001148156425 | 0.929918495 |
| C[C@H]1COc2c(N3CCN(C)CC3)c(F)cc3c(=O)c(C(=O)NCCn4ccnc4)cn1c32 | ZINC001148155262 | 0.929898602 |
| Cc1cnc(O)nc1NC(=O)c1cn2c3c(cc(F)c(N4CCN(C)CC4)c3OC[C@H]2C)c1=O | ZINC001148154305 | 0.929885143 |
| O=C1S/C(=N/C2CCCCC2)N(C2CCCCC2)/C1=C1\C(=O)S/C(=N\C2CCCCC2)N1C1CCCCC1 | ZINC000104270994 | 0.929783437 |
| CO/N=C(\C(=O)N[C@@H]1C(=O)N2C(C(=O)NC3(CC4CC4)CC3)=CCS[C@H]12)c1csc(N)n1 | ZINC001185591403 | 0.929762256 |
| C[C@H]1COc2c(N3CCN(C)CC3)c(F)cc3c(=O)c(C(=O)NCc4ncccc4O)cn1c32 | ZINC001148162340 | 0.929696038 |
| COc1c(F)cc(F)cc1N1[C@H]2CN3C4=C(C(=O)C(N)=C(C)C4=O)[C@@H](COC(=N)O)[C@@]3(OC)[C@H]21 | ZINC001170237051 | 0.929516879 |
| O=C1CSC(=S)N1N1C(=O)[C@H]2[C@H](C1=O)C1C=CC2[C@H]2C(=O)N(N3C(=O)CSC3=S)C(=O)[C@H]21 | ZINC000025501600 | 0.929494266 |
| O=C1CSC(=S)N1N1C(=O)[C@H]2[C@@H](C1=O)C1C=CC2[C@@H]2C(=O)N(N3C(=O)CSC3=S)C(=O)[C@H]21 | ZINC000195528756 | 0.929494265 |

FIG. 14 (Continued)

| | | |
|---|---|---|
| C[C@H]1COc2c(N3CCN(C)CC3)c(F)cc3c(=O)c(C(=O)NCc4nccn4C)cn1c32 | ZINC001148155948 | 0.929482883 |
| C=C1c2cccc(O)c2C(O)=C2C(=O)[C@]3(O)C(=O)C(C(N)=O)=C(O)[C@@H](N(C)C)[C@@H]3[C@@H](O)[C@H]12 | ZINC000199797578 | 0.929371318 |
| CC(=O)N/C(=C\c1cc(F)ccc1F)C(=O)N1CN[C@H](N)[C@@H]2NCN[C@@H]21 | ZINC001185743138 | 0.929347238 |
| C[C@H]1COc2c(N3CCN(C)CC3)c(F)cc3c(=O)c(C(=O)n4[nH]c5ccnc(=O)c-5c4N)cn1c32 | ZINC001148163812 | 0.929327148 |
| Cc1nnc(SCC2=C(C(=O)O)N3C(=O)[C@@H](NC(=O)Cn4nc(C(F)F)c(Cl)c4C4CC4)[C@@H]3SC2)s1 | ZINC000002798379 | 0.9293136 |
| C[C@@H]1C[C@@H](CNC(=O)c2cn3c4c(cc(F)c(N5CCN(C)CC5)c4OC[C@@H]3C)c2=O)CN1 | ZINC001219684530 | 0.929275244 |
| Cc1nnc(SCC2=C(C(=O)O)N3C(=O)[C@@H](NC(=O)Cn4cc(Cl)c(=O)c(Cl)c4)[C]3SC2)s1 | ZINC001560405402 | 0.929259479 |
| CCOC(=O)[C@](NC(=O)CC(C)C)(N1CCN(c2cc3c(cc2F)c(=O)c(C(=O)O)cn3C2CC2)CC1)C(F)(F)F | ZINC000004047814 | 0.929242477 |
| COC(C)(CNC(=O)c1cn2c3c(cc(F)c(N4CCN(C)CC4)c3OC[C@H]2C)c1=O)OC | ZINC001148162722 | 0.929179049 |
| CO/N=C(/C(=O)N[C@@H]1C(=O)N2C(C(=O)O)=C(CSc3nnc(C)s3)CS[C@H]12)c1csc(N)c1 | ZINC000101645989 | 0.928840107 |
| Cc1cc(=O)c(N)c(C)n1C(=O)c1cn2c3c(cc(F)c(N4CCN(C)CC4)c3OC[C@H]2C)c1=O | ZINC001148155745 | 0.928819615 |
| C[C@@H]1COc2c(N3CCN(C)CC3)c(F)cc3c2n1cc(C(=O)n1ccc(=N)c(N)c1)c3=O | ZINC001218694478 | 0.928783005 |
| CO/N=C(\C(=O)N[C@@H]1C(=O)N2C(C(=O)N[C@H]3CCCNC3)=CCS[C@H]12)c1csc(N)n1 | ZINC001220890686 | 0.928732762 |

FIG. 14 (Continued)

| | | |
|---|---|---|
| CO/N=C(\C(=O)N[C@@H]1C(=O)N2C(C(=O)N[C@@H](C)c3ccno3)=CCS[C@H]12)c1csc(N)n1 | ZINC001185592349 | 0.928664035 |
| Cc1nnc(SCC2=C(C(=O)O)N3C(=O)[C@H](NC(=O)c4cc(F)c(F)cc4Cl)[C@H]3SC2)s1 | ZINC000017356885 | 0.928659973 |
| C[C@H]1COc2c(N3CCN(C)CC3)c(F)cc3c(=O)c(C(=O)NC[C@H]4COCCN4C)cn1c32 | ZINC001148163098 | 0.928541204 |
| C[C@H]1COc2c(N3CCN(C)CC3)c(F)cc3c(=O)c(C(=O)NC[C@H]4CC(=O)N(C)C4)cn1c32 | ZINC001148162427 | 0.928409645 |
| C[C@H]1COc2c(N3CCN(C)CC3)c(F)cc3c(=O)c(C(=O)N(CCN)S(C)(=O)=O)cn1c32 | ZINC001148155296 | 0.928338563 |
| C[C@H]1c2ccc(N)c(O)c2C(=O)C2=C(O)[C@]3(O)C(=O)C(C(N)=O)=C(O)[C@@H](N(C)C)[C@H]3[C@@H](O)[C@@H]21 | ZINC000095616385 | 0.928331232 |
| CNCCCCNC(=O)C1=CCS[C@@H]2[C@H](NC(=O)/C(=N\OC)c3csc(N)n3)C(=O)N12 | ZINC001220077601 | 0.928228226 |
| CCN=c1ccc(N)cn1C(=O)c1cn2c3c(cc(F)c(N4CCN(C)CC4)c3OC[C@H]2C)c1=O | ZINC001148155773 | 0.928144333 |
| C[C@@H]1COc2c(N3CCN(C)CC3)c(F)cc3c(=O)c(C(=O)N4CC(=O)N(C)C[C@@H]4C)cn1c32 | ZINC001148157319 | 0.928042275 |
| CC(=O)N/C(=C/c1cc(F)ccc1F)C(=O)N1CN[C@H](N)[C@@H]2NCN[C@H]21 | ZINC001185743128 | 0.927953881 |
| CCOC(=O)c1cn(C2CC2)c2cc(N3CCN([C@@H]4CN[C@@H](C(=O)OC)C4)CC3)c(F)cc2c1=O | ZINC001246943457 | 0.927893123 |
| C[C@@H](O)[C@H]1C(=O)N2C(C(=O)N3CN[C@H](N)[C@H]4NCN[C@H]43)=C([C@H]3CCCO3)S[C@H]12 | ZINC001183464026 | 0.927779785 |

FIG. 14 (Continued)

| | | |
|---|---|---|
| C=C1c2cccc(O)c2C(O)=C2C(=O)[C@]3(O)C(=O)/C(=C(/N)O)C(=O)[C@H](N(C)C)[C@@H]3[C@H](O)[C@H]12 | ZINC000111327805 | 0.927754182 |
| C[C@H]1COc2c(N3CCN(C)CC3)c(F)cc3c(=O)c(C(=O)N4CCC[C@H]4C(N)=O)cn1c32 | ZINC001161034386 | 0.927679396 |
| CCn1cc(C(=O)O)c(=O)c2cc(F)c(N3CCN([C@@H]4CC(=O)N(c5cnccn5)C4=O)CC3)cc21 | ZINC000517414974 | 0.927667627 |
| CO/N=C(\C(=O)N[C@@H]1C(=O)N2C(C(=O)N[C@H]3CCCN(C)C3)=CCS[C@H]12)c1csc(N)n1 | ZINC001185592144 | 0.927563742 |
| C[C@@H]1COc2c(N3CCN(C)CC3)c(F)cc3c(=O)c(C(=O)N[C@@H]4CS(=O)(=O)C[C@@H]4O)cn1c32 | ZINC000888104977 | 0.927479592 |
| CCN1CCN(C(=O)N[C@@H](C(=O)N[C@]2(OC)C(=O)N3C(C(=O)O)=C(CSc4nnnn4C)CS[C@@H]32)[C@H](C)O)C(=O)C1=O | ZINC000004215229 | 0.927390209 |
| CN(C)[C@@H]1C(O)=C(C(N)=O)C(=O)[C@]2(O)C(O)=C3C(=O)c4c(O)cccc4[C@@](C)(O)[C@H]3[C@@H](O)[C@@H]12 | ZINC000035947013 | 0.927364701 |
| C[C@H]1COc2c(N3CCN(C)CC3)c(F)cc3c(=O)c(C(=O)N4CCN(c5ncccn5)CC4)cn1c32 | ZINC000012645296 | 0.927353781 |
| N[C@@H]1NCN(C(=O)CSc2nnc(S)s2)[C@H]2NCN[C@H]21 | ZINC001177346744 | 0.92731154 |
| CO/N=C(\C(=O)N[C@@H]1C(=O)N2C(C(=O)N3CC(C)(N(C)C)C3)=CCS[C@H]12)c1csc(N)n1 | ZINC001185590965 | 0.927199519 |
| CCOC(=O)c1cn(C2CC2)c2cc(N3CCN(c4ccc(C(N)=O)nn4)CC3)c(F)cc2c1=O | ZINC001157808757 | 0.927145782 |
| COCCCNC(=O)C1=CCS[C@@H]2[C@H](NC(=O)/C(=N\OC)c3csc(N)n3)C(=O)N12 | ZINC001185590820 | 0.927067396 |

FIG. 14 (Continued)

| | | |
|---|---|---|
| Cc1cnc(NC(=O)c2cn3c4c(cc(F)c(N5CCN(C)CC5)c4OC[C@H]3C)c2=O)c(=O)[nH]1 | ZINC001148163022 | 0.9270567 |
| CO/N=C(\C(=O)N[C@@H]1C(=O)N2C(C(=O)O)=C(CSC(=O)c3ccco3)CS[C@H]12)c1csc(N)n1 | ZINC000004215267 | 0.926841131 |
| CO/N=C(/C(=O)N[C@@H]1C(=O)N2C(C(=O)O)=C(COC(C)=O)CS[C@@H]12)c1csc(N)n1 | ZINC000003830438 | 0.926836795 |
| CCn1cc(C(=O)O)c(=O)c2c(N)c(F)c(F)c(F)c21 | ZINC000001428777 | 0.92674966 |
| CO/N=C(\C(=O)N[C@H]1C(=O)N2C(C(=O)O)=C[C@@H](C[n+]3cccc4c3CCC4)S[C@@H]12)c1csc(N)n1 | ZINC000584577518 | 0.926749402 |
| CN(C)[C@H]1C(O)=C(C(N)=O)C(=O)[C@@]2(O)C(O)=C3C(=O)c4c(O)ccc(Cl)c4[C@@](C)(O)[C@H]3C[C@@H]12 | ZINC000022054932 | 0.926726976 |
| C[C@@H]1c2cccc(O)c2C(O)=C2C(=O)[C@]3(O)C(O)=C(C(N)=O)C(=O)[C@H](N(C)C)[C@@H]3[C@@H](O)[C@H]21 | ZINC000252586750 | 0.926719049 |
| O=C1S/C(=N/C2CCCCC2)N(C2CCCCC2)/C1=C1/C(=O)S/C(=N\C2CCCCC2)N1C1CCCCC1 | ZINC000104270982 | 0.926505488 |
| CON=C(C(=O)N[C@H]1C(=O)N2C(C(=O)O)=C(CSc3nc(C)c(CC(=O)O)s3)CS[C@@H]12)c1csc(N)n1 | ZINC000252676467 | 0.926500529 |
| CSc1nc(Cl)c(/C=N/O)c(N2CN[C@H](N)[C@H]3NCN[C@H]32)n1 | ZINC001162436704 | 0.926174507 |
| O=c1c(=O)c2c1NCCCN2 | ZINC000020458415 | 0.926117477 |
| CO/N=C(\C(=O)N[C@@H]1C(=O)N2C(C(=O)n3ccc(CN)cc3=N)=CCS[C@H]12)c1csc(N)n1 | ZINC001185591657 | 0.925970164 |
| C[C@H]1COc2c(N3CCN(C)CC3)c(F)cc3c(=O)c(C(=O)Nc4c(N)ccnc4O)cn1c32 | ZINC001148157077 | 0.925939521 |

FIG. 14 (Continued)

| | | |
|---|---|---|
| Cc1nonc1CNC(=O)c1cn2c3c(cc(F)c(N4CCN(C)CC4)c3OC[C@H]2C)c1=O | ZINC001148154230 | 0.92593897 |
| C[C@@H]1COc2c(N3CCN(C)CC3)c(F)cc3c(=O)c(C(=O)N[C@H]4CCCN(C)C4=O)cn1c32 | ZINC001148163254 | 0.925937602 |
| C[C@H]1COc2c(N3CCN(C)CC3)c(F)cc3c(=O)c(C(=O)NC[C@@H](O)CO)cn1c32 | ZINC001148154336 | 0.92574988 |
| COC(=O)[C@@H]1C[C@@H](NC(=O)c2cn3c4c(cc(F)c(N5CCN(C)CC5)c4OC[C@@H]3C)c2=O)CN1 | ZINC001219967822 | 0.9257366 |
| O=C1S/C(=N\C2CCCCC2)N(C2CCCCC2)/C1=C1/C(=O)S/C(=N\C2CCCCC2)N1C1CCCCC1 | ZINC000104270977 | 0.925656721 |
| C[C@H]1COc2c(N3CCN(C)CC3)c(F)cc3c(=O)c(C(=O)N4CCOC[C@H]4CN(C)C)cn1c32 | ZINC001148155792 | 0.925407487 |
| Cc1nc(CNC(=O)c2cn3c4c(cc(F)c(N5CCN(C)CC5)c4OC[C@H]3C)c2=O)n[nH]1 | ZINC001148162686 | 0.925276133 |
| C[C@@H]1c2cccc(O)c2C(O)=C2C(=O)[C@]3(O)C(=O)/C(=C(\N)O)C(=O)[C@H](N(C)C)[C@@H]3[C@H](O)[C@@H]21 | ZINC000001530626 | 0.925203827 |
| Cc1nnc(SCC2=C(C(=O)O)N3C(=O)[C@@H](NC(=O)Cn4cc(Cl)c(=O)c(Cl)c4)[C@H]3SC2)s1 | ZINC000001567521 | 0.925203398 |
| C[C@H]1COc2c(F)c(F)cc3c(=O)c(C(=O)N[C@H](CO)C(N)=O)cn1c32 | ZINC001152654514 | 0.9251315 |
| Cc1nc(CCN(C)C(=O)c2cn3c4c(cc(F)c(N5CCN(C)CC5)c4OC[C@H]3C)c2=O)no1 | ZINC001148157103 | 0.925126225 |
| Cc1nnc(SCC2=C(C(=O)O)N3C(=O)[C@@H](NC(=O)Cn4nc(C(F)F)cc4C4CC4)[C@H]3SC2)s1 | ZINC000002732726 | 0.925072435 |
| C[C@@H]1COc2c(N3CCN(C)CC3)c(F)cc3c(=O)c(C(=O)N[C@H]4CCC[C@H]4CO)cn1c32 | ZINC001148163275 | 0.925006431 |

FIG. 14 (Continued)

| | | |
|---|---|---|
| CO/N=C(\C(=O)N[C@@H]1C(=O)N2C(C(=O)N[C@H]3C[C@@](C)(N)C3)=CCS[C@H]12)c1csc(N)n1 | ZINC001221240998 | 0.924957782 |
| CN(C)[C@@H]1C(=O)[C@H](C(N)=O)C(=O)[C@@]2(O)C(=O)[C@H]3C(=O)c4c(O)cccc4[C@@](C)(O)[C@H]3C[C@@H]12 | ZINC000169686737 | 0.924788526 |
| CN1CCN(c2c(F)cc3c(=O)c(C(=O)Nc4cc(F)c(F)cc4N)cn4c3c2OCN4C)CC1 | ZINC000015659813 | 0.924765548 |
| C[C@H]1COc2c(N3CCN(C)CC3)c(F)cc3c(=O)c(C(=O)NCc4ccnn4CCF)cn1c32 | ZINC001148162520 | 0.924637789 |
| CC[C@H](C)[C@@H](NC)C(=O)N1[C@H]2CN3C4=C(C(=O)C(N)=C(C)C4=O)[C@@H](COC(=N)O)[C@@]3(OC)[C@H]21 | ZINC001220471496 | 0.924632213 |
| CN(C)[C@@H]1C(=O)[C@@H](C(N)=O)C(=O)[C@@]2(O)C(=O)[C@@H]3C(=O)c4c(O)cccc4[C@@](C)(O)[C@H]3C[C@@H]12 | ZINC000169686734 | 0.924629679 |
| OC[C@H]1CC(F)(F)CN1c1c(F)c(F)nc(F)c1F | ZINC000780612019 | 0.924586008 |
| CSCC[C@H](NC(=O)c1cn2c3c(cc(F)c(N4CCN(C)CC4)c3OC[C@@H]2C)c1=O)C(N)=O | ZINC001148162784 | 0.924578831 |
| CO/N=C(\C(=O)N[C@@H]1C(=O)N2C(C(=O)O)=C(C)CS[C@@H]12)c1csc(N)n1 | ZINC000011616979 | 0.924529991 |
| CON=C(C(=O)N[C@@H]1C(=O)N2C(C(=O)O)=C(C[N+]3(C)CCCC3)CS[C@H]12)c1csc(N)n1 | ZINC000252669539 | 0.924516264 |
| C[C@H]1c2cccc(O)c2C(=O)C2=C(O)[C@]3(O)C(=O)C(C(N)=O)=C(O)[C@@H](N(C)C)[C@H]3[C@@H](O)[C@H]21 | ZINC000016248871 | 0.924503204 |
| C[C@H]1COc2c(N3CCN(C)CC3)c(F)cc3c(=O)c(C(=O)N4CCC(=O)C(F)(F)C4)cn1c32 | ZINC001148157989 | 0.924392188 |
| C[C@@H]1COc2c(N3CCN(C)CC3)c(F)cc3c(=O)c(C(=O)NC[C@@H](F)C(C)(C)O)cn1c32 | ZINC001148163249 | 0.924357679 |

FIG. 14 (Continued)

| | | |
|---|---|---|
| CCOC(=O)c1cn(C2CC2)c2cc(N3CCN([C@@H]4CN[C@H](C(=O)OC)C4)CC3)c(F)cc2c1=O | ZINC001246943454 | 0.924304122 |
| CN[C@H](C(=O)N1[C@H]2CN3C4=C(C(=O)C(N)=C(C)C4=O)[C@@H](COC(=N)O)[C@@]3(OC)[C@H]21)[C@@H](C)O | ZINC001220471644 | 0.924303311 |
| C[C@H]1CC(=O)NN1C(=O)[C@H]1[C@@H](CN)C1(F)F | ZINC001576581710 | 0.924275729 |
| O=C1N[C@@H](CF)C(=O)N1[C@@H]1COc2cc(F)cc(F)c21 | ZINC000672813398 | 0.924210301 |
| CN(C)CCNc1c(=O)c(=O)c1N1CCN(C)CC1 | ZINC000101677319 | 0.924197185 |
| CCOC(=O)c1cn(C2CC2)c2cc(N3CCN(c4cncc(C(N)=O)n4)CC3)c(F)cc2c1=O | ZINC001157809734 | 0.924137875 |
| C[C@H]1c2ccc(N)c(O)c2C(=O)C2=C(O)[C@]3(O)C(=O)C(C(N)=O)=C(O)[C@@H](N(C)C)[C@@H]3[C@@H](O)[C@H]21 | ZINC000095616382 | 0.924084467 |
| CCOC(=O)c1cn(-c2nc(-c3ccc(Cl)cc3)cs2)c2c(F)c(N3C[C@@H](C)O[C@H](C)C3)c(F)cc2c1=O | ZINC000002050037 | 0.924034587 |
| CCOC(=O)c1cn(-c2nc(-c3ccc(Cl)cc3)cs2)c2c(F)c(N3C[C@H](C)O[C@@H](C)C3)c(F)cc2c1=O | ZINC000002050038 | 0.924034581 |
| Cc1ccnc(CNC(=O)c2cn3c4c(cc(F)c(N5CCN(C)CC5)c4OC[C@H]3C)c2=O)n1 | ZINC001148155512 | 0.923989645 |
| C[C@H]1c2cccc(O)c2C(=O)C2=C(O)[C@@]3(O)C(=O)C(C(N)=O)=C(O)[C@@H](N(C)C)[C@@H]3[C@@H](O)[C@@H]21 | ZINC000004245687 | 0.923989075 |
| CC(C)[C@](C)(NC(=O)c1cn2c3c(cc(F)c(N4CCN(C)CC4)c3OC[C@@H]2C)c1=O)C(N)=O | ZINC001148155361 | 0.923937485 |
| O=C1N[C@H]2N[C@H]3NC(=O)N[C@@H]3N[C@H]2N1 | ZINC000022942313 | 0.923918173 |

FIG. 14 (Continued)

| | | |
|---|---|---|
| C[C@@H]1COc2c(N3CCN(C)CC3)c(F)cc3c(=O)c(C(=O)N4CCN(C)C(=O)C4)cn1c32 | ZINC001148155952 | 0.923873407 |
| COc1c(N2CCN(C(=S)N[C@H]3C[C@H]4CC[C@H]3C4)[C@H](C)C2)c(F)cc2c(=O)c(C(=O)O)cn(C3CC3)c21 | ZINC000251781951 | 0.923741826 |
| C[C@H]1COc2c(N3CCN(C)CC3)c(F)cc3c(=O)c(C(=O)N4C[C@@H](CO)CC(F)(F)C4)cn1c32 | ZINC001148153941 | 0.923617819 |
| CON=C(C(=O)N[C@@H]1C(=O)N2[C]1SCC(CSc1nnnn1C)=C2C(=O)O)c1csc(N)n1 | ZINC001560407482 | 0.923484129 |
| CO/N=C(\C(=O)N[C@@H]1C(=O)N2C(C(=O)N[C@@H]3CCOC[C@@H]3F)=CCS[C@H]12)c1csc(N)n1 | ZINC001185592291 | 0.923268735 |
| C[C@@H]1COc2c(N3CCN(C)CC3)c(F)cc3c(=O)c(C(=O)NCCC[C@@H]4C=NNC4=O)cn1c32 | ZINC001148157632 | 0.923186296 |
| COC[C@H](NC(=O)C1=CCS[C@@H]2[C@H](NC(=O)/C(=N\OC)c3csc(N)n3)C(=O)N12)C1CC1 | ZINC001185591335 | 0.923033902 |
| COc1c(F)ccc2c(=O)c(C(=O)N3CN[C@H](N)[C@@H]4NCN[C@@H]43)cn(C3CC3)c21 | ZINC001154388540 | 0.922979289 |
| CCNC(=O)CN(C)C(=O)c1cn2c3c(cc(F)c(N4CCN(C)CC4)c3OC[C@H]2C)c1=O | ZINC001148156766 | 0.922797176 |
| CN(C)[C@@H]1C(=O)C(C(N)=O)=C(O)[C@]2(O)C(=O)C3=C(O)c4c(O)cccc4[C@](C)(O)[C@@H]3[C@H](O)[C@H]12 | ZINC000199197726 | 0.922752792 |
| CN(C)[C@H]1C(O)=C(C(N)=O)C(=O)[C@@]2(O)C(O)=C3C(=O)c4c(O)ccc(Cl)c4[C@@](C)(O)[C@@H]3C[C@@H]12 | ZINC000016605477 | 0.922739697 |
| N[C@@H]1NCN(c2nc(Cl)nc(Cl)c2[N+](=O)[O-])[C@H]2NCN[C@H]21 | ZINC001162436119 | 0.922736657 |
| C[C@H]1COc2c(N3CCN(C)CC3)c(F)cc3c(=O)c(C(=O)NCCN4CCC(F)(F)C4)cn1c32 | ZINC001148163066 | 0.922618523 |

FIG. 14 (Continued)

| | | |
|---|---|---|
| Cn1[nH]c(=O)c(=O)nc1SCC1=C(C(=O)O)N2C(=O)[C@@H](NC(=O)[C@H]3C[C@@]3(F)Cl)[C@H]2SC1 | ZINC001181674720 | 0.922523862 |
| COC(=O)[C@H](CCCN)NC(=O)c1cn2c3c(cc(F)c(N4CCN(C)CC4)c3OC[C@@H]2C)c1=O | ZINC001221190199 | 0.922513467 |
| CCOC(=O)c1cn(-c2nc(-c3ccc(Cl)cc3)cs2)c2c(F)c(N3C[C@@H](C)O[C@@H](C)C3)c(F)cc2c1=O | ZINC000017297156 | 0.92245926 |
| C[C@H]1COc2c(N3CCN(C)CC3)c(F)cc3c(=O)c(C(=O)Nc4nnccc4C#N)cn1c32 | ZINC001148153975 | 0.922429189 |
| C[C@@H]1c2cccc(O)c2C(O)=C2C(=O)[C@]3(O)C(=O)C(C(N)=O)=C(O)[C@H](N(C)C)[C@@H]3[C@@H](O)[C@H]21 | ZINC000271778035 | 0.922423664 |
| CO/N=C(/C(=O)N[C@@H]1C(=O)N2C(C(=O)O)=C(CSC(=O)c3ccco3)CS[C@H]12)c1csc(N)n1 | ZINC000038141711 | 0.922405249 |
| C=C1c2cccc(O)c2C(O)=C2C(=O)[C@]3(O)C(O)=C(C(N)=O)C(=O)[C@H](N(C)C)[C@@H]3[C@@H](O)[C@@H]12 | ZINC000256010999 | 0.922299951 |
| Cc1cc(NC(=O)c2cn3c4c(cc(F)c(N5CCN(C)CC5)c4OC[C@@H]3C)c2=O)n(N)c(=O)c1 | ZINC001148162791 | 0.922213626 |
| Cc1cc(CNC(=O)c2cn3c4c(cc(F)c(N5CCN(C)CC5)c4OC[C@H]3C)c2=O)n[nH]1 | ZINC001148158021 | 0.922163901 |
| CN(C)[C@@H]1C(O)=C(C(N)=O)C(=O)[C@@]2(O)C(O)=C3C(=O)c4c(O)cccc4[C@@](C)(O)[C@@H]3[C@H](O)[C@@H]12 | ZINC000013719195 | 0.922080231 |
| CC(C)OC(=O)[C@H](C)NC(=O)c1cn2c3c(cc(F)c(N4CCN(C)CC4)c3OC[C@H]2C)c1=O | ZINC001148157811 | 0.922041047 |
| C[C@H]1COc2c(N3CCN(C)CC3)c(F)cc3c(=O)c(C(=O)NC[C@@]4(F)CCCNC4)cn1c32 | ZINC001219772201 | 0.921844172 |

FIG. 14 (Continued)

| | | |
|---|---|---|
| COc1c(N2CCN(C(=S)N[C@H]3C[C@H]4CC[C@H]3C4)[C@@H](C)C2)c(F)cc2c(=O)c(C(=O)O)cn(C3CC3)c21 | ZINC000169690047 | 0.921611625 |
| COC1(OC)C(=N/O)/C(=N/O)C(OC)(OC)C(=N/O)/C1=N/O | ZINC000100342039 | 0.921610965 |
| CO/N=C(\C(=O)N[C@@H]1C(=O)N2C(C(=O)N[C@@H]3C[C@H](O)C3(C)C)=CCS[C@H]12)c1csc(N)n1 | ZINC001185592433 | 0.921562645 |
| CCc1ncsc1NC(=O)C1=CCS[C@@H]2[C@H](NC(=O)/C(=N\OC)c3csc(N)n3)C(=O)N12 | ZINC001185591876 | 0.921491075 |
| O=C(O)c1cn(C2CC2)c2cc(N3CCN(C(=S)NC(=O)C4c5ccccc5Oc5ccccc54)CC3)c(F)cc2c1=O | ZINC000098005935 | 0.921350905 |
| CN(C)[C@@H]1C(O)=C(C(N)=O)C(=O)[C@]2(O)C(=O)[C@H]3C(=O)c4c(O)ccc(Cl)c4[C@@](C)(O)[C@H]3C[C@H]12 | ZINC000104097007 | 0.921350536 |
| COC(=O)c1c(-c2ccc(C)cc2)csc1NC(=S)N1CCN(c2c(F)cc3c(=O)c(C(=O)O)cn(C4CC4)c3c2OC)C[C@@H]1C | ZINC000098008262 | 0.921194053 |
| COC(=O)c1c(-c2ccc(C)cc2)csc1NC(=S)N1CCN(c2c(F)cc3c(=O)c(C(=O)O)cn(C4CC4)c3c2OC)C[C@H]1C | ZINC000098008263 | 0.921151844 |
| N[C@@H]1NCN(c2nc(Cl)ccc2F)[C@H]2NCN[C@@H]21 | ZINC001162435510 | 0.921104267 |
| NC(=O)c1nc(Cl)nc(Cl)c1N1CN[C@H](N)[C@H]2NCN[C@H]21 | ZINC001162438753 | 0.921036044 |
| CO/N=C(\C(=O)N[C@@H]1C(=O)N2C(C(=O)N[C@@H]3CCCNC3)=CCS[C@H]12)c1csc(N)n1 | ZINC001220890687 | 0.920963243 |
| CN(C)[C@@H]1C(O)=C(C(N)=O)C(=O)[C@@]2(O)C(=O)C3=C(C[C@@H]12)[C@](C)(O)c1c(Cl)ccc(O)c1C3=O | ZINC000015290514 | 0.920764482 |

FIG. 14 (Continued)

| | | |
|---|---|---|
| C[C@H]1S/C(=N\C(=N)N)NC1=O | ZINC000019819671 | 0.920520172 |
| Cc1nnc(SCC2=C(C(=O)O)N3C(=O)[C@@H](NC(=O)c4ccc(COc5c(F)c(F)cc(F)c5F)o4)[C@@H]3SC2)s1 | ZINC000150385911 | 0.920504045 |
| CCOC(=O)CC(=N)NC(=O)C1=CCS[C@@H]2[C@H](NC(=O)/C(=N\OC)c3csc(N)n3)C(=O)N12 | ZINC001185591709 | 0.920503348 |
| COC(CN(C)C(=O)c1cn2c3c(cc(F)c(N4CCN(C)CC4)c3OC[C@@H]2C)c1=O)OC | ZINC001148153902 | 0.920328778 |
| CN(C)[C@@H]1C(O)=C(C(N)=O)C(=O)[C@@]2(O)C(O)=C3C(=O)c4c(O)cccc4[C@@](C)(O)[C@H]3[C@H](O)[C@H]12 | ZINC000008681704 | 0.920313346 |
| C[C@@H]1NC(=S)N(c2cc(F)c(F)cc2F)C1=O | ZINC000171770188 | 0.920206222 |
| Cc1nccn1CCNC(=O)c1cn2c3c(cc(F)c(N4CCN(C)CC4)c3OC[C@H]2C)c1=O | ZINC001148153931 | 0.920144778 |
| CCn1cc(Cl)c(C(=O)N[C@H]2C(=O)N3C(C(=O)O)=C(CSc4nnc(C)s4)CS[C@H]23)n1 | ZINC000002747826 | 0.920053416 |
| CCOC(=O)c1cn(-c2nc(-c3ccc(Cl)cc3)cs2)c2c(F)c(N3CCCCC3)c(F)cc2c1=O | ZINC000002049998 | 0.920027721 |
| CCN(C(=O)c1cn2c3c(cc(F)c(N4CCN(C)CC4)c3OC[C@@H]2C)c1=O)C1CN(C)C1 | ZINC001148154689 | 0.919998789 |
| C[C@H]1CCc2cc(F)cc3c(=O)c(C(=O)NC=N)cn1c23 | ZINC001150148884 | 0.919964457 |
| CN(C)[C@H]1C(O)=C(C(N)=O)C(=O)[C@@]2(O)C(O)=C3C(=O)c4c(O)ccc(Cl)c4[C@H](O)[C@H]3C[C@@H]12 | ZINC000013783337 | 0.919956914 |
| COC[C@@H](NC(=O)C1=CCS[C@@H]2[C@H](NC(=O)/C(=N\OC)c3csc(N)n3)C(=O)N12)C1CC1 | ZINC001185591337 | 0.91993314 |
| C[C@@H]1COc2c(N3CCN(C)CC3)c(F)cc3c(=O)c(C(=O)Nc4cnc(O)nc4N)cn1c32 | ZINC001148156936 | 0.919911817 |

FIG. 14 (Continued)

| | | |
|---|---|---|
| C=C1c2cccc(O)c2C(O)=C2C(=O)[C@]3(O)C(O)=C(C(N)=O)C(=O)[C@@H](N(C)C)[C@@H]3[C@H](O)[C@H]12 | ZINC000004574570 | 0.91981822 |
| CCN1CCN(c2cc3c(cc2F)c(=O)c(C(=O)OCC(=O)NCCCOC)cn3C2CC2)CC1 | ZINC000051364307 | 0.919485343 |
| CN(C)[C@H]1C(O)=C(C(=O)NCN[C@@H]2C(=O)N3[C@H]2SC(C)(C)[C@H]3C(=O)O)C(=O)[C@@]2(O)C(O)=C3C(=O)c4c(O)cccc4[C@@](C)(O)[C@@H]3C[C@@H]12 | ZINC000004430815 | 0.919450018 |
| C[C@@H]1c2cccc(O)c2C(=O)C2=C(O)[C@@]3(O)C(=O)C(C(N)=O)=C(O)[C@@H](N(C)C)[C@@H]3[C@@H](O)[C@@H]21 | ZINC000036386945 | 0.919442406 |
| CN[C@H]1CC(=O)N(C2CC2)C1=O | ZINC000036850897 | 0.919401595 |
| C[C@H]1COc2c(N3CCN(C)CC3)c(F)cc3c(=O)c(C(=O)NC[C@@H]4CNC(=O)C4)cn1c32 | ZINC001148155471 | 0.919335392 |
| CO/N=C(\C(=O)N[C@@H]1C(=O)N2C(C(=O)N[C@@H](CO)C(C)(C)C)=CCS[C@H]12)c1csc(N)n1 | ZINC001185591644 | 0.919180611 |
| C[C@@H]1c2cccc(O)c2C(O)=C2C(=O)[C@]3(O)C(O)=C(C(N)=O)C(=O)[C@H](N(C)C)[C@@H]3[C@@H](O)[C@@H]21 | ZINC000206171961 | 0.919158077 |
| CO/N=C(\C(=O)N[C@@H]1C(=O)N2C(C(=O)N(C)C)=CCS[C@H]12)c1csc(N)n1 | ZINC001185591313 | 0.919001457 |
| O=C(O)c1cn(C2CC2)c2cc(N3CCN(C(=S)NC(=O)c4ccc(Cl)cc4)CC3)c(F)cc2c1=O | ZINC000029748026 | 0.91897051 |
| CC(=O)NC[C@@H](C)CNC(=O)c1cn2c3c(cc(F)c(N4CCN(C)CC4)c3OC[C@H]2C)c1=O | ZINC001148162394 | 0.918959525 |
| COc1cc(F)c(C(=O)N2CN[C@H](N)[C@H]3NCN[C@H]32)cc1F | ZINC001193989505 | 0.918915278 |
| C[C@@H]1CC(=O)NN1C(=O)[C@H]1[C@@H](CN)C1(F)F | ZINC001576581711 | 0.918868062 |

FIG. 14 (Continued)

| | | |
|---|---|---|
| C[C@@H]1COc2c(N3CCN(C)CC3)c(F)cc3c(=O)c(C(=O)N4CCN(CCF)CC4)cn1c32 | ZINC001148156183 | 0.918849432 |
| C[C@@H]1COc2c(N3CCN(C)CC3)c(F)cc3c(=O)c(C(=O)NCc4cccnn4)cn1c32 | ZINC001148155394 | 0.918844905 |
| COC(=O)[C@H](C)N(C)C(=O)c1cn2c3c(cc(F)c(N4CCN(C)CC4)c3OC[C@@H]2C)c1=O | ZINC001148153922 | 0.918823126 |
| CC[C@H](CC#N)NC(=O)C1=CCS[C@@H]2[C@H](NC(=O)/C(=N\OC)c3csc(N)n3)C(=O)N12 | ZINC001185591437 | 0.918691677 |
| CCC(=O)N1C2C3N(C(=O)CC)C4C(N3C(=O)CC)N(C(=O)CC)C(C1N4C(=O)CC)N2C(=O)CC | ZINC000018090096 | 0.918629912 |
| C[C@H]1COc2c(N3CCN(C)CC3)c(F)cc3c(=O)c(C(=O)NC[C@H]4COCCN4)cn1c32 | ZINC001220432037 | 0.918561941 |
| CO/N=C(C(\O)=N/[C@@H]1C(=O)N2C(C(=O)O)=C(CSc3[nH]c(=O)c(O)n[n+]3C)CS[C@H]12)/c1csc(N)n1 | ZINC000328577255 | 0.918448576 |
| C[C@H]1c2cccc(O)c2C(=O)C2=C(O)[C@@]3(O)C(=O)C(C(N)=O)=C(O)[C@@H](N(C)C)[C@@H]3[C@H](O)[C@H]21 | ZINC000035024605 | 0.918372282 |
| O=C(Cn1cnnn1)N[C@H]1C(=O)N2C(C(=O)O)=C(CSc3nnc(O)s3)CS[C@@H]12 | ZINC000010494678 | 0.918276048 |
| C[C@H]1COc2c(N3CCN(C)CC3)c(F)cc3c(=O)c(C(=O)NC[C@@H]4COCCN4C)cn1c32 | ZINC001148163100 | 0.918244344 |
| CO[C@@]12[C@H]3N[C@H]3CN1C1=C(C(=O)C(N)=C(C)C1=O)[C@@H]2COC(N)=O | ZINC000001530537 | 0.918238142 |
| CO/N=C(\C(=O)N[C@H]1C(=O)N2C(C(=O)O)=C(CN3Cc4cccn[n+]4C3)CS[C@@H]12)c1nsc(N)n1 | ZINC000021986096 | 0.918196064 |
| CO/N=C(\C(=O)N[C@@H]1C(=O)N2C(C(=O)N(C)CC3(C)COC3)=CCS[C@H]12)c1csc(N)n1 | ZINC001185591175 | 0.918175215 |

FIG. 14 (Continued)

| | | |
|---|---|---|
| CO/N=C(/C(=O)N[C@H]1C(=O)N2C(C(=O)OCOC(=O)C(C)(C)C)=C(/C=C/c3scnc3C)CS[C@@H]12)c1csc(N)n1 | ZINC000059660417 | 0.918160492 |
| CN(C)[C@@H]1C(O)=C(C(N)=O)C(=O)[C@]2(O)C(O)=C3C(=O)c4c(O)cccc4[C@](C)(O)[C@H]3[C@@H](O)[C@@H]12 | ZINC000036384720 | 0.918140391 |
| C[C@@H](O)[C@H]1C(=O)N2C(C(=O)N3CN[C@H](N)[C@@H]4NCN[C@H]43)=C([C@H]3CCCO3)S[C@H]12 | ZINC001183464035 | 0.918092701 |
| C[C@H]1COc2c(N3CCN(C)CC3)c(F)cc3c(=O)c(C(=O)N4C[C@H](CO)CC(F)(F)C4)cn1c32 | ZINC001148153943 | 0.91789414 |
| CO/N=C(\C(=O)N[C@H]1C(=O)N2[C@@H]1CCC(/C=C/c1scnc1C)=S2C(=O)OCOC(=O)C(C)(C)C)c1csc(N)n1 | ZINC001570001715 | 0.917689231 |
| CCN=c1ncc(N)cn1C(=O)c1cn2c3c(cc(F)c(N4CCN(C)CC4)c3OC[C@@H]2C)c1=O | ZINC001148157382 | 0.917679667 |
| CCCCC(=O)[C@H](C)NC(=O)C1=CCS[C@@H]2[C@H](NC(=O)/C(=N\OC)c3csc(N)n3)C(=O)N12 | ZINC001185591463 | 0.917634583 |
| C[C@@H]1COc2c(N3CCN(C)CC3)c(F)cc3c(=O)c(C(=O)N[C@@H]4[C@H]5C=C[C@@H](C5)[C@@H]4C(N)=O)cn1c32 | ZINC001148162466 | 0.91760346 |
| C[C@H]1COc2c(N3CCN(C)CC3)c(F)cc3c(=O)c(C(=O)NCCc4cc[nH]n4)cn1c32 | ZINC001148157386 | 0.91750364 |
| C[C@H]1c2ccc(N)c(O)c2C(=O)C2=C(O)[C@]3(O)C(=O)C(C(N)=O)=C(O)[C@@H](N(C)C)[C@@H]3[C@@H](O)[C@@H]21 | ZINC000095616384 | 0.917497864 |
| COCCNc1c(=O)c(=O)c1N1CCN(C)CC1 | ZINC000101676256 | 0.917456731 |
| C[C@@H](O)[C@H]1C(=O)N2C(C(=O)N3CN[C@H](N)[C@H]4NCN[C@@H]43)=C([C@H]3CCCO3)S[C@H]12 | ZINC001183464040 | 0.917280707 |
| N[C@@H]1NCN(c2nc(Cl)ncc2F)[C@@H]2NCN[C@@H]21 | ZINC001162436491 | 0.917196545 |

FIG. 14 (Continued)

| | | |
|---|---|---|
| CCOC(=O)c1cn(-c2nc(-c3ccc([N+](=O)[O-])cc3)cs2)c2c(F)c(N3CCCC3)c(F)cc2c1=O | ZINC000002049994 | 0.917107642 |
| C[C@H]1COc2c(N3CCN(C)CC3)c(F)cc3c(=O)c(C(=O)N4CCOC[C@H]4C#N)cn1c32 | ZINC001148155344 | 0.917086074 |
| CN(C)[C@H]1C(O)=C(C(N)=O)C(=O)[C@]2(O)C(O)=C3C(=O)c4c(O)cccc4[C@](C)(O)[C@@H]3[C@@H](O)[C@H]12 | ZINC000004533581 | 0.917008898 |
| C[C@@H]1COc2c(N3CCN(C)CC3)c(F)cc3c(=O)c(C(=O)NC[C@H]4CNC[C@@H](C)C4)cn1c32 | ZINC001219653795 | 0.916918328 |
| CO/N=C(\C(=O)N[C@@H]1C(=O)N2C(c3nnc(C4CCCC4)o3)=CCS[C@H]12)c1csc(N)n1 | ZINC001257561186 | 0.916805401 |
| CON=C(C(=O)N[C@H]1C(=O)N2C(C(=O)O)=C(CSc3nc(C)c(CC(=O)O)s3)CS[C@H]12)c1csc(N)n1 | ZINC000252676468 | 0.916725573 |
| C[C@H]1COc2c(N3CCN(C)CC3)c(F)cc3c(=O)c(C(=O)NC[C@H]4CCC(=O)N4)cn1c32 | ZINC001148154698 | 0.9166336 |
| C[C@H]1COc2c(N3CCN(C)CC3)c(F)cc3c(=O)c(C(=O)NC[C@@H](O)c4ccco4)cn1c32 | ZINC001148154942 | 0.916571739 |
| CO/N=C(\C(=O)N[C@@H]1C(=O)N2C(C(=O)N[C@@H]3CNC(=O)C3(C)C)=CCS[C@H]12)c1csc(N)n1 | ZINC001185591021 | 0.916545638 |
| C[C@H]1c2cccc(O)c2C(=O)C2=C(O)[C@]3(O)C(=O)C(C(N)=O)=C(O)[C@@H](N(C)C)[C@H]3[C@@H](O)[C@@H]21 | ZINC000016248873 | 0.916428414 |
| C[C@@H]1COc2c(N3CCN(C)CC3)c(F)cc3c(=O)c(C(=O)NCC4(N)CCCC4)cn1c32 | ZINC001220496933 | 0.916344696 |
| COCCCNc1c(=O)c(=O)c1N1CCN(C)CC1 | ZINC000101677296 | 0.916269255 |

FIG. 14 (Continued)

| | | |
|---|---|---|
| CNCC1CCN(C(=O)c2cn3c4c(cc(F)c(N5CCN(C)CC5)c4OC[C@H]3C)c2=O)CC1 | ZINC001160459611 | 0.91619992 |
| CO/N=C(\C(=O)N[C@@H]1C(=O)N2C(C(=O)N[C@@H](C#N)c3ccccc3)=CCS[C@H]12)c1csc(N)n1 | ZINC001185591245 | 0.916132867 |
| COCn1cc(NC(=O)c2cn3c4c(cc(F)c(N5CCN(C)CC5)c4OC[C@H]3C)c2=O)cn1 | ZINC001148156535 | 0.916002348 |
| CCC1(NC(=O)C2=CCS[C@@H]3[C@H](NC(=O)/C(=N\OC)c4csc(N)n4)C(=O)N23)CCCCC1 | ZINC001185591675 | 0.915967745 |
| C[C@H]1COc2c(N3CCN(C)CC3)c(F)cc3c(=O)c(C(=O)N(C)C[C@H]4CCCNC4)cn1c32 | ZINC001160698978 | 0.915943575 |
| CO/N=C(\C(=O)N[C@@H]1C(=O)N2C(c3nnc(C4CCC4)o3)=CCS[C@H]12)c1csc(N)n1 | ZINC001255221061 | 0.915812334 |
| C[C@@H]1c2cccc(O)c2C(O)=C2C(=O)[C@]3(O)C(=O)C(C(N)=O)=C(O)[C@H](N(C)C)[C@@H]3[C@@H](O)[C@@H]21 | ZINC000271778042 | 0.915530261 |
| O=C1CSC(=S)N1N1C(=O)[C@H]2[C@@H](C1=O)[C@@H]1C=C[C@H]2[C@@H]2C(=O)N(N3C(=O)CSC3=S)C(=O)[C@@H]21 | ZINC000245285086 | 0.915493669 |
| CCOC(=O)C1(NC(=O)c2cn3c4c(cc(F)c(N5CCN(C)CC5)c4OC[C@@H]3C)c2=O)CNC1 | ZINC001220853345 | 0.915400678 |
| C[C@H]1COc2c(N3CCN(C)CC3)c(F)cc3c(=O)c(C(=O)Nc4cnc(N)cn4)cn1c32 | ZINC001148156769 | 0.915294623 |
| COC(CCCNC(=O)c1cn2c3c(cc(F)c(N4CCN(C)CC4)c3OC[C@@H]2C)c1=O)OC | ZINC001148162628 | 0.91525313 |
| C[C@@H](N)c1cc(F)c(N(C(=O)[C@H]2N[C@@H]3[C@H](O)C[C@@H]2[C@H]3O)S(C)(=O)=O)c(F)c1 | ZINC001221260312 | 0.915250224 |
| CO/N=C(\C(=O)N[C@@H]1C(=O)N2C(C(=O)O)=C(COC(C)=O)CS[C@H]12)c1csc(N)n1 | ZINC000004468780 | 0.915249607 |

FIG. 14 (Continued)

| | | |
|---|---|---|
| C[C@@H]1c2cccc(O)c2C(=O)C2=C(O)[C@@]3(O)C(=O)C(C(N)=O)=C(O)[C@@H](N(C)C)[C@@H]3[C@H](O)[C@H]21 | ZINC000035024602 | 0.915222076 |
| COc1cc(-n2c(N)csc2=N)c(F)cc1F | ZINC001176108065 | 0.915102223 |
| CO/N=C(\C(=O)N[C@@H]1C(=O)N2C(C(=O)N3CCN(CCF)CC3)=CCS[C@H]12)c1csc(N)n1 | ZINC001185591319 | 0.915025258 |
| C[C@H]1COc2c(N3CCN(C)CC3)c(F)cc3c(=O)c(C(=O)N4CCNC5(CC5)C4)cn1c32 | ZINC001161552405 | 0.914950815 |
| C[C@@H]1c2cccc(O)c2C(O)=C2C(=O)[C@]3(O)C(O)=C(C(N)=O)C(=O)[C@H](N(C)C)[C@@H]3[C@H](O)[C@H]21 | ZINC000252586751 | 0.914904028 |
| C[C@@H]1COc2c(N3CCN(C)CC3)c(F)cc3c(=O)c(C(=O)N4CCC[C@H]5NC[C@H]54)cn1c32 | ZINC001158421805 | 0.914881438 |
| C[C@@H]1COc2c(F)c(F)cc3c(=O)c(C(=O)N[C@@H](CO)C(N)=O)cn1c32 | ZINC001152654512 | 0.91485993 |
| CC/C=C(\C(=O)N[C@@H]1C(=O)N2C(C(=O)O)=C(COC(N)=O)CS[C@H]12)c1csc(N)n1 | ZINC000004215231 | 0.914751419 |
| CO/N=C(\C(=O)N[C@@H]1C(=O)N2C(C(=O)NCCn3cccc3)=CCS[C@H]12)c1csc(N)n1 | ZINC001185591486 | 0.914701352 |
| C[C@H]1COc2c(N3CCN(C)CC3)c(F)cc3c(=O)c(C(=O)N4CCN5C(=O)OC[C@H]5C4)cn1c32 | ZINC001148157957 | 0.914665607 |
| COc1cc(F)c(-n2c(Cl)ncc(N)c2=N)cc1F | ZINC001174926018 | 0.91461964 |
| CN(C)[C@H]1C(O)=C(C(N)=O)C(=O)[C@@]2(O)C(O)=C3C(=O)c4c(O)ccc(Cl)c4[C@](C)(O)[C@H]3C[C@@H]12 | ZINC000044019566 | 0.914583427 |
| COCC1=C(C(=O)O[C@@H](C)OC(=O)OC(C)C)N2C(=O)[C@@H](NC(=O)/C(=N\OC)c3csc(N)n3)[C@H]2SC1 | ZINC000014235259 | 0.914475846 |

FIG. 14 (Continued)

| | | |
|---|---|---|
| C[C@@H]1COc2c(N3CCN(C)CC3)c(F)cc3c(=O)c(C(=O)Nc4cccnc4CN)cn1c32 | ZINC001148162790 | 0.914461842 |
| CO/N=C(\C(=O)N[C@H]1C(=O)N2C(C(=O)O)=C[C@H](C[n+]3cccc4c3CCC4)S[C@@H]12)c1csc(N)n1 | ZINC000584577515 | 0.914425275 |
| Cc1nccnc1CNC(=O)c1cn2c3c(cc(F)c(N4CCN(C)CC4)c3OC[C@H]2C)c1=O | ZINC001148162482 | 0.914396909 |
| N[C@@H]1NCN(C(=O)c2cc(F)nc(F)c2F)[C@H]2NCN[C@H]21 | ZINC001189183030 | 0.914387304 |
| Cc1nnc(SCC2=C(C(=O)O)N3C(=O)[C@@H](NC(=O)Cn4nc(C(F)F)cc4C4CC4)[C@@H]3SC2)s1 | ZINC000002732725 | 0.914363471 |
| O=C1CSC(=S)N1/N=C\c1ccc([N+](=O)[O-])s1 | ZINC000005327885 | 0.914334875 |
| COCC1=C(C(=O)O[C@H](C)OC(=O)OC(C)C)N2C(=O)[C@@H](NC(=O)/C(=N\OC)c3csc(N)n3)[C@H]2SC1 | ZINC000004468725 | 0.914282301 |
| CCCCCc1nnc(C2=CCS[C@@H]3[C@H](NC(=O)/C(=N\OC)c4csc(N)n4)C(=O)N23)o1 | ZINC001256107282 | 0.914257476 |
| C[C@@H]1COc2c(N3CCN(C)CC3)c(F)cc3c(=O)c(C(=O)N[C@H]4CO[C@@H]5CNC[C@H]45)cn1c32 | ZINC001219856580 | 0.914147076 |
| C[C@@H]1COc2c(N3CCN(C)CC3)c(F)cc3c(=O)c(C(=O)NC[C@@H]4CCN(C)C4)cn1c32 | ZINC001148163751 | 0.914110431 |
| CO/N=C(\C(=O)N[C@@H]1C(=O)N2C(C(=O)N[C@H]3COCC[C@@H]3O)=CCS[C@H]12)c1csc(N)n1 | ZINC001185591661 | 0.91410844 |
| CN1CCN(c2c(=O)c(=O)c2NCCCO)CC1 | ZINC000101686190 | 0.914066496 |
| C[C@H]1COc2c(N3CCN(C)CC3)c(F)cc3c(=O)c(C(=O)NC[C@@H]4CC(=O)N(C)C4)cn1c32 | ZINC001148162425 | 0.914058131 |

FIG. 14 (Continued)

| | | |
|---|---|---|
| CNC(=O)[C@H](C)NC(=O)C1=CCS[C@@H]2[C@H](NC(=O)/C(=N\OC)c3csc(N)n3)C(=O)N12 | ZINC001185591670 | 0.913976571 |
| C[C@H]1COc2c(N3CCN(C)CC3)c(F)cc3c(=O)c(C(=O)NCC(=O)NC4CCCC4)cn1c32 | ZINC001148153984 | 0.913778678 |
| CC(=O)N/C(=C/c1cc(F)ccc1F)C(=O)N1CN[C@H](N)[C@@H]2NCN[C@@H]21 | ZINC001185743134 | 0.91376684 |
| C[C@H]1COc2c(N3CCN(C)CC3)c(F)cc3c(=O)c(C(=O)N[C@@H]4CCCNC(=O)C4)cn1c32 | ZINC001148162739 | 0.913737866 |
| CCOC(=O)[C@@H](C)CNC(=O)c1cn2c3c(cc(F)c(N4CCN(C)CC4)c3OC[C@H]2C)c1=O | ZINC001148163685 | 0.913688025 |
| C[C@@H]1COc2c(N3CCN(C)CC3)c(F)cc3c(=O)c(C(=O)N4CCC[C@@H]5NC[C@H]54)cn1c32 | ZINC001158421804 | 0.913686651 |
| CCOC(=O)CN(CCN)C(=O)c1cn2c3c(cc(F)c(N4CCN(C)CC4)c3OC[C@H]2C)c1=O | ZINC001148162472 | 0.913545546 |
| CO/N=C(\C(=O)N[C@@H]1C(=O)N2C(C(=O)N[C@H](C#N)c3ccccc3)=CCS[C@H]12)c1csc(N)n1 | ZINC001185591241 | 0.91343855 |
| C[C@H]1COc2c(N3CCN(C)CC3)c(F)cc3c(=O)c(C(=O)Nc4c[nH]ccc4=O)cn1c32 | ZINC001148154340 | 0.913382527 |
| N[C@@H]1NCN(c2nc(Cl)ccc2F)[C@@H]2NCN[C@H]21 | ZINC001162435513 | 0.913081583 |
| CSc1nc(Cl)c(/C=N/O)c(N2CN[C@H](N)[C@@H]3NCN[C@H]32)n1 | ZINC001162436707 | 0.913068259 |
| CCOC(=O)c1cn(C2CC2)c2cc(N3CCN(CC4(O)CCNCC4)CC3)c(F)cc2c1=O | ZINC001246062042 | 0.913024062 |
| C[C@H]1COc2c(N3CCN(C)CC3)c(F)cc3c(=O)c(C(=O)Nc4nccnc4C(N)=O)cn1c32 | ZINC001148155236 | 0.91298663 |
| O/N=C1\N[C@H](O)[C@H](O)N\C1=N/O | ZINC000016137386 | 0.912977646 |

FIG. 14 (Continued)

| | | |
|---|---|---|
| CC(=O)NC[C@H](C)CNC(=O)c1cn2c3c(cc(F)c(N4CCN(C)CC4)c3OC[C@H]2C)c1=O | ZINC001148162395 | 0.912958235 |
| C[C@@H]1COc2c(N3CCN(C)CC3)c(F)cc3c(=O)c(C(=O)NCCc4nncs4)cn1c32 | ZINC001148164278 | 0.912875643 |
| CCOC(=O)c1cn(C2CC2)c2cc(N3CCN(C[C@H]4CNCCO4)CC3)c(F)cc2c1=O | ZINC001236432924 | 0.912872425 |
| C[C@@H]1CNC[C@@H](CNC(=O)c2cn3c4c(cc(F)c(N5CCN(C)CC5)c4OC[C@@H]3C)c2=O)C1 | ZINC001219653796 | 0.912624204 |
| CO/N=C(\C(=O)N[C@@H]1C(=O)N2C(C(=O)N[C@@H](C)C3CC3)=CCS[C@H]12)c1csc(N)n1 | ZINC001185591634 | 0.912611008 |
| C[C@@H]1COc2c(N3CCN(C)CC3)c(F)cc3c(=O)c(C(=O)NC4(CO)CCN(C)CC4)cn1c32 | ZINC001148162391 | 0.912583247 |
| C[C@H]1COc2c(N3CCN(C)CC3)c(F)cc3c(=O)c(C(=O)NC[C@H]4CN(C)CCO4)cn1c32 | ZINC001148157002 | 0.912579465 |
| C[C@H]1COc2c(N3CCN(C)CC3)c(F)cc3c(=O)c(C(=O)N4CC(=O)NC[C@@]45CCNC5)cn1c32 | ZINC001158101291 | 0.912436637 |
| C[C@H]1COc2c(N3CCN(C)CC3)c(F)cc3c(=O)c(C(=O)NCc4cc5n(n4)CCCO5)cn1c32 | ZINC001148164410 | 0.91243352 |
| CO/N=C(/C(=O)N[C@H]1C(=O)N2C(C(=O)O)=C(COC(C)=O)CS[C@@H]12)c1csc(N)c1 | ZINC000004066587 | 0.91231643 |
| CO/N=C(\C(=O)N[C@@H]1C(=O)N2C(C(=O)NCS(=O)(=O)O)=CCS[C@H]12)c1csc(N)n1 | ZINC001185592117 | 0.912298012 |
| N[C@@H]1NCN(C(=O)CSc2nnc(S)s2)[C@H]2NCN[C@@H]21 | ZINC001177346742 | 0.912204307 |
| CCOC(=O)c1cn(C2CC2)c2cc(N3CCN(C[C@@]4(O)CCNC4)CC3)c(F)cc2c1=O | ZINC001246060105 | 0.912165567 |

FIG. 14 (Continued)

| | | |
|---|---|---|
| COc1c(N2CCN(C(=S)N[C@@H]3C[C@H]4CC[C@H]3C4)[C@H](C)C2)c(F)cc2c(=O)c(C(=O)O)cn(C3CC3)c21 | ZINC000102762348 | 0.91213569 |
| C[C@@H]1COc2c(N3CCN(C)CC3)c(F)cc3c(=O)c(C(=O)N[C@@H]4C=CS(=O)(=O)C4)cn1c32 | ZINC001148155759 | 0.911895284 |
| N[C@@H]1NCN(c2nnc(Cl)cc2F)[C@H]2NCN[C@H]21 | ZINC001162439954 | 0.911849767 |
| COc1nn(C)cc1NC(=O)c1cn2c3c(cc(F)c(N4CCN(C)CC4)c3OC[C@H]2C)c1=O | ZINC001148155298 | 0.911794579 |
| CO/N=C(\C(=O)N[C@@H]1C(=O)N2C(C(=O)O)=C(CSc3nc(=O)c(O)nn3C)CS[C@H]12)c1csc(/N=C/c2ccc(O)cc2)n1 | ZINC000095101146 | 0.911764482 |
| CCN1C(=O)N(CC)[C@@H](NNC(N)=S)[C@H]1NNC(N)=S | ZINC000012411918 | 0.911639637 |
| C[C@H]1COc2c(N3CCN(C)CC3)c(F)cc3c(=O)c(C(=O)NCCc4cn(C)cn4)cn1c32 | ZINC001148155025 | 0.911635473 |
| C[C@H]1NC(=S)N(c2cc(F)cc(F)c2F)C1=O | ZINC000814184250 | 0.911541581 |
| CC(=O)NCCCCCNC(=O)c1cn2c3c(cc(F)c(N4CCN(C)CC4)c3OC[C@H]2C)c1=O | ZINC001148162741 | 0.911451456 |
| CN(C)[C@H]1C(O)=C(C(N)=O)C(=O)[C@@]2(O)C(O)=C3C(=O)c4c(O)ccc(Cl)c4[C@](C)(O)[C@@H]3C[C@@H]12 | ZINC000090424177 | 0.911419648 |
| CO/N=C(/C(=O)N[C@@H]1C(=O)N2C(C(=O)O)=C(CSc3nnnn3C)CS[C@@H]12)c1csc(N)c1 | ZINC000013563727 | 0.911358586 |
| CCOC(=O)C1=C(NC(=O)c2cn3c4c(cc(F)c(N5CCN(C)CC5)c4OC[C@H]3C)c2=O)CNC1 | ZINC001220830013 | 0.911316198 |
| C[C@H]1c2cccc(O)c2C(=O)C2=C(O)[C@]3(O)C(=O)C(C(N)=O)=C(O)[C@@H](N(C)C)[C@@H]3[C@@H](O)[C@H]21 | ZINC000008681705 | 0.911297983 |

FIG. 14 (Continued)

| | | |
|---|---|---|
| CCC[C@@H](CCO)NC(=O)C1=CCS[C@@H]2[C@H](NC(=O)/C(=N\OC)c3csc(N)n3)C(=O)N12 | ZINC001185591639 | 0.91125046 |
| COCC1=NN(c2cc(F)c(F)cc2F)C(=O)C1 | ZINC000112351417 | 0.911223224 |
| Cc1nnc(SCC2=C(C(=O)O)N3C(=O)[C@@H](NC(=O)Cn4cc(Cl)c(=O)c(Cl)c4)[C@@H]3SC2)s1 | ZINC000001567520 | 0.911160907 |
| Cn1[nH]c(=O)c(=O)nc1SCC1=C(C(=O)O)N2C(=O)[C@@H](NC(=O)[C@H]3C[C@]3(F)Cl)[C@H]2SC1 | ZINC001181674708 | 0.91112313 |
| CO/N=C(\C(=O)N[C@@H]1C(=O)N2C(C(=O)NC3=CC(=O)CCC3)=CCS[C@H]12)c1csc(N)n1 | ZINC001185592175 | 0.911057526 |
| CO/N=C(\C(=O)N[C@@H]1C(=O)N2C(C(=O)Nc3ncccn3)=CCS[C@H]12)c1csc(N)n1 | ZINC001185590080 | 0.911016023 |
| C=C1c2cccc(O)c2C(O)=C2C(=O)[C@]3(O)C(O)=C(C(N)=O)C(=O)[C@H](N(C)C)[C@@H]3[C@@H](O)[C@H]12 | ZINC000256011000 | 0.910970494 |
| CN(C)[C@@H]1C(O)=C(C(N)=O)C(=O)[C@]2(O)C(=O)[C@H]3C(=O)c4c(O)ccc(Cl)c4[C@](C)(O)[C@H]3C[C@H]12 | ZINC000104097002 | 0.910909924 |
| C[C@@H]1COc2c(N3CCN(C)CC3)c(F)cc3c(=O)c(C(=O)N4CCC[C@H]5NC[C@@H]54)cn1c32 | ZINC001158421806 | 0.910657689 |
| C[C@@H]1c2cccc(O)c2C(O)=C2C(=O)[C@]3(O)C(=O)C(C(N)=O)=C(O)[C@H](N(C)C)[C@@H]3[C@H](O)[C@H]21 | ZINC000271778049 | 0.910576448 |
| CCc1nc(Cl)nc(Cl)c1N1CN[C@H](N)[C@H]2NCN[C@H]21 | ZINC001162446230 | 0.910511544 |
| C[C@@H]1COc2c(N3CCN(C)CC3)c(F)cc3c(=O)c(C(=O)N4CCN[C@H](C#N)C4)cn1c32 | ZINC001160652570 | 0.910464224 |

FIG. 14 (Continued)

| | | |
|---|---|---|
| C[C@H]1COc2c(N3CCN(C)CC3)c(F)cc3c(=O)c(C(=O)N4CCN(C(N)=O)CC4)cn1c3 2 | ZINC001148155718 | 0.910456938 |
| COCC1=NN(c2c(F)cc(F)cc2F)C(=O)C1 | ZINC000899362036 | 0.910315406 |
| CN(C)[C@@H]1C(=O)C(C(N)=O)=C(O)[C@]2(O)C(=O)C3=C(O)c4c(O)ccc(Cl)c4[ C@H](O)[C@H]3C[C@@H]12 | ZINC000198711495 | 0.910238117 |
| N[C@@H]1NCN(C(=O)CSc2nnc(S)s2)[C@@H]2NCN[C@H]21 | ZINC001177346745 | 0.910234895 |
| C[C@H]1COc2c(N3CCN(C)CC3)c(F)cc3c(=O)c(C(=O)NC[C@]4(F)CCCNC4)cn1c3 2 | ZINC001219772203 | 0.910178584 |
| Cc1nnc(CNC(=O)c2cn3c4c(cc(F)c(N5CCN(C)CC5)c4OC[C@@H]3C)c2=O)o1 | ZINC001148163048 | 0.9100851 |
| C[C@H]1COc2c(N3CCN(C)CC3)c(F)cc3c(=O)c(C(=O)N4CCOC[C@@H]4CN(C)C) cn1c32 | ZINC001148155794 | 0.909952193 |
| CO/N=C(\C(=O)N[C@@H]1C(=O)N2C(C(=O)N[C@@](C)(C(N)=O)C(C)C)=CCS[ C@H]12)c1csc(N)n1 | ZINC001185591362 | 0.909834749 |
| CO[C@@H]1COCC[C@H]1NC(=O)c1cn2c3c(cc(F)c(N4CCN(C)CC4)c3OC[C@@H ]2C)c1=O | ZINC001148158022 | 0.909818295 |
| CCN(C(=O)C1=CCS[C@@H]2[C@H](NC(=O)/C(=N\OC)c3csc(N)n3)C(=O)N12)C1 CN(C)C1 | ZINC001185590380 | 0.909808475 |
| CO/N=C(\C(=O)N[C@@H]1C(=O)N2C(C(=O)N3CCNC(=O)[C@H]3C)=CCS[C@H ]12)c1csc(N)n1 | ZINC001185590326 | 0.909785831 |
| CO/N=C(/C(=O)N[C@H]1C(=O)N2C(C(=O)OCOC(=O)C(C)(C)C)=C(/C=C/c3scnc3 C)CS[C@H]12)c1csc(N)n1 | ZINC000059660408 | 0.909781086 |
| O=C(O)c1cn(C2CC2)c(=O)[nH]c1=O | ZINC000044225906 | 0.909724435 |

FIG. 14 (Continued)

| | | |
|---|---|---|
| C[C@H]1COc2c(N3CCN(C)CC3)c(F)cc3c(=O)c(C(=O)N[C@H]4CCCNC(=O)C4)cn1c32 | ZINC001148162737 | 0.909690878 |
| Cn1[nH]c(=O)c(=O)nc1SCC1=C(C(=O)O)N2C(=O)[C@@H](NC(=O)[C@@H]3C[C@@H](N)CN3)[C@H]2SC1 | ZINC001221383386 | 0.909668875 |
| CCC(CO)(CO)NC(=O)c1cn2c3c(cc(F)c(N4CCN(C)CC4)c3OC[C@@H]2C)c1=O | ZINC001148155808 | 0.909586897 |
| COc1c(N2CCN(C(=S)N[C@@H]3C[C@H]4CC[C@H]3C4)[C@@H](C)C2)c(F)cc2c(=O)c(C(=O)O)cn(C3CC3)c21 | ZINC000102762350 | 0.909548214 |
| C[C@@H]1COc2c(N3CCN(C)CC3)c(F)cc3c(=O)c(C(=O)NC4=CC(=O)NCC4)cn1c32 | ZINC001221316928 | 0.909453794 |
| CO/N=C(/C(=O)N[C@@H]1C(=O)N2C(C(=O)O)=C(COC(C)=O)CS[C@H]12)c1csc(N)n1 | ZINC000003830437 | 0.909447724 |
| COc1ccc(CNC(=O)c2cn3c4c(cc(F)c(N5CCN(C)CC5)c4OC[C@H]3C)c2=O)nn1 | ZINC001148162380 | 0.909439602 |
| CCc1nc(Cl)c(F)c(N2[C@H]3CN4C5=C(C(=O)C(N)=C(C)C5=O)[C@@H](COC(=N)O)[C@@]4(OC)[C@H]32)n1 | ZINC001170236372 | 0.909363991 |
| CO/N=C(\C(=O)N[C@@H]1C(=O)N2C(C(=O)Nc3cccnc3F)=CCS[C@H]12)c1csc(N)n1 | ZINC001185591821 | 0.909246039 |
| CO/N=C(\C(=O)N[C@@H]1C(=O)N2C(C(=O)N[C@H](C)c3cnn(C)c3)=CCS[C@H]12)c1csc(N)n1 | ZINC001185592224 | 0.90922322 |
| CCOC(=O)c1c2c(sc1NC(=S)N1CCN(c3cc4c(cc3F)c(=O)c(C(=O)O)cn4CC)CC1)CCCCC2 | ZINC000098005936 | 0.909013575 |
| N[C@@H]1NCN(c2nc(Cl)nc(Cl)c2[N+](=O)[O-])[C@H]2NCN[C@@H]21 | ZINC001162436126 | 0.908900422 |

FIG. 14 (Continued)

| | | |
|---|---|---|
| C[C@@H]1COc2c(N3CCN(C)CC3)c(F)cc3c(=O)c(C(=O)N(C)CC(=O)N(C)C)cn1c32 | ZINC001148156428 | 0.908807871 |
| Cn1nnnc1SCC1=C(C(=O)O)N2C(=O)[C@@H](NC(=O)Cn3nc(C(F)F)cc3C3CC3)[C@H]2SC1 | ZINC000002732933 | 0.908752179 |
| CO/N=C(\C(=O)N[C@@H]1C(=O)N2C(C(=O)NC[Si](C)(C)C)=CCS[C@H]12)c1csc(N)n1 | ZINC001185591396 | 0.908715189 |
| CCn1cc(C(=O)O)c(=O)c2cc(F)c(N3CCN(C(=S)NC(=O)c4ccc(Cl)cc4Cl)CC3)cc21 | ZINC000001260828 | 0.9086925 |
| C[C@H]1COc2c(N3CCN(C)CC3)c(F)cc3c(=O)c(C(=O)NC4(CCO)COC4)cn1c32 | ZINC001148156453 | 0.908651301 |
| CN(C)[C@@H]1C(=O)[C@H](C(N)=O)C(=O)[C@@]2(O)C(=O)[C@@H]3C(=O)c4c(O)cccc4[C@@](C)(O)[C@H]3C[C@@H]12 | ZINC000169686735 | 0.908639094 |
| COCC1(NC(=O)C2=CCS[C@@H]3[C@H](NC(=O)/C(=N\OC)c4csc(N)n4)C(=O)N23)CCC1 | ZINC001185591357 | 0.908629611 |
| C[C@@H]1COc2c(N3CCN(C)CC3)c(F)cc3c(=O)c(C(=O)Nc4cnn(C5CNC5)c4)cn1c32 | ZINC001218641408 | 0.908538461 |
| CN(C)[C@@H]1C(O)=C(C(N)=O)C(=O)[C@]2(O)C(O)=C3C(=O)c4ccccc4[C@](C)(O)[C@@H]3[C@@H](O)[C@@H]12 | ZINC000256601875 | 0.908425748 |
| N[C@@H]1NCN(C(=O)c2cc(F)c(O)cc2F)[C@H]2NCN[C@H]21 | ZINC001192887429 | 0.908316466 |
| CCOC(=O)[C@H](C)CNC(=O)c1cn2c3c(cc(F)c(N4CCN(C)CC4)c3OC[C@H]2C)c1=O | ZINC001148163683 | 0.908223984 |
| COC1(OC)C(=N/O)/C(=N\O)C(OC)(OC)C(=N/O)/C1=N\O | ZINC000100506795 | 0.908199865 |
| C=CC1=C(C(=O)O)N2C(=O)[C@@H](NC(=O)/C(=N/OCC(=O)O)c3csc(N)n3)[C@H]2SC1 | ZINC000012503147 | 0.908182693 |

FIG. 14 (Continued)

| | | |
|---|---|---|
| CN[C@@H](C)C(=O)N1[C@H]2CN3C4=C(C(=O)C(N)=C(C)C4=O)[C@@H](COC(=N)O)[C@@]3(OC)[C@H]21 | ZINC001220471406 | 0.908179644 |
| C[C@H]1COc2c(N3CCN(C)CC3)c(F)cc3c(=O)c(C(=O)N4C[C@@H](N)C5(COC5)C4)cn1c32 | ZINC001161511177 | 0.908095586 |
| N=C(N)N/N=C\C(=N\NC(=N)N)[C@@H](O)CO | ZINC000104122033 | 0.908093673 |
| C[C@H]1COc2c(N3CCN(C)CC3)c(F)cc3c(=O)c(C(=O)NC[C@H]4C[C@H]5CNCCN5C4)cn1c32 | ZINC001219765897 | 0.908027714 |
| CN(C)[C@@H]1C(O)=C(C(N)=O)C(=O)[C@@]2(O)C(O)=C3C(=O)c4c(O)cccc4[C@@](C)(O)[C@@H]3[C@H](O)[C@H]12 | ZINC000013783193 | 0.907986444 |
| C[C@@H]1COc2c(N3CCN(C)CC3)c(F)cc3c(=O)c(C(=O)NCc4ncccc4O)cn1c32 | ZINC001148162341 | 0.907924837 |
| C[C@@H]1C[C@H]1NC(=O)C(=O)Nc1c(F)cc(F)cc1F | ZINC000076281422 | 0.90772227 |
| C[C@H]1COc2c(N3CCN(C)CC3)c(F)cc3c(=O)c(C(=O)NC[C@H]4CNC(=O)O4)cn1c32 | ZINC001148163225 | 0.907684729 |
| Cc1cnc(O)nc1NC(=O)c1cn2c3c(cc(F)c(N4CCN(C)CC4)c3OC[C@@H]2C)c1=O | ZINC001148154306 | 0.90761193 |
| N=c1c(N)cnc(Cl)n1-c1cc(F)c(O)cc1F | ZINC001215572462 | 0.907569563 |
| NC(=O)c1nc(Cl)nc(Cl)c1N1CN[C@H](N)[C@@H]2NCN[C@H]21 | ZINC001162438752 | 0.907494402 |
| CCOC(=O)C(F)(F)CNC(=O)c1cn2c3c(cc(F)c(N4CCN(C)CC4)c3OC[C@H]2C)c1=O | ZINC001148153938 | 0.907437277 |
| CC(C)(O/N=C(/C(=O)N[C@@H]1C(=O)N2C(C(=O)O)=C(C[n+]3ccccc3)CS[C@@H]12)c1csc(N)n1)C(=O)O | ZINC000003830471 | 0.907368305 |
| Cc1cnc(CCNC(=O)c2cn3c4c(cc(F)c(N5CCN(C)CC5)c4OC[C@H]3C)c2=O)nc1 | ZINC001148154214 | 0.907345122 |

FIG. 14 (Continued)

| | | |
|---|---|---|
| CO/N=C(\C(=O)N[C@@H]1C(=O)N2C(C(=O)N[C@H](C)c3cnccn3)=CCS[C@H]12)c1csc(N)n1 | ZINC001185592422 | 0.907304704 |
| NC(=O)OC[C@@H]1[C@H](NC(=O)/C(=N\OCC(=O)O)c2csc(N)n2)C(=O)N1S(=O)(=O)O | ZINC000003917496 | 0.907296705 |
| C[C@@H]1COc2c(N3CCN(C)CC3)c(F)cc3c(=O)c(C(=O)N4CC5CC4(CN)C5)cn1c32 | ZINC001158191636 | 0.907261962 |
| C[C@H]1COc2c(N3CCN(C)CC3)c(F)cc3c(=O)c(C(=O)NC[C@H](O)c4ccco4)cn1c32 | ZINC001148154944 | 0.907232031 |
| C[C@H]1COc2c(N3CCN(C)CC3)c(F)cc3c(=O)c(C(=O)NCCC4(O)CNC4)cn1c32 | ZINC001219696299 | 0.907160449 |
| CO/N=C(\C(=O)N[C@@H]1C(=O)N2C(C(=O)N[C@H](C)CCCC(C)C)=CCS[C@H]12)c1csc(N)n1 | ZINC001185591080 | 0.907126769 |
| CO[C@@]12[C@H]3N[C@@H]3CN1C1=C(C(=O)C(N)=C(C)C1=O)[C@@H]2COC(N)=O | ZINC000100006731 | 0.907075158 |
| C[C@@H]1COc2c(N3CCN(C)CC3)c(F)cc3c(=O)c(C(=O)N[C@H]4CC[C@H](C)NC4)cn1c32 | ZINC001219589607 | 0.907003796 |
| Cc1cc(=O)c(N)c(C)n1C(=O)c1cn2c3c(cc(F)c(N4CCN(C)CC4)c3OC[C@@H]2C)c1=O | ZINC001148155744 | 0.906886458 |
| CCc1nc(Cl)c(N2CN[C@H](N)[C@H]3NCN[C@H]32)c(Cl)n1 | ZINC001162446141 | 0.906837076 |
| C[C@@H]1COc2c(N3CCN(C)CC3)c(F)cc3c(=O)c(C(=O)n4[nH]c5ccnc(=O)c-5c4N)cn1c32 | ZINC001148163811 | 0.906828061 |
| C[C@H]1COc2c(N3CCN(C)CC3)c(F)cc3c(=O)c(C(=O)NCc4ccncn4)cn1c32 | ZINC001148154333 | 0.906702876 |

FIG. 14 (Continued)

| | | |
|---|---|---|
| C[C@H]1COc2c(N3CCN(C)CC3)c(F)cc3c(=O)c(C(=O)N4CCNC(=O)C4(C)C)cn1c32 | ZINC001148157384 | 0.906689337 |
| CO[C@]1(NC(=O)C2SC(=C(C(N)=O)C(=O)O)S2)C(=O)[C@@H]2C(C(=O)O)=C(CSc3nnnn3C)CS[C@H]21 | ZINC000584578710 | 0.906654245 |
| Nc1nnc(Sc2ncc([N+](=O)[O-])s2)s1 | ZINC000008716875 | 0.906628424 |
| CO/N=C(\C(=O)N[C@@H]1C(=O)N2C(C(=O)NC[C@H](C)OC)=CCS[C@H]12)c1csc(N)n1 | ZINC001185592182 | 0.906488243 |
| O=C1CSC(=S)N1N1C(=O)[C@H]2[C@H](C1=O)C1C=CC2[C@H]2C(=O)N(N3C(=O)CSC3=S)C(=O)[C@@H]21 | ZINC000025501609 | 0.906462257 |
| C[C@@H]1COc2c(N3CCN(C)CC3)c(F)cc3c(=O)c(C(=O)N4CCN(c5ncccn5)CC4)cn1c32 | ZINC000012645293 | 0.906443208 |
| Cc1cnn(CCO)c1NC(=O)c1cn2c3c(cc(F)c(N4CCN(C)CC4)c3OC[C@H]2C)c1=O | ZINC001148157995 | 0.906339556 |
| CSc1nc(Cl)c([N+](=O)[O-])c(N2CN[C@H](N)[C@H]3NCN[C@H]32)n1 | ZINC001162434677 | 0.906310049 |
| Cn1[nH]c(=O)c(=O)nc1SCC1=C(C(=O)O)N2C(=O)[C@@H](NC(=O)CBr)[C@H]2SC1 | ZINC000164933862 | 0.906227183 |
| Cn1[nH]c(=O)c(=O)nc1SCC1=C(C(=O)O)N2C(=O)[C@@H](N[C@H]3CNC(=O)C3)[C@H]2SC1 | ZINC001246500912 | 0.906167629 |
| CO/N=C(\C(=O)N[C@@H]1C(=O)N2C(C(=O)N3CC(=O)N(C)C[C@@H]3C)=CCS[C@H]12)c1csc(N)n1 | ZINC001185590061 | 0.906149173 |
| CO/N=C(\C(=O)N[C@@H]1C(=O)N2C(C(=O)N3CCN(C)C(=O)C3)=CCS[C@H]12)c1csc(N)n1 | ZINC001185590060 | 0.906120262 |

FIG. 14 (Continued)

| | | |
|---|---|---|
| CN(C)[C@@H]1C(O)=C(C(N)=O)C(=O)[C@]2(O)C(O)=C3C(=O)c4c(O)cccc4[C@](C)(O)[C@@H]3[C@@H](O)[C@@H]12 | ZINC000239119603 | 0.906092328 |
| CN(C)[C@H]1C(O)=C(C(=O)NCN[C@@H]2C(=O)N3[C@H]2SC(C)(C)[C@@H]3C(=O)O)C(=O)[C@@]2(O)C(O)=C3C(=O)c4c(O)cccc4[C@@](C)(O)[C@@H]3C[C@@H]12 | ZINC000004430814 | 0.905955657 |
| COc1cc(F)c(C(=O)N2CN[C@H](N)[C@H]3NCN[C@@H]32)cc1F | ZINC001193989498 | 0.905840561 |
| N=C(N)N/N=C(\C=N/NC(=N)N)[C@@H](O)CO | ZINC000104122038 | 0.905650532 |
| CON=C(C(=O)N[C@@H]1C(=O)N2C(C(=O)O)=C(CSc3cnns3)CS[C@H]12)c1csc(N)n1 | ZINC000299888282 | 0.905521122 |
| CO/N=C(\C(=O)N[C@@H]1C(=O)N2C(C(=O)O)=C(C)CS[C@H]12)c1csc(N)n1 | ZINC000004215237 | 0.9055051 |
| CO/N=C(\C(=O)N[C@@H]1C(=O)N2C(C(=O)N(C)CC3CCCCC3)=CCS[C@H]12)c1csc(N)n1 | ZINC001185590018 | 0.905502871 |
| O=C1CSC(=S)N1N1C(=O)[C@H]2[C@H](C1=O)C1C=CC2[C@@H]2C(=O)N(N3C(=O)CSC3=S)C(=O)[C@H]21 | ZINC000025501605 | 0.905412717 |
| Cc1nnc(SCC2=C(C(=O)O)N3C(=O)[C@H](NC(=O)c4cc(F)c(F)cc4Cl)[C@@H]3SC2)s1 | ZINC000017356883 | 0.905394733 |
| O=C(Nc1c(F)cc(F)cc1F)C(=O)NC(CF)CF | ZINC000453797051 | 0.905361038 |
| C[C@@H]1COc2c(N3CCN(C)CC3)c(F)cc3c(=O)c(C(=O)NC[C@H]4CC(=O)N(C)C4)cn1c32 | ZINC001148162426 | 0.905359271 |
| CO/N=C(\C(=O)N[C@H]1C(=O)N2C(C(=O)O)=C(CN3Cc4cccn[n+]4C3)CS[C@H]12)c1nsc(N)n1 | ZINC000021986099 | 0.905339953 |
| CCN=c1ccc(N)cn1C(=O)c1cn2c3c(cc(F)c(N4CCN(C)CC4)c3OC[C@@H]2C)c1=O | ZINC001148155772 | 0.905237877 |

FIG. 14 (Continued)

| | | |
|---|---|---|
| CN(C)[C@@H]1C(O)=C(C(N)=O)C(=O)[C@@]2(O)C(O)=C3C(=O)c4c(O)ccc(Cl)c4[C@@H](O)[C@H]3C[C@@H]12 | ZINC000100036924 | 0.905232322 |
| CO/N=C(\C(=O)N[C@@H]1C(=O)N2C(C(=O)N[C@H]3C=CS(=O)(=O)C3)=CCS[C@H]12)c1csc(N)n1 | ZINC001185591321 | 0.905222026 |
| CCn1cc(C(=O)O)c(=O)c2cc(F)c(Cl)nc21 | ZINC000039290862 | 0.905110183 |
| C[C@@H]1c2cccc(O)c2C(=O)C2=C(O)[C@@]3(O)C(=O)C(C(N)=O)=C(O)[C@H](N(C)C)[C@H]3[C@H](O)[C@H]21 | ZINC000021984604 | 0.905085105 |
| C[C@@H]1c2cccc(O)c2C(O)=C2C(=O)[C@]3(O)C(O)=C(C(N)=O)C(=O)[C@H](N(C)C)[C@@H]3[C@H](O)[C@@H]21 | ZINC000252586752 | 0.905069214 |
| Cn1[nH]c(=O)c(=O)nc1SCC1=C(C(=O)O)N2C(=O)[C@@H](N[C@H]3CCNC3)[C@H]2SC1 | ZINC001246503849 | 0.904931697 |
| CO[C@@H](CN)C(=O)N1[C@H]2CN3C4=C(C(=O)C(N)=C(C)C4=O)[C@@H](COC(=N)O)[C@@]3(OC)[C@H]21 | ZINC001220471554 | 0.904820019 |
| CO/N=C(/C(=O)N[C@H]1C(=O)N2C(C(=O)OCOC(=O)C(C)(C)C)=C(Cn3nnc(C)n3)CS[C@@H]12)c1csc(N)n1 | ZINC000011616468 | 0.904811484 |
| C[C@H]1COc2c(N3CCN(C)CC3)c(F)cc3c(=O)c(C(=O)Nc4cc(=O)n(C)c(O)n4)cn1c32 | ZINC001148163312 | 0.904796544 |
| C[C@H]1C[C@@H](CO)N(C(=O)c2cn3c4c(cc(F)c(N5CCN(C)CC5)c4OC[C@@H]3C)c2=O)C1 | ZINC001148157366 | 0.904787982 |
| CN(C)[C@@H]1C(=O)C(C(N)=O)=C(O)[C@]2(O)C(=O)C3=C(O)c4c(O)ccc(Cl)c4[C@H](O)[C@@H]3C[C@@H]12 | ZINC000256418753 | 0.904777336 |
| CSc1nc(Cl)c(/C=N/O)c(N2CN[C@H](N)[C@H]3NCN[C@@H]32)n1 | ZINC001162436709 | 0.904682317 |

FIG. 14 (Continued)

| | | |
|---|---|---|
| O=C(O)c1cc(F)cc(NCCn2cccn2)c1F | ZINC001610812188 | 0.904629886 |
| Cn1[nH]c(=O)c(=O)nc1SCC1=C(C(=O)O)N2C(=O)[C@@H](NC(=O)[C@H]3CNC[C@@H]3N)[C@H]2SC1 | ZINC001221382939 | 0.904586673 |
| C[C@@H](O)[C@H]1C(=O)N2C(C(=O)N3CN[C@H](N)[C@@H]4NCN[C@@H]43)=C([C@H]3CCCO3)S[C@H]12 | ZINC001183464034 | 0.904477066 |
| CO/N=C(\C(=O)N[C@@H]1C(=O)N2C(C(=O)N[C@H]3CCCN(C)C3=O)=CCS[C@H]12)c1csc(N)n1 | ZINC001185591425 | 0.904453835 |
| CCOC(=O)c1cn(C2CC2)c2cc(N3CCN(C[C@]4(O)CCNC4)CC3)c(F)cc2c1=O | ZINC001246060101 | 0.90437095 |
| C[C@H]1COc2c(N3CCN(C)CC3)c(F)cc3c(=O)c(C(=O)N4CC(N5CCNC(=O)C5)C4)cn1c32 | ZINC001148156196 | 0.904356408 |
| CCn1cc(C(=O)N2CN[C@H](N)[C@H]3NCN[C@H]32)c(=O)c2cc3c(cc21)OCO3 | ZINC001152730493 | 0.904321906 |
| C[C@@H]1COc2c(N3CCN(C)CC3)c(F)cc3c(=O)c(C(=O)NCCn4ccnc4)cn1c32 | ZINC001148155263 | 0.904248747 |
| COc1c(N2CCN(C(=S)N[C@@H]3C[C@H]4CC[C@@H]3C4)[C@H](C)C2)c(F)cc2c(=O)c(C(=O)O)cn(C3CC3)c21 | ZINC000217441147 | 0.9042429 |
| CO/N=C(\C(=O)N[C@@H]1C(=O)N2C(C(=O)N[C@@H](C)c3cnccn3)=CCS[C@H]12)c1csc(N)n1 | ZINC001185592420 | 0.90418939 |
| CCOC(=O)c1cn(C2CC2)c2cc(N3CCN(C[C@@H]4CNCCO4)CC3)c(F)cc2c1=O | ZINC001236432923 | 0.90417079 |
| N/N=C1/C(=O)NC(=O)[C@H]1C(N)=O | ZINC000198719270 | 0.90407832 |
| CO/N=C(\C(=O)N[C@@H]1C(=O)N2C(C(=O)N[C@@]3(C)CCCN(C)C3)=CCS[C@H]12)c1csc(N)n1 | ZINC001185591377 | 0.904073337 |

FIG. 14 (Continued)

| | | |
|---|---|---|
| C=C/C(=N\COC)N1[C@H]2CN3C4=C(C(=O)C(N)=C(C)C4=O)[C@@H](COC(=N)O)[C@@]3(OC)[C@H]21 | ZINC001170237453 | 0.904042503 |
| C=C1c2cccc(O)c2C(O)=C2C(=O)[C@]3(O)C(O)=C(C(N)=O)C(=O)[C@H](N(C)C)[C@H]3[C@H](O)[C@H]12 | ZINC000004574571 | 0.903933033 |
| C[C@H]1COc2c(N3CCN(C)CC3)c(F)cc3c(=O)c(C(=O)NC[C@@H]4COCCN4)cn1c32 | ZINC001220432039 | 0.903859413 |
| CC1(C)[C@@H]2C(=O)NN(c3c(F)cc(F)cc3F)C(=O)[C@H]21 | ZINC000899363082 | 0.903855371 |
| C[C@H]1COc2c(N3CCN(C)CC3)c(F)cc3c(=O)c(C(=O)NCc4ccn(C)c(=O)c4)cn1c32 | ZINC001148156545 | 0.90379636 |
| Cn1[nH]c(=O)c(=O)nc1SCC1=C(C(=O)O)N2C(=O)[C@@H](NC(=O)[C@H]3NCC[C@H]3O)[C@H]2SC1 | ZINC001221383400 | 0.903777424 |
| CN(C)[C@@H]1C(=O)C(C(N)=O)=C(O)[C@]2(O)C(=O)C3=C(O)c4c(O)ccc(Cl)c4[C@H](O)[C@H]3C[C@H]12 | ZINC000198711525 | 0.903765783 |
| Cn1[nH]c(=O)c(=O)nc1SCC1=C(C(=O)O)N2C(=O)[C@@H](NC(=O)[C@H]3C[C@@H]3F)[C@H]2SC1 | ZINC001143446877 | 0.903652501 |
| CCN(C)C(=O)C1=CCS[C@@H]2[C@H](NC(=O)/C(=N\OC)c3csc(N)n3)C(=O)N12 | ZINC001185591694 | 0.903631899 |
| CC[C@H]1NC(=O)N([C@H]2COc3cc(F)cc(F)c32)C1=O | ZINC000683340190 | 0.903621054 |
| CO/N=C(\C(=O)N[C@@H]1C(=O)N2C(C(=O)NC[C@H]3C[C@@H](N)C3)=CCS[C@H]12)c1csc(N)n1 | ZINC001220150239 | 0.903536719 |
| CCOC(=O)C(C)(C)NC(=O)c1cn2c3c(cc(F)c(N4CCN(C)CC4)c3OC[C@H]2C)c1=O | ZINC001148157045 | 0.903483814 |
| C[C@@H]1COc2c(N3CCN(C)CC3)c(F)cc3c(=O)c(C(=O)NC[C@H]4CNC(=O)C4)cn1c32 | ZINC001148155482 | 0.903472444 |

FIG. 14 (Continued)

| | | |
|---|---|---|
| CO/N=C(\C(=O)N[C@@H]1C(=O)N2C(C(=O)N3CCC[C@H]4NC[C@H]43)=CCS[C@H]12)c1csc(N)n1 | ZINC001158424257 | 0.903411558 |
| C=C1c2cccc(O)c2C(O)=C2C(=O)[C@]3(O)C(O)=C(C(N)=O)C(=O)[C@H](N(C)C)[C@@H]3[C@H](O)[C@@H]12 | ZINC000256010998 | 0.903325206 |
| C[C@H]1CC[C@@H](CO)N1C(=O)c1cn2c3c(cc(F)c(N4CCN(C)CC4)c3OC[C@H]2C)c1=O | ZINC001148156527 | 0.903314662 |
| CO/N=C(\C(=O)N[C@@H]1C(=O)N2C(C(=O)N[C@@](C)(C#N)CC(C)C)=CCS[C@H]12)c1csc(N)n1 | ZINC001185591615 | 0.903217795 |
| CO/N=C(\C(=O)N[C@@H]1C(=O)N2C(C(=O)N3CCNC(=O)[C@@H]3C)=CCS[C@H]12)c1csc(N)n1 | ZINC001185590331 | 0.903142768 |
| CCOC(=O)C1=C(NC(=S)N2CCN(c3cc4c(cc3F)c(=O)c(C(=O)O)cn4CC)CC2)S[C@H]2CCCCC[C@@H]12 | ZINC000101572644 | 0.903113103 |
| O=C1CSC(=S)N1N1C(=O)[C@H]2[C@@H](C1=O)C1C=CC2[C@@H]2C(=O)N(N3C(=O)CSC3=S)C(=O)[C@@H]21 | ZINC000195528757 | 0.903093925 |
| O=C1N[C@H]2N[C@H]3NC(=O)N[C@@H]3N[C@@H]2N1 | ZINC000022859090 | 0.903090878 |
| O=C(Cn1cnnn1)N[C@H]1C(=O)N2C(C(=O)O)=C(CSc3nncs3)CS[C@@H]12 | ZINC000003830474 | 0.903084254 |
| C[C@H]1COc2c(N3CCN(C)CC3)c(F)cc3c(=O)c(C(=O)N4CCN5C(=O)COC[C@H]5C4)cn1c32 | ZINC001148154320 | 0.903055358 |
| COc1cc(F)c(C(=O)N2CN[C@H](N)[C@@H]3NCN[C@H]32)cc1F | ZINC001193989503 | 0.90290311 |
| C[C@H]1COc2c(N3CCN(C)CC3)c(F)cc3c(=O)c(C(=O)NC4COC(C)(C)OC4)cn1c32 | ZINC001148162285 | 0.902892601 |
| CN(C)[C@@H]1C(=O)C(C(N)=O)=C(O)[C@]2(O)C(=O)C3=C(O)c4c(O)ccc(Cl)c4[C@](C)(O)[C@H]3C[C@@H]12 | ZINC000199209020 | 0.902878511 |

FIG. 14 (Continued)

| | | |
|---|---|---|
| CO/N=C(\C(=O)N[C@@H]1C(=O)N2C(C(=O)N[C@H]3CCOC[C@H]3C)=CCS[C@H]12)c1csc(N)n1 | ZINC001185591693 | 0.902854264 |
| C[C@H]1COc2c(N3CCN(C)CC3)c(F)cc3c(=O)c(C(=O)N4CCOCC(F)(F)C4)cn1c32 | ZINC001148156793 | 0.902850327 |
| C[C@H]1COc2c(N3CCN(C)CC3)c(F)cc3c(=O)c(C(=O)NC[C@H]4CCNCC4(F)F)cn1c32 | ZINC001220189197 | 0.902841961 |
| Cc1cnc(NC(=O)c2cn3c4c(cc(F)c(N5CCN(C)CC5)c4OC[C@@H]3C)c2=O)c(=O)[nH]1 | ZINC001148163023 | 0.902718583 |
| COC(=O)[C@H](CS)NC(=O)c1cn2c3c(cc(F)c(N4CCN(C)CC4)c3OC[C@@H]2C)c1=O | ZINC001148157998 | 0.902673471 |
| CO/N=C(\C(=O)N[C@@H]1C(=O)N2C(C(=O)N[C@@H]3CCOC[C@H]3OC)=CCS[C@H]12)c1csc(N)n1 | ZINC001185591043 | 0.90262095 |
| CCCNC1=C(C)C(=O)C2=C(C1=O)[C@@H](COC(N)=O)[C@@]1(OC)[C@H]3N[C@@H]3CN21 | ZINC000101254171 | 0.902594382 |
| C[C@H]1COc2c(N3CCN(C)CC3)c(F)cc3c(=O)c(C(=O)N(C)C[C@H]4CNCCO4)cn1c32 | ZINC001157721514 | 0.902565372 |
| N[C@@H]1NCN(c2nc(Cl)ncc2Cl)[C@H]2NCN[C@H]21 | ZINC001162434653 | 0.90244804 |
| C[C@H]1COc2c(N3CCN(C)CC3)c(F)cc3c(=O)c(C(=O)N(C)C[C@@H]4CCCNC4)cn1c32 | ZINC001160698976 | 0.902309915 |
| Nc1nc(/C(=N/O)C(=O)O)cs1 | ZINC000006661600 | 0.902300328 |
| CO/N=C(\C(=O)N[C@@H]1C(=O)N2C(C(=O)N[C@H]3CCC[C@H]3CO)=CCS[C@H]12)c1csc(N)n1 | ZINC001185592177 | 0.902254826 |
| Clc1c(Cl)c2c(Cl)c(Cl)c3c(Cl)c(Cl)c(Cl)c4c(Cl)c(Cl)c(c1Cl)c2c34 | ZINC000059321687 | 0.902115346 |

FIG. 14 (Continued)

| | | |
|---|---|---|
| COc1c(N2CCN(C(=S)N[C@@H]3C[C@H]4CC[C@@H]3C4)[C@@H](C)C2)c(F)cc2c(=O)c(C(=O)O)cn(C3CC3)c21 | ZINC000217441219 | 0.902101114 |
| C[C@H]1COc2c(N3CCN(C)CC3)c(F)cc3c(=O)c(C(=O)N[C@H]4CCC(=O)N(C)C4)cn1c32 | ZINC001148155997 | 0.901960585 |
| C[C@@H]1COc2c(N3CCN(C)CC3)c(F)cc3c(=O)c(C(=O)N4CCC[C@@H]5NC[C@@H]54)cn1c32 | ZINC001158421803 | 0.901931924 |
| CN(C)[C@@H]1C(=O)/C(=C(\N)O)C(=O)[C@]2(O)C(=O)C3=C(O)c4c(O)cccc4[C@](C)(O)[C@H]3C[C@@H]12 | ZINC000135883177 | 0.901927733 |
| C[C@H]1COc2c(N3CCN(C)CC3)c(F)cc3c(=O)c(C(=O)NCc4ccnc(O)c4)cn1c32 | ZINC001148155802 | 0.901881003 |
| CO/N=C(\C(=O)N[C@@H]1C(=O)N2C(C(=O)N[C@@H]3CCOC[C@H]3C)=CCS[C@H]12)c1csc(N)n1 | ZINC001185591686 | 0.90185892 |
| CO/N=C(\C(=O)N[C@@H]1C(=O)N2C(C(=O)N3CCC[C@@H]4NC[C@H]43)=CCS[C@H]12)c1csc(N)n1 | ZINC001158424254 | 0.901764923 |
| O=C1N[C@@H](C2CC2)C(=O)N1[C@H]1COc2cc(F)cc(F)c21 | ZINC000373890406 | 0.901755857 |
| C[C@H]1COc2c(N3CCN(C)CC3)c(F)cc3c(=O)c(C(=O)NCCc4cnn(C)c4)cn1c32 | ZINC001148162786 | 0.9016886 |
| C[C@H]1COc2c(N3CCN(C)CC3)c(F)cc3c(=O)c(C(=O)N4CCN5CCC4CC5)cn1c32 | ZINC001148157860 | 0.901685724 |
| N[C@@H]1NCN(c2nc(Cl)nc(Cl)c2[N+](=O)[O-])[C@@H]2NCN[C@H]21 | ZINC001162436125 | 0.901684415 |
| C[C@H]1COc2c(N3CCN(C)CC3)c(F)cc3c(=O)c(C(=O)N4CC(N5CC(F)C5)C4)cn1c32 | ZINC001148154997 | 0.901674674 |
| C[C@@H]1c2cccc(O)c2C(O)=C2C(=O)[C@]3(O)C(=O)C(C(N)=O)=C(O)[C@H](N(C)C)[C@@H]3[C@H](O)[C@@H]21 | ZINC000271778055 | 0.901644284 |

FIG. 14 (Continued)

| | | |
|---|---|---|
| CO/N=C(\C(=O)N[C@@H]1C(=O)N2C(C(=O)N3C4CCC3CC4)=CCS[C@H]12)c1csc(N)n1 | ZINC001185591915 | 0.901634258 |
| CO/N=C(\C(=O)N[C@@H]1C(=O)N2C(c3nnc(CC(C)C)o3)=CCS[C@H]12)c1csc(N)n1 | ZINC001256463941 | 0.901459211 |
| COc1ncc(NC(=O)c2cn3c4c(cc(F)c(N5CCN(C)CC5)c4OC[C@H]3C)c2=O)cn1 | ZINC001148154067 | 0.901317745 |
| CO/N=C(\C(=O)N[C@@H]1C(=O)N2C(c3nnc(CCC(C)C)o3)=CCS[C@H]12)c1csc(N)n1 | ZINC001258322327 | 0.901216659 |
| C[C@H]1COc2c(N3CCN(C)CC3)c(F)cc3c(=O)c(C(=O)Nc4cn(C)nc4C#N)cn1c32 | ZINC001148155779 | 0.901197635 |
| C[C@@H]1COc2c(N3CCN(C)CC3)c(F)cc3c(=O)c(C(=O)NCc4nccn4C)cn1c32 | ZINC001148155949 | 0.901193139 |
| C[C@@H]1COc2c(N3CCN(C)CC3)c(F)cc3c(=O)c(C(=O)N4CCC(=O)C(F)(F)C4)cn1c32 | ZINC001148157988 | 0.901130015 |
| CO/N=C(\C(=O)N[C@@H]1C(=O)N2C(C(=O)N(C)Cc3ncccn3)=CCS[C@H]12)c1csc(N)n1 | ZINC001185591009 | 0.9010887 |
| CC(C)(O/N=C(\C(=O)N[C@@H]1C(=O)N2C(C(=O)O)=C(C[n+]3ccccc3)CS[C@@H]12)c1csc(N)n1)C(=O)O | ZINC000008035456 | 0.90087949 |
| N[C@@H]1NCN(C(=O)Cc2cc(F)cc(F)c2F)[C@H]2NCN[C@H]21 | ZINC001179846391 | 0.900806066 |
| O=C(Cn1cnnn1)N[C@H]1C(=O)N2C(C(=O)O)=C(CSc3nnc(O)s3)CS[C@H]12 | ZINC000010494670 | 0.900784853 |
| CO/N=C(/C(=O)N[C@@H]1C(=O)N2C(C(=O)O)=C(C)CS[C@H]12)c1csc(N)n1 | ZINC000026892317 | 0.900759667 |
| C[C@@H]1COc2c(N3CCN(C)CC3)c(F)cc3c(=O)c(C(=O)NC[C@H]4COCCN4C)cn1c32 | ZINC001148163097 | 0.900705045 |

FIG. 14 (Continued)

| | | |
|---|---|---|
| C[C@@H]1COc2c(N3CCN(C)CC3)c(F)cc3c(=O)c(C(=O)NC[C@@H]4CNC[C@@H](C)C4)cn1c32 | ZINC001219653794 | 0.900683293 |
| CCNC1=C(N2CC2)C(=O)C(NCC)=C(N2CC2)C1=O | ZINC000104182129 | 0.900541435 |
| C[C@H]1COc2c(N3CCN(C)CC3)c(F)cc3c(=O)c(C(=O)NCCS(C)(=O)=O)cn1c32 | ZINC001148154880 | 0.900467572 |
| CO/N=C(\C(=O)N[C@@H]1C(=O)N2C(C(=O)NCCCS)=CCS[C@H]12)c1csc(N)n1 | ZINC001185592363 | 0.900321776 |
| CO/N=C(\C(=O)N[C@@H]1C(=O)N2C(C(=O)NC[C@@H](F)C(C)(C)O)=CCS[C@H]12)c1csc(N)n1 | ZINC001185591811 | 0.90020538 |
| Cn1[nH]c(=O)c(=O)nc1SCC1=C(C(=O)O)N2C(=O)[C@@H](NC(=O)C3(F)CNC3)[C@H]2SC1 | ZINC001221383237 | 0.900194871 |
| C[C@H]1COc2c(N3CCN(C)CC3)c(F)cc3c(=O)c(C(=O)N4CC(=O)NC5(CCCC5)C4)cn1c32 | ZINC001148153982 | 0.900113925 |
| Cn1[nH]c(=O)c(=O)nc1SCC1=C(C(=O)O)N2C(=O)[C@@H](N[C@@H]3CNC(=O)C3)[C@H]2SC1 | ZINC001246500908 | 0.900013304 |
| O=C1N[C@H](CF)C(=O)N1[C@H]1COc2cc(F)cc(F)c21 | ZINC000672813399 | 0.899870926 |
| CCCC(/C=N\NC(=N)N)=N/NC(=N)N | ZINC000104271999 | 0.89982594 |
| CN[C@@H](CCCCN)C(=O)N1[C@H]2CN3C4=C(C(=O)C(N)=C(C)C4=O)[C@@H](COC(=N)O)[C@@]3(OC)[C@H]21 | ZINC001220471576 | 0.899806359 |
| CCOC(=O)c1cn(-c2nc(-c3ccc(Cl)c(Cl)c3)cs2)c2c(F)c(N3CCOCC3)c(F)cc2c1=O | ZINC000002049995 | 0.899653316 |
| CCOC(=O)c1cn(-c2nc(-c3ccc(Br)cc3)cs2)c2c(F)c(N3C[C@H](C)O[C@@H](C)C3)c(F)cc2c1=O | ZINC000008445214 | 0.899633646 |

FIG. 14 (Continued)

| | | |
|---|---|---|
| CCOC(=O)c1cn(-c2nc(-c3ccc(Br)cc3)cs2)c2c(F)c(N3C[C@@H](C)O[C@H](C)C3)c(F)cc2c1=O | ZINC000008445213 | 0.899633637 |
| CO/N=C(\C(=O)N[C@@H]1C(=O)N2C(C(=O)N[C@]3(C)CCCN(C)C3)=CCS[C@H]12)c1csc(N)n1 | ZINC001185591374 | 0.899491853 |
| C[C@@H]1CCN(C(=O)c2cn3c4c(cc(F)c(N5CCN(C)CC5)c4OC[C@@H]3C)c2=O)C[C@@H]1N | ZINC001157810430 | 0.899483353 |
| CN(C)[C@@H]1C(=O)C(C(N)=O)=C(O)[C@@]2(O)C(=O)C3=C(O)c4c(O)cccc4[C@@](C)(O)[C@H]3C[C@@H]12 | ZINC000100303069 | 0.899380311 |
| C[C@H]1[C@H](NS(=O)(=O)c2cc(F)c(F)cc2F)C(=O)N1S(=O)(=O)O | ZINC001259043140 | 0.899298319 |
| NC(=O)[C@H]1CN(c2c(F)c(F)nc(F)c2F)CCN1 | ZINC000268072775 | 0.899244854 |
| C[C@H]1COc2c(N3CCN(C)CC3)c(F)cc3c(=O)c(C(=O)N[C@@H](CO)Cc4cnc[nH]4)cn1c32 | ZINC001148162507 | 0.899175864 |
| CO/N=C(\C(=O)N[C@@H]1C(=O)N2C(C(=O)N[C@H]3CCOC[C@@H]3C)=CCS[C@H]12)c1csc(N)n1 | ZINC001185591688 | 0.898935932 |
| C[C@H]1COc2c(N3CCN(C)CC3)c(F)cc3c(=O)c(C(=O)Nc4nc(O)nc5[nH]cnc54)cn1c32 | ZINC001148163281 | 0.898910347 |
| C[C@@H]1COc2c(N3CCN(C)CC3)c(F)cc3c(=O)c(C(=O)Nc4c(N)ccnc4O)cn1c32 | ZINC001148157076 | 0.898877311 |
| CO/N=C(\C(=O)N[C@@H]1C(=O)N2C(C(=O)N(C)[C@H]3CCCC[C@H]3N)=CCS[C@H]12)c1csc(N)n1 | ZINC001161065003 | 0.898867121 |
| CCn1cc(C(=O)O)c(=O)c2cc(F)c(N3CCN(C(=S)N[C@H](C)c4ccc(F)cc4)CC3)cc21 | ZINC000001443367 | 0.898792064 |
| CCOC(=O)C1=C(NC(=S)N2CCN(c3cc4c(cc3F)c(=O)c(C(=O)O)cn4CC)CC2)S[C@H]2CCCCC[C@H]12 | ZINC000101572647 | 0.898688653 |

FIG. 14 (Continued)

| | | |
|---|---|---|
| CO/N=C(/C(=O)N[C@@H]1C(=O)N2C(C(=O)O)=C(C[n+]3ccn4ncccc43)CS[C@@H]12)c1nsc(N)n1 | ZINC000011615948 | 0.898648703 |
| CO/N=C(\C(=O)N[C@@H]1C(=O)N2C(C(=O)N(C)CC(C)=O)=CCS[C@H]12)c1csc(N)n1 | ZINC001185590460 | 0.898520088 |
| CO/N=C(\C(=O)N[C@@H]1C(=O)N2C(C(=O)NC(C)(C)CC(C)(C)C)=CCS[C@H]12)c1csc(N)n1 | ZINC001185592234 | 0.898470393 |
| CO/N=C(\C(=O)N[C@@H]1C(=O)N2C(C(=O)Nc3ncccc3N)=CCS[C@H]12)c1csc(N)n1 | ZINC001185590538 | 0.89838849 |
| CCn1cc(C(=O)O)c(=O)c2cc(N)c(Cl)cc21 | ZINC000072434064 | 0.898194584 |
| C[C@@H]1COc2c(N3CCN(C)CC3)c(F)cc3c(=O)c(C(=O)N(CCN)S(C)(=O)=O)cn1c32 | ZINC001148155295 | 0.898187628 |
| Cn1c(=O)c2cc(Cl)c3c4c(Cl)cc5c(=O)n(C)c(=O)c6cc(Cl)c(c7c(Cl)cc(c1=O)c2c37)c4c56 | ZINC000100034447 | 0.898115301 |
| CO/N=C(\C(=O)N[C@@H]1C(=O)N2C(C(=O)NCC(C)(C)C(N)=O)=CCS[C@H]12)c1csc(N)n1 | ZINC001185591054 | 0.898082271 |
| C[C@H]1COc2c(N3CCN(C)CC3)c(F)cc3c(=O)c(C(=O)NC[C@@H]4CN(C)CCO4)cn1c32 | ZINC001148157013 | 0.898050806 |
| OC[C@@H]1CC(F)(F)CN1c1c(F)c(F)nc(F)c1F | ZINC000780612017 | 0.898023883 |
| Cc1cnc(CCNC(=O)c2cn3c4c(cc(F)c(N5CCN(C)CC5)c4OC[C@H]3C)c2=O)[nH]1 | ZINC001148154360 | 0.897950354 |
| C[C@H]1COc2c(N3CCN(C)CC3)c(F)cc3c(=O)c(C(=O)NC[C@@H]4CCC(=O)N4)cn1c32 | ZINC001148154696 | 0.897939631 |

FIG. 14 (Continued)

| | | |
|---|---|---|
| C[C@H]1COc2c(N3CCN(C)CC3)c(F)cc3c(=O)c(C(=O)N4CCOC[C@@H]4C#N)cn1c32 | ZINC001148155342 | 0.897923157 |
| N[C@@H]1NCN(c2nc(Cl)nc3c(Cl)nc(Cl)nc32)[C@H]2NCN[C@H]21 | ZINC001162435853 | 0.89769965 |
| O=c1oc(=O)c2cc(Cl)c3c4c(Cl)cc5c(=O)oc(=O)c6cc(Cl)c(c7c(Cl)cc1c2c73)c4c65 | ZINC000100007728 | 0.897689763 |
| CO/N=C(\C(=O)N[C@@H]1C(=O)N2C(C(=O)N[C@](C)(C#N)CC(C)C)=CCS[C@H]12)c1csc(N)n1 | ZINC001185591616 | 0.8976879 |
| CCOC(=O)c1cn(C2CC2)c2cc(N3CCN([C@H]4CCNC5(CNC5)C4)CC3)c(F)cc2c1=O | ZINC001246946539 | 0.897668472 |
| C[C@@H]1COc2c(N3CCN(C)CC3)c(F)cc3c(=O)c(C(=O)Nc4nnccc4C#N)cn1c32 | ZINC001148153974 | 0.897536781 |
| C[C@@H]1c2cccc(O)c2C(=O)C2=C(O)[C@]3(O)C(=O)C(C(N)=O)=C(O)[C@@H](N(C)C)[C@@H]3[C@@H](O)[C@@H]21 | ZINC000008034239 | 0.897524568 |
| CCNC(=O)CN(C)C(=O)c1cn2c3c(cc(F)c(N4CCN(C)CC4)c3OC[C@@H]2C)c1=O | ZINC001148156763 | 0.897478208 |
| COC[C@H]1C(=O)N[C@H](c2cc(F)c(F)cc2F)N1C | ZINC000334874613 | 0.89745267 |
| O=C1N[C@@H]2N[C@H]3NC(=O)N[C@@H]3N[C@H]2N1 | ZINC000035185463 | 0.897364578 |
| C=CC1=C(C(=O)O)N2C(=O)[C@@H](NC(=O)/C(=N/OCC(=O)O)c3csc(N)n3)[C@@H]2SC1 | ZINC000003830410 | 0.897314852 |
| Cc1nc(CCN(C)C(=O)c2cn3c4c(cc(F)c(N5CCN(C)CC5)c4OC[C@@H]3C)c2=O)no1 | ZINC001148157102 | 0.89731003 |
| COC(C)(CNC(=O)c1cn2c3c(cc(F)c(N4CCN(C)CC4)c3OC[C@@H]2C)c1=O)OC | ZINC001148162704 | 0.897267547 |
| CCOC(=O)c1cn(C2CC2)c2cc(N3CCN(C[C@@H](O)C(=O)OC)CC3)c(F)cc2c1=O | ZINC001252425176 | 0.89722271 |
| Cc1ccnc(CNC(=O)c2cn3c4c(cc(F)c(N5CCN(C)CC5)c4OC[C@@H]3C)c2=O)n1 | ZINC001148155511 | 0.897171348 |

FIG. 14 (Continued)

| | | |
|---|---|---|
| CO/N=C(\C(=O)N[C@@H]1C(=O)N2C(C(=O)NCC(C)(C)S)=CCS[C@H]12)c1csc(N)n1 | ZINC001185591796 | 0.897145355 |

FIG. 14 (Continued)

| ZINC Index | SMILES String | Prediction Score | Antibiotics Neighbor | Neighbor Tanimoto | Clinical Toxicity (low=less Tox) |
|---|---|---|---|---|---|
| ZINC000022865640 | O/N=C1\N[C@H]2NCCN[C@H]2N\C1=N/O | 0.992158172 | N[C@@H]1CONC1=O | 0.1 | |
| ZINC000169457956 | CC(=O)N1C2C3N(C©=O)[C@H]4N[C@H]1[C@@H](N[C@H]4N3C©=O)N2C©=O | 0.989006802 | CC(=O)C1C(=O)C=C©OC1=O | 0.130434783 | |
| ZINC000098210492 | COC(=O)c1cc(F)c(N2CCN©CC2)cc1F | 0.97141532 | CCn1cc(C(=O)O)c(=O)c2cc(F)c(N3CCN©CC3)cc21 | 0.368421053 | 0.952547169 |
| ZINC000005510605 | O/N=C1\N[C@@H](O)[C@H](O)N\C1=N/O | 0.953537351 | N[C@@H]1CONC1=O | 0.085714286 | |
| ZINC000001735150 | O=C1CSC(=S)N1/N=C/c1ccc([N+](=O)[O-])s1 | 0.941529986 | C1COC(=O)N1/N=C/C2=CC=C(O2)[N+](=O)[O-] | 0.283333333 | 0.000304384 |
| ZINC000018090096 | CCC(=O)N1C2C3N(C(=O)CC)C4C(N3C(=O)CC)N(C(=O)CC)C(C1N4C(=O)CC)N2C(=O)CC | 0.918629912 | CCCCCCCCC(=O)O | 0.166666667 | |
| ZINC000101676256 | COCCNc1c(=O)c(=O)c1N1CCN©CC1 | 0.917456731 | CN1CCN(c2c(F)cc3c(=O)c(C(=O)O)cn(CCF)c3c2F)CC1 | 0.240963855 | |
| ZINC000100506795 | COC1(OC)C(=N/O)/C(=N\O)C(OC)(OC)C(=N/O)/C1=N\O | 0.908199865 | Coc1ccc(C(=O)O)cc1 | 0.135135135 | |

FIG. 15A

| | | | | | |
|---|---|---|---|---|---|
| ZINC000006661600 | Nc1nc(/C(=N/O)C(=O)O)cs1 | 0.902300328 | C=CC1=C(C(=O)O)N2C(=O)[C@@H](NC(=O)/C(=N\O)c3csc(N)n3)[C@H]2SC1 | 0.355263158 | |
| ZINC000006719085 | CN©CCNC(=O)/C(=N/O)c1csc(N)n1 | 0.891840497 | COCC1=C(C(=O)O)N2C(=O)[C@@H](NC(=O)/C(=N\O)c3csc(N)n3)[C@H]2SC1 | 0.351648352 | |
| ZINC000584578353 | O=c1oc(=O)c2cc(Cl)c3c4c(Cl)cc5c(=O)oc(=O)c6c(Cl)cc(c7c(Cl)cc1c2c73)c4c56 | 0.881675141 | Oc1c(I)cc(Cl)c2cccnc12 | 0.118421053 | |
| ZINC000225434673 | O=[N+]([O-])C(Br)(Br)/[N+](O)=N/c1nonc1/N=N\c1nonc1/N=[N+](\O)C(Br)(Br)[N+](=O)[O-] | 0.881357093 | NC(=O)c1cc([N+](=O)[O-])cc([N+](=O)[O-])c1 | 0.157894737 | 2.37E-05 |
| ZINC000038586996 | CCO/N=C(\C(=O)O)c1nsc(N)n1 | 0.875853644 | CO/N=C(\C(=O)N[C@@H]1C(=O)N2C(C(=O)O)=C(C[n+]3ccn4ccccc43)CS[C@H]12)c1nsc(N)n1 | 0.238938053 | |
| ZINC000019771150 | CN1CCN(/N=C/c2ccc([N+](=O)[O-])s2)CC1 | 0.874699378 | O=C1OCCN1/N=C/c1ccc([N+](=O)[O-])o1 | 0.213333333 | 0.28520993 |
| ZINC000004481415 | N=C1[C@@H](C(N)=O)SC(=S)N1/N=C(\N)S | 0.872656737 | C[C@@H](O)[C@H]1C(=O)N2C(C(=O)O)=C(COC(N)=O)S[C@H]12 | 0.144736842 | 0.004137098 |

FIG. 15A (Continued)

| | | | | | |
|---|---|---|---|---|---|
| ZINC000004623615 | C[C@@H]1CN(c2cc(N)c([N+](=O)[O-])cc2F)C[C@H]©N1 | 0.870749618 | C[C@H]1CN(c2c(F)c(N)c3c(=O)c(C(=O)O)cn(C4CC4)c3c2F)C[C@@H]©N1 | 0.258426966 | 0.001678272 |
| ZINC000001387673 | O=C1CCC(=O)N1N1C(=O)CSC1=S | 0.869396894 | O=C1C[C@H]2SOC=CN12 | 0.1875 | |
| ZINC000101675810 | Cc1ccn(CCNc2c(=O)c(=O)c2N2CCN©CC2)n1 | 0.868850151 | CN1CCN(c2c(F)cc3c(=O)c(C(=O)O)cn(CCF)c3c2F)CC1 | 0.225806452 | |
| ZINC000015134557 | N=C1N[C@H]2[C@@H](N1)N(C=O)[C@H]1NC(N)=N[C@H]1N2C=O | 0.860230324 | NCCCC(N)CC(=O)NC1CNC(=O)C(C2CC(O)NC(N)=N2)NC(=O)C(=CNC(N)=O)NC(=O)C(CO)NC(=O)C(CO)NC1=O.O=S(=O)(O)O | 0.103703704 | |
| ZINC000238901709 | CN1N[C@H](c2cccs2)[C@H]2C(=O)NC(=O)[C@H]21 | 0.857387473 | CC1©S[C@@H]2[C@H](N3C(=O)[C@@H](c4ccccc4)NC3©C)C(=O)N2[C@H]1C(=O)O | 0.166666667 | 0.573262084 |
| ZINC000006599408 | NC(=S)N/N=C/c1c(Cl)nc2sccn12 | 0.856743827 | NC(=O)OC[C@@H]1[C@H](NC(=O)/C(=N\OCC(=O)O)c2csc(N)n2)C(=O)N1S(=O)(=O)O | 0.126126126 | |
| ZINC000013517522 | CCN1C(=O)N(CC)[C@H]2NS(=O)(=O)N[C@H]21 | 0.856085099 | CC1©[C@H](C(=O)O)N2C(=O)C[C@H]2S1(=O)=O | 0.196078431 | |

FIG. 15A (Continued)

| | | | | | |
|---|---|---|---|---|---|
| ZINC000100032716 | C[C@H]1CN(c2cc3c(cc2[N+](=O)[O-])c(=O)c(C(=O)O)cn3C2CC2)CCN1/N=N/c1ccc(S(N)(=O)=O)cc1 | 0.850668466 | CCN1CCN(c2cc3c(cc2F)c(=O)c(C(=O)O)cn3C2CC2)CC1 | 0.383928571 | 0.010021057 |

FIG. 15A (Continued)

| ZINC Index | Neighbor Name |
|---|---|
| ZINC000022865640 | D-cycloserine cycloserine 68-41-7 Seromycin orientomycin Oxamycin Cyclorin Cyclo-D-serine Cicloserina Farmiserina Miroseryn Tisomycin Wasserina Closina D-4-amino-3-isoxazolidinone (R)-4-AMINOISOXAZOLIDIN-3-ONE alpha-Cycloserine (+)-4-Amino-3-isoxazolidinone Cycloserinum Miroserina D-4-amino-3-isoxazolidone Oxamicina (4R)-4-aminoisoxazolidin-3-one PA 94 (+)-Cycloserine (4R)-4-amino-1,2-oxazolidin-3-one Oxamicina [Italian] Cycloserin Micoserina Cicloserina [Italian] PA-94 Tebemicina Novoserin (R)-4-AMINO-ISOXAZOLIDIN-3-ONE D-Oxamycin D-CS Cycloserinum [INN-Latin] E-733-A Cicloserina [INN-Spanish] D-4-Amino-3-isossazolidone D-(+)-Cycloserine RO-1-9213 3-Isoxazolidinone, 4-amino-, (R)- HSDB 3218 D-Oxamicina 3-Isoxazolidinone, 4-amino-, d- K-300 UNII-95IK5KI84Z I-1431 3-Isoxazolidinone, 4-amino-, (+)- D-4-Amino-3-isossazolidone [Italian] NSC 154851 3-Isoxazolidinone, 4-amino-, (4R)- (R)-4-Amino-3-isoxazolidinone CHEBI:40009 AI3-50153 D-Cycloserine, synthetic EINECS 200-688-4 (R)-(+)-4-Amino-3-isoxazolidinone CHEMBL771 BRN 0080798 Closerin SC-49088 95IK5KI84Z DYDCUQKUCUHJBH-UWTATZPHSA-N MFCD00005353 CAS-68-41-7 NCGC00016306-01 D-Cycloserine, 98% DSSTox_CID_2870 3-Isoxazolidinone, 4-amino-, (+)- (8CI) DSSTox_RID_76766 DSSTox_GSID_22870 Cycloserine, D- .alpha.-Cycloserine (R)-Cycloserine Seromycin (TN) 4AX CPD000058313 SMR000058313 R-4-Amino-3-isoxazolidinone Cycloserine [INN:BAN:JAN] (S)-(-)-Cycloserine R-(+)-Cycloserine (4R)-4-Amino-3-isoxazolidinone 4-Amino-isoxazolidin-3-one SR-01000075432 DRG-0195 (R)-(+)-Cycloserine D-Cycloserine synth. BP 88 D-amino-3-isoxazolidinone (R)-4-Amino-3-isoxazolidone Serine, cyclo- 3-Isoxazolidinone, 4-amino-, D R(+)-4-Amino-3-isoxazolidinone Cycloserine [USP:INN:BAN:JAN] 3-Isoxazolidinone, 4-amino-, (R) PubChem5763 D-Cycloserine, powder Spectrum_000860 1pb9 CYCLOSERINE (D) Prestwick0_001089 Prestwick1_001089 Prestwick2_001089 Prestwick3_001089 Spectrum2_000084 Spectrum3_000371 Spectrum4_000305 Spectrum5_000797 Lopac-C-1159 Lopac-C-3909 Lopac-C-7005 3-Isoxazolidinone, 4-amino-, (4R)- (9CI) C 3909 C-9390 C-9400 AC1Q4UA7 Lopac0_000252 SCHEMBL34322 BSPBio_001138 BSPBio_002121 KBioGR_000890 KBioSS_001340 4-27-00-05549 (Beilstein Handbook Reference) MLS000758215 MLS001423962 MLS002548887 BIDD:GT0707 DivK1c_000098 SPECTRUM1500215 SPBio_000008 SPBio_003029 AC1L1M33 BPBio1_001252 FA6C7F8B-D080-4EA3-978F-1ECFB5A29D09 GTPL9489 Cycloserine (JP17/USP/INN) 4-Amino-3-isoxazolidinone, D- DTXSID8022870 HMS500E20 KBio1_000098 KBio2_001340 KBio2_003908 KBio2_006476 KBio3_001341 MolPort-000-858-643 NINDS_000098 HMS1571I20 HMS1920C06 HMS2051C15 HMS2091I14 HMS2098I20 HMS2232F03 HMS3259L19 HMS3260D06 HMS3715I14 NJ-21 Pharmakon1600-01500215 R (+)-4-amino-3-isoxazolidinone (R)-3-Isoxazolidinone, 4-amino- 4-Amino-3-isoxazolidinone, (R)- ACT04767 HY-B0030 KS-00001FB7 |

FIG. 15B

| | |
|---|---|
| | Tox21_110361 Tox21_500252 BDBM50038178 BDBM50103516 CCG-39705 D-Cycloserine, >=96.0% (NT) FC1270 LMPK14000007 NSC756712 s1998 ZINC34676245 4-Isoxazolidinamine, 3-oxo-, (D)- AKOS015994626 Tox21_110361_1 AC-4721 CS-2395 DB00260 HS-0079 LP00252 MCULE-4212827696 NC00050 NC00676 NSC-756712 RL04615 IDI1_000098 SMP1_000167 NCGC00015213-01 NCGC00015213-02 NCGC00015213-03 NCGC00016306-02 NCGC00016306-03 NCGC00016306-04 NCGC00016306-05 NCGC00016306-07 NCGC00016306-08 NCGC00093713-01 NCGC00093713-02 NCGC00260937-01 AJ-89953 AK-26256 AN-11678 BR-26256 CAS-339-72-0 K138 LS-86757 SAM001247014 SAM002264599 SC-06256 ST075697 SBI-0050240.P004 AB0007232 AB2000415 ST2408171 AB00443920 EU-0100252 FT-0624464 (4R)-4-amino-2,4,5-trihydroisoxazol-3-one C08057 D00877 AB00443920_09 AB00443920_10 005C353 101039-EP2295402A2 101039-EP2301544A1 SR-01000759389 SR-01000075432-1 SR-01000075432-2 SR-01000075432-5 SR-01000075432-9 SR-01000759389-4 SR-01000075432-10 F2173-1228 Z1522567171 Cycloserine, United States Pharmacopeia (USP) Reference Standard Cycloserine, Pharmaceutical Secondary Standard; Certified Reference Material |
| ZINC000169457956 | DEHYDROACETIC ACID 520-45-6 3-Acetyl-6-methyl-2H-pyran-2,4(3H)-dione Methylacetopyronone Dehydracetic acid Biocide 470F Acetic acid, dehydro- 3-Acetyl-6-methyl-2,4-pyrandione 2H-Pyran-2,4(3H)-dione, 3-acetyl-6-methyl- NSC 8770 3-Acetyl-6-methyl-pyran-2,4-dione 3-Acetyl-6-methyldihydropyrandione-2,4 PGRHXDWITVMQBC-UHFFFAOYSA-N 3-Acetyl-6-methylpyrandione-2,4 Dehydroacetic acid, 98% 3-acetyl-6-methyl-3,4-dihydro-2H-pyran-2,4-dione 2-Acetyl-5-hydroxy-3-oxo-4-hexenoic acid, .delta.-lactone 3-acetyl-6-methyl-2,4-dioxo-3H-pyran Dehydroacetic acid [ISO] PubChem9713 DH AA DSSTox_CID_14 AC1Q5CBR AC1L3VH5 DSSTox_RID_75321 DSSTox_GSID_20014 SCHEMBL17787 3-Acetyl-6-methyl-2-pyranone DTXSID6020014 CTK6B2865 PGRHXDWITVMQBC-UHFFFAOYSA- NSC8770 CHEBI:137426 MolPort-000-860-873 4-Hexenoic acid, .delta.-lactone HMS3264K05 Pharmakon1600-01301016 3-acetyl-6-methylpyran-2,4-dione HY-B1211 NSC-8770 2H-Pyran-2, 3-acetyl-6-methyl- Tox21_302764 WLN: T6OV DV CHJ CV1 F1 BBL013155 MFCD00066709 NSC760135 s4522 SBB056765 STL163953 Dehydroacetic acid, >=98.0% (T) AKOS000119576 AKOS016038058 CCG-213725 CS-4810 EBD1328048 LS-2659 NSC-760135 KS-00000G03 3-acetyl-6-methyl-3H-pyran-2,4-dione NCGC00256469-01 3-Acetyl-6-methyl-2,4(3H)-pyrandione AC-10441 AK-73000 AN-18654 BR-73000 CAS-520-45-6 DS-15291 E265 ST2410411 D0039 FT-0624496 ST50308131 3-Acetyl-6-Methyldihydropyrandione-2,4(3H) Pyran-2,4(3H)-dione, 3-acetyl-6-methyl- M-6038 3-Acetyl-6-methyl-2,3-dihydropyran-2,4-dione AB01510434_02 AH-034/32463001 SR-01000389026 I04-0246 SR-01000389026-1 3-?acetyl-?4-?hydroxy-?6-?methyl-2H-?Pyran-?2-?one 3-Acetyl-6-methyl-2H-pyran-2,4(3H)-dione, enol form 3-Acetyl-6-methyl-2H-pyran-2,4(3H)-dione, ion(1-) F0191-0260 4-Hexenoic acid, 2-acetyl-5-hydroxy-3-oxo-, .delta.-lactone |

FIG. 15B (Continued)

| | |
|---|---|
| | Dehydroacetic acid, United States Pharmacopeia (USP) Reference Standard Dehydroacetic acid, Pharmaceutical Secondary Standard; Certified Reference Material InChI=1/C8H8O4/c1-4-3-6(10)7(5(2)9)8(11)12-4/h3,7H,1-2H3 |
| ZINC000098210492 | Pefloxacin 70458-92-3 Pefloxacine Pefloxacino Pefloxacinum PFLX Pefloxacin [INN-French] Pefloxacinum [INN-Latin] Pefloxacino [INN-Spanish] AM-725 1-ethyl-6-fluoro-7-(4-methylpiperazin-1-yl)-4-oxo-1,4-dihydroquinoline-3-carboxylic acid 1584RB UNII-2H52Z9F2Q5 EU 5306 EU-5306 C17H20FN3O3 1-ethyl-6-fluoro-7-(4-methylpiperazin-1-yl)-4-oxo-quinoline-3-carboxylic acid EINECS 274-611-8 1589 RB BRN 0567618 CHEBI:50199 2H52Z9F2Q5 1-ethyl-6-fluoro-7-(4-methylpiperazin-1-yl)-4-oxoquinoline-3-carboxylic acid 1-Ethyl-6-fluoro-1,4-dihydro-4-oxo-7-(4-methyl-1-piperazinyl)-3-quinolinecarboxylic acid 1-Ethyl-6-fluoro-1,4-dihydro-7-(4-methyl-1-piperazinyl)-4-oxo-3-quinolinecarboxylic acid Abactal BAS 00463355 Silver Pefloxacin P-1198 3-Quinolinecarboxylic acid, 1-ethyl-6-fluoro-1,4-dihydro-7-(4-methyl-1-piperazinyl)-4-oxo 3-Quinolinecarboxylic acid, 1-ethyl-6-fluoro-1,4-dihydro-7-(4-methyl-1-piperazinyl)-4-oxo- PERFLOXACIN Labocton MLS001049009 3-Quinolinecarboxylic acid, 1,4-dihydro-1-ethyl-6-fluoro-7-(4-methyl-1-piperazinyl)-4-oxo- SMR000273037 Pefloxacin [USAN:BAN:INN] SR-01000356843 Pefloxacin (USAN/INN) SMR000387024 Pefloxacin [USAN:INN:BAN] CCRIS 8210 Pefloxacin,(S) AC1L1AEA Spectrum2_000034 Spectrum3_001971 AC1Q5RD0 ACMC-1C1J6 Oprea1_063677 Oprea1_546341 SCHEMBL34292 BSPBio_003571 MLS000713556 MLS006011797 SPBio_000127 CHEMBL267648 cid_119525 ZINC1894 DTXSID3048493 BDBM57936 CTK0G9599 KBio3_002945 FHFYDNQZQSQIAI-UHFFFAOYSA-N MolPort-000-883-203 HMS1613E05 HMS2090H09 HMS3713G04 BCP20511 HY-B0147 3962AH BBL008795 STK169677 AKOS000280245 API0009117 CCG-111464 CS-1961 DB00487 MCULE-3576829094 1-ethyl-6-fluoro-7-(4-methyl-1-piperazinyl)-4-oxo-1,4-dihydro-3-quinolinecarboxylic acid 70458-95-6 (MESYLATE) NCGC00177986-04 2589 R.B AN-37702 SC-74449 SC-75585 ST095166 SBI-0206758.P001 AB0106989 LS-141589 RT-005170 FT-0630798 H2906 VU0243371-6 D02306 AB00600922-12 AB00600922-14 AB00600922_15 AB00600922_16 458P923 C-20124 Pefloxacin, Antibiotic for Culture Media Use Only SR-01000356843-1 SR-01000356843-6 BRD-K55034111-001-02-0 BRD-K55034111-066-02-3 BRD-K55034111-066-07-2 F5577-0091 1-ETHYL-6-FLUORO-7-(4-METHYLPIPERAZIN-1-YL)-4-OXO- 1-Ethyl-6-fluoro-1,4-dihydro-4-oxo-7-(4-methylpiperazinyl)quinoline-3-carboxylic Acid 1-Ethyl-6-fluoro-1,4-dihydro-7-(4-methyl-1- piperazinyl)-4-oxo-3-quinolinecarboxylic acid 1-ethyl-6-fluoro-4-keto-7-(4-methylpiperazino)quinoline-3-carboxylic acid;mesylic acid 1-Ethyl-6-fluoro-7-(4-methyl-piperazin-1-yl)-4-oxo-1,4-dihydro-quinoline-3-carbo 1-ethyl-6-fluoro-7-(4-methylpiperazinyl)-4-oxohydroquinoline-3-carboxylic acid 3-Quinolinecarboxylic acid,1-ethyl-6-fluoro-1,4-dihydro-7-(4-methyl-1-piperazinyl)-4-oxo- 1-ethyl-6- |

FIG. 15B (Continued)

| | |
|---|---|
| | fluoranyl-7-(4-methylpiperazin-1-yl)-4-oxidanylidene-quinoline-3-carboxylic acid;methanesulfonic acid 1-ethyl-6-fluoro-7-(4-methyl-1-piperazinyl)-4-oxo-3-quinolinecarboxylic acid;methanesulfonic acid |
| ZINC000005510605 | D-cycloserine cycloserine 68-41-7 Seromycin orientomycin Oxamycin Cyclorin Cyclo-D-serine Cicloserina Farmiserina Miroseryn Tisomycin Wasserina Closina D-4-amino-3-isoxazolidinone (R)-4-AMINOISOXAZOLIDIN-3-ONE alpha-Cycloserine (+)-4-Amino-3-isoxazolidinone Cycloserinum Miroserina D-4-amino-3-isoxazolidone Oxamicina (4R)-4-aminoisoxazolidin-3-one PA 94 (+)-Cycloserine (4R)-4-amino-1,2-oxazolidin-3-one Oxamicina [Italian] Cycloserin Micoserina Cicloserina [Italian] PA-94 Tebemicina Novoserin (R)-4-AMINO-ISOXAZOLIDIN-3-ONE D-Oxamycin D-CS Cycloserinum [INN-Latin] E-733-A Cicloserina [INN-Spanish] D-4-Amino-3-isossazolidone D-(+)-Cycloserine RO-1-9213 3-Isoxazolidinone, 4-amino-, (R)- HSDB 3218 D-Oxamicina 3-Isoxazolidinone, 4-amino-, d- K-300 UNII-95IK5KI84Z I-1431 3-Isoxazolidinone, 4-amino-, (+)- D-4-Amino-3-isossazolidone [Italian] NSC 154851 3-Isoxazolidinone, 4-amino-, (4R)- (R)-4-Amino-3-isoxazolidinone CHEBI:40009 AI3-50153 D-Cycloserine, synthetic EINECS 200-688-4 (R)-(+)-4-Amino-3-isoxazolidinone CHEMBL771 BRN 0080798 Closerin SC-49088 95IK5KI84Z DYDCUQKUCUHJBH-UWTATZPHSA-N MFCD00005353 CAS-68-41-7 NCGC00016306-01 D-Cycloserine, 98% DSSTox_CID_2870 3-Isoxazolidinone, 4-amino-, (+)- (8CI) DSSTox_RID_76766 DSSTox_GSID_22870 Cycloserine, D- .alpha.-Cycloserine (R)-Cycloserine Seromycin (TN) 4AX CPD000058313 SMR000058313 R-4-Amino-3-isoxazolidinone Cycloserine [INN:BAN:JAN] (S)-(-)-Cycloserine R-(+)-Cycloserine (4R)-4-Amino-3-isoxazolidinone 4-Amino-isoxazolidin-3-one SR-01000075432 DRG-0195 (R)-(+)-Cycloserine D-Cycloserine synth. BP 88 D-amino-3-isoxazolidinone (R)-4-Amino-3-isoxazolidone Serine, cyclo- 3-Isoxazolidinone, 4-amino-, D R(+)-4-Amino-3-isoxazolidinone Cycloserine [USP:INN:BAN:JAN] 3-Isoxazolidinone, 4-amino-, (R) PubChem5763 D-Cycloserine, powder Spectrum_000860 1pb9 CYCLOSERINE (D) Prestwick0_001089 Prestwick1_001089 Prestwick2_001089 Prestwick3_001089 Spectrum2_000084 Spectrum3_000371 Spectrum4_000305 Spectrum5_000797 Lopac-C-1159 Lopac-C-3909 Lopac-C-7005 3-Isoxazolidinone, 4-amino-, (4R)- (9CI) C 3909 C-9390 C-9400 AC1Q4UA7 Lopac0_000252 SCHEMBL34322 BSPBio_001138 BSPBio_002121 KBioGR_000890 KBioSS_001340 4-27-00-05549 (Beilstein Handbook Reference) MLS000758215 MLS001423962 MLS002548887 BIDD:GT0707 DivK1c_000098 SPECTRUM1500215 SPBio_000008 SPBio_003029 AC1L1M33 BPBio1_001252 FA6C7F8B-D080-4EA3-978F-1ECFB5A29D09 GTPL9489 Cycloserine (JP17/USP/INN) 4-Amino-3-isoxazolidinone, D- DTXSID8022870 HMS500E20 KBio1_000098 KBio2_001340 KBio2_003908 KBio2_006476 KBio3_001341 MolPort-000-858-643 NINDS_000098 HMS1571I20 HMS1920C06 HMS2051C15 HMS2091I14 HMS2098I20 HMS2232F03 HMS3259L19 HMS3260D06 HMS3715I14 NJ-21 Pharmakon1600-01500215 R (+)-4-amino-3-isoxazolidinone (R)-3- |

FIG. 15B (Continued)

| | |
|---|---|
| | Isoxazolidinone, 4-amino- 4-Amino-3-isoxazolidinone, (R)- ACT04767 HY-B0030 KS-00001FB7 Tox21_110361 Tox21_500252 BDBM50038178 BDBM50103516 CCG-39705 D-Cycloserine, >=96.0% (NT) FC1270 LMPK14000007 NSC756712 s1998 ZINC34676245 4-Isoxazolidinamine, 3-oxo-, (D)- AKOS015994626 Tox21_110361_1 AC-4721 CS-2395 DB00260 HS-0079 LP00252 MCULE-4212827696 NC00050 NC00676 NSC-756712 RL04615 IDI1_000098 SMP1_000167 NCGC00015213-01 NCGC00015213-02 NCGC00015213-03 NCGC00016306-02 NCGC00016306-03 NCGC00016306-04 NCGC00016306-05 NCGC00016306-07 NCGC00016306-08 NCGC00093713-01 NCGC00093713-02 NCGC00260937-01 AJ-89953 AK-26256 AN-11678 BR-26256 CAS-339-72-0 K138 LS-86757 SAM001247014 SAM002264599 SC-06256 ST075697 SBI-0050240.P004 AB0007232 AB2000415 ST2408171 AB00443920 EU-0100252 FT-0624464 (4R)-4-amino-2,4,5-trihydroisoxazol-3-one C08057 D00877 AB00443920_09 AB00443920_10 005C353 101039-EP2295402A2 101039-EP2301544A1 SR-01000759389 SR-01000075432-1 SR-01000075432-2 SR-01000075432-5 SR-01000075432-9 SR-01000759389-4 SR-01000075432-10 F2173-1228 Z1522567171 Cycloserine, United States Pharmacopeia (USP) Reference Standard Cycloserine, Pharmaceutical Secondary Standard; Certified Reference Material |
| ZINC000001735150 | CHEBI:5195 CAS-67-45-8 Furanzolidone,(S) AC1NS4EQ Epitope ID:116184 CHEMBL1572167 ZINC113418 FZL NCGC00016299-01 ZB003810 (E)-3-((5-nitrofuran-2-yl)methyleneamino) (E)-3-((5-nitrofuran-2-yl)methyleneamino)oxazolidin-2-one (E)-3-(((5-nitrofuran-2-yl)methylene)amino)oxazolidin-2-one 3-[(Z)-(5-nitrofuran-2-yl)methylideneamino]-1,3-oxazolidin-2-one |
| ZINC000018090096 | NONANOIC ACID Pelargonic acid 112-05-0 n-Nonanoic acid Nonylic acid Pelargic acid Nonoic acid n-Nonylic acid n-Nonoic acid 1-Octanecarboxylic acid Pelargon Cirrasol 185A Hexacid C-9 Emfac 1202 Nonanoate 1-nonanoic acid Fatty acids, C8-10 Pelargon [Russian] 1-Octanecarboxyic acid Nonansaeure Pelargonsaeure pergonic acid Fatty acids, C6-12 nonoate NSC 62787 UNII-97SEH7577T FEMA No. 2784 HSDB 5554 EINECS 203-931-2 68937-75-7 EPA Pesticide Chemical Code 217500 BRN 1752351 CH3-[CH2]7-COOH AI3-04164 CHEBI:29019 FBUKVWPVBMHYJY-UHFFFAOYSA-N 97SEH7577T pergonate n-nonanoate MFCD00004433 1-nonanoate octan-1 carboxylic acid 1-octanecarboxylate n-Nonanoic acid, 97% DSSTox_CID_1641 DSSTox_RID_76255 DSSTox_GSID_21641 Q-201488 nonans CAS-112-05-0 Nonanoicacid n-Pelargonate n-Nonylate n-Nonoate NoEthaCoEa n-pelargonic acid KNA EINECS 273-086-2 Nonanoic Acid Anion Acid C9 Caprylic-Capric Acid Nonanoic acid, 96% 3sz1 Emery's L-114 Pelargonic Acid 1202 Emery 1202 Emery 1203 octane-1-carboxylic acid Nonanoic acid, >=97% ACMC-2099ce bmse000499 EC 203-931-2 EC 273-086-2 AC1L1QE7 AC1Q2VX7 AC1Q5W5X Caprylic-Capric Acid 658 WLN: QV8 NCIOpen2_000142 NCIOpen2_000179 NCIOpen2_001763 NCIOpen2_002882 NCIOpen2_003483 |

FIG. 15B (Continued)

| | |
|---|---|
| | SCHEMBL21966 Emery 1202 (Salt/Mix) 4-02-00-01018 (Beilstein Handbook Reference) KSC175A3N MLS001066339 IioA inverted question markuEa CHEMBL108436 Nonanoic acid, >=96%, FG QSPL 030 Jsp000917 DTXSID3021641 CTK0H5036 7640-78-0 (zinc salt) 5112-16-3 (cadmium salt) MolPort-000-881-522 HMS2269L08 Nonanoic acid, analytical standard 29813-38-5 (calcium salt) BB_SC-07262 KS-00000UO4 Nonanoic acid, natural, 98%, FG NSC62787 ZINC1529234 23282-34-0 (potassium salt) Tox21_202426 Tox21_300022 ANW-16380 BBL027459 LMFA01010009 NSC-62787 SBB058693 STL372710 14047-60-0 (hydrochloride salt) AKOS000118981 NONANOIC ACID MFC9 H18 O2 CCG-231471 LS-2986 MCULE-4736597375 RTR-002359 NCGC00164328-01 NCGC00164328-02 NCGC00164328-03 NCGC00253958-01 NCGC00259975-01 AN-43106 C9:0 SMR000112203 TR-002359 FT-0660055 N0288 P0952 ST51037369 C01601 83478-EP2305655A2 A802476 S04-0163 F0001-2447 Z1258948135 F57B4D17-8824-403B-AE1B-FA425608BB39 InChI=1/C9H18O2/c1-2-3-4-5-6-7-8-9(10)11/h2-8H2,1H3,(H,10,11 58253-02-4 |
| ZINC000101676256 | fleroxacin 79660-72-3 Megalone Fleroxacino Fleroxacinum Fleroxicin Megalocin Quinodis Fleroxacine 6,8-Difluoro-1-(2-fluoroethyl)-1,4-dihydro-7-(4-methyl-1-piperazinyl)-4-oxo-3-quinolinecarboxylic acid Fleroxacine [French] Fleroxacinum [Latin] Fleroxacino [Spanish] AM 833 AM-833 Ro 23-6240 Fleroxacin (Quinodis) Ro 23-6240/000 UNII-N804LDH51K CCRIS 3972 C17H18F3N3O3 Ro-236240 BRN 4300996 N804LDH51K CHEBI:31810 6,8-difluoro-1-(2-fluoroethyl)-7-(4-methylpiperazin-1-yl)-4-oxo-1,4-dihydroquinoline-3-carboxylic acid NCGC00167558-01 6,8-difluoro-1-(2-fluoroethyl)-7-(4-methylpiperazin-1-yl)-4-oxo-quinoline-3-carboxylic acid 6,8-difluoro-1-(2-fluoroethyl)-7-(4-methylpiperazin-1-yl)-4-oxoquinoline-3-carboxylic acid DSSTox_CID_26714 DSSTox_RID_81846 DSSTox_GSID_46714 3-Quinolinecarboxylic acid, 6,8-difluoro-1-(2-fluoroethyl)-1,4-dihydro-7-(4-methyl-1-piperazinyl)-4-oxo-Megalosin Megalocin (TN) Megalone (TN) 3-Quinolinecarboxylic acid, 1,4-dihydro-6,8-difluoro-1-(2-fluoroethyl)-7-(4-methyl-1-piperazinyl)-4-oxo- SMR000466302 CAS-79660-72-3 FLRX Fleroxacin [USAN:BAN:INN:JAN] SR-01000759379 Fleroxacin (JAN/USAN/INN) Fleroxacin,(S) Fleroxacin [USAN:INN:BAN:JAN] F0646 Ro-23-6240/000 AC1L1FR2 AC1Q3ZU5 CHEMBL6273 SCHEMBL48145 6,8-difluoro-1-(2-fluoroethyl)-7-(4-methyl-1-piperazinyl)-4-oxo-1,4-dihydro-3-quinolinecarboxylic acid KSC492E5H MLS000759401 MLS006010715 AC1Q4N64 DTXSID1046714 CTK3J2253 KS-00000XUW MolPort-003-847-381 XBJBPGROQZJDOJ-UHFFFAOYSA-N HMS2090I08 HMS3715B11 BCP28939 HY-B0414 RKL10075 ZINC3786299 Tox21_112553 ANW-42889 s2469 ZINC03786299 AKOS015907011 Tox21_112553_1 API0003278 CCG-221125 CS-2518 DB04576 KS-5124 RTR-025289 VQ10280 NCGC00167558-02 6,8-Difluoro-1-(2-fluoroethyl)-1,4-dihydro-7-(4-methylpiperazino)-4-oxo-3-quinolinecarboxylic acid AM-833;AM833;AM 833 AN-36581 CC-28438 CPD000466302 SAM001246535 SC-58138 AB1010903 LS-141577 Ro-236240000 TR-025289 FT-0630874 C13179 D01716 Fleroxacin, |

FIG. 15B (Continued)

| | |
|---|---|
| | VETRANAL(TM), analytical standard J10168 AB00640001-02 AB00640001-03 AB00640001_04 660F723 A839732 C-21096 SR-01000759379-2 SR-01000759379-3 6,8-difluoro-1-(2-fluoroethyl)-7-(4-methyl-1-piperazinyl)-4-oxo-3-quinolinecarboxylic acid 6,8-bis(fluoranyl)-1-(2-fluoranylethyl)-7-(4-methylpiperazin-1-yl)-4-oxidanylidene-quinoline-3-carboxylic acid 6,8-Difluoro-1-(2-Fluoroethyl)-1,4-Dihydro-7-(4-Methyl-1-Piperazinyl)-4-Oxo-3-Quinolinecarboxylic Ac 6,8-difluoro-1-(2-fluoroethyl)-1,4-dihydro-7-(4-methyl-1-piperazinyl)-4-oxo-3-quinolinecarboxylic acid- 6,8-Difluoro-1-(2-fluoroethyl)-1,4-dihydro-7-(4-methyl-1-piperazinyl)-4-oxo-3-quinolinecarboxylic acid; Megalone 79660-53-0 |
| ZINC000100506795 | 4-METHOXYBENZOIC ACID p-Anisic acid 100-09-4 ANISIC ACID p-Methoxybenzoic acid Draconic acid 4-Anisic acid Benzoic acid, 4-methoxy- ANISIC ACID, PARA para-anisic acid Anisic acid, p-isomer 4-methoxy-benzoic acid Kyselina 4-methoxybenzoova UNII-4SB6Y7DMM3 4-Methoxy benzoic acid P-Methoxy Benzoic Acid Methoxybenzoic acid Kyselina 4-methoxybenzoova [Czech] EINECS 202-818-5 NSC 32742 1335-08-6 BRN 0508910 4SB6Y7DMM3 AI3-00893 CHEBI:40813 ZEYHEAKUIGZSGI-UHFFFAOYSA-N p-methoxybenzoate p-Anisic acid, 98% 73424-02-9 ANN anisoic acid 4-Carboxyanisole EINECS 215-618-8 4-methoxylbenzoic acid PubChem23856 1sv3 paramethoxy benzoic acid ACMC-1BLVJ P-ANISIC ACID, 4-(methoxy)benzoic acid AC1L1OUP ANISIC ACID(P-) 4-(methyloxy)benzoic acid ANISIC ACID, 4- bmse000356 bmse010012 AC1Q4A1W NCIOpen2_004706 SCHEMBL43335 4-10-00-00346 (Beilstein Handbook Reference) CHEMBL21932 536-45-8 (sodium) Jsp000058 RARECHEM AL BO 0059 DTXSID4059205 SCHEMBL12015259 FEMA 3945 p-Anisic acid, >=99%, FG TIMTEC-BB SBB037872 52509-81-6 (potassium) NSC7926 MolPort-000-871-566 OTAVA-BB 1779304 P-METHYLHYDROXYBENZOIC ACID BDBM243072 HMS1760M22 HMS3604D05 p-Anisic acid, analytical standard ZINC332748 CS-B1766 NSC-7926 NSC32742 STR02874 AKOS BBS-00003715 p-Anisic acid, natural, 99%, FG AB2885 ANW-14157 HTS006404 LABOTEST-BB LT00781808 LABOTEST-BB LT03327667 LABOTEST-BB LT03330798 MFCD00002542 NSC-32742 SBB037872 STK498216 4-Methoxybenzoic acid; p-Anisic acid 73424-02-9 (copper+2) AKOS000118883 AM86179 AS00727 AS03913 DB02795 LS11457 MCULE-7627915900 PS-3382 TRA0034183 AC-11353 AJ-19560 AK-41188 AN-24541 BP-10768 LS-20071 SC-16070 ST080859 AB1002335 DB-023671 RT-001038 TL8006996 A0482 FT-0653005 FT-0658638 ST24032813 4-Methoxybenzoic acid, ReagentPlus(R), 99% C02519 M-5859 p-Anisic acid, Vetec(TM) reagent grade, 98% 31543-EP2308858A1 31543-EP2311816A1 31543-EP2311817A1 AE-848/32075009 I01-1731 Q-200489 Melting point standard 182-184C, analytical standard Z56931884 F1335- |

FIG. 15B (Continued)

| | |
|---|---|
| | 0001 4-Methoxybenzoic acid, certified reference material, TraceCERT(R) InChI=1/C8H8O3/c1-11-7-4-2-6(3-5-7)8(9)10/h2-5H,1H3,(H,9,10 |
| ZINC000006661600 | cefdinir 91832-40-5 UNII-61G2M33IGF 178601-88-2 61G2M33IGF (E)-Cefdinir E-Cefdinir Cefdinir, E-C14H13N5O5S2 bmy28488 SCHEMBL36996 MLS006010415 AC1O4R30 SCHEMBL5919457 CHEBI:94470 MolPort-003-845-683 MolPort-044-724-244 RTXOFQZKPXMALH-GHXIOONMSA-N ZINC3927198 AKOS015964069 AC-1246 API0001887 AS-14294 BC213681 K673 SW197768-3 BRD-K52735702-001-01-2 BRD-K52735702-001-02-0 (6r-(6-alpha,7-beta(z)))-)(hydroxyiminoacetyl)amino)-3-ethenyl-8-oxo (6R,7R)-7-[[(2E)-(2-Amino-4-thiazolyl)(hydroxyimino)acetyl]amino]-3-ethenyl-8-oxo-5-thia-1-azabicyclo[4.2.0]oct-2-ene-2-carboxylic Acid (6R,7R)-7-[[(2E)-2-(2-amino-1,3-thiazol-4-yl)-2-hydroxyiminoacetyl]amino]-3-ethenyl-8-oxo-5-thia-1-azabicyclo[4.2.0]oct-2-ene-2-carboxylic acid (z)-7beta-[2-(2-amino-4-thiazolyl)-2-(hydroxyimino)acetamido]-3-vinyl-3-cephem-4-carboxylic acid 5-Thia-1-azabicyclo[4.2.0]oct-2-ene-2-carboxylic acid, 7-[[(2E)-2-(2-amino-4-thiazolyl)-2-(hydroxyimino)acetyl]amino]-3-ethenyl-8-oxo-, (6R,7R)- 7beta-[(Z)-2-(2-AMINO-4-THIAZOLYL)-2-HYDROXYIMINO ACETAMIDO]-3-VINYL-3-CEPHEM-4-CARBOXYLIC ACID 7beta-[2-(2-amino-4-thiazolyl)-2-(z-hydroxyimino)acetamido]-3-vinyl-3-cephem-4-carboxylic acid 8-[2-(2-amino-1,3-thiazol-4-yl)-1-hydroxy-2-nitroso-ethenyl]amino-4-ethenyl-7-oxo-2-thia-6-azabicyclo[4.2.0]oct-4-ene-5-carboxylicacid |
| ZINC000006719085 | SCHEMBL417203 ZINC3926191 RU-29246 |
| ZINC000584578353 | clioquinol 130-26-7 5-Chloro-7-iodoquinolin-8-ol Iodochlorhydroxyquin Chinoform Chloroiodoquin Chloroiodoquine 5-Chloro-8-hydroxy-7-iodoquinoline Iodochloroxyquinoline Cliquinol Vioform Iodochlorohydroxyquinoline Chlorojodochin Enteroquinol Iodochloroquine Iodochloroxine Iodoenterol 7-Iodo-5-chloroxine 5-Chloro-7-iodo-8-quinolinol Entero-Vioform Iodochlorhydroxyquinoline Iodoxyquinoline Alchloquin Barquinol Budoform Cifoform Dermaform Dioquinol Domeform Eczecidin Enteroseptol Enterozol Enterseptol Entrokin Iodenterol Lekosept Mycoquin Quinambicide Quinoform Rheaform Amebil Amoenol Bactol Emaform Nioform Rometin 5-Chloro-7-iodo-8-hydroxyquinoline Entero-Bioform Iodochlorohydroxyquin Hi-Enterol Iodochlorhydroxyquinol Hydriodide-enterol Quin-O-Creme Chinoformum Cliochinolum Clioquinolum Entero-Septol Enterum locorten Domeform-HC 8-Quinolinol, 5-chloro-7-iodo- 7-Iodo-5-chloro-8-hydroxyquinoline Enterovalodon Alioform Chloro-8-hydroxyiodoquinoline Enteritan Jodchloroxychinolinum Corque Cortin Oralcer Iodo Iodochloroxychinolinum Cremo-quin Entero-bio form Entero-Vioformio Ala-Quin Quinoform (antiseptic) 5-Chloro-7-iodo-quinolin-8-ol UAD Lotion Vioform n.n.r. Cliochinolo Cliochinolo [DCIT] Caswell No. 193 5-Chlor-7-jod-8-hydroxy-chinolin Formtone-HC Lidaform- |

FIG. 15B (Continued)

| | |
|---|---|
| | HC Quinoform (VAN) Clioquinolum [INN-Latin] Quinoline, chloro-8-hydroxyiodo- loquinol C9H5ClINO Vioformio Hi-eneterol Rheaform boluses Iodochlorhydroxyquin Cream Vioform-Hydrocortisone Mild UNII-7BHQ856EJ5 Rheaform Boluses (Veterinary) CCRIS 6050 HSDB 6843 5-Chlor-7-jod-8-hydroxy-chinolin [German] NSC 3531 EINECS 204-984-4 EPA Pesticide Chemical Code 024001 BRN 0153637 AI3-16451 7BHQ856EJ5 CHEBI:74460 QCDFBFJGMNKBDO-UHFFFAOYSA-N MFCD00006787 NCGC00016391-05 CAS-130-26-7 TG2-36-2 DSSTox_CID_2837 DSSTox_RID_76751 PBT-1 DSSTox_GSID_22837 22112-03-4 SMR000058282 Clioquinol [INN:BAN] SR-01000002987 Linolasept Clioqinol Clioquinol [USP:INN:BAN] Cloquinol Clioquinol (CQ) component of Hyquin Vioform N.N.R NSC 74938 Nystaform (Salt/Mix) PubChem16777 Clioquinol (USP/INN) AC1L1EGW component of Formtone-HC component of Heb-Cort V Prestwick0_000886 Prestwick1_000886 Prestwick2_000886 Prestwick3_000886 Formtone-HC (Salt/Mix) ACMC-1CD8U CHEMBL497 EC 204-984-4 cid_2788 SCHEMBL3967 NCIOpen2_009062 Oprea1_438281 BSPBio_000672 BSPBio_002466 5-21-03-00294 (Beilstein Handbook Reference) ksc-8-192 MLS000069389 MLS002454410 SPECTRUM1505114 SPBio_002891 BPBio1_000740 component of Hyquin (Salt/Mix) DTXSID7022837 8-Quinolinol,5-chloro-7-iodo- BDBM32188 CTK4B6611 NSC3531 MolPort-000-146-025 WLN: T66 BNJ GG II JQ HMS1570B14 HMS1648J07 HMS2093I12 HMS2097B14 HMS2230I20 HMS3372J20 HMS3714B14 KUC105859N Pharmakon1600-01505114 ALBB-031653 component of Cort-Quin (Salt/Mix) NSC-3531 ZINC6409735 Tox21_110416 Tox21_200291 ANW-19167 IN1375 LS-725 NSC759822 s4601 SBB032280 STK399761 5-chloro-8-hydroxy-7-iodo-quinoline component of Heb-Cort V (Salt/Mix) AKOS000120779 Tox21_110416_1 AC-6792 AN-9693 CCG-213339 DB04815 MCULE-5389218452 NSC-759822 RTR-035598 TRA0054336 SMP1_000073 NCGC00016391-01 NCGC00016391-02 NCGC00016391-03 NCGC00016391-04 NCGC00016391-06 NCGC00016391-07 NCGC00016391-08 NCGC00016391-09 NCGC00016391-10 NCGC00016391-13 NCGC00021665-03 NCGC00021665-04 NCGC00021665-05 NCGC00257845-01 S4601 5-Chloro-8-hydroxy-7-iodoquin AJ-56165 AS-14597 HY-14603 L813 SBI-0206782.P001 TR-035598 AB00384254 FT-0603209 ST24032993 ST50585810 V2416 Clioquinol, VETRANAL(TM), analytical standard component of Vioform-Hydrocortisone (Salt/Mix) D03538 AB00384254_17 5-Chloro-7-iodo-8-quinolinol, >=95.0% (HPLC) CU-01000000767-2 I01-1475 Q-200875 SR-01000002987-2 SR-01000002987-3 SR-01000002987-4 BRD-K09255212-001-04-2 Z2768770393 Clioquinol, British Pharmacopoeia (BP) Reference Standard Clioquinol, European Pharmacopoeia (EP) Reference Standard Clindamycin phosphate, Antibiotic for Culture Media Use Only Clioquinol, United States Pharmacopeia (USP) Reference Standard InChI=1/C9H5ClINO/c10-6-4-7(11)9(13)8-5(6)2-1-3-12-8/h1-4,13 736176-41-3 CQL |

FIG. 15B (Continued)

| | |
|---|---|
| ZINC000225434673 | 3,5-Dinitrobenzamide nitromide 121-81-3 Tristat Unistat Benzamide, 3,5-dinitro- component of Unistat-3 Nitromide [USAN] component of Tristat Nitroamide UNII-9DUJ3CMK8S C7H5N3O5 EINECS 204-499-8 NSC 60719 9DUJ3CMK8S BRN 1981935 UUKWKUSGGZNXGA-UHFFFAOYSA-N NSC60719 Nitromide (USAN) NCGC00094736-01 DSSTox_CID_25836 DSSTox_RID_81163 DSSTox_GSID_45836 unistat-3 CAS-121-81-3 SR-05000002028 Spectrum_001065 ACMC-20anc0 AC1L1IBY AC1Q5AHS Spectrum2_001044 Spectrum3_000519 Spectrum4_000077 Spectrum5_001200 BSPBio_002077 KBioGR_000633 KBioSS_001545 4-09-00-01351 (Beilstein Handbook Reference) MLS002207159 3,5-Dinitrobenzamide, 97% DivK1c_000813 SCHEMBL193674 SPECTRUM1500435 SPBio_000968 3,5-DINITRO BENZAMIDE CHEMBL1437065 DTXSID0045836 CTK0H4630 HMS502I15 KBio1_000813 KBio2_001545 KBio2_004113 KBio2_006681 KBio3_001577 UUKWKUSGGZNXGA-UHFFFAOYSA-MolPort-002-461-990 NINDS_000813 HMS1920B06 HMS2091J06 Pharmakon1600-01500435 ACT07882 HY-B0945 ZINC1690424 Tox21_111321 5264AH CCG-39929 MFCD00007985 NSC-60719 NSC757245 SBB057213 AKOS001434379 Tox21_111321_1 MCULE-9213012419 NSC-757245 TRA0037962 VZ25861 IDI1_000813 UPCMLD0ENAT5895628:001 NCGC00094736-02 NCGC00094736-03 NCGC00094736-05 AN-43407 CJ-28117 LS-26754 NCI60_004694 SC-47147 SMR001306736 SBI-0051459.P003 AB0004874 DB-022109 TC-169911 FT-0614715 ST50308244 Nitromide, VETRANAL(TM), analytical standard A-8855 D05191 AB00052054_04 A804791 I01-3079 J-004683 SR-05000002028-1 SR-05000002028-3 BRD-K76381435-001-02-9 BRD-K76381435-001-04-5 I14-10501 InChI=1/C7H5N3O5/c8-7(11)4-1-5(9(12)13)3-6(2-4)10(14)15/h1-3H,(H2,8,11) |
| ZINC000038586996 | AC1OAHM8 SCHEMBL3073045 ZINC3871946 (6R,7R)-7-[[(2E)-2-(5-amino-1,2,4-thiadiazol-3-yl)-2-methoxyiminoacetyl]amino]-3-(imidazo[1,2-b]pyridazin-4-ium-1-ylmethyl)-8-oxo-5-thia-1-azabicyclo[4.2.0]oct-2-ene-2-carboxylic acid |
| ZINC000019771150 | CHEBI:5195 CAS-67-45-8 Furanzolidone,(S) AC1NS4EQ Epitope ID:116184 CHEMBL1572167 ZINC113418 FZL NCGC00016299-01 ZB003810 (E)-3-((5-nitrofuran-2-yl)methyleneamino) (E)-3-((5-nitrofuran-2-yl)methyleneamino)oxazolidin-2-one (E)-3-(((5-nitrofuran-2-yl)methylene)amino)oxazolidin-2-one 3-[(Z)-(5-nitrofuran-2-yl)methylideneamino]-1,3-oxazolidin-2-one |
| ZINC000004481415 | Ritipenem Ritipenem [INN] UNII-D4SL77931L 84845-57-8 C10H12N2O6S D4SL77931L (5R,6S)-6-((1R)-1-Hydroxyethyl)-3-(hydroxymethyl)-7-oxo-4-thia-1-azabicyclo(3.2.0)hept-2-ene-2-carboxylic acid, 3-carbamate 4-Thia-1-azabicyclo(3.2.0)hept-2-ene-2-carboxylic acid, 3-(((aminocarbonyl)oxy)methyl)-6-(1-hydroxyethyl)-7-oxo-, (5R-(5alpha,6alpha(R*)))- AC1L23NQ fce22101 CHEMBL70088 SCHEMBL155886 s121 84845-58- |

FIG. 15B (Continued)

| | |
|---|---|
| | 9 (Parent) ZINC4217416 LS-149906 (5R,6S)-3-(carbamoyloxymethyl)-6-[(1R)-1-hydroxyethyl]-7-oxo-4-thia-1-azabicyclo[3.2.0]hept-2-ene-2-carboxylic acid |
| ZINC000004623615 | sparfloxacin 110871-86-8 Zagam AT-4140 CI-978 Esparfloxacino Sparfloxacine Sparfloxacinum Spara CI 978 PD-131501 AT 4140 Sparfloxacine [INN-French] Sparfloxacinum [INN-Latin] DRG-0143 SPFX Esparfloxacino [INN-Spanish] PD 131501 UNII-Q90AGA787L CHEBI:9212 CP 103826 BRN 3658018 Q90AGA787L 5-Amino-1-cyclopropyl-7-(cis-3,5-dimethyl-1-piperazinyl)-6,8-difluoro-1,4-dihydro-4-oxo-3-quinolinecarboxylic acid 5-amino-1-cyclopropyl-7-[(3R,5S)-3,5-dimethylpiperazin-1-yl]-6,8-difluoro-4-oxo-1,4-dihydroquinoline-3-carboxylic acid cis-5-Amino-1-cyclopropyl-7-(3,5-dimethyl-1-piperazinyl)-6,8-difluoro-1,4-dihydro-4-oxo-3-quinolinecarboxylic acid DSSTox_CID_3590 DSSTox_RID_77097 DSSTox_GSID_23590 5-amino-1-cyclopropyl-7-((3R,5S)-3,5-dimethylpiperazin-1-yl)-6,8-difluoro-4-oxo-1,4-dihydroquinoline-3-carboxylic acid 5-amino-1-cyclopropyl-7-[(3R,5S)-3,5-dimethylpiperazin-1-yl]-6,8-difluoro-4-oxoquinoline-3-carboxylic acid 111542-93-9 Parox 3-Quinolinecarboxylic acid, 1,4-dihydro-5-amino-1-cyclopropyl-6,8-difluoro-7-(3,5-dimethyl-1-piperazinyl)-4-oxo-, cis- 3-Quinolinecarboxylic acid, 5-amino-1-cyclopropyl-7-((3R,5S)-3,5-dimethyl-1-piperazinyl)-6,8-difluoro-1,4-dihydro-4-oxo-, rel- 3-Quinolinecarboxylic acid, 5-amino-1-cyclopropyl-7-(3,5-dimethyl-1-piperazinyl)-6,8-difluoro-1,4-dihydro-4-oxo-, cis- 3-Quinolinecarboxylic acid, 5-amino-1-cyclopropyl-7-[(3R,5S)-3,5-dimethyl-1-piperazinyl]-6,8-difluoro-1,4-dihydro-4-oxo-, rel- 5-amino-1-cyclopropyl-7-((3S,5R)-3,5-dimethylpiperazin-1-yl)-6,8-difluoro-4-oxo-1,4-dihydroquinoline-3-carboxylic acid 5-amino-1-cyclopropyl-7-[(3S,5R)-3,5-dimethylpiperazin-1-yl]-6,8-difluoro-4-oxo-quinoline-3-carboxylic acid CAS-110871-86-8 Zagam (TN) sparfloxacin, cis-isomer SR-05000001521 Sparfloxacin [USAN:BAN:INN:JAN] Sparfloxacin & RU 40555 PD 1315-1 Sparfloxacin (JAN/USAN/INN) Liposome-encapsulated sparfloxacin Sparfloxacin,(S) NCGC00159333-02 Sparfloxacin [USAN:INN:BAN:JAN] Sparfloxacin trihydrate PD131501 RP-64206 CP-103826 CHEMBL850 Epitope ID:119065 AC1L1TB5 SCHEMBL41311 MLS000759417 AC1Q29E9 DTXSID9023590 DZZWHBIBMUVIIW-DTORHVGOSA-N MolPort-002-507-759 HMS2090N19 HMS3715J13 ZINC538362 HY-B0308 RKL10082 Sparfloxacin, >=98.0% (HPLC) Tox21_111580 BBL010957 BDBM50366822 MFCD00869619 s1884 STK802067 AKOS005622503 Tox21_111580_1 API0004214 CCG-221166 CS-2347 DB01208 KS-5009 MCULE-1827276157 NCGC00166294-01 NCGC00166294-02 NCGC00166294-03 (cis)-5-amino-1-cyclopropyl-7-(3,5-dimethyl-1-piperazinyl)-6,8-difluoro-1,4-dihydro-4-oxo-3-quinolinecarboxylic acid 5-Amino-1-cyclohexyl-7-(cis-3,5-dimethylpiperazino)-6,8-difluoro-1,4-dihydro-4-oxo-3-quinolinecarboxylic acid 5-Amino-1-cyclopropyl-7-(cis-3,5-dimethyl-1-piperazinyl)- 6,8-difluoro-1,4-dihydro-4-oxo-3-quinolinecarboxylic acid AC-11574 AJ-23393 AK115680 AN-33527 CPD000466312 SAM001246566 SC-96745 SMR000466312 AX8151779 LS-141521 RT-015760 FT-0631055 FT-0674635 |

FIG. 15B (Continued)

| | |
|---|---|
| | S0896 ST24031663 SW199632-2 C07662 D00590 AB00639950-02 AB00639950_03 Sparfloxacin, VETRANAL(TM), analytical standard 871S868 A802376 SR-01000759357 I06-1320 Sparfloxacin, Antibiotic for Culture Media Use Only SR-01000759357-2 SR-05000001521-1 SR-05000001521-2 BRD-K07612980-001-07-9 5-amino-1-cyclopropyl-6,8-difluoro-7-(cis-3,5-dimethyl-1-piperazinyl)-1,4-dihydro-4-oxoquinoline-3-carboxylic acid 5-Amino-1-cyclopropyl-7-(cis-3,5-dimethyl)-6,8- difluoro-1,4-dihydro-4-oxo-3-quinolinecarboxylic acid & RU 40555 5-Amino-1-cyclopropyl-7-(cis-3,5-dimethyl-1-piperazinyl)-6,8-difluoro-1,4-dihydro-4-oxoquinoline-3-carboxylic Acid 5-amino-1-cyclopropyl-7-[(3R,5S)-3,5-dimethylpiperazin-1-yl]-6,8-difluoro-4-oxo-quinoline-3-carboxylic acid 5-amino-1-cyclopropyl-7-[(3S,5R)-3,5-dimethyl-1-piperazinyl]-6,8-difluoro-4-oxo-3-quinolinecarboxylic acid 5-azanyl-1-cyclopropyl-7-[(3S,5R)-3,5-dimethylpiperazin-1-yl]-6,8-bis(fluoranyl)-4-oxidanylidene-quinoline-3-carboxylic acid |
| ZINC000001387673 | oxacephem |
| ZINC000101675810 | fleroxacin 79660-72-3 Megalone Fleroxacino Fleroxacinum Fleroxicin Megalocin Quinodis Fleroxacine 6,8-Difluoro-1-(2-fluoroethyl)-1,4-dihydro-7-(4-methyl-1-piperazinyl)-4-oxo-3-quinolinecarboxylic acid Fleroxacine [French] Fleroxacinum [Latin] Fleroxacino [Spanish] AM 833 AM-833 Ro 23-6240 Fleroxacin (Quinodis) Ro 23-6240/000 UNII-N804LDH51K CCRIS 3972 C17H18F3N3O3 Ro-236240 BRN 4300996 N804LDH51K CHEBI:31810 6,8-difluoro-1-(2-fluoroethyl)-7-(4-methylpiperazin-1-yl)-4-oxo-1,4-dihydroquinoline-3-carboxylic acid NCGC00167558-01 6,8-difluoro-1-(2-fluoroethyl)-7-(4-methylpiperazin-1-yl)-4-oxo-quinoline-3-carboxylic acid 6,8-difluoro-1-(2-fluoroethyl)-7-(4-methylpiperazin-1-yl)-4-oxoquinoline-3-carboxylic acid DSSTox_CID_26714 DSSTox_RID_81846 DSSTox_GSID_46714 3-Quinolinecarboxylic acid, 6,8-difluoro-1-(2-fluoroethyl)-1,4-dihydro-7-(4-methyl-1-piperazinyl)-4-oxo-Megalosin Megalocin (TN) Megalone (TN) 3-Quinolinecarboxylic acid, 1,4-dihydro-6,8-difluoro-1-(2-fluoroethyl)-7-(4-methyl-1-piperazinyl)-4-oxo- SMR000466302 CAS-79660-72-3 FLRX Fleroxacin [USAN:BAN:INN:JAN] SR-01000759379 Fleroxacin (JAN/USAN/INN) Fleroxacin,(S) Fleroxacin [USAN:INN:BAN:JAN] F0646 Ro-23-6240/000 AC1L1FR2 AC1Q3ZU5 CHEMBL6273 SCHEMBL48145 6,8-difluoro-1-(2-fluoroethyl)-7-(4-methyl-1-piperazinyl)-4-oxo-1,4-dihydro-3-quinolinecarboxylic acid KSC492E5H MLS000759401 MLS006010715 AC1Q4N64 DTXSID1046714 CTK3J2253 KS-00000XUW MolPort-003-847-381 XBJBPGROQZJDOJ-UHFFFAOYSA-N HMS2090I08 HMS3715B11 BCP28939 HY-B0414 RKL10075 ZINC3786299 Tox21_112553 ANW-42889 s2469 ZINC03786299 AKOS015907011 Tox21_112553_1 API0003278 CCG-221125 CS-2518 DB04576 KS-5124 RTR-025289 VQ10280 NCGC00167558-02 6,8-Difluoro-1-(2-fluoroethyl)-1,4-dihydro-7-(4-methylpiperazino)-4-oxo-3-quinolinecarboxylic acid AM-833;AM833;AM 833 AN-36581 CC-28438 CPD000466302 SAM001246535 |

FIG. 15B (Continued)

| | |
|---|---|
| | SC-58138 AB1010903 LS-141577 Ro-236240000 TR-025289 FT-0630874 C13179 D01716 Fleroxacin, VETRANAL(TM), analytical standard J10168 AB00640001-02 AB00640001-03 AB00640001_04 660F723 A839732 C-21096 SR-01000759379-2 SR-01000759379-3 6,8-difluoro-1-(2-fluoroethyl)-7-(4-methyl-1-piperazinyl)-4-oxo-3-quinolinecarboxylic acid 6,8-bis(fluoranyl)-1-(2-fluoranylethyl)-7-(4-methylpiperazin-1-yl)-4-oxidanylidene-quinoline-3-carboxylic acid 6,8-Difluoro-1-(2-Fluoroethyl)-1,4-Dihydro-7-(4-Methyl-1-Piperazinyl)-4-Oxo-3-Quinolinecarboxylic Ac 6,8-difluoro-1-(2-fluoroethyl)-1,4-dihydro-7-(4-methyl-1-piperazinyl)-4-oxo-3-quinolinecarboxylic acid- 6,8-Difluoro-1-(2-fluoroethyl)-1,4-dihydro-7-(4-methyl-1-piperazinyl)-4-oxo-3-quinolinecarboxylic acid; Megalone 79660-53-0 |
| ZINC000015134557 | NONE |
| ZINC000238901709 | hetacillin Hetacilina Hetacilline Hetacillinum Phenazacillin 3511-16-8 Versapen UNII-TN4JSC48CV BRL 804 BL-P 804 TN4JSC48CV CHEBI:5683 BRL-804 Etacillina [DCIT] Versapen-k Hetacilina [INN-Spanish] Hetacilline [INN-French] Hetacillinum [INN-Latin] (2S,5R,6R)-6-[(4R)-2,2-dimethyl-5-oxo-4-phenylimidazolidin-1-yl]-3,3-dimethyl-7-oxo-4-thia-1-azabicyclo[3.2.0]heptane-2-carboxylic acid Etacillina EINECS 222-512-5 7-(2,2-dimethyl-5-oxo-4-phenyl-imidazolidin-1-yl)-3,3-dimethyl-6-oxo-2-thia-5-azabicyclo[3.2.0]heptane-4-carboxylic acid N,N'-Isopropylidene-A-amino-benzyl penicillin 6-(2,2-Dimethyl-5-oxo-4-phenyl-1-imidazolidinyl)penicillansaeure Hetacillin [USAN:USP:INN:BAN] Versapen (TN) (2S,%R,6R)-6-(2,2-Dimethyl-5-oxo-4-phenyl-1-imidazolidinyl)-3,3-dimethyl-7-oxo-4-thia-1-azabicyclo(3.2.0)heptan-2-carbonsaeure 6-(2,2-Dimethyl-5-oxo-4-phenyl-1-imidazolidinyl)-3,3-dimethyl-7-oxo-4-thia-1-azabicyclo(3.2.0)heptane-2-carboxylic acid AC1L9EKH Hetacillin (USAN/INN) SCHEMBL34131 CHEMBL1201116 DXVUYOAEDJXBPY-NFFDBFGFSA-N 4-Thia-1-azabicyclo(3.2.0)heptane-2-carboxylic acid, 6-(2,2-dimethyl-5-oxo-4-phenyl-1-imidazolidinyl)-3,3-dimethyl-7-oxo-, (2S-(2alpha,5alpha,6beta(S*)))- BL-P-804 ZINC4102186 HY-16251A AKOS027381814 CS-4870 DB00739 CC-29245 FT-0771485 N.N'-Isopropylidene-A-amino-benzyl penicillin C11729 D01074 C-23897 6beta-[(4R)-2,2-dimethyl-5-oxo-4-phenylimidazolidin-1-yl]penicillanic acid (2S,5R,6R)-6-((R)-2,2-dimethyl-5-oxo-4-phenylimidazolidin-1-yl)-3,3-dimethyl-7-oxo-4-thia-1-azabicyclo[3.2.0]heptane-2-carboxylic acid 6beta-[(4R)-2,2-dimethyl-5-oxo-4-phenylimidazolidin-1-yl]-2,2-dimethylpenam-3alpha-carboxylic acid |
| ZINC000006599408 | carlliiionaln AC1OAHJZ Epitope ID:120377 antibiotic ro 17-2301 SCHEMBL49607 CHEMBL1256767 UIMOJFJSJSIGLV-JNHMLNOCSA-N ZINC3917496 RP18119 Ro 17-2301 (3S,4S)-3-[(Z)-2-(2-amino-4-thiazolyl)-2-[(carboxymethoxy)imino]acetamido]-4-carbamoyloxymethyl-2-oxo-1-azetidinesulphonic acid 2- |

FIG. 15B (Continued)

| | |
|---|---|
| | [(E)-[1-(2-amino-1,3-thiazol-4-yl)-2-[[(2S,3S)-2-(carbamoyloxymethyl)-4-oxo-1-sulfoazetidin-3-yl]amino]-2-oxoethylidene]amino]oxyacetic acid |
| ZINC000013517522 | SULBACTAM 68373-14-8 sulbactam acid Betamaze Sulbactamum Penicillanic Acid Sulfone (2S,5R)-3,3-dimethyl-7-oxo-4-thia-1-azabicyclo[3.2.0]heptane-2-carboxylic acid 4,4-dioxide penicillanic acid 1,1-dioxide UNII-S4TF6I2330 CP 45899 CHEMBL403 CHEBI:9321 S4TF6I2330 Sulbactam;Penicillanic acid sulfone (2S,5R)-3,3-Dimethyl-7-oxo-4-thia-1-azabicyclo(3.2.0)heptane-2-carboxylic acid 4,4-dioxide Sulbactam [INN:BAN] CP-45,899 Sulbactamum [INN-Latin] DSSTox_CID_3605 (2S,5R)-3,3-dimethyl-4,4,7-trioxo-4$l^{6}-thia-1-azabicyclo[3.2.0]heptane-2-carboxylic acid DSSTox_RID_77104 DSSTox_GSID_23605 2,2-dimethyl-1,1-dioxidopenam-3alpha-carboxylic acid EINECS 269-878-2 CP-45899 SMR000387064 Sulbactam free acid CAS-68373-14-8 MFCD00867005 SR-01000760610 C8H11NO5S Penicillanic acid dioxide (2S,5R)-3,3-Dimethyl-7-oxo-4-thia-1-azabicyclo(3.2.0)heptan-2-carbonsaeure 4,4-dioxid Sulbactam,(S) Sulbactam (INN) 4-Thia-1-azabicyclo(3.2.0)heptane-2-carboxylic acid, 3,3-dimethyl-7-oxo-, 4,4-dioxide, (2S-cis)-Sulbactam acid (base) NCGC00159487-06 Sulbactam; Sulbactam Acid SCHEMBL47781 MLS001048859 MLS001304017 Penicillanic acid S,S-dioxide Sodium 1,1-Dioxypenicillanate AC1L2X62 DTXSID1023605 CTK2F3300 FKENQMMABCRJMK-RITPCOANSA-N MolPort-002-499-832 HMS2090E07 HMS2269A12 HMS3651C06 HMS3715B09 ZINC897244 BCP13271 EX-A2000 HY-B0334 KS-00000XO5 Tox21_113642 ANW-43630 BBL033518 BDBM50021954 s1958 STK801889 AKOS004119988 Tox21_113642_1 CCG-221124 CS-2376 DB09324 KS-5198 MCULE-8384465258 Sulbactam, analytical reference material NCGC00159336-02 NCGC00159336-03 NCGC00159336-05 AC-18973 AN-14929 SC-12203 AB0014047 AB2000391 FT-0630775 S0868 ST24049316 A-2179 C07770 D08533 AB00698109-06 AB00698109-08 AB00698109_09 373S148 A836122 SR-01000760610-2 SR-01000760610-3 BRD-K44133266-001-10-0 Z1563146038 Sulbactam, European Pharmacopoeia (EP) Reference Standard Sulbactam, United States Pharmacopeia (USP) Reference Standard (2S,5R)-2-Carboxylato-3,3-dimethyl-7-oxo-4-thia-1-azabicyclo[3.2.0]heptane4,4-dioxide 3,3-Dimethyl-4,4,7-trioxo-4lambda*6*-thia-1-aza-bicyclo[3.2.0]heptane-2-carboxylic acid Sulbactam for peak identification, European Pharmacopoeia (EP) Reference Standard ((2S-cis)-3,3-Dimethyl-7-oxo-4-thia-1-azabicyclo[3,2,0]heptane-2-carboxylic acid 4,4-dioxide ) (2S,5R)-3,3-dimethyl-4,4,7-trioxo-4?^{6}-thia-1-azabicyclo[3.2.0]heptane-2-carboxylic acid (2S,5R)-3,3-Dimethyl-4,4,7-trioxo-4lambda*6*-thia-1-aza-bicyclo[3.2.0]heptane-2-carboxylic acid (2S,5R)-3,3-dimethyl-4,4,7-trioxo-4lambda-thia-1-azabicyclo[3.2.0]heptane-2-carboxylic acid (2S,5R)-3,3-dimethyl-4,4,7-trioxo-4lambda6-thia-1-azabicyclo[3.2.0]heptane-2-carboxylic acid (2S,5R)-3,3-dimethyl-4,4,7-tris(oxidanylidene)-4$l^{6}-thia-1-azabicyclo[3.2.0]heptane-2-carboxylic acid (2S,5R)?-?3,3-?dimethyl-?7-?oxo-?4-?thia-?1-?azabicyclo[3.2.0]?heptane-?2-?carboxylic acid 4,4-dioxide (S)-3,3-Dimethyl-7-(R)-oxo-4,4-dioxo- |

FIG. 15B (Continued)

| | |
|---|---|
| | 4lambda*6*-thia-1-aza-bicyclo[3.2.0]heptane-2-carboxylic acid 0RN 3,3-Dimethyl-4,4,7-trioxo-4lambda*6*-thia-1-aza-bicyclo[3.2.0]heptane-2-carboxylic acid (Sulbactam) 4-Thia-1-azabicyclo[3.2.0]heptane-2-carboxylic acid, 3,3-dimethyl-7-oxo-,4,4-dioxide, (2S, cis) 4-Thia-1-azabicyclo[3.2.0]heptane-2-carboxylicacid, 3,3-dimethyl-7-oxo-, 4,4-dioxide, (2S,5R)- |
| ZINC000100032716 | Enrofloxacin 93106-60-6 Baytril Enrofloxacine CFPQ Enrofloxacino Enrofloxacinum endrofloxicin BAY VP 2674 Bay-Vp-2674 Enrofloxacine [French] Enrofloxacinum [Latin] Enrofloxacino [Spanish] UNII-3DX3XEK1BN Baytril (TN) N-Ethylciprofloxacin ERFX 1-cyclopropyl-7-(4-ethylpiperazin-1-yl)-6-fluoro-4-oxo-1,4-dihydroquinoline-3-carboxylic acid Enrofloxacin [USAN:BAN:INN] HSDB 6952 3DX3XEK1BN Enrofloxacin (USAN/INN) BRN 5307824 1-Cyclopropyl-7-(4-ethyl-1-piperazinyl)-6-fluoro-1,4-dihydro-4-oxo-3-quinolinecarboxylic acid 3-Quinolinecarboxylic acid, 1-cyclopropyl-7-(4-ethyl-1-piperazinyl)-6-fluoro-1,4-dihydro-4-oxo- MLS000069441 C19H22FN3O3 CHEBI:35720 SPFYMRJSYKOXGV-UHFFFAOYSA-N NCGC00018143-04 AK323592 CPD000059011 SMR000059011 1,4-Dihydro-1-cyclopropyl-7-(4-ethyl-1-piperazinyl)-6-fluoro-4-oxo-3-quinolinecarboxylic acid DSSTox_CID_25619 DSSTox_RID_81007 DSSTox_GSID_45619 1-cyclopropyl-7-(4-ethylpiperazin-1-yl)-6-fluoro-4-oxo-quinoline-3-carboxylic acid 1-cyclopropyl-7-(4-ethylpiperazin-1-yl)-6-fluoro-4-oxoquinoline-3-carboxylic acid 1-cyclopropyl-7-(4-ethylpiperazinyl)-6-fluoro-4-oxohydroquinoline-3-carboxylic acid 1-Cyclopropyl-7-(4-ethyl-1-piperazinyl)-6-Fluoro-1,4-Dihydro-4-Oxo-3-Quinolonecarboxylic Acid 1-Cyclopropyl-7-(4-ethyl-1-piperazinyl)-6-fluoro-1,4-dihydro-4-oxoquinoline-3-carboxylic Acid 3-Quinolinecarboxylic acid, 1,4-dihydro-1-cyclopropyl-7-(4-ethyl-1-piperazinyl)-6-fluoro-4-oxo- CAS-93106-60-6 CCRIS 8214 Enrofloxacin [USAN:USP:INN:BAN] AC1L2FPD Opera_ID_1106 MLS001076496 MLS001424169 CHEMBL15511 SCHEMBL149150 SPECTRUM1503721 DTXSID1045619 KS-00000JRV MolPort-001-738-732 HMS2052O09 HMS2090E12 HMS2093I21 HMS2234M11 HMS3373P14 HMS3394O09 HMS3715B18 Pharmakon1600-01503721 ZINC597112 ALBB-030792 BCP15457 HY-B0502 Enrofloxacin, >=98.0% (HPLC) Tox21_110831 BBL009982 DL-384 GA3066 HTS028366 KM3166 MFCD00792463 NSC758616 s3059 SBB012586 STK711109 AKOS005530685 Tox21_110831_1 AC-7614 AN-8830 AN-8831 API0007273 CCG-101102 CS-2699 KS-5010 MCULE-6446074322 NC00352 NSC-758616 NCGC00018143-01 NCGC00018143-02 NCGC00018143-03 NCGC00018143-05 NCGC00021632-03 CC-27475 H734 PD160788 SAM001246856 SC-16013 ST072197 ACM1173021925 SBI-0206725.P001 AB0013220 AB1009369 LS-141553 B1742 E0786 FT-0625663 D02473 AB00384269-16 AB00384269_17 AB00384269_18 Enrofloxacin, VETRANAL(TM), analytical standard 106E606 A844445 C-20873 SR-01000000045 SR-01000000045-3 BRD-K76534306-001-11-0 Enrofloxacin, European Pharmacopoeia (EP) Reference Standard Enrofloxacin, United States Pharmacopeia (USP) Reference Standard 1-cyclopropyl-7-(4-ethyl-1-piperazinyl)-6-fluoro-4-oxo-3- |

FIG. 15B (Continued)

| | |
|---|---|
| | quinolinecarboxylic acid Enrofloxacin for system suitability, European Pharmacopoeia (EP) Reference Standard Enrofloxacin, Pharmaceutical Secondary Standard; Certified Reference Material 1-cyclopropyl-6-fluoro-1,4-dihydro-4-oxo-7-(4-ethyl-1-piperazinyl)-3-quinoline-carboxylic acid 1-cyclopropyl-6-fluoro-1,4-dihydro-4-oxo-7-(4-ethyl-1-piperazinyl)-3-quinolinecarboxylic acid 1-Cyclopropyl-7-(4-ethyl-1-piperazinyl)-6-fluoro-1,4-dihydro-4-oxo-3-quinolinecarboxylic acid, 9CI 1-cyclopropyl-7-(4-ethylpiperazin-1-yl)-6-fluoranyl-4-oxidanylidene-quinoline-3-carboxylic acid |

FIG. 15B (Continued)

SEQUENCE LISTING

```
<160> NUMBER OF SEQ ID NOS: 4

<210> SEQ ID NO 1
<211> LENGTH: 70
<212> TYPE: DNA
<213> ORGANISM: Artificial
<220> FEATURE:
<223> OTHER INFORMATION: Synthetic

<400> SEQUENCE: 1

tagccgggca gatgcccggc aagagagaat tacacttcgg ttaaggtgat attccgggga      60

tccgtcgacc                                                             70


<210> SEQ ID NO 2
<211> LENGTH: 70
<212> TYPE: DNA
<213> ORGANISM: Artificial
<220> FEATURE:
<223> OTHER INFORMATION: Synthetic

<400> SEQUENCE: 2

accttgtaat ctgctggcac gcaaaattac tttcacatgg agtctttatg tgtaggctgg      60

agctgcttcg                                                             70


<210> SEQ ID NO 3
<211> LENGTH: 40
<212> TYPE: DNA
<213> ORGANISM: Artificial
<220> FEATURE:
<223> OTHER INFORMATION: Synthetic

<400> SEQUENCE: 3

tgcaaaataa tatgcaccac gacggcggtc agaaaaataa                            40


<210> SEQ ID NO 4
<211> LENGTH: 40
```

-continued

```
<212> TYPE: DNA
<213> ORGANISM: Artificial
<220> FEATURE:
<223> OTHER INFORMATION: Synthetic

<400> SEQUENCE: 4

gaagcgttac ttcgcgatct gatcaacgat tcgtggaatc                    40
```

IN SILICO DISCOVERY OF EFFECTIVE ANTIMICROBIALS

CROSS REFERENCE TO RELATED APPLICATIONS

This application is a national stage application, filed under 35 U.S.C. § 371, of international application No. PCT/US2020/049830, filed Sep. 9, 2020, which claims the benefit of U.S. Provisional Application No. 62/898,363, filed Sep. 10, 2019, entitled "In Silico Discovery of Effective Antimicrobials," and of U.S. Provisional Application No. 62/971,801, filed Feb. 7, 2020, also entitled "In Silico Discovery of Effective Antimicrobials," The entire contents of the aforementioned applications are incorporated herein by reference.

STATEMENT REGARDING FEDERALLY SPONSORED RESEARCH

The invention was made with government support under Grant No. HDTRA1-15-1-0051, awarded by the Department of Defense. The government has certain rights in the invention.

FIELD OF THE INVENTION

The current disclosure relates to compositions capable of killing or decreasing the growth of microbes, particularly bacteria, and associated methods for discovery and use of antimicrobial compositions.

BACKGROUND OF THE INVENTION

The prevalence of antibiotic resistance is rapidly increasing on a global scale, with broad deleterious impact, particularly for nosocomial infections, among others. Concurrently, the steadily declining productivity in clinically implementing new antibiotics due to the high risk of early discovery and low return on investment has been further exacerbating this problem (E. D. Brown and Wright, 2016). A need therefore exists for new, next-generation antimicrobial/antibiotic agents, and for new approaches capable of substantially decreasing the cost and increasing the rate of antibiotic discovery.

BRIEF SUMMARY OF THE INVENTION

The current disclosure relates, at least in part, to the discovery of multiple structurally distinct compounds each possessing antibacterial activity, identified through construction and use of machine learning-informed in silico modeling performed upon a vast number test compounds that collectively occupy a highly diverse chemical space. One of the compounds, halicin, was discovered to be effective against the bacteria *C. difficile*, pan-resistant *A. baumannii*, carbapenem-resistant Enterobacteriaceae (CRE) species, *M. tuberculosis*, and Methicillin-resistant *Staphylococcus aureus* (MRSA). In addition, fifteen other structurally distinct compounds were discovered and experimentally validated as exhibiting antimicrobial properties. Certain aspects of the instant disclosure also relate to use of in silico model-predicted antimicrobial compounds in pharmaceutical compositions, e.g., for treating a subject having or at risk of developing a bacterial infection (particularly an antibiotic-resistant and/or antibiotic-tolerant bacterial infection), as well as to the methods employed herein to predict the antimicrobial efficacy of surveyed compounds. Advantageously, the empirically validated antimicrobials of the instant disclosure were initially discovered in silico, and then validated in vivo, which has greatly lowered the time and cost of the approach of the instant disclosure, as compared to preclinical screening efforts known in the art.

In one aspect, the instant disclosure provides a pharmaceutical composition for treating or preventing a microbial infection in a subject, the pharmaceutical composition including:

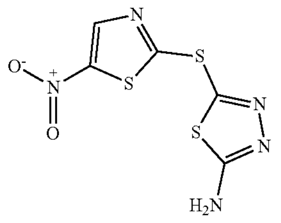

5-[(5-nitro-1,3-thiazol-2-yl)sulfanyl]-1,3,4-thiadiazol-2-amine, or a pharmaceutically acceptable salt or stereoisomer thereof, and a pharmaceutically acceptable carrier.

In one embodiment, the microbial infection is resistant to or tolerant to one or more antimicrobial agents.

In some embodiments, the microbial infection is a bacterial infection. Optionally, the bacterial infection is antibiotic resistant or antibiotic tolerant.

In certain embodiments, the microbial infection is caused by one or more of the following bacteria *Acinetobacter* spp. (including *Acinetobacter baumannii*), *Escherichia* spp. (including *Escherichia coli*), *Campylobacter, Neisseria gonorrhoeae, Providencia* spp., *Enterobacter* spp. (including *Enterobacter cloacae, Enterobacter aerogenes*, and carbpanem-resistant Enterobacteriaceae), *Klebsiella* spp. (including *Klebsiella pneumoniae*), *Salmonella, Pasteurella* spp., *Proteus* spp. (including *Proteus mirabilis*), *Serratia* spp. (including *Serratia marcescens*), *Citrobacter* spp., *Acinetobacter, Morganella morganii, Pseudomonas aeruginosa, Burkholderia pseudomallei, Burkholderia cenocepacia, Helicobacter pylori, Treponema pallidum* and *Hemophilus influenza, Clostridium difficile, Enterococcus* (e.g., *E. faecalis, E. faecium, E. casseliflavus, E. gallinarum, E. raffinosus*, including vanomycin-resistant *Enteroccocus* (VRE)), *Mycobacterium tuberculosis, Mycobacterium avium* complex (including *Mycobacterium intracellulare* and *Mycobacterium avium*), *Mycobacterium smegmatis, Mycoplasms genitalium, Staphylococcus aureus* (including methicillin-resistant *Staphylococcus aureus* (MRSA)), *Streptococcus pyogenes, Streptococcus pneumoniae*, and *Mycobaterium leprae, Listeria* spp. (including *Listeria monocytogenes*); or by one or more of the following fungi: *Aspergillus, Blastomyces, Candida* (including *Candida auris*), *Coccidioides, C. neoformans, C. gattii, Histoplasma, Mucormycetes, Mycetoma, Pneumocytsis jirovencii, Trichophyton, Microsporum, Epiderophyton, Sporothrix, Paracoccidioidomycosis, Talaromycosis*, and *Cryptococcus.*

An additional aspect of the instant disclosure provides a pharmaceutical composition for treating or preventing a microbial infection in a subject that includes a therapeutically effective amount of a compound of FIG. 14, or a pharmaceutically acceptable salt or stereoisomer thereof, and a pharmaceutically acceptable carrier.

Another aspect of the disclosure provides a pharmaceutical composition that includes one or more of the following compounds:

| Name | Compound |
| --- | --- |
| 3-[(5-nitrothiophen-2-yl)methylideneamino]-2-sulfanylidene-1,3-thiazolidin-4-one | 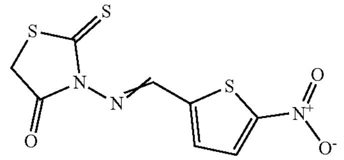 [SMILES: O=C1CSC(=S)N1N=Cc1ccc([N+](=O)[O-])s1] |
| 7-[2-(4-chloro-3-methylpyrazol-1-yl)propanoylamino]-3-[(5-methyl-1,3,4-thiadiazol-2-yl)sulfanylmethyl]-8-oxo-5-thia-1-azabicyclo[4.2.0]oct-2-ene-2-carboxylic acid | 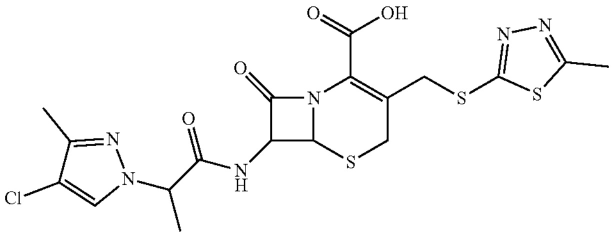 [SMILES: Cc1nnc(SCC2=C(C(=O)O)N3C(=O)C(NC(=O)C(C)n4cc(Cl)c(C)n4)C3SC2)s1] |
| 7-[2-(5-methyl-3-nitropyrazol-1-yl)propanoylamino]-3-[(5-methyl-1,3,4-thiadiazol-2-yl)sulfanylmethyl]-8-oxo-5-thia-1-azabicyclo[4.2.0]oct-2-ene-2-carboxylic acid | 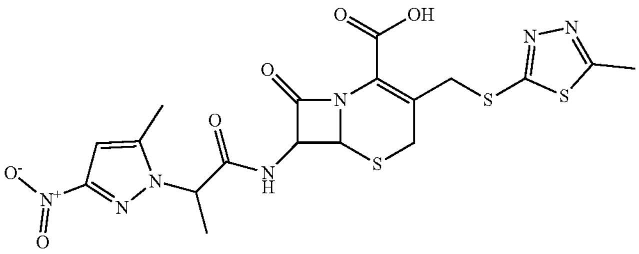 [SMILES: Cc1nnc(SCC2=C(C(=O)O)N3C(=O)C(NC(=O)C(C)n4nc([N+](=O)[O-])cc4C)C3SC2)s1] |
| 7-[[2-(5-aminothiophen-3-yl)-2-methoxyiminoacetyl]amino]-3-[(5-methyl-1,3,4-thiadiazol-2-yl)sulfanylmethyl]-8-oxo-5-thia-1-azabicyclo[4.2.0]oct-2-ene-2-carboxylic acid | 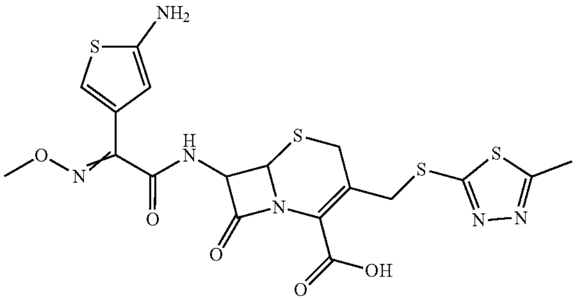 |
| Levofloxacin Q-acid (6,7-difluoro-2-methyl-10-oxo-4-oxa-1-azatricyclo[7.3.1.05,13]trideca-5(13),6,8,11-tetraene-11-carboxylic acid) | 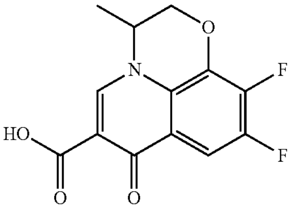 [SMILES: CC1COc2c(F)c(F)cc3c(=O)c(C(=O)O)cn1c23] |
| 7-[4-(1-cyclopropyl-2,5-dioxopyrrolidin-3-yl)piperazin-1-yl]-1-ethyl-6-fluoro-4-oxo-1,4-dihydroquinoline-3-carboxylic acid | 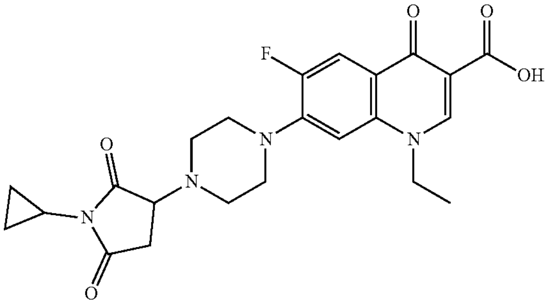 [SMILES: CCn1cc(C(=O)O)c(=O)c2cc(F)c(N3CCN(C4CC(=O)N(C5CC5)C4=O)CC3)cc21] |

-continued

| Name | Compound |
|---|---|
| 1-cyclopropyl-7-[4-[1-(3,5-dichlorophenyl)-2,5-dioxopyrrolidin-3-yl]piperazin-1-yl]-6-fluoro-4-oxoquinoline-3-carboxylic acid | 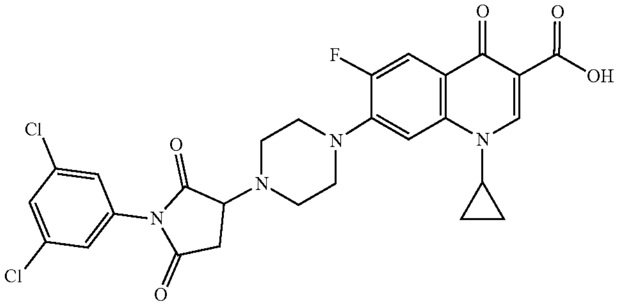 [SMILES: O=C(O)c1cn(C2CC2)c2cc(N3CCN(C4CC(=O)N(c5cc(Cl)cc(Cl)c5)C4=O)CC3)c(F)cc2c1=O] |
| Methyl 2,5-difluoro-4-(4-methylpiperazin-1-yl)benzoate (ZINC000098210492) | 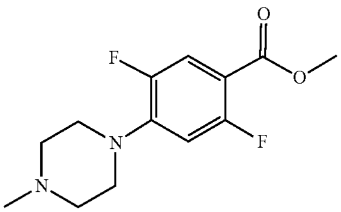 |
| 3-[(Z)-(5-Nitrothiophen-2-yl)methylideneamino]-2-sulfanylidene-1,3-thiazolidin-4-one (ZINC000001735150) | 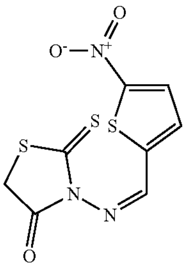 [SMILES: O=C1CSC(=S)N1/N=C\c1ccc([N+](=O)[O-])s1] |
| [Dibromo(nitro)methyl]-[[4-[[4-[[[dibromo(nitro)methyl]-oxoazaniumyl]amino]-1,2,5-oxadiazol-3-yl]diazenyl]-1,2,5-oxadiazol-3-yl]amino]-oxoazanium (ZINC000225434673) | 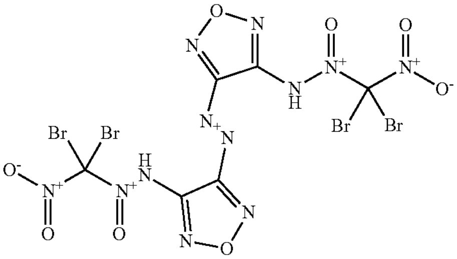 |
| 5-Nitro-2-[(4-methylpiperazin-1-yl)iminomethyl]thiophene (ZINC000019771150) | 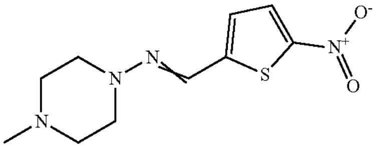 [SMILES: CN1CCN(N=Cc2ccc([N+](=O)[O-])s2)CC1] |
| (5S)-3-(Carbamothioylamino)-4-imino-2-sulfanylidene-1,3-thiazolidine-5-carboxamide (ZINC000004481415) | 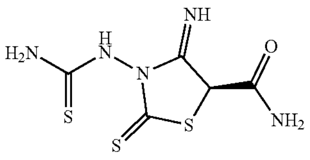 [SMILES: N=C1[C@@H](C(N)=O)SC(=S)N1NC(N)=S] |

-continued

| Name | Compound |
|---|---|
| 5-[(3S,5R)-3,5-Dimethylpiperazin-1-yl]-4-fluoro-2-nitroaniline (ZINC000004623615) | 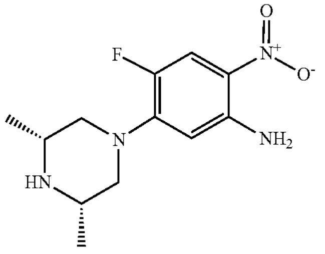 [SMILES: C[C@@H]1CN(c2cc(N)c([N+](=O)[O-])cc2F)C[C@H](C)N1] |
| (3S,3Ar,6aS)-1-methyl-3-thiophen-2-yl-2,3,3a,6a-tetrahydropyrrolo[3,4-c]pyrazole-4,6-dione (ZINC000238901709) | 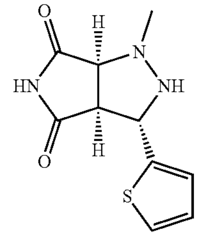 |
| 1-Cyclopropyl-7-[(3S)-3-methyl-4-[(4-sulfamoylphenyl)diazenyl]piperazin-1-yl]-6-nitro-4-oxoquinoline-3-carboxylic acid (ZINCOOO100032716) | 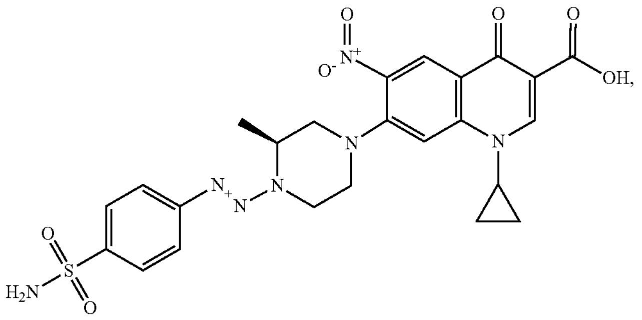 |

or a pharmaceutically acceptable salt or stereoisomer thereof, and a pharmaceutically acceptable carrier.

In embodiments, the pharmaceutical composition is for treatment of a microbial infection in a subject.

Another aspect of the disclosure provides a pharmaceutical composition that includes a compound of FIG. 14, or a pharmaceutically acceptable salt or stereoisomer thereof, and a pharmaceutically acceptable carrier.

An additional aspect of the disclosure provides a method of treating or preventing a microbial infection involving administering to a subject in need thereof a therapeutically-effective amount of a pharmaceutical composition that includes one or more of the following compounds:

| Name | Compound |
|---|---|
| Halicin (5-[(5-nitro-1,3-thiazol-2-yl)sulfanyl]-1,3,4-thiadiazol-2-amine) | 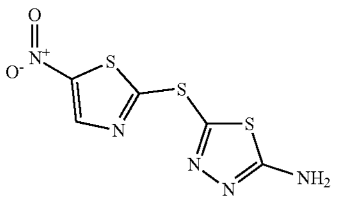 |
| 3-[(5-nitrothiophen-2-yl)methylideneamino]-2-sulfanylidene-1,3-thiazolidin-4-one | 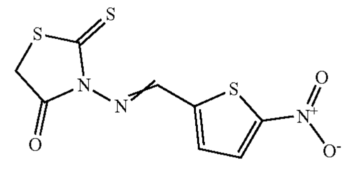 [SMILES: O=C1CSC(=S)N1N=Cc1ccc([N+](=O)[O-])s1] |

-continued

| Name | Compound |
|---|---|
| 7-[2-(4-chloro-3-methylpyrazol-1-yl)propanoylamino]-3-[(5-methyl-1,3,4-thiadiazol-2-yl)sulfanylmethyl]-8-oxo-5-thia-1-azabicyclo[4.2.0]oct-2-ene-2-carboxylic acid | 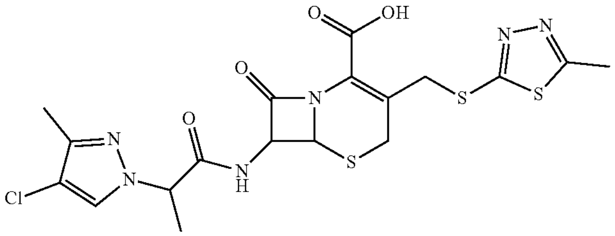 [SMILES: Cc1nnc(SCC2=C(C(=O)O)N3C(=O)C(NC(=O)C(C)n4cc(Cl)c(C)n4)C3SC2)s1] |
| 7-[2-(5-methyl-3-nitropyrazol-1-yl)propanoylamino]-3-[(5-methyl-1,3,4-thiadiazol-2-yl)sulfanylmethyl]-8-oxo-5-thia-1-azabicyclo[4.2.0]oct-2-ene-2-carboxylic acid | 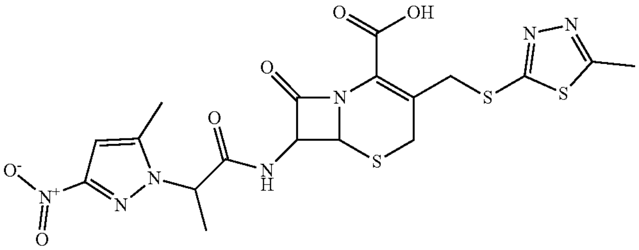 [SMILES: Cc1nnc(SCC2=C(C(=O)O)N3C(=O)C(NC(=O)C(C)n4nc([N+](=O)[O-])cc4C)C3SC2)s1] |
| 7-[[2-(5-aminothiophen-3-yl)-2-methoxyiminoacetyl]amino]-3-[(5-methyl-1,3,4-thiadiazol-2-yl)sulfanylmethyl]-8-oxo-5-thia-1-azabicyclo[4.2.0]oct-2-ene-2-carboxylic acid | 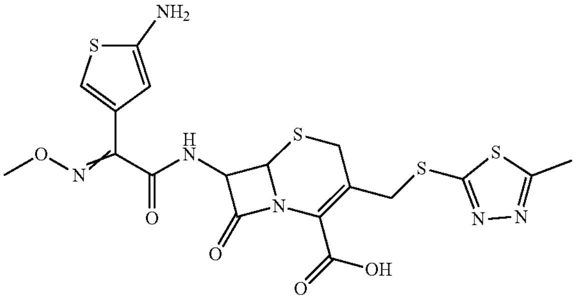 |
| Levofloxacin Q-acid (6,7-difluoro-2-methyl-10-oxo-4-oxa-1-azatricyclo[7.3.1.05,13]trideca-5(13),6,8,11-tetraene-11-carboxylic acid) | 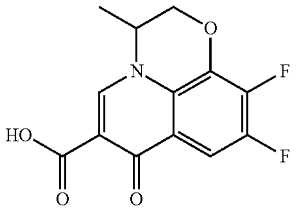 |
| 7-[4-(1-cyclopropyl-2,5-dioxopyrrolidin-3-yl)piperazin-1-yl]-1-ethyl-6-fluoro-4-oxo-1,4-dihydroquinoline-3-carboxylic acid | 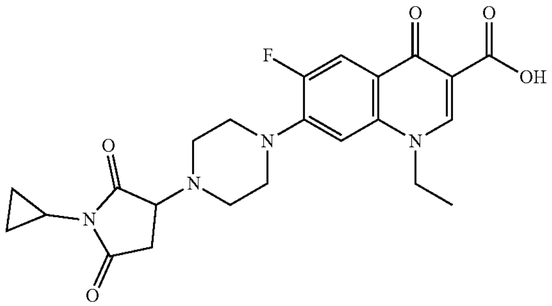 [SMILES: CCn1cc(C(=O)O)c(=O)c2cc(F)c(N3CCN(C4CC(=O)N(C5CC5)C4=O)CC3)cc21] |

-continued

| Name | Compound |
|---|---|
| 1-cyclopropyl-7-[4-[1-(3,5-dichlorophenyl)-2,5-dioxopyrrolidin-3-yl]piperazin-1-yl]-6-fluoro-4-oxoquinoline-3-carboxylic acid | 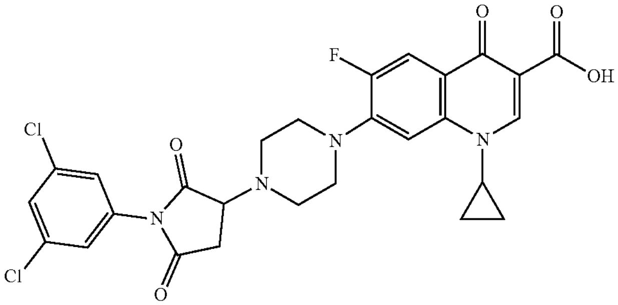 [SMILES: O=C(O)c1cn(C2CC2)c2cc(N3CCN(C4CC(=O)N(c5cc(Cl)cc(Cl)c5)C4=O)CC3)c(F)cc2c1=O] |
| Methyl 2,5-difluoro-4-(4-methylpiperazin-1-yl)benzoate | 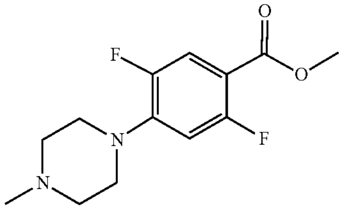 |
| 3-[(Z)-(5-Nitrothiophen-2-yl)methylideneamino]-2-sulfanylidene-1,3-thiazolidin-4-one | 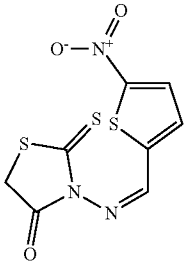 [SMILES: O=C1CSC(=S)N1/N=C\c1ccc([N+](=O)[O-])s1] |
| [Dibromo(nitro)methyl]-[[4-[[4-[[[dibromo(nitro)methyl]-oxoazaniumyl]amino]-1,2,5-oxadiazol-3-yl]diazenyl]-1,2,5-oxadiazol-3-yl]amino]-oxoazanium | 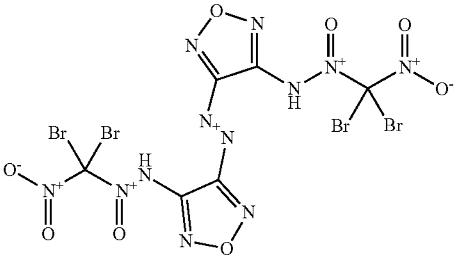 |
| 5-Nitro-2-[(4-methylpiperazin-1-yl)iminomethyl]thiophene | 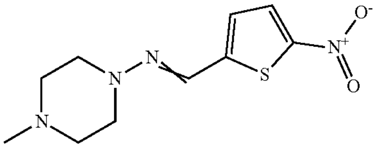 [SMILES: CN1CCN(N=Cc2ccc([N+](=O)[O-])s2)CC1] |
| (5S)-3-(Carbamothioylamino)-4-imino-2-sulfanylidene-1,3-thiazolidine-5-carboxamide | 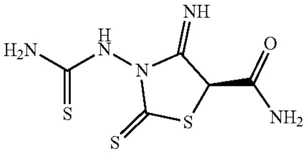 [SMILES: N=C1[C@@H](C(N)=O)SC(=S)N1NC(N)=S] |

-continued

| Name | Compound |
|---|---|
| 5-[(3S,5R)-3,5-Dimethylpiperazin-1-yl]-4-fluoro-2-nitroaniline | 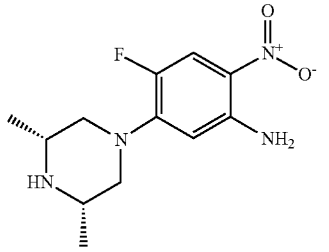 [SMILES: C[C@@H]1CN(c2cc(N)c([N+](=O)[O-])cc2F)C[C@H](C)N1] |
| (3S,3Ar,6aS)-1-methyl-3-thiophen-2-yl-2,3,3a,6a-tetrahydropyrrolo[3,4-c]pyrazole-4,6-dione | 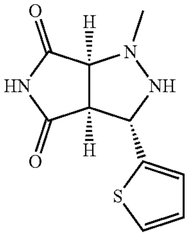 [SMILES: CN1N[C@H](c2cccs2)[C@H]2C(=O)NC(=O)[C@H]21] |
| 1-Cyclopropyl-7-[(3S)-3-methyl-4-[(4-sulfamoylphenyl)diazenyl]piperazin-1-yl]-6-nitro-4-oxoquinoline-3-carboxylic acid | 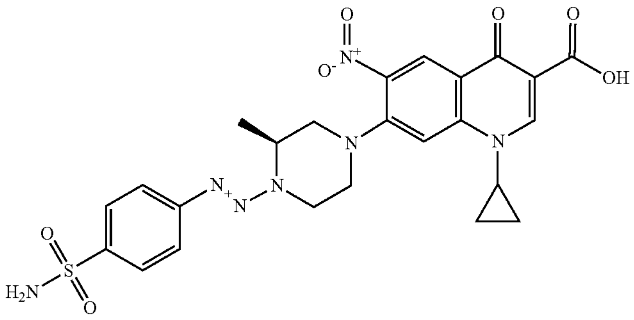 |

Another aspect of the instant disclosure provides a method of treating or preventing a microbial infection involving administering to a subject in need thereof a therapeutically-effective amount of a pharmaceutical composition that includes a compound of FIG. 14.

A further aspect of the instant disclosure provides a method for identifying one or more molecules as predicted to possess antimicrobial activity, the method involving: a) providing a first training set of molecules for which antimicrobial activity is known, where one or more molecules of the first training set of molecules possesses antimicrobial activity; b) applying a machine learning algorithm to the first training set of molecules, thereby generating a machine learning model; c) assessing the ability of the machine learning model to predict antimicrobial activity of the molecules in the first training set; d) applying the machine learning model to a second training set of molecules; e) assessing the ability of the machine learning model to predict antimicrobial activity of the molecules in the second training set; f) altering the machine learning model to integrate results obtained in step (e), thereby generating an updated machine learning model; and g) applying the updated machine learning model to a test set of molecules that includes molecules unknown to the updated machine learning model, thereby identifying one or more molecules of the test set of molecules as a molecule predicted to possess antimicrobial activity.

In one embodiment, the first training set includes about 1500-4000 diverse molecules.

In another embodiment, one or more molecules of the first training set of molecules is known to inhibit the growth of *E. coli.*

In certain embodiments, the second training set includes about 4000 to 10000 molecules. Optionally, the second training set includes about 6100 molecules. Optionally, the second training set includes a drug repurposing library.

In embodiments, the second training set includes an anti-tuberculosis library.

In another embodiment, the test set of molecules includes a selection of molecules of the ZINC15 database.

In some embodiments, the machine learning algorithm includes a directed message passing neural network for predicting molecular properties directly from graph structures of molecules.

In certain embodiments, the machine learning algorithm includes a process that identifies the set of atoms and bonds of each molecule. Optionally, a feature vector is initialized for each atom and bond of each molecule based on the atom and bond features of the molecule.

In another embodiment, the machine learning algorithm applies a series of message passing steps that include aggregating information from neighboring atoms and bonds to build an understanding of local chemistry.

In some embodiments, the machine learning algorithm classifies molecules in a binary manner and generates an output that is 0 or 1 as a prediction of whether the molecules inhibit growth of a microbe. Optionally, the microbe is *E. coli.*

In embodiments, step (b) employs the following Bayesian hyperparameters:

| Hyperparameter | Range | Value |
|---|---|---|
| Number of message-passing steps | [2, 6] | 5 |
| Neural network hidden size | [300, 2400] | 1600 |
| Number of feed-forward layers | [1, 3] | 1 |
| Dropout probability | [0, 0.4] | 0.35 |

In some embodiments, step (f) includes ensembling a group of models (optionally a group of about 5-50 models), where each model is trained on a different random split of data.

In certain embodiments, the method further includes determining antimicrobial activity of a molecule empirically. Optionally, the antimicrobial activity of the molecule is determined by assessing microbe concentration after contact with the molecule. Optionally, an endpoint of $OD_{600}$ of 20% of the starting concentration indicates antimicrobial activity of the molecule. In a related embodiment, a molecule is selected for determining antimicrobial activity of the molecule empirically if a model-generated prediction score for the molecule is greater than about 0.5. Optionally, greater than about 0.6, greater than about 0.7, greater than about 0.8, greater than about 0.9, greater than about 0.95, or greater than about 0.99.

In some embodiments, the test data set includes 50,000,000 or more unique molecules. Optionally, the test data set includes one or more of the following tranches of the ZINC15 dataset: 'AA', 'AB', 'BA', 'BB', 'CA', 'CB', 'CD', 'DA', 'DB', 'EA', 'EB', 'FA', 'FB', 'GA', 'GB', 'H A', 'HB', 'IA', 'IB', 'JA', 'JB', 'JC', 'JD', 'KA', 'KB', 'KC', 'KD', 'KE', 'KF', 'KG', 'KH', 'KI', 'KJ', and 'KK'. Optionally, the test data set includes 107,349,233 unique molecules.

In some embodiments, a molecule is selected for determining antimicrobial activity of the molecule empirically via clustering of molecules into k=between about 10-200 clusters.

In some embodiments, a molecule is prioritized for selection for determining antimicrobial activity of the molecule empirically based upon clinical trial toxicity and/or FDA-approval status of the molecule.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%,6%,5%,4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about." The term "infection" as used herein includes presence of bacteria, in or on a subject, which, if its growth were inhibited or if killing and/or clearing of the bacteria from a site of infection were to occur, would result in a benefit to the subject. The term "infection" therefore refers to any undesirable form of bacteria that is present on or in a subject. As such, the term "infection" in addition to referring to the presence of bacteria also refers to normal flora, which are not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection. The term "therapeutic treatment" refers to administering treatment to a subject already suffering from infection. The term "treat", "treating" or "treatment" as used herein also refers to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibiotic or a pharmaceutical composition is the amount of the antibiotic or the pharmaceutical composition required to produce a desired therapeutic effect as may be judged by clinical trial results, model animal infection studies, and/or in vitro studies (e.g., in agar or broth media). The pharmaceutically effective amount depends on several factors, including but not limited to, the microorganism (e.g., bacteria) involved, characteristics of the subject (for example height, weight, sex, age and medical history), severity of infection and the particular type of the antibiotic used. For prophylactic treatments, a therapeutically or prophylactically effective amount is that amount which would be effective to prevent a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In case of a pharmaceutical composition that comprises more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "antibiotic" as used herein refers to any substance, compound or a combination of substances or a combination of compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibiotic" also refers to compounds capable of decreasing infectivity or virulence of bacteria.

As used herein, the term "antimicrobial agent" refers to any compound known to one of ordinary skill in the art that will inhibit or reduce the growth of, or kill, one or more microorganisms, including bacterial species and fungal species.

The term "growth" as used herein refers to a growth of one or more microorganisms and includes reproduction or population expansion of the microorganism (e.g., bacteria). The term also includes maintenance of on-going metabolic processes of a microorganism, including processes that keep the microorganism alive.

The term, "effectiveness" as used herein refers to ability of a treatment or a composition or one or more pharmaceutically active ingredients to produce a desired biological effect in a subject. For example, the term "antibiotic effectiveness" of a composition or a beta-lactam antibiotic refers to the ability of the composition or the beta-lactam antibiotic to prevent or treat the microbial (e.g., bacterial) infection in a subject.

The term "synergistic" or "synergy" as used herein refers to the interaction of two or more agents so that their combined effect is greater than their individual effects.

By "control" or "reference" is meant a standard of comparison. Methods to select and test control samples are within the ability of those in the art. Determination of statistical significance is within the ability of those skilled in the art, e.g., the number of standard deviations from the mean that constitute a positive result.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the term "tissue" is intended to mean an aggregation of cells, and, optionally, intercellular matter. Typically the cells in a tissue are not free floating in solution and instead are attached to each other to form a multicellular structure. Exemplary tissue types include muscle, nerve, epidermal and connective tissues.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As used herein, the term "machine learning" refers to the use of algorithms and statistical models to computationally perform a task without explicit instructions, instead relying on patterns and inference.

As used herein, the term "ensembling" refers to a process where several copies of the same machine learning model architecture possessing different random initial weights are trained and their predictions are averaged.

Unless specifically stated or obvious from context, as used herein, the term "or" is understood to be inclusive. Unless specifically stated or obvious from context, as used herein, the terms "a", "an", and "the" are understood to be singular or plural.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The embodiments set forth below and recited in the claims can be understood in view of the above definitions.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 2A shows primary screening data for the growth inhibition of *E. coli* by a total of 2,560 molecules from both the FDA-approved drug library (1,760 molecules) and a natural product collection (800 molecules). Shown is the mean of two biological replicates. Red are growth inhibitory molecules; blue are non-growth inhibitory molecules. FIG. 2B shows an ROC-AUC plot demonstrating model performance after training. Dark blue is the mean of six individual trials (cyan). FIG. 2C shows the rank-ordered prediction scores of Broad Repurposing Hub molecules that were not present in the training dataset. FIG. 2D shows that the top 99 predictions from the data shown in FIG. 2C were curated for empirical testing for growth inhibition of *E. coli*. Fifty-one of the 99 molecules were validated as true positives based on a cut-off of $OD_{600}<0.2$. Shown is the mean of two biological replicates. Red are growth inhibitory molecules; blue are non-growth inhibitory molecules. FIG. 2E shows that for all molecules in FIG. 2D, ratios of $OD_{600}$ to prediction score were calculated and these values were plotted based on the prediction score for each corresponding molecule. This demonstrated that a higher prediction score generally correlated with a greater probability of growth inhibition. FIG. 2F demonstrates that the bottom 63 predictions from the data shown in FIG. 2C were also curated for empirical testing for growth inhibition of *E. coli*. Two of the 63 molecules tested as false negatives. Shown is the mean of two biological replicates. Red are growth inhibitory molecules; blue are non-growth inhibitory molecules. FIG. 2G shows the t-SNE of all molecules from the training dataset (blue) and the Broad Repurposing Hub (red), which revealed chemical relationships between these libraries. Halicin is shown as a black and orange circle. FIG. 2H shows the Tanimoto similarity between halicin (structure inset) and each molecule in the de-duplicated training dataset. The Tanimoto nearest neighbor is the antiprotozoal drug nithiamide (score=0.37), with metronidazole being the nearest antibiotic (score=0.21). FIG. 21 shows the growth inhibition of *E. coli* by halicin. Shown is the mean of two biological replicates. Bars denote absolute error. See also FIGS. 7A and 7B, and FIGS. 13 through 15A and 15B.

FIG. 3A demonstrates the observed effect on *E. coli* death in LB media in response to halicin concentration with incubation periods of 1 hour (blue), 2 hours (cyan), 3 hours (green), and 4 hours (red). The initial cell density was ~$10^6$ CFU/ml. Shown is the mean of two biological replicates. Bars denote absolute error. FIG. 3B demonstrates the observed effect on *E. coli* death in PBS in response to halicin concentration with incubation periods of 2 hours (blue), 4 hours (cyan), 6 hours (green), and 8 hours (red). The initial cell density was ~$10^6$ CFU/ml. Shown is the mean of two biological replicates. Bars denote absolute error. FIG. 3C demonstrates the observed effect of *E. coli* persister cell death by halicin after treatment with 10 μg/ml (10×MIC) of ampicillin. Light blue is no halicin. Green is 5×MIC halicin. Blue is 10×MIC halicin. Red is 20×MIC halicin. Shown is the mean of two biological replicates. Bars denote absolute error. FIG. 3D demonstrates the observed minimum inhibitory concentration (MIC) of halicin against *E. coli* strains harboring a range of plasmid-borne, functionally diverse, antibiotic-resistance determinants. The mcr-1 gene was expressed in *E. coli* BW25113. All other resistance genes were expressed in *E. coli* BW25113 AbamBAtolC. Experiments were conducted using two biological replicates. FIG. 3E demonstrates the growth inhibition of *M. tuberculosis* by halicin. Shown is the mean of three biological replicates. Bars denote standard deviation. FIG. 3F demonstrates the observed effect of *M. tuberculosis* death by halicin in 7H9 media at 16 μg/ml (lx MIC). Shown is the mean of three biological replicates. Bars denote standard deviation. FIG. 3G demonstrates the MIC of halicin against 36-strain panels of Carbapenem resistant Enterobacteriaceae (CRE) isolates (green), *A. baumannii* isolates (red), and *P. aeruginosa* isolates (blue). Experiments were conducted using two biological replicates. Halicin exhibited robust activity against *M. tuberculosis*, CRE, and *A. baumannii*. See also FIGS. 8A-8M.

FIG. 4A demonstrates the evolution of resistance to halicin (blue) or ciprofloxacin (red) in *E. coli* after 30 days of serial passaging in liquid LB medium in the presence of varying concentrations of antibiotic. Cells were passaged every 24 hours. FIG. 4B demonstrates the whole transcriptome hierarchical clustering of the relative gene expression of *E. coli* treated with halicin at 4× the MIC for 1 hour, 2 hours, 3 hours, and 4 hours. Shown is the mean transcript abundance of two biological replicates of halicin-treated cells relative to untreated control cells on a $\log_2$-fold scale. Genes enriched in cluster b are involved in locomotion ($p \approx 10^{-20}$); genes enriched in cluster c are involved in ribosome structure/function ($p \approx 10^{-30}$); and genes enriched in cluster d are involved in membrane protein complexes ($p \approx 10^{-15}$). Clusters a, e, and f were not highly enriched for specific biological functions. In the growth curve, blue represents untreated cells; red represents halicin-treated cells. FIG. 4C demonstrates observed halicin induced growth inhibition of *E. coli* in pH-adjusted media. Shown is the mean of two biological replicates. Bars denote absolute error. FIG. 4D demonstrates $DiSC_3(5)$ relative fluorescence intensity in *E. coli* upon exposure to polymyxin B (PMB), halicin at varying concentrations, and DMSO. Halicin-induced decreases in fluorescence intensity indicated that halicin dissipated the ΔpH component of the proton motive force. FIG. 4E illustrates growth inhibition checkerboards of halicin in combination with tetracycline (left), kanamycin (center), and $FeCl_3$ (right). Chemical interactions between halicin and both tetracycline and kanamycin were consistent with ΔpH dissipation. The interaction of halicin and $FeCl_3$ in growth inhibition assays suggested that halicin sequestered $FeCl_3$ in the *E. coli* cell, forming a complex that inhibited growth via ΔpH dissipation. The observed synergy with $FeCl_3$ indicated that complexation of halicin and $Fe^{3+}$ could underlie the observed ΔpH dissipation. Dark blue represents greater growth. See also FIGS. 9A-9H.

FIG. 5A shows observed growth inhibition of pan-resistant *A. baumannii* CDC 288 by halicin in vitro. Shown is the mean of two biological replicates. Bars denote absolute error. FIG. 5B shows the observed growth inhibition of *A. baumannii* CDC 288 in PBS in the presence of varying concentrations of halicin after 2 hours (blue), 4 hours (cyan), 6 hours (green), and 8 hours (red). The initial cell density was ~$10^8$ CFU/ml. Shown is the mean of two biological replicates. Bars denote absolute error. FIG. SC shows that in a wound infection model, mice were infected with *A. baumannii* CDC 288 for 1 hour and treated with either vehicle (green; 0.5% DMSO; n=6) or halicin (blue; 0.5% w/v; n=6) periodically over 24 hours. Bacterial load from the wound tissue after treatment was determined by selective plating. Black lines represent the geometric mean of the bacterial load for each treatment group. FIG. SD demonstrates halicin-induced growth inhibition of *C. difficile* 630 in vitro. Shown is the mean of two biological replicates. Bars denote absolute error. FIG. 5E shows the experimental design for *C. difficile* infection and treatment. FIG. 5F shows the bacterial load of *C. difficile* 630 in feces of infected mice after treatment. Metronidazole (red; 50 mg/kg; n=6) did not result in enhanced rates of clearance relative to vehicle controls (green; 10% PEG 300; n=7). Halicin-treated mice (blue; 15 mg/kg; n=4) displayed sterilization beginning at 72 hours after treatment, with 100% of mice being free of infection at 96 hours after treatment. Lines represent the geometric mean of the bacterial load for each treatment group. See also FIGS. 10A and 10B.

FIGS. 6A-6I demonstrate the prediction accomplished herein of new antibiotic candidates from chemical libraries of heretofore unprecedented scale. FIG. 6A shows tranches of the ZINC15 database, colored based on the proportion of hits from the original training dataset of 2,335 molecules within each tranche. Darker blue tranches have a higher proportion of molecules that are growth inhibitory against *E. coli*. Yellow tranches are those selected for predictions. FIG. 6B shows a histogram of the number of ZINC15 molecules from selected tranches within a corresponding prediction score range. FIG. 6C shows the prediction scores and Tanimoto nearest neighbor antibiotic of the 23 predictions that were empirically tested for growth inhibition. Yellow circles represent those molecules that displayed detectable growth inhibition of at least one pathogen. Grey circles represent inactive molecules. ZINC numbers of active molecules are shown on the right. FIG. 6D demonstrates the MIC values (g/ml) of eight predictions from the ZINC15 database against *E. coli* (EC), *S. aureus* (SA), *K pneumoniae* (KP), *A. baumannii* (AB), and *P. aeruginosa* (PA). Blank regions represent no detectable growth inhibition at 128 μg/ml. Structures are shown in the same order (top to bottom) as their corresponding ZINC numbers in FIG. 6C. FIG. 6E shows the MIC of ZINC000100032716 (1-Cyclopropyl-7-[(3S)-3-methyl-4-[(4-sulfamoylphenyl)diazenyl]piperazin-1-yl]-6-nitro-4-oxoquinoline-3-carboxylic acid) against *E. coli* strains harboring a range of plasmid-borne, functionally diverse, antibiotic-resistance determinants. The mcr-1 gene was expressed in *E. coli* BW25113. All other resistance genes were expressed in *E. coli* BW25113 AbamBAtolC. Experiments were conducted with two biological replicates. Note the minor increase in MIC in the presence of aac(6')-Ib-cr. FIG. 6F shows the shows the MIC of ZINC000225434673 ([Dibromo(nitro)methyl]-[[4-[[4-[[[dibromo(nitro)methyl]-oxoazaniumyl]amino]-1,2,5-oxadiazol-3-yl]diazenyl]-1,2,5-oxadiazol-3-yl]amino]-oxoazanium) against *E. coli* strains harboring a range of plasmid-borne, functionally diverse, antibiotic-resistance determinants. The mcr-1 gene was expressed in *E. coli* BW25113. All other resistance genes were expressed in *E. coli* BW25113 AbamBAtolC. Experiments were conducted with two biological replicates. FIG. 6G shows the effect on *E. coli* cell death in LB media in the presence of varying concentrations of ZINC000100032716 after 0 hr (blue) and 4 hr (red). The initial cell density is ~$10^6$ CFU/ml. Shown is the mean of two biological replicates. Bars denote absolute error. FIG. 6H shows the effect on *E. coli* cell death in LB media in the presence of varying concentrations of ZINC000225434673 after 0 hr (blue) and 4 hr (red). The initial cell density is ~$10^6$ CFU/ml. Shown is the mean of two biological replicates. Bars denote absolute error.

FIG. 6I shows the t-SNE of all molecules from the primary training dataset (blue), the Broad Repurposing Hub (red), the WuXi anti-tuberculosis library (green), the ZINC15 molecules with prediction scores>0.9 (pink), false positive predictions (grey), and true positive predictions (yellow), highlighting relationships between these discrete sets of molecules. See also FIGS. 11A-11M and FIGS. 14 through 15A and 15B.

FIG. 7A shows primary screening data for observed growth inhibition of *E. coli* by 2,560 molecules within the FDA-approved drug library supplemented with a natural product collection. Red are growth inhibitory molecules; blue are non-growth inhibitory molecules. FIG. 7B shows rank-ordered de-duplicated screening data containing 2,335 molecules. Shown is the mean of two biological replicates. Red are growth inhibitory molecules; blue are non-growth inhibitory molecules.

FIG. 8A shows the observed death of *E. coli* in LB media in the presence of varying concentrations of halicin after 1 hour (blue), 2 hours (cyan), 3 hours (green), and 4 hours (red) with an initial cell density of ~$10^8$ CFU/ml. Shown is the mean of two biological replicates. Bars denote absolute error. FIG. 8B shows the observed death of *E. coli* in LB media in the presence of varying concentrations of halicin after 1 hour (blue), 2 hours (cyan), 3 hours (green), and 4 hours (red) with an initial cell density of ≈$10^7$ CFU/ml. Shown is the mean of two biological replicates. Bars denote absolute error. FIG. 8C shows the observed death of *E. coli* in PBS as a function of halicin concentration after 2 hours (blue), 4 hours (cyan), 6 hours (green), and 8 hours (red) incubation with an initial cell density of ≈$10^8$ CFU/ml. Shown is the mean of two biological replicates. Bars denote absolute error. FIG. 8D shows the observed death of *E. coli* in PBS as a function of halicin concentration after 2 hours (blue), 4 hours (cyan), 6 hours (green), and 8 hours (red) incubation, as in FIG. 8C with an initial cell density of ≈$10^7$ CFU/ml. Shown is the mean of two biological replicates. Bars denote absolute error. FIG. 8E shows the observed death of *E. coli* in PBS as a function of ampicillin concentration after 2 hours (blue), 4 hours (cyan), 6 hours (green), and 8 hours (red) with an initial cell density of $10^8$ CFU/ml. Shown is the mean of two biological replicates. Bars denote absolute error. FIG. 8F shows the observed death of *E. coli* in PBS as a function of ampicillin concentration after 2 hours (blue), 4 hours (cyan), 6 hours (green), and 8 hours (red) with an initial cell density of ≈$10^7$ CFU/ml. Shown is the mean of two biological replicates. Bars denote absolute error. FIG. 8G shows the observed death of *E. coli* in PBS as a function of ampicillin concentration after 2 hours (blue), 4 hours (cyan), 6 hours (green), and 8 hours (red) with an initial cell density of =$10^6$ CFU/ml. Shown is the mean of two biological replicates. Bars denote absolute error. FIG. 8H shows the observed death of *E. coli* in LB media as a function of ampicillin concentration after 1 hour (blue), 2 hours (cyan), 3 hours (green), and 4 hours (red) with an initial cell density of ≈$10^8$ CFU/ml. Shown is the mean of two biological replicates. Bars denote absolute error. FIG. 8I shows the observed death of. *coli* in LB media as a function of ampicillin concentration after 1 hour (blue), 2 hours (cyan), 3 hours (green), and 4 hours (red) with an initial cell density of ≈$10^7$ CFU/ml. Shown is the mean of two biological replicates. Bars denote absolute error. FIG. 8J shows the observed death of *E. coli* in LB media as a function of ampicillin concentration after 1 hour (blue), 2 hours (cyan), 3 hours (green), and 4 hours (red) with an initial cell density of $10^6$ CFU/ml. Shown is the mean of two biological replicates. Bars denote absolute error. FIG. 8K shows the observed MIC of various antibiotics against *E. coli* strains harboring a range of plasmid-borne, functionally diverse, antibiotic-resistance determinants. The mcr-1 gene was expressed in *E. coli* BW25113. All other resistance genes were expressed in *E. coli* BW25113 AbamBAtolC. "WT" indicates wildtype *E. coli*. "R" indicates *E. coli* harboring a resistance plasmid. "Chlor" indicates chloramphenicol. "Amp" indicates ampicillin. "Gent" indicates gentamicin. "Levo" indicates levofloxacin. Experiments were conducted with two biological replicates. FIG. 8L demonstrates observed growth inhibition of wildtype *E. coli* (blue) and ΔnfsAΔnfsB *E. coli* (green) by halicin. Shown is the mean of two biological replicates. Bars denote absolute error. FIG. 8M demonstrates observed growth inhibition of wildtype *E. coli* (blue) and ΔnfsAΔnfsB *E. coli* (green) by nitrofurantoin. Shown is the mean of two biological replicates. Bars denote absolute error.

FIG. 9A shows the evolution of spontaneous resistance that occurred against halicin (top) and ciprofloxacin (bottom). *E. coli* BW25113 (~$10^9$ CFU) was plated onto non-selective or selective media and incubated for 7 days prior to imaging. Re-streaking of colonies was done into fresh non-selective or selective media. 20 μg/ml halicin and 20 ng/ml ciprofloxacin, respectively, were used for suppressor mutant evolution. Note that the colonies that emerged at the edge of halicin-supplemented plates after 7 days grew well on LB non-selective media, but did not re-streak onto halicin-supplemented media. All seven selected ciprofloxacin-resistant colonies grew on both non-selective and ciprofloxacin-supplemented media. FIG. 9B shows whole transcriptome hierarchical clustering of *E. coli* treated with halicin at 0.25×MIC for 1 hour, 2 hours, 3 hours, and 4 hours. Shown is the mean transcript abundance of two biological replicates of halicin-treated cells relative to untreated control cells on a $log_2$-fold scale. In the growth curve, blue represents untreated cells; red represents halicin-treated cells. FIG. 9C shows whole transcriptome hierarchical clustering of *E. coli* treated with halicin at 1×MIC for 1 hour, 2 hours, 3 hours, and 4 hours. Shown is the mean transcript abundance of two biological replicates of halicin-treated cells relative to untreated control cells on a log 2-fold scale. In the growth curve, blue represents untreated cells; red represents halicin-treated cells. FIG. 9D shows the growth inhibition by halicin against *S. aureus* USA300 in pH-adjusted media. Shown is the mean of two biological replicates. Bars denote absolute error. FIG. 9E shows the growth inhibition by halicin against *E. coli* in LB (blue) or LB supplemented with 25 mM sodium bicarbonate (red), which dissipates the ΔpH component of the proton motive force. FIG. 9F at left shows the $DiSC_3(5)$ fluorescence intensity in *S. aureus* upon exposure to valinomycin (64 g/ml; known to dissipate Δψ), nigericin (16 μg/ml; known to dissipate ΔpH), halicin (4 μg/ml), or DMSO. At right is a zoom inset of the time of treatment addition. Halicin induced initial fluorescence changes that appeared more similar to nigericin than to valinomycin, suggesting that halicin dissipated the ΔpH component of the proton motive force. The right panel is a magnified image of the drug-induced decrease in fluorescence shown in the left. FIG. 9G shows the $DiSC_3(5)$ fluorescence in *S. aureus* upon exposure to valinomycin, nigericin, halicin, or DMSO after 4 hour of exposure. FIG. 9H shows observed growth inhibition by daptomycin (left) and halicin (right) against *S. aureus* RN4220 (blue) or a daptomycin-resistant RN4220 strain (Δdsp1; red) in LB media. The mean of two biological replicates is shown. Bars denote absolute error.

FIG. 10A shows the death of *A. baumannii* in PBS as a function of halicin concentration after 2 hours (blue), 4 hours (cyan), 6 hours (green), and 8 hours (red). The initial cell density was ≈$10^7$ CFU/ml. Shown is the mean of two biological replicates. Bars denote absolute error. FIG. JOB shows the death of *A. baumannii* in PBS as a function of halicin concentration after 2 hours (blue), 4 hours (cyan), 6 hours (green), and 8 hours (red). The initial cell density was ≈$10^6$ CFU/ml. Shown is the mean of two biological replicates. Bars denote absolute error.

FIG. 11A shows rank-ordered prediction scores of WuXi anti-tuberculosis library molecules. The overall low prediction scores are notable. FIG. 11B shows the top 200 predictions from the data shown in FIG. 11A curated for empirical testing of growth inhibition of *E. coli*. None were validated as true positives. Shown is the mean of two biological replicates. FIG. 11C shows the bottom 100 predictions from the data shown in FIG. 11A curated for empirical testing of growth inhibition of *E. coli*. None were validated as growth inhibitory. Shown is the mean of two biological replicates. FIGS. 11D to 11M show the growth inhibition by the eight positively validated ZINC15 predictions (from the 23 predictions curated based on both prediction score and Tanimoto similarity, which were empirically tested for growth inhibition), against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11D shows the growth inhibition with ZINC000098210492 against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11E shows the growth inhibition with ZINC000019771150 against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11F shows the growth inhibition of with ZINC000225434673 against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11G shows the growth inhibition with ZINC000004481415 against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11H shows the growth inhibition with ZINC000001735150 against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11 shows the growth inhibition of with ZINC000004623615 against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11J shows the growth inhibition with ZINC000238901709 against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11K shows the growth inhibition with ZINC000100032716 against *E. coli* (blue), *S. aureus*(green), *K. pneumoniae* (purple), *A. baumannii* (pink), and *P. aeruginosa* (red) in LB media. Shown is the mean of two biological replicates. Bars denote absolute error. FIG. 11L shows the growth inhibition by ZINC000100032716 against *E. coli* BW25113 (blue) or a ciprofloxacin-resistant gyrA S83A mutant of BW25113 (red). Shown is the mean of two biological replicates. Bars denote absolute error. FIG. 11M shows the growth inhibition by cipfrofloxacin against. *coli* BW25113 (blue) or a ciprofloxacin-resistant gyrA S83A mutant of BW25113 (red). Shown is the mean of two biological replicates. Bars denote absolute error. Note the 4-fold smaller change in MIC with ZINC000100032716 between the gyrA mutant and wildtype *E. coli* relative to ciprofloxacin.

FIG. 12A shows the prediction scores and Tanimoto nearest neighbor antibiotic of the 15 predictions generated based on prediction score alone that were empirically tested for growth inhibition of *E. coli*. Stars indicate molecules that inhibited the growth of. *coli*. Circles represent inactive molecules that were not observed to inhibit *E. coli* growth. Compounds represented by red circles are varied in structure. FIG. 12G shows the structures and corresponding growth inhibitory activities of the seven active predictions from the ZINC15 database. Shown are the MICs of each compound for each bacterial species in μg/ml. "EC" is *E. coli*; "SA" is MRSA; "KP" is *K. pneumoniae*; "AB" is *A. baumannii*; "PA" is *P. aeruginosa*. Blanks represent instances where the MIC was greater than 128 μg/ml. FIG. 12H shows the t-SNE of all molecules from the primary training dataset (blue), the Broad Repurposing Hub (red), the WuXi anti-tuberculosis library (green), the ZINC15 molecules with prediction scores>0.9 (pink), the eight false positive predictions (grey), and the seven true positive predictions (black and orange), demonstrating the relationships between these discrete sets of molecules. See also FIGS. 11A-11C above and FIG. 14. FIGS. 12I to 12W show the growth inhibition of *E. coli* by the 15 compounds possessing the highest prediction scores of the ZINC15 database. FIG. 121 shows the growth inhibition of *E. coli* with compound 1 of the predicted compounds. Shown is the mean of two biological replicates. Bars denote absolute error. Color denotes structural relationships described in FIG. 6I. FIG. 12W shows the growth inhibition of *E. coli* with compound 15 of the predicted compounds. Shown is the mean of two biological replicates. Bars denote absolute error. Color denotes structural relationships described in FIG. 6I.

FIG. 13 shows the rank-ordered prediction scores, Broad identifier, compound name, compound SMILES string, and clinical toxicity score (where a low score indicates less toxicity) of molecules from the Drug Repurposing Hub that were not found in the training dataset. FIG. 13 supports the data in FIG. 2 above.

FIG. 14 shows the compound SMILEs string, Zinc Index, and prediction score of molecules with prediction scores greater than 0.7. FIG. 14 supports the data in FIG. 6 above.

FIGS. 15A and 15B show the ZINC 15 prediction molecules (curated based on prediction score and Tanimoto score) used for empirical validation. FIG. 15A shows the ZINC Index, SMILES string, prediction score, antibiotics neighbor, Tanimoto score to neighbor, and clinical toxicity score (where a low score indicates less toxicity) of the molecules used for empirical validation. FIG. 15B shows the ZINC Index of the molecule tested and the names or other identifiers of the neighbor molecule referenced in FIG. 15A. FIGS. 15A and 15B support the data in FIG. 6 above.

DETAILED DESCRIPTION OF THE INVENTION

Figure 1:
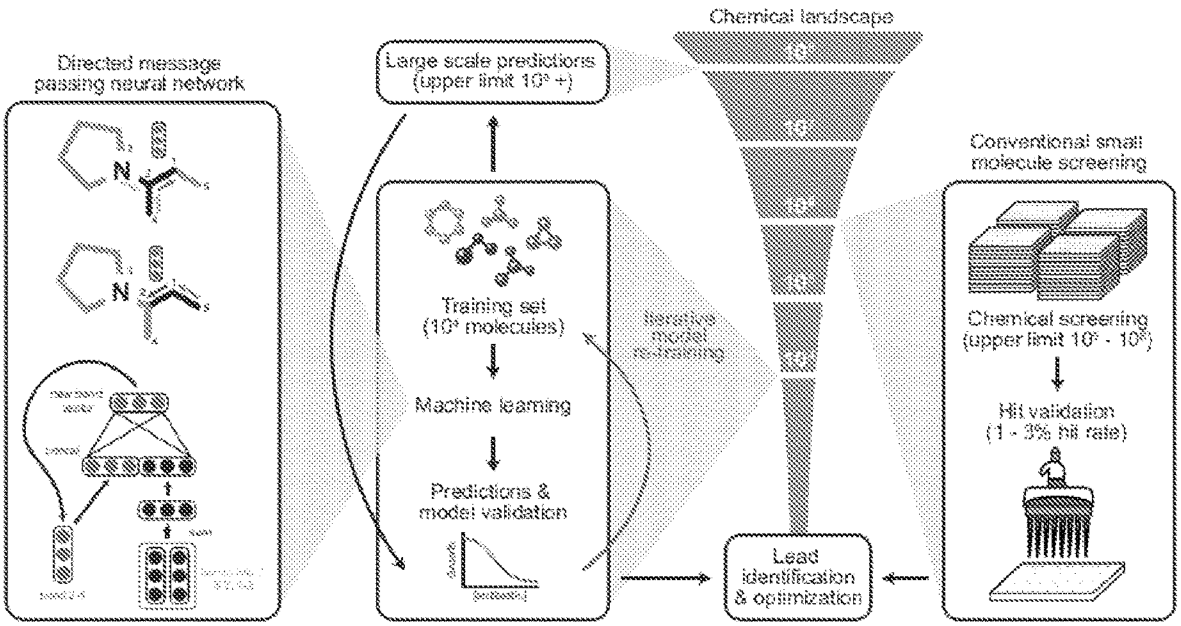
FIG. 1 demonstrates the instant disclosure's approach to utilizing machine learning in antibiotic discovery. Modem approaches to antibiotic discovery often include screening large chemical libraries for those that elicit a phenotype of interest directly on a sample. These screens, which are upper bounded by hundreds of thousands to a few million molecules, are expensive, time consuming, and can fail to capture an expansive breadth of chemical space. In contrast, machine learning approaches enable the rapid and inexpensive exploration of vast chemical spaces in silico. Briefly, aspects of the instant disclosure's deep neural network model work by building a molecular graph based on a specific property, in the instant case as currently exemplified the inhibition of the growth of *E. coli*, using a directed message passing neural network. The neural network model presented in the instant disclosure was trained using a collection of a few thousand diverse molecules including those known to inhibit the growth of *E. coli*. The model was then augmented with a set of molecular features, hyperparameter optimization, and ensembling. Next, the model was applied to multiple discrete chemical libraries comprising >107 million molecules, to identify potential lead compounds with activity against *E. coli*. The candidates were ranked according to the model's predicted score, and a list of promising candidates was selected based on a pre-defined threshold.

The current disclosure relates, at least in part, to the discovery of in silico methods that use machine learning to achieve robust and accurate predictive identification of effective antimicrobial compounds from compound databases, and to the specific compounds that have been identified through use of the instant methods (and in a number of instances empirically validated). One compound identified by the machine learning-informed in silico modeling of the instant disclosure, herein renamed "halicin", was discovered to be effective against the bacteria *C. difficile* and pan-resistant *A. baumannii*. In addition, fifteen other compounds, eight of which are structurally distinct from other antibiotics, were discovered and experimentally validated to possess antimicrobial properties. Certain aspects of the instant disclosure relate to use of compounds predicted herein to possess antimicrobial activity in pharmaceutical compositions, e.g., for treating a subject having or at risk of developing a bacterial infection (particularly an antibiotic-resistant and/or antibiotic-tolerant bacterial infection). Advantageously, the empirically validated antimicrobials disclosed herein were initially discovered in silico, and then validated in vivo, which has greatly lowered the time and cost of the approach of the instant disclosure, as compared to preclinical screening efforts known in the art.

The dissemination of antibiotic-resistance determinants threatens the stability of healthcare systems worldwide. In particular, due to the rapid emergence of antibiotic-resistant bacteria, there is a growing need to discover new antibiotics. To increase the rate at which antibiotics can be discovered, a deep neural network was trained herein to be capable of predicting molecules with antibacterial activity. Model-directed predictions were performed herein upon multiple chemical libraries and a first molecule—termed "halicin" herein (a molecule of the Drug Repurposing Hub)—that displayed bactericidal activity against a wide phylogenetic spectrum of pathogens (including *Mycobacterium tuberculosis* and carbapenem-resistant Enterobacteriaceae) was discovered. Excitingly, halicin effectively treated Clostridioides *difficile* and pan-resistant *Acinetobacter baumannii* infections in murine models. Additionally, from a discrete set of 23 empirically tested antibiotic predictions obtained from a library comprising more than 107 million molecules (curated from the ZINC15 database), the model of the instant disclosure identified fifteen molecules as possessing antibiotic activity, including three new β-lactams, three new fluoroquinolones, and remarkably, nine novel compounds structurally distant from known antibiotics. Altogether, the instant disclosure (1) has identified a number of molecules not previously identified as antibiotics as in fact possessing antibacterial efficacy, (2) has provided a machine learning-enhanced process for antibiotic and/or antimicrobial compound discovery, and (3) the results presented herein highlight the significant impact that machine learning is capable of exerting towards discovering new antibiotics, by increasing the true positive rate of lead compound discovery and decreasing the cost of preclinical screening. Among other useful discoveries, the instant disclosure therefore highlights the utility of deep learning approaches to expand the antibiotic arsenal through the discovery of structurally novel antibacterial molecules.

Since the discovery of penicillin, antibiotics have become a cornerstone of modern medicine. However, the continued efficacy of these essential drugs—of which there are on the order of a couple hundred in clinical use—is uncertain due to the persistent global dissemination of antibiotic-resistance determinants. Moreover, the decreasing development of new antibiotics in the private sector that has resulted from a lack of economic incentives is exacerbating this already dire problem (E. D. Brown and Wright, 2016); only ten antibiotics, nearly all from existing classes, have been approved by the FDA since 2014 (PEW, 2019). Indeed, without immediate action to discover and develop new antibiotics, it has been projected that deaths attributable to resistant infections will reach 10 million per year by 2050 (O'Neill, 2014).

Historically, antibiotics were discovered largely through screening soil-dwelling microbes for secondary metabolites that prevented the growth of pathogenic bacteria in vitro (Clardy et al., 2006; Wright, 2017). This approach resulted in the majority of clinically used classes of antibiotics, including β-lactams, aminoglycosides, tetracyclines, polymyxins, and glycopeptides, among others. Semi-synthetic derivatives of these scaffolds maintained a viable clinical arsenal of antibiotics by increasing potency, decreasing toxicity, and sidestepping pre-existing resistance determinants. Furthermore, entirely synthetic antibiotics of the structurally diverse pyrimidine, quinolone, oxazolidinone, and sulfa classes have found prolonged clinical utility, and continue to be chemically optimized for the aforementioned biological properties.

Unfortunately, the discovery of new antibiotics has become increasingly difficult. Indeed, natural product discovery has been plagued by the de-replication problem, wherein the same molecules are being repeatedly discovered from discrete species that inhabit similar ecological niches (Cox et al., 2017). Moreover, given the rapid expansion of chemical spaces that are accessible by the derivatization of complex scaffolds (Ortholand and Ganesan, 2004), engineering next-generation versions of existing antibiotics can result in substantially more failures than leads. With these challenges, many contemporary antibiotic discovery programs have turned to screening large synthetic chemical libraries generated by high-throughput combinatorial synthesis (Tommasi et al., 2015). However, these libraries, which can contain hundreds of thousands to a few million molecules, are often prohibitively costly to curate, limited in chemical diversity, and fail to reflect the chemistry that is inherent to antibiotic molecules (D. G. Brown et al., 2014). Since the implementation of high-throughput screening in the late 1980s, no new clinical antibiotics have been discovered using this approach.

Clearly, novel approaches to antibiotic discovery have heretofore been critically needed, to increase the rate at which new antibiotics are identified and simultaneously decrease the associated cost of early lead discovery. As disclosed and applied herein, recent advancements in machine learning (Camacho et al., 2018) have rendered the antibiotic discovery field ripe for the application of algorithmic solutions for molecular property prediction, to identify novel structural classes of antibiotics, as well as new analogs of existing scaffolds. Indeed, adopting methodologies that allow early drug discovery to be performed largely in silico, as in certain approaches disclosed herein, enables the exploration of vast chemical spaces that has been beyond the reach of current experimental approaches due to prohibitive cost, labor, and time constraints.

The concept of analytical exploration in drug design has been previously described: decades of prior work in chemoinformatics has developed models for molecular property prediction, including both bioactivity and ADME (absorption, distribution, metabolism, and excretion) properties (Mayr et al., 2018; Wu et al., 2017). However, the accuracy of these models has heretofore been insufficient to substantially change the traditional drug discovery pipeline. With recent algorithmic advancements in modelling neural network-based molecular representations, there exists the opportunity to change the paradigm of drug discovery (K. Yang et al., 2019). A significant development has related to how molecules are represented; traditionally, molecules were represented by their fingerprint vectors, which reflected the presence or absence of certain functional groups in the molecule, or by descriptors that include computable molecular properties and require expert knowledge to construct (Mauri et al., 2006; Moriwaki et al., 2018; Rogers and Hahn, 2010). Even though the mapping from these representations to properties was learned automatically, the fingerprints and descriptors themselves were designed manually. The innovation of neural network approaches lies in their ability to learn this representation automatically, mapping molecules into continuous vectors which are subsequently used to predict their properties. This design results in molecular representations that have been highly attuned to the desired property, yielding significant gains in property prediction accuracy over manually crafted representations (K. Yang et al., 2019).

While neural network models have narrowed the performance gap between analytical and experimental approaches, a difference still exists. As disclosed herein, the combination of in silico predictions and empirical investigations has led to the discovery of new antibiotics (FIG. 1). In one aspect of the invention, the approach to discovery of a new antibiotic involves three stages: first, a deep neural network model was trained to predict growth inhibition of *Escherichia coli* using a collection of 2,335 diverse molecules; second, in order to identify unknown potential lead compounds with activity against *E. coli*, the resulting model was applied to several discrete chemical libraries, comprising greater than 10' million molecules; third, after ranking the candidates according to the model's predicted score, a list of promising candidates based on a pre-specified prediction score threshold, chemical structure, and availability were selected.

Through the approach of the instant disclosure, the c-Jun N-terminal kinase inhibitor SU3327 (De et al., 2009; Jang et al., 2015) (renamed "halicin" herein) was identified. Halicin is structurally divergent from conventional antibiotics and is a potent inhibitor of *E. coli* growth. Further investigation revealed that halicin displayed growth inhibitory properties against a wide phylogenetic spectrum of human pathogens, apparently (and without wishing to be bound by theory) through selective dissipation of the bacterial transmembrane ΔpH potential. Without wishing to be bound by theory, this mechanism, which is uncommon amongst clinical antibiotics, endows halicin with bactericidal activity against both metabolically active and antibiotic-tolerant cells. Importantly, halicin showed efficacy against Clostridioides *difficile* and pan-resistant *Acinetobacter baumannii* infections in murine models. Of note, the World Health Organization designated *A. baumannii* as the highest priority pathogen against which new antibiotics are urgently required, due to its propensity to acquire antibiotic-resistance determinants at high frequency and the broad spectrum of diseases it can cause, particularly in wounded soldiers (Lee et al., 2017; Perez et al., 2007). In addition to halicin, from a distinct set of 37 empirically tested predictions, fifteen compounds not previously identified as possessing antibacterial properties were identified: three new β-lactams, three new fluoroquinolones, and nine novel compounds structurally distant from previously known clinical antibiotics, all of which were found to exhibit antibacterial activity. Altogether, this work highlights the significant impact that machine learning has now exerted herein (and can exert in the future) upon early antibiotic discovery efforts, by simultaneously increasing the accuracy rate of lead compound identification and decreasing the cost of preclinical screening efforts.

Given that halicin is well-tolerated in vivo, this molecule, or analogs thereof, could represent a novel structural class of antibiotics with efficacy against antibiotic-resistant and antibiotic-tolerant bacterial pathogens. The additional fifteen molecules identified have activity against one or more of *E. coli*, MRSA, *K. pneumoniae, A. baumannii*, and *P. aeruginosa*, and are likely also to be useful antibiotics. Halicin displayed potent activity against MRSA, *C. difficile*, and *M. tuberculosis*, as well as Gram-negative bacteria, showing broad-spectrum coverage. It is expressly contemplated that halicin and derivatives thereof can be used against a wide range of bacterial infections. Use of halicin with other antimicrobial agents is also expressly contemplated, optionally in an additive and/or synergistic matter. For halicin, it is contemplated that the most probable synergistic partners are molecules that dissipate the psi component of the proton motive force, since it is well known that pH dissipating molecules are synergistic with psi dissipating compounds.

The development of new approaches that can substantially decrease the cost and increase the rate of antibiotic discovery is essential to reinfuse the world's drug pipeline with a steady stream of candidates that show promise as next-generation therapeutics. Excitingly, the adoption of machine learning approaches is ideally suited to address these fundamental hurdles. Indeed, modem neural molecular representations have the potential to: (1) decrease the cost of lead molecule identification since high-throughput screening is limited to gathering appropriate training data, (2) increase the true positive rate of identifying compounds with the desired bioactivity, and (3) decrease the time and labor required to find these ideal compounds from months or years to weeks.

In the instant disclosure, neural molecular representations were applied to predict antibacterial compounds in silico from a collection of greater than $10^7$ million compounds from numerous libraries. The deep neural network model of the instant disclosure was first trained with empirical data analyzing *E. coli* growth inhibition achieved by molecules from a widely available FDA-approved drug library supplemented with a modest natural product library, totaling 2,335 molecules. Next, the resulting model was applied to predict antibacterial compounds from the Broad Repurposing Hub, a substantially larger library of 6,111 molecules that contains clinical and preclinical entities. Excitingly, amongst the most highly predicted molecules, the model performed well (51.5% accuracy) and ultimately resulted in identifying halicin as a broad-spectrum bactericidal antibiotic with exceptional in vivo efficacy. Two features of this molecule were particularly unique in relation to the existing antibiotic arsenal. First, halicin's susceptibility to existing antibiotic-resistance determinants, as well as the spontaneous frequency of resistance, was minimal. Second, halicin, due to its mechanism of action, is capable of killing metabolically repressed, antibiotic-tolerant cells. Furthermore, the structural relationship to the nearest neighbor antibiotic, metronidazole (Tanimoto similarity≈0.21), showed that the approach of the instant disclosure was capable of generalization, thereby permitting access to new antibiotic chemistry.

Subsequently, the prediction space was expanded to include the WuXi anti-tuberculosis library containing 9,997 molecules, as well as a subset of the ZINC15 database comprising 107,349,233 molecules, to identify additional candidate antibacterial molecules. Growth inhibition was not observed from any molecules empirically tested from the WuXi library, in agreement with the correspondingly low model predictions (upper limit z 0.37). However, from amongst the 37 molecules from the ZINC15 database that were curated for empirical testing, fifteen were validated as true positives in at least one of the tested pathogens.

The models were curated based on prediction scores alone, as well on low Tanimoto similarities to known antibiotics. Of the fifteen molecules with the highest prediction scores based on prediction scores alone, four were β-lactam derivatives and five were fluoroquinolone derivatives. The prediction scores associated with these molecules were entirely consistent with the training set on which the model was trained: β-lactams and fluoroquinolones are two large classes of antibiotics with activity against *E. coli*, and as such were highly represented in the training dataset. Of these 15 molecules with high prediction scores, seven were validated experimentally as new antibiotic compounds. Interestingly, three of these validated compounds were β-lactam derivatives, three were fluoroquinolone derivatives, and only one was structurally distant from other antibiotics. The fact that the model could correctly predict 3 out of 4 of the empirically assayed β-lactams and 3 out of 5 of the fluoroquinolones indicated that the model distinguished the physiologic importance of chemical features distal to the core structures that define various antibiotic classes. Therefore, aside from applying learned molecular representations to discover new structures, the model was well-suited to accurately predict novel derivatives of existing antibiotic classes without requiring extensive derivatization efforts.

Importantly, when the compounds were curated not only on the basis of high prediction scores, but also on low Tanimoto similarities to known antibiotics, the model was generalized to new chemistries. Remarkably, two of these eight molecules, ZINC000100032716 (1-Cyclopropyl-7-[(3S)-3-methyl-4-[(4-sulfamoylphenyl)diazenyl]piperazin-1-yl]-6-nitro-4-oxoquinoline-3-carboxylic acid) and ZINC000225434673 ([Dibromo(nitro)methyl]-[[4-[[4-[[[dibromo(nitro)methyl]-oxoazaniumyl]amino]-1,2,5-oxadiazol-3-yl]diazenyl]-1,2,5-oxadiazol-3-yl]amino]-oxoazanium), displayed broad-spectrum activity and maintained excellent growth inhibitory potency against *E. coli* harboring an array of resistance determinants. It is particularly important that ZINC000100032716, which contains structural features of both quinolones and sulfa drugs, was only weakly sensitive to resistance via expression of aac(6')-Ib-cr or mutations in gyrA. Moreover, ZINC000225434673, which is structurally distinct from any known antibacterial agent (Tanimoto nearest antibiotic=0.16), was able to rapidly sterilize cultures of *E. coli*, suggesting that this compound might represent a powerful novel structural class of antibiotic. Indeed, ZINC000225434673 is sufficiently promising to warrant further investigation into its mechanism of action, its in vivo efficacy, as well the basis for potency of the compound.

Machine learning is imperfect, and the success of deep neural network model-guided antibiotic discovery rests heavily upon the coupling of these approaches to appropriate experimental designs. Indeed, this is captured by the varying degrees of overlap between the model predictions of the instant invention and those molecules predicted by discrete architectures. A contemplated first consideration for assay design relates to training: specifically, what is the biological outcome that is desired after cells are exposed to compounds? For the instant disclosure, conventional growth inhibition was selected as the biological property on which training data were gathered, since this generally resulted in a reasonable proportion of active compounds relative to the size of the screening library, and quite easily generated reproducible data. However, the number of bacterial phenotypes contemplated for use in the current modeling approaches for prediction of efficacious antibiotics is expansive (Farha and E. D. Brown, 2015; Kohanski et al., 2010)—it is contemplated that as long as it is possible to gather a sufficient quantity of reproducible hit compounds from a primary screen, deep neural network approaches are well-suited to predict additional molecules with the desired biological property. Indeed, where the screen of the instant disclosure was largely agnostic to the mechanism of action, it is contemplated that incorporation of phenotypic screening conditions that enrich for molecules against specific biological targets (Stokes and E. D. Brown, 2015; Stokes et al., 2016; 2017; J. H. Yang et al., 2019) can be incorporated into the current processes, thereby further enabling prediction of molecules possessing structurally and functionally diverse mechanisms of action as effective.

A second consideration is the composition of the training data itself: specifically, on what chemistry should the model be trained? Without wishing to be bound by theory, it appears to be important to use training data that have sufficient chemical diversity in both active and inactive compounds, as well as appropriate pharmacology/ADME/toxicity properties for downstream in vivo application. If all active molecules are structurally similar, a model can be rendered unable to generalize to new scaffolds. Moreover, model accuracy deteriorates as the training set and prediction set diverge. As such, there exists a tension of sorts between prediction accuracy and chemical generalization, and it is advantageous to have the broadest structural variation possible in the training phase to maximize the probability of successful generalization in new chemical spaces. In the instant case, the intent to train on a supplemented FDA-approved drug library offered the capacity to perform a small screen and, simultaneously, capture substantial chemical diversity with desired pharmacology/ADME/toxicity properties. While mining pre-existing screening datasets could have been implemented, it was reasoned that at this early stage in the application of machine learning for antibiotic discovery, a high-quality and carefully controlled training set allowed for more tractable predictions that avoided potentially unfavorable molecules. Nevertheless, given the increasing volume of antibiotic screening data that exists (Wang et al., 2017), it is contemplated that carefully leveraging these resources can result in millions of molecular graph-biological property relationships, provided that the data are of adequate quality and methodological uniformity so that erroneous predictions are minimized.

A third consideration is in prediction prioritization: specifically, what is the most appropriate approach to selecting tens of molecules for follow-up investigation from perhaps tens of thousands of strongly predicted compounds? Without wishing to be bound by theory, because a primary aim is to identify new antibacterial candidates, the prioritization scheme employed in the instant disclosure involved the selection of molecules that were (1) given a high prediction score, (2) structurally unique relative to clinical antibiotics based on Tanimoto nearest neighbor analyses, and in some cases (3) unlikely to display toxicity. Indeed, this approach allowed for the identification of new analogs of existing antibiotic classes, as well as a novel structure in halicin, thereby highlighting the ability of the molecular graph approach to generalize between discrete molecular scaffolds. It should be noted here, however, that investigators can encounter limitations in acquiring predicted compounds in quantities sufficient to perform experiments. This can be due to the inability to synthesize predicted molecules, prohibitive costs of synthesizing those that can be synthesized, and/or compound instability in aqueous solution. Nonetheless, emerging models in retrosynthesis and physicochemical property prediction are expected to overcome these limitations in the near future (Coley et al., 2019; Gao et al., 2018), thereby increasing the quantity and chemical diversity of compounds that can be empirically validated in the laboratory.

Where the deep neural network model of the instant disclosure was trained using a targeted dataset, other endeavors that aim to assemble chemical libraries designed for model training on a task-by-task basis, which could contain on the order of perhaps $\approx 10^5$ compounds of diverse structure, are also contemplated. Without wishing to be bound by theory, in the context of antibacterial discovery, these training libraries are contemplated to contain molecules with physicochemical properties consistent with antibacterial drugs (Tommasi et al., 2015), yet sufficiently diverse such that the model can generalize to unconventional chemistry during training. Furthermore, with repeated training cycles across phylogenetically diverse species, it is likely to be possible to predict molecules with activity against a specified spectrum of pathogens. Application of such an approach is contemplated to result in identification of narrow-spectrum agents that can be administered systemically without damaging the host microbiota. Moreover, by training on multidrug-resistant pathogens, it is contemplated that entirely novel scaffolds or structural analogs of existing classes that overcome pre-existing resistance determinants can be identified. In a similar manner, model training against a spectrum of drug-resistant variants of a specific target is also contemplated, which is likely to help inform on the design of molecules against which conventional target mutations are difficult to confer resistance. Overall, the results of the instant disclosure establish the utility in applying modem machine learning approaches to antibiotic discovery—further application of machine learning approaches, including the approaches disclosed herein, are contemplated as enabling an increase in the rate at which new molecular entities are discovered, while decreasing the resources required to identify these molecules, and also decreasing associated costs. Deep learning approaches are therefore contemplated as enabling drug discovery to outpace the emergence of multidrug-resistant pathogens, with global benefit.

Microbes

In certain embodiments, antimicrobial compounds are identified via use of predictive algorithms as disclosed herein. Exemplary microbes to which such compounds are directed include, but are not limited to, the following.

Bacteria

In certain aspects, the present disclosure provides compositions and/or methods designed to inhibit the growth of and/or kill bacteria, particularly harmful bacteria and/or bacteria that have become or are at risk of becoming tolerant of and/or resistant to commonly administered antibiotics (e.g., amoxicillin, ampicillin, nafcillin, piperacillin, penicillin G, etc.). Tolerance specifically refers to an inability of high concentrations of antibiotics—typically lethal concentrations that are above the growth-inhibitory threshold for a given strain—to kill bacteria. Tolerance levels can be influenced by genetic mutations or induced by environmental conditions. Bacteria can often develop antibiotic tolerance and/or resistance. Resistance can tend to arise via mutations that confer increased survival, which are selected for in natural selection, and which can arise quickly in bacteria because lifespans and production of new generations can be on a timescale of mere hours. Tolerant and/or resistant microbes are more difficult to treat, requiring alternative medications or higher doses of antimicrobials. These approaches may be more expensive, more toxic or both. Microbes resistant to multiple antimicrobials are called multidrug resistant (MDR). Those considered extensively drug resistant (XDR) or totally drug resistant (TDR) are sometimes called "superbugs".

*Escherichia* is a genus of Gram-negative, non-spore-forming, facultatively anaerobic, rod-shaped bacteria from the family Enterobacteriaceae. A number of the species of *Escherichia* are pathogenic. The *Escherichia* genus includes, but is not limited to, *Escherichia coli* (*E. coli*). *E. coli* is one of the most commonly used bacteria in microbiology experiments. *E. coli* is a rod-shaped, Gram-negative bacteria. Gram-negative bacteria contain an outer membrane surrounding the cell wall that provides a barrier to certain antibiotics. Most strains of *E. coli* are harmless, but some serotypes cause illnesses such as food poisoning. Cells are able to survive outside the body for a limited amount of time, which makes them ideal indicator organisms to test environmental samples for fecal contamination. The bacterium can also be grown easily and inexpensively in a laboratory setting.

*Pseudomonas* is a genus of Gram-negative, Gammaproteobacteria, belonging to the family Pseudomonadaceae and containing 191 validly described species. The members of the genus demonstrate a great deal of metabolic diversity and consequently are able to colonize a wide range of niches. Their ease of culture in vitro and availability of an increasing number of *Pseudomonas* strain genome sequences has made the genus favorable for scientific research. A number of the species of *Escherichia* are pathogenic to plants and animals, including humans. The *Pseudomonas* genus includes, but is not limited to, the strains commonly used in a lab setting: *Pseudomonas aeruginosa, Pseudomonas fluorescens, Pseudomonas citronellolis, Pseudomonas chlororaphis, veronii, Pseudomonas aurantiaca, Pseudomonas putida*, and *Pseudomonas syringae.*

An exemplary but not comprehensive list of bacteria for use with the compositions and methods of the instant disclosure includes *Achromobacter* spp, *Acidaminococcus fermentans, Acinetobacter calcoaceticus, Actinomyces* spp, *Actinomyces viscosus, Actinomyces naeslundii, Aeromonas* spp, *Aggregatibacter actinomycetemcomitans, Anaerobiospirillum* spp, *Alcaligenes faecalis, Arachnia propionica, Bacillus* spp, *Bacteroides* spp, *Bacteroides gingivalis, Bacteroides fragilis, Bacteroides intermedius, Bacteroides melaninogenicus, Bacteroides pneumosintes, Bacterionema matruchotii, Bifidobacterium* spp, *Buchnera aphidicola, Butyriviberio fibrosolvens, Campylobacter* spp, *Campylobacter coli, Campylobacter sputorum, Campylobacter upsaliensis, Capnocytophaga* spp, *Clostridium* spp, *Citrobacter freundii, Clostridium difficile, Clostridium sordellii, Corynebacterium* spp, *Eikenella corrodens, Enterobacter cloacae, Enterococcus* spp, *Enterococcus faecalis, Enterococcus faecium, Escherichia coli, Eubacterium* spp, *Flavobacterium* spp, *Fusobacterium* spp, *Fusobacterium nucleatum, Gordonia Bacterium* spp, *Haemophilus parainfluenzae, Haemophilus paraphrophilus, Lactobacillus* spp, *Leptotrichia buccalis, Methanobrevibacter smithii, Morganella morganii, Mycobacteria* spp, *Mycoplasma* spp, *Micrococcus* spp, *Mycoplasma* spp, *Mycobacterium chelonae, Neisseria* spp, *Neisseria sicca, Peptococcus* spp, *Peptostreptococcus* spp, *Plesiomonas shigelloides, Porphyromonas gingivalis, Propionibacterium* spp, *Propionibacterium acnes, Providencia* spp, *Pseudomonas aeruginosa, Ruminococcus bromii, Rothia dentocariosa, Ruminococcus* spp, *Sarcina* spp, *Staphylococcus aureus, Staphylococcus epidermidis, Streptococcus anginosus, Streptococcus mutans, Streptococcus oralis, Streptococcus pneumoniae, Streptococcus sobrinus, Streptococcus viridans, Torulopsis glabrata, Treponema denticola, Treponema refringens, Veillonella* spp, *Vibrio* spp, *Vibrio sputorum, Wolinella succinogenes* and *Yersinia enterocolitica.*

An exemplary list of Gram-positive bacteria expressly contemplated for targeting with the compositions and methods of the instant disclosure include, without limitation, *Clostridium difficile, Enterococcus* (e.g., *E. faecalis, E. faecium, E. casseliflavus, E. gallinarum, E. raffinosus*), *Mycobacterium tuberculosis, Mycobacterium avium* complex (including *Mycobacterium intracellulare* and *Mycobacterium avium*), *Mycobacterium smegmatis, Mycoplasms genitalium, Staphylococcus aureus, Streptococcus pyogenes, Streptococcus pneumoniae*, and *Mycobaterium leprae.*

An exemplary list of Gram-negative bacteria expressly contemplated for targeting with the compositions and methods of the instant disclosure include, without limitation, *Acinetobacter* spp. (including *Acinetobacter baumannii*), *Campylobacter, Neisseria gonorrhoeae, Providencia* spp., *Enterobacter* spp. (including *Enterobacter cloacae* and *Enterobacter aerogenes*), *Klebsiella* spp. (including *Klebsiella pneumoniae*), *Salmonella, Pasteurella* spp., *Proteus* spp. (including *Proteus mirabilis*), *Serratia* spp. (including *Serratia marcescens*), *Citrobacter* spp., *Escherichia* spp. (including *Escherichia coli*), *Acinetobacter, Morganella morganii, Pseudomonas aeruginosa, Burkholderia pseudomallei, Burkholderia cenocepacia, Helicobacter pylori, Treponema pallidum* and *Hemophilus influenza*. (See, e.g., Cohen et al. Cell Host & Microbe 13: 632-642, the contents of which are incorporated by reference herein in their entirety.) The instant disclosure expressly contemplates targeting of any of (or any combination of) the above-listed forms of Gram-positive and/or Gram-negative bacteria, particularly those forms of the above-recited bacteria that possess or are at risk of developing tolerance and/or resistance to antibiotics previously known in the art.

In embodiments, a composition and/or formulation of the instant disclosure can be administered to a subject to treat mixed infections that comprise different types of Gram-negative bacteria, different types of Gram-positive bacteria, or which comprise both Gram-positive and Gram-negative bacteria. These types of infections include, without limitation, intra-abdominal infections and obstetrical/gynecological infections.

Algae

*Chlamydomonas* is a genus of green algae consisting of about 325 species, all unicellular *flagellates*, found in stagnant water, damp soil, freshwater, seawater, and snow. *Chlamydomonas* is used as a model organism for molecular biology, especially studies of flagellar motility and chloroplast dynamics, biogeneses, and genetics. *Chlamydomonas* contain ion channels that are directly activated by light. The *Chlamydomonas* genus includes, but is not limited to, the strain *Chlamydomonas reinhardtii. Chlamydomonas reinhardtii* is an especially well studied biological model organism, partly due to its ease of culturing and the ability to manipulate its genetics (e.g., *Chlamydomonas reinhardtii* CC-503 auto-fluorescent strain).

Yeast

Yeasts are unicellular organisms belonging to one of three classes: *Ascomycetes, Basidiomycetes* and fungi imperfecti. Pathogenic yeast strains, including mutants thereof, are expressly contemplated for use and/or targeting in the instant disclosure. Explicitly contemplated yeast strains include *Saccharomyces, Candida, Cryptococcus, Hansenula, Kluyveromyces, Pichia, Rhodotorula, Schizosaccharomyces* and *Yarrowia*. Exemplary species include *Saccharomyces cerevisiae, Saccharomyces pastorianus, Candida albicans, Candida tropicalis, Candida stellatoidea, Candida glabrata, Candida krusei, Candida parapsilosis, Candida guilliermondii, Candida viswanathii, Candida lusitaniae, Candida kefyr, Candida laurentii, Cryptococcus neoformans, Hansenula anomala, Hansenula polymorpha, Kluyveromyces fragilis, Kluyveromyces lactis, Kluyveromyces marxianus* var. *Lactis, Pichia pastoris, Rhodotorula rubra, Schizosaccharomyces pombe, Leucosporidium frigidum, Saccharomyces telluris, Candida slooffi, Torulopsis, Trichosporon cutaneum, Dekkera intermedia, Candida blankii, Cryptococcus gattii, Rhodotorula mucilaginosa, Brettanomyces bruxellensis, Candida stellata, Torulaspora delbrueckii, Zygosaccharomyces baiii, Brettanomyces anomalus, Brettanomyces custersianus, Brettanomyces naardenensis, Brettanomyces nanus, Dekkera bruxellensis, Dekkera anomala* and *Yarrowia lipolytica*. As will be understood to one of ordinary skill in the art, a number of these species include a variety of subspecies, types and subtypes, etc. that are to be understood as included within the aforementioned species.

Other Microbes

Other expressly contemplated microbes include, without limitation, *Aspergillus, Blastomyces, Coccidioides, C. neoformans, C. gattii, Histoplasma, Mucormycetes, Mycetoma, Pneumocytsis jirovencii, Trichophyton, Microsporum, Epidermophyton, Sporothrix, Paracoccidioidomycosis, Talaromycosis*, and *Cryptococcus*.

Methods of Treatment

The compositions and methods of the present disclosure may be used in the context of a number of therapeutic or prophylactic applications. Compositions of the instant disclosure can be selected and/or administered as a single agent, or to augment the efficacy of another therapy (second therapy), it may be desirable to combine these compositions and methods with one another, or with other agents and methods effective in the treatment, amelioration, or prevention of infections and/or diseases.

In certain embodiments of the instant disclosure, one or more antimicrobial compounds can be administered to a subject. It is contemplated that in certain embodiments, one or more antimicrobial compounds of the instant disclosure can be co-administered and/or administration of one antimicrobial compound of the instant disclosure can precede or follow administration of a second antimicrobial agent. It is also expressly contemplated that the antimicrobial agent compositions and methods of the instant disclosure can optionally be administered in further combination with other agents, including, e.g., other agents capable of enhancing antimicrobial agent efficacy (such as, e.g., β-lactamase inhibitors, among other antibiotic potentiators/adjuvants that are known in the art).

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing a bacterial infection) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers or diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, non-therapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, PA, 17th ed. (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977):1-19, incorporated herein by reference. The salts can be prepared in situ during the final isolation and purification of the compounds of the application, or separately by reacting a free base or free acid function with a suitable reagent, as described generally below. For example, a free base function can be reacted with a suitable acid. Furthermore, where the compounds to be administered of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved compound where administered to a human subject) or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent, such as an antibiotic compound, in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease/infection to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with an antibiotic) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 μg/kg, followed by a weekly maintenance dose of about 100 g/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 μg/kg to about 2 mg/kg (such as about 3 μg/kg, about 10 g/kg, about 30 μg/kg, about 100 g/kg, about 300 μg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer β-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

To prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such as magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., an antibiotic) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Drugs provided herein can be formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for oral delivery or intravenous injection to a subject.

The exact amount of an agent required to achieve an effective amount will vary from subject to subject, depending, for example, on species, age, and general condition of a subject, severity of the side effects or disorder/infection, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., an antibiotic) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

A drug or other therapy of the instant disclosure is administered to the subject in an amount sufficient to achieve a desired effect at a desired site (e.g., reduction of bacterial infection, bacterial abundance, symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 g/kg/day, at least 100 μg/kg/day, at least 250 μg/kg/day, at least 500 μg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 μg/kg/day, and less than 500 μg/kg/day.

In certain embodiments, when multiple doses are administered to a subject or applied to a tissue, the frequency of administering the multiple doses to the subject or applying the multiple doses to the tissue is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., an antibiotic) described herein. In certain embodiments, a dose described herein includes independently between 1 mg and 3 mg, inclusive, of an agent (e.g., an antibiotic) described herein. In certain embodiments, a dose described herein includes independently between 3 mg and 10 mg, inclusive, of an agent (e.g., an antibiotic) described herein. In certain embodiments, a dose described herein includes independently between 10 mg and 30 mg, inclusive, of an agent (e.g., an antibiotic) described herein. In certain embodiments, a dose described herein includes independently between 30 mg and 100 mg, inclusive, of an agent (e.g., an antibiotic) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., an antibiotic) or composition, as described herein, can be administered in combination with one or more additional pharmaceutical agents (e.g., therapeutically and/or prophylactically active agents), which are different from the agent or composition and may be useful as, e.g., combination therapies.

The agents or compositions can be administered in combination with additional pharmaceutical agents that improve their activity (e.g., activity (e.g., potency and/or efficacy) in treating a disease or infection (e.g., an antibiotic tolerant or resistant bacterial infection) in a subject in need thereof, in preventing a disease or infection in a subject in need thereof, in reducing the risk of developing a disease or infection in a subject in need thereof, etc. in a subject or tissue. In certain embodiments, a pharmaceutical composition described herein including an agent (e.g., an antibiotic) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an immunotherapy, an antioxidant, an antiinflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease or infection described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, additional antibiotics, antimicrobials, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure. Kits of the instant disclosure may include one or more containers comprising an agent (e.g., an antibiotic) and/or composition of this disclosure. In some embodiments, the kits further include instructions for use in accordance with the methods of this disclosure. In some embodiments, these instructions comprise a description of administration of the agent to treat or prevent, e.g., an infection and/or disease. In some embodiments, the instructions comprise a description of how to administer an antibiotic to a bacterial population, and/or to a subject infected or suspected to be infected or at risk of infection with a bacteria.

The instructions generally include information as to dosage, dosing schedule, and route of administration for the intended use/treatment. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable. Instructions may be provided for practicing any of the methods described herein. The kits of this disclosure are in suitable packaging. Suitable packaging includes, but is not limited to, vials, bottles, jars, flexible packaging (e.g., sealed Mylar or plastic bags), and the like. The container may further comprise a pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Chemical Screening

*E. coli* BW25113 was grown overnight in 3 ml Luria-Bertani (LB) medium and diluted 1/10,000 into fresh LB. 99 µl of cells was added to each well of a 96-well flat-bottom plate (Corning) using a multichannel pipette. Next, 1 µl of a 5 mM stock of each molecule from an FDA-approved drug library supplemented with a natural product library (2,560 molecules total; MicroSource Discovery Systems) was added using an Agilent Bravo liquid handler, in duplicate. The final screening concentration was 50 µM. Plates were then incubated in sealed plastic bags at 37° C. without shaking for 16 hours, and subsequently read at 600 nm using a SpectraMax M3 plate reader (Molecular Devices) to quantify cell growth. Plate data were normalized based on the interquartile mean of each plate.

Model Training and Predictions

A directed message passing neural network (Chemprop), like other message passing neural networks, learns to predict molecular properties directly from the graph structure of the molecule, where atoms are represented as nodes and bonds are represented as edges. In the instant disclosure, a molecular graph was constructed for every molecule corresponding to each compound's SMILES string. The set of atoms and bonds were then determined using the open source package RDKit (Landrum, 2006). Next, a feature vector was initialized, as described in (K. Yang et al., 2019), for each atom and bond based on the following computable features:

1. Atom features: atomic number, number of bonds for each atom, formal charge, chirality, number of bonded hydrogens, hybridization, aromaticity, atomic mass
2. Bond features: bond type (single/double/triple/aromatic), conjugation, ring membership, stereochemistry The model of the instant disclosure applied a series of message passing steps where it aggregated information from neighboring atoms and bonds to build an understanding of local chemistry. In Chemprop, on each step of message passing, each bond's featurization is updated by summing the featurization of neighboring bonds, concatenating the current bond's featurization with the sum, and then applying a single neural network layer with non-linear activation. After a fixed number of message-passing steps, the learned featurizations across the molecule are summed to produce a single featurization for the whole molecule. Finally, this featurization is fed through a feed-forward neural network that outputs a prediction of the property of interest. Since the property of interest in the instant disclosure was the binary classification of whether a molecule inhibited the growth of *E. coli*, the model was trained to output a number between 0 and 1 which represented its belief about whether the input molecule was growth inhibitory. In addition to the basic D-MPNN architecture described above, three model optimizations (K. Yang et al., 2019) were employed:

1. Additional molecule-level features: While the message passing paradigm is excellent for extracting features that depend on local chemistry, it can struggle to extract global molecular features. This is especially true for large molecules, where the longest path through the molecule may be longer than the number of message-passing iterations performed, meaning information from one side of the molecule does not inform the features on the other side of the molecule. For this reason, concatenatation of the molecular representation that is learned via message passing with 200 additional molecule-level features computed with RDKit was performed.
2. Hyperparameter optimization: The performance of machine learning models is known to depend critically on the choice of hyperparameters, such as the size of the neural network layers, which control how and what the model is able to learn. In the instant disclosure, bayesian hyperparameter optimization scheme was employed, with 20 iterations of optimization to improve the hyperparameters of the model (see the table below). Bayesian hyperparameter optimization learns to select optimal hyperparameters based on performance using prior hyperparameter settings, allowing for rapid identification of the best set of hyperparameters for any model.

| Hyperparameter | Range | Value |
|---|---|---|
| Number of message-passing steps | [2, 6] | 5 |
| Neural network hidden size | [300, 2400] | 1600 |
| Number of feed-forward layers | [1, 3] | 1 |
| Dropout probability | [0, 0.4] | 0.35 |

3. Ensembling: Another standard machine learning technique used to improve performance is ensembling, where several copies of the same model architecture with different random initial weights are trained and their predictions are averaged. An ensemble of 20 models was employed in the instant disclosure, with each model trained on a different random split of the data (Dietterich, 2000). The initial training dataset of the instant disclosure consisted of 2,335 molecules, with 120 compounds (5.14%) showing growth inhibitory activity against *E. coli*, as defined by an endpoint of $OD_{600}$ less than 0.2. Predictions were performed on the Broad Repurposing Hub, consisting of 6,111 unique molecules; the WuXi anti-tuberculosis library, consisting of 9,997 unique molecules; and tranches of the ZINC15 database. The ZINC15 tranches that were used for molecular predictions were selected based on their likelihood to contain antibiotic-like molecules. The aforementioned ZINC15 tranches included: 'AA', 'AB', 'BA', 'BB', 'CA', 'CB', 'CD', 'DA', 'DB', 'EA', 'EB', 'FA', 'FB', 'GA', 'GB', 'HA', 'HB', 'IA', 'IB', 'JA', 'JB', 'JC', 'JD', 'KA', 'KB', 'KC', 'KD', 'KE', 'KF', 'KG', 'KH', 'KI', 'KJ', and 'KK', constituting a dataset of 107,349,233 unique molecules.

In one embodiment, the experimental procedure for discovery of novel antibiotics involved four phases: (1a) a training phase to evaluate the optimized but non-ensembled model and (1b) training the ensemble of optimized models; (2) a prediction phase; (3) a retraining phase; and (4) a final prediction phase. To determine the best performance of any given model under these conditions, the initial optimized but non-ensembled model was evaluated using the training set of 2,335 molecules with all optimizations except that of ensembling. Then, the dataset was split randomly into 80% training data, 10% validation data, and 10% test data. The model was trained on the training data for 30 epochs, wherein an epoch is defined as a single pass through all of the training data, and wherein the validation data was evaluated at the completion of each epoch. After the training was complete, the model parameters that performed best on the validation data were chosen and the model was tested with those parameters on the test data. This procedure was repeated with 20 different random splits of the data and the results were averaged. After the model performance proved to be sufficiently accurate, predictions were then performed on new datasets. To maximize the amount of training data, and because test data was no longer needed, new models were trained on the training data using 20 random splits, each split with 90% training data, 10% validation data, and no test data. The ensemble consisting of these 20 models is the model in the instant disclosure that was then applied to the Broad Repurposing Hub and WuXi anti-tuberculosis library.

The aforementioned model of the instant disclosure was used to make predictions on the Broad Repurposing Hub and Wuxi datasets. First the highest and lowest predicted molecules from both libraries were tested empirically for growth inhibition against *E. coli*. Subsequently all of these data were added to the original training set to create a new training set. The updated training set contained 2,911 unique molecules, with 232 (7.97%) showing growth inhibitory activity. The model of the instant disclosure was retrained on the new data and then was used to make predictions on the subset of the ZINC15 database described above. All molecules with a prediction score greater than 0.7 were selected, resulting in 6,820 candidate compounds. These compounds were clustered into k=50 clusters using k-means clustering on Morgan fingerprints with radius 2 and with 2048 bits to curate molecules with structural diversity. All molecules selected for curation were subsequently cross-referenced with SciFinder to ensure that these molecules were not already employed as clinical antibiotics.

Lastly a comparison was done between the prediction outputs of the augmented D-MPNN with a D-MPNN without RDKit features, a feedforward DNN model with the same depth as t D-MPNN model with hyperparameter optimization using RDKit features only, the same DNN instead using Morgan fingerprints (radius 2) as the molecular representation, and RF and SVM models using the same Morgan fingerprint representations. The scikit-learn implementation of a random forest classifier with all default parameters, except for number of trees, was used, wherein 500 trees were used instead of 10. To make predictions, the growth inhibition probability output for each molecule was determined according to the random forest, i.e. the proportion of trees in the model that predicts a 1 for that molecule. Similarly, the scikit-learn implementation of a support vector machine with all default parameters was used. To make predictions, the signed distance between the Morgan fingerprint of the molecule and the separating hyperplane was learned by the SVM. This number represents the model's prediction of the likelihood of a molecule to be antibacterial, with large positive distances indicating most likely to be antibacterial and large negative distances meaning most likely to not be antibacterial. Although the signed distance is not a probability, it can still be used to rank the molecules according to how likely they are to be antibacterial.

In one embodiment, to predict the toxicity of candidate molecules for possible in vivo applications, a Chemprop model was trained on the ClinTox dataset. This dataset consisted of 1,478 molecules, each with two binary properties: (a) clinical trial toxicity and (b) FDA-approval status. Of these 1,478 molecules, 94 (6.36%) had clinical toxicity and 1,366 (92.42%) were FDA approved. Using the same methodology as described in phase (1) above, in one embodiment, the Chemprop model was trained simultaneously on both clinical toxicity and FDA approval, wherein the model of the instant disclosure learned a single molecular representation that was used by the feed-forward neural network layers to predict toxicity. The same RDKit features were used as in other models described herein, except that the ClinTox model was an ensemble of five models and used the following optimal hyperparameters: message-passing steps=6; neural network hidden size=2200; number of feed-forward layers=3, and dropout probability=0.15. This ensemble of models was subsequently used to make toxicity predictions on candidate molecules.

Growth inhibition assays Cells were grown overnight in 3 ml LB medium and diluted 1/10,000 into fresh LB. In 96-well flat-bottom plates (Corning), cells were then introduced to compound at a final concentration of 50 M, or to compound at two-fold serial dilutions, in final volumes of 100 μl. Plates were then incubated at 37° C. without shaking until untreated control cultures reached stationary phase, at which time they were read at 600 nm using a SpectraMax M3 plate reader. The incubation time required to reach stationary phase differed between species but was generally between 12 hours and 18 hours. For ZINC15 compound validation, the strains were *E. coli* BW25113, *S. aureus* USA 300, *K. pneumoniae* ATCC 700721, *A. baumannii* ATCC 17978, and *P. aeruginosa* PA01. *C. difficile* growth inhibition was performed as described above, except cells were grown in BHI+0.1% taurocholate for 18 hours in an anaerobic chamber (Coy Laboratory Products). *M. tuberculosis* H37Rv was grown at 37° C. in Middlebrook 7H9 broth supplemented with 10% OADC (oleic acid-albumin-dextrose complex, vol/vol), 0.2% glycerol, and 0.05% Tween-80, or on Middlebrook 7H10 plates supplemented with 10% OADC and 0.5% glycerol. Cells were grown to mid-log phase, then added to 96-well plates at $OD_{600}$=0.0025, in a total of 50 μl of 7H9 medium. In addition, each well contained 45 μl of 7H9 medium and varying compound concentrations diluted in a total of 5 μl of medium. Plates were incubated at 37° C. in a humidified container for 14 days. $OD_{600}$ was measured using a SpectraMax M5 plate reader.

Bacterial Cell Killing Assays

Cells were grown overnight in 3 ml LB medium and diluted 1/10,000 into fresh LB. In 96-well flat-bottom plates (Corning), cells were grown to the required density, at which time antibiotic was added at the indicated concentration and cultures were incubated for the required duration. Cells were then pelleted in plates by centrifugation at 4000×g for 15 minutes at 4° C. and washed in ice cold PBS. After washing, cells were 10-fold serially diluted in PBS and plated on LB to quantify cell viability. In experiments where cells were incubated with antibiotic in nutrient-depleted conditions, cells were grown to the required density in LB media, washed in PBS, and subsequently re-suspended in PBS prior to the addition of antibiotic. After cultures were incubated for the required duration, cells were pelleted in plates by centrifugation at 4000×g for 15 minutes at 4° C. and washed in ice cold PBS. After washing, cells were 10-fold serially diluted in PBS and plated on LB to quantify cell viability. *M. tuberculosis* M37Rv was grown to mid-log phase, then 30,000 cells were added to a 24 well plate in 1 ml of 7H9 medium. A sample from each well was taken as time=0, prior to halicin addition, then halicin was added to each well at 16 μg/ml (1×MIC). At the indicated time points, samples were taken from each well and plated on 7H 10. Control wells contained the relevant DMSO concentration without halicin. Plates were incubated at 37° C. and counted twice, once after 4 weeks and once after 6 weeks.

Mutant Generation

For serial passage evolution, *E. coli* BW25113 was grown overnight in 3 ml LB medium and diluted 1/10,000 into fresh LB. Cells were grown in 96-well flat-bottom plates (Corning), in the presence of varying concentrations of halicin (or ciprofloxacin) at two-fold serial dilutions, in final volumes of 100 μl. Plates were incubated at 37° C. without shaking for 24 hours, at which time they were read at 600 nm using a SpectraMax M3 plate reader. After 24 hours, cells that grew in the presence of the highest concentration of halicin (or ciprofloxacin) were diluted 1/10,000 into fresh LB, and once again introduced to varying concentrations of halicin at two-fold serial dilutions. This procedure was performed every 24 hours over the course of 30 days. For spontaneous suppressor generation, ≈$10^9$ CFU of *E. coli* BW25113 grown in LB media was spread onto LB agar in 10 cm petri dishes, either without antibiotics or supplemented with ciprofloxacin (Millipore Sigma) or halicin (TCI Chemicals) at the indicated concentrations. Plates were subsequently incubated at 37° C. for seven days, at which time colonies from each plate were re-streaked onto LB and LB supplemented with antibiotics at the same concentration on which the colonies were originally grown. These plates were grown at 37° C. overnight to monitor re-growth. For strain engineering, *E. coli* BW25113 ΔnsfA::kan ΔnfsB::cat was derived from BW25113 ΔnsfA::kan via introduction of a cat gene to disrupt the nfsB ORF using the Lambda Red method (Datsenko and Wanner, 2000). Briefly, 2 ml of 2×YT media with BW25113 ΔnsfA::kan carrying the temperature-sensitive plasmid pKD46 at 30° C. was induced with 20 mM arabinose. Upon reaching mid log phase ($OD_{600}$≈0.5), cells were pelleted at 6000×g for 2 min, then washed three times with 1 ml 15% glycerol. The final pellet was re-suspended in 200 μl of 15% glycerol, and 50 μl was mixed with 300 ng of disruption fragment (generated using primers AB5044 and AB5045 on pKD32 to amplify the FRT-flanked cat cassette). Cells were electroporated at 1800 kV, then allowed to recover overnight in 5 ml 2×YT at 30° C. Cells were then pelleted at 6000×g for 2 min, re-suspended in 200 μl deionized water and plated on 2×YT agar plates with 15 μg/ml kanamycin (Millipore Sigma) and 20 μg/ml chloramphenicol (Millipore Sigma). Plates were incubated at 37° C. for 24-48 hr. Single colonies were PCR checked (primers AB5046, AB5047) for loss of the nfsB gene (1069 bp) and appearance of the cat gene insertion (1472 bp). Finally, positive colonies were assayed for loss of pKD46 at 37° C. by replica plating on 15 μg/ml kanamycin and 20 g/ml chloramphenicol with or without 50 μg/ml carbenicillin (Millipore Sigma).

```
AB5044
                                              (SEQ ID NO: 1)
TAGCCGGGCAGATGCCCGGCAAGAGAGAATTACACTTCGGTTAAGGTGAT

ATTCCGGGGATCCGTCGACC
```

-continued

AB5045

(SEQ ID NO: 2)
ACCTTGTAATCTGCTGGCACGCAAAATTACTTTCACATGGAGTCTTTATG

TGTAGGCTGGAGCTGCTTCG

AB5046

(SEQ ID NO: 3)
tgcaaaataatatgcaccacgacggcggtcagaaaaataa

AB5047

(SEQ ID NO: 4)
gaagcgttacttcgcgatctgatcaacgattcgtggaatc

RNA Sequencing

Cells were grown overnight in 3 ml LB medium and diluted 1/10,000 into 50 ml fresh LB. When cultures reached ≈$10^7$ CFU/ml, halicin was added at 0.25×MIC (0.5 μg/ml), 1×MIC (2 sg/ml), or 4×MIC (8 μg/ml) and cells were incubated for the noted durations. After incubation, cells were harvested via centrifugation at 15,000×g for 3 minutes at 4° C., and RNA was purified using the Zymo Direct-zol 96-well RNA purification kit (R2056). Briefly, ≈$10^7$ to $10^8$ CFU pellets were lysed in 500 μl hot Trizol reagent (Life Technologies). 200 μl chloroform (Millipore Sigma) was added, and samples were centrifuged at 15,000×g for 3 minutes at 4° C. 200 μl of the aqueous phase was added to 200 μl anhydrous ethanol (Millipore Sigma), and RNA was purified using a Zymo-spin plate as per the manufacturer's instructions. After purification, Illumina cDNA libraries were generated using a modified version of the RNAtag-seq protocol (Shishkin et al., 2015). Briefly, 500 ng to 1 μg of total RNA was fragmented, depleted of genomic DNA, dephosphorylated, and ligated to DNA adapters carrying 5'-AN8-3' barcodes of known sequence with a 5' phosphate and a 3' blocking group. Barcoded RNAs were pooled and depleted of rRNA using the RiboZero rRNA depletion kit (Epicentre). Pools of barcoded RNAs were converted to Illumina cDNA libraries in two main steps: (1) reverse transcription of the RNA using a primer designed to the constant region of the barcoded adaptor with addition of an adapter to the 3' end of the cDNA by template switching using SMARTScribe (Clontech), as previously described (Zhu et al., 2018); (2) PCR amplification using primers whose 5' ends target the constant regions of the 3' or 5' adaptors and whose 3' ends contain the full Illumina P5 or P7 sequences. cDNA libraries were sequenced on the Illumina NextSeq 500 platform to generate paired end reads. Following sequencing, reads from each sample in a pool were demultiplexed based on their associated barcode sequence using custom scripts. Up to one mismatch in the barcode was allowed, provided it did not make assignment of the read to a different barcode possible. Barcode sequences were removed from the first read as were terminal G's from the second read that may have been added by SMARTScribe during template switching. Next, reads were aligned to the *E. coli* MG1655 genome (NC_000913.3) using BWA (Li et al., 2009) and read counts were assigned to genes and other genomic features. Differential expression analysis was conducted with DESeq2 (Love et al., 2014) and/or edgeR (Robinson et al., 2010). To verify coverage, visualization of raw sequencing data and coverage plots in the context of genome sequences and gene annotations was conducted using GenomeView (Abeel et al., 2012). To determine biological response of cells as a function of halicin exposure, hierarchical clustering was performed of the gene expression profiles using the clustergram function in Matlab 2016a. The Euclidean distance was selected as the metric to define the pairwise distance between observations, which measures a straight-line distance between two points. The use of Euclidian distance has been considered as the most appropriate to cluster log-ratio data (D'haeseleer, 2005). With a metric defined, the average linkage was selected as the clustering method. The average linkage uses the algorithm termed "unweighted pair group method with arithmetic mean (UPGMA)", which is currently the most employed and most preferred algorithm for hierarchical data clustering (Jaskowiak et al., 2014; Loewenstein et al., 2008). UPGMA uses the mean similarity across all cluster data points to combine the nearest two clusters into a higher-level cluster. UPGMA assumes there is a constant rate of change among species (genes) analyzed. All alternative clustering metrics available (i.e., Speannan, Hamming, cosine, etc.) were tested in the pdist function within the clustergram function in Matlab and concluded that the Euclidean metric together with the average linkage allow the clearest and likely most meaningful definition of clusters for the data set of this embodiment of the instant disclosure. Transcript cluster enrichment was performed using EcoCyc Pathway Tools (Karp, 2001; Karp et al., 2016; Keseler et al., 2013). P values were calculated using Fisher's exact test.

$DiSC_3(5)$ Assays

*S. aureus* USA300 and *E. coli* MC1061 were streaked onto LB agar and grown overnight at 37° C. Single colonies were picked and used to inoculate 50 ml LB in 250 ml baffled flasks, which were incubated for 3.5 hour in a 37° C. incubator shaking at 250 rpm. Cultures were pelleted at 4000×g for 15 minutes and washed 3 times in buffer. For *E. coli*, the buffer was 5 mM HEPES with 20 mM glucose (pH 7.2). For *S. aureus*, the buffer was 50 mM HEPES with 300 mM KCl and 0.1% glucose (pH 7.2). Both cell densities were normalized to $OD_{600}$≈0.1, loaded with 1 μM DiSC3(5) dye (3,3'-dipropylthiadicarbocyanine iodide), and left to rest for 10 minutes in the dark for probe fluorescence to stabilize. Fluorescence was measured in a cuvette-based fluorometer with stirring (Photon Technology International) at 620 nm excitation and 670 nm emission wavelengths. A time-course acquisition was performed, with compounds injected after 60 sec of equilibration to measure increases or decreases in fluorescence. For *E. coli*, polymyxin B was used as a control to monitor $\Delta\psi$ dissipation. For *S. aureus*, valinomycin was used as a $\Delta\psi$ control and nigiricin was used as a ΔpH control. Upon addition of antibiotic, fluorescence was read continuously for 3 minutes and at an endpoint of 4 hours.

*a. Baumannii* Mouse Infection Model

Experiments were conducted according to guidelines set by the Canadian Council on Animal Care, using protocols approved by the Animal Review Ethics Board at McMaster University under Animal Use Protocol #17-03-10. Before infection, mice were relocated at random from a housing cage to treatment or control cages. No animals were excluded from analyses, and blinding was considered unnecessary. Six- to eight-week old Balb/c mice were pretreated with 150 mg/kg (day −4) and 100 mg/kg (day −1) of cyclophosphamide to render mice neutropenic. Mice were then anesthetized using isofluorane and administered the analgesic buprenorphine (0.1 mg/kg) intraperitoneally. A 2 $cm^2$ abrasion on the dorsal surface of the mouse was inflicted through tape-stripping to the basal layer of epidermis using approximately 25-30 pieces of autoclave tape. Mice were infected with $2.5\times10^5$ CFU *A. baumannii* CDC 288 directly pipetted on the wounded skin. The infection was established for one hour prior to treatment with Glaxal Base supplemented with vehicle (0.5% DMSO) or halicin (0.5% w/v). Groups of mice were treated 1 hour, 4 hours, 8 hours, 12 hours, 20 hours, and 24 hours post-infection. Mice were euthanized at the experimental endpoint of 25 hours and the wounded tissue collected, homogenized, and plated onto LB to quantify bacterial load.

*C. difficile* Mouse Infection Model

Experiments were conducted according to protocol IS00000852-3, approved by Harvard Medical School Institutional Animal Care and Use Committee and the Committee on Microbiological Safety. *C. difficile* 630 spores were prepared from a single batch and stored long term at 4° C., as previously reported (Edwards and McBride, 2016). To disrupt colonization resistance and enable infection with *C. difficile*, four colonies (n=20) of six- to eight-week-old C57BL/6 mice were administered 200 mg/kg ampicillin every 24 hours for 72 hours via intraperitoneal injection. Antibiotic-treated mice were given 24 hours to recover prior to infection with *C. difficile*. A total of $5\times10^3$ spores of *C. difficile* strain 630 was delivered via oral gavage and mice were randomly assigned to three treatment groups: 50 mg/kg metronidazole (n=7), 15 mg/kg halicin (n=7) and 10% PEG 300 vehicle (n=6). Three mice from the halicin treatment group failed to display *C. difficile* colonization. Beginning at 24 hours after *C. difficile* challenge, mice were gavaged with antibiotics or vehicle control every 24 hours for five days. To monitor *C. difficile* colonization, fecal samples were collected, weighed and diluted under anaerobic conditions with anaerobic PBS. CFUs were quantified using TCCFA plates supplemented with 50 μg/ml erythromycin at 37° C. under anaerobic conditions, as previously described (Winston et al., 2016).

Chemical Analyses

The Tanimoto similarity was utilized to understand the chemical relationship between molecules predicted in the model of the instant disclosure. The Tanimoto similarity of two molecules is a measure of the proportion of shared chemical substructures in the molecules. To compute Tanimoto similarity, Morgan fingerprints (computed using RDKit) were first determined for each molecule using a radius of 2 and using 2048-bit fingerprint vectors. Tanimoto similarity was then computed as the number of chemical substructures contained in both molecules divided by the total number of unique chemical substructures in either molecule. The Tanimoto similarity is thus a number between 0 and 1, with 0 indicating least similar (no substructures are shared) and 1 indicating most similar (all substructures are shared). Morgan fingerprints with radius R and B bits were generated by looking at each atom and determining all of the substructures centered at that atom that included atoms up to R bonds away from the central atom. The presence or absence of these substructures was encoded as 1 and 0 in a vector of length B, which represented the fingerprint. For t-SNE analyses, plots were created using scikit-learn's implementation of t-Distributed Stochastic Neighbor Embedding. RDKit was first used to compute Morgan fingerprints for each molecule using a radius of 2 and using 2048-bit fingerprint vectors. Subsequently, t-SNE using the Jaccard (Tanimoto) distance metric was employed to reduce the data points from 2048 dimensions to the two dimensions that were plotted. The Jaccard distance is a common term for Tanimoto distance, wherein the Tanimoto distance is defined as: Tanimoto distance=1−Tanimoto similarity. Thus, the distance between points in the t-SNE plots is an indication of the Tanimoto similarity of the corresponding molecules, with greater distance between molecules indicating lower Tanimoto similarity. Scikit-leam's default values were used for all t-SNE parameters apart from the distance metric.

Code Availability

Chemprop code is available at: www.github.com/swansonk14/chemprop.

Figure 2A:
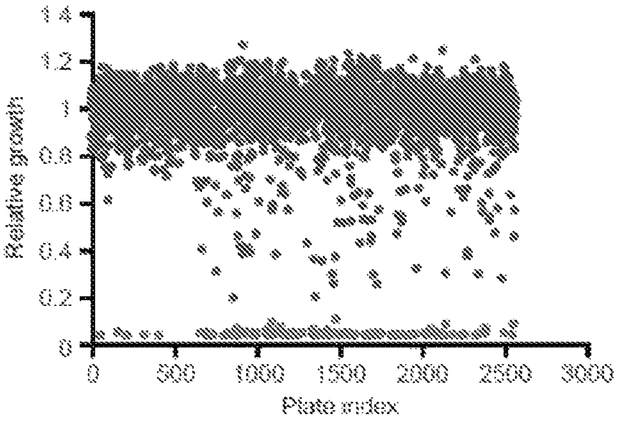
FIGS. 2A-2I demonstrate initial model training and the notable identification of halicin (5-[(5-nitro-1,3-thiazol-2-yl)sulfanyl]-1,3,4-thiadiazol-2-amine).
Figure 7A:
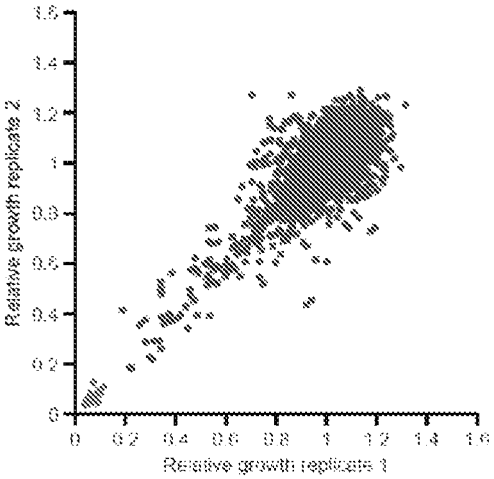
FIGS. 7A and 7B shows data from the primary screening and initial model training (in further support of FIGS. 2A-2I above).
Figure 7B:
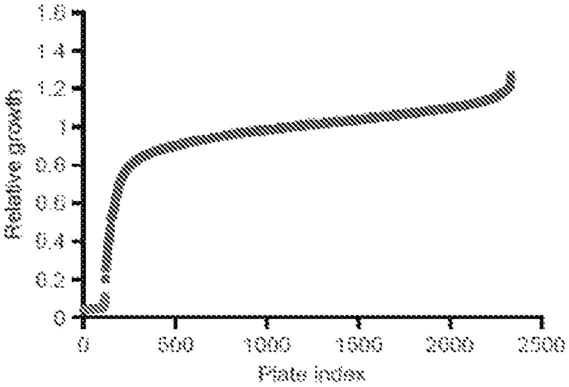

Example 2: Initial Model Training and Identification of Halicin as an Effective Antibacterial An initial goal of the instant disclosure was to obtain a training dataset de novo that was inexpensive, chemically diverse, and that did not require sophisticated laboratory resources. Such a training dataset would allow for the development of a robust model with which new antibiotics could be predicted, without the practical hurdles associated with large-scale antibiotic screening efforts. To meet these fundamental criteria, growth inhibition against *E. coli* BW25113 (Zampieri et al., 2017) was screened for using a widely available FDA-approved drug library consisting of 1,760 molecules of diverse structure and function. To supplement these molecules and further increase chemical diversity, an additional 800 natural products isolated from plant, animal, and microbial sources were included, resulting in a primary training set of 2,560 molecules (FIG. 2A and FIG. 7A), or a total of 2,335 unique compounds when de-duplicated (FIG. 7B). Using 80% growth inhibition as a hit cut-off, this primary screen resulted in the identification of 120 molecules with growth inhibitory activity against *E. coli*.

Figure 2B:
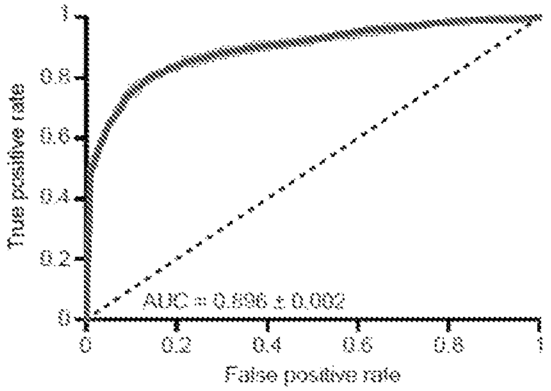
Figure 2C:
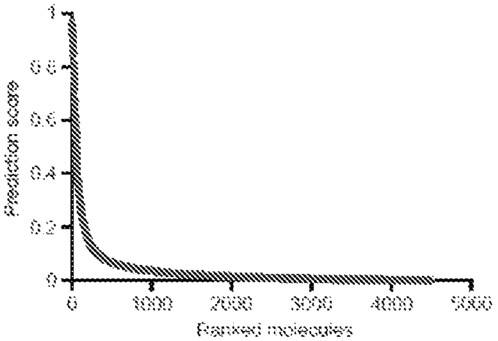

Next, all 2,335 compounds from the primary training dataset were binarized as hit or non-hit. After binarization, these data were used to train a binary classification model that predicted the probability of whether a new compound inhibited the growth of *E. coli* based on its molecular structure. For this purpose, the directed-message passing deep neural network model developed at MIT (K. Yang et al., 2019) was utilized. This model translates the graph representation of a molecule into a continuous vector via a directed bond-based message passing approach, building a molecular representation by iteratively aggregating the features of individual atoms and bonds. The model operates by passing "messages" along bonds which encode information about neighboring atoms and bonds. By applying this message passing operation multiple times, the model constructs higher-level bond messages that contain information about larger chemical substructures. The highest-level bond messages are then combined into a single continuous vector representing the entire molecule. Given the limited amount of data available for training the model, it was important to ensure that the model generalized without overfitting the training data. To this end, the learned representation was augmented with molecular features computed by RDKit (Landrum, 2006), thereby yielding a hybrid molecular representation. The algorithm's robustness was further increased by utilizing an ensemble of classifiers and estimating hyperparameters with Bayesian optimization. The resulting model achieved an ROC-AUC of 0.896 on the test data (FIG. 2B). After model development and optimization using the training dataset of 2,335 molecules, an ensemble of models trained on all twenty folds was subsequently applied to identify potential antibacterial molecules from the Drug Repurposing Hub (Corsello et al., 2017) housed at the Broad Institute. This library consists of 6,111 molecules at various stages of investigation for human diseases, including those in phase 1, 2, and 3 clinical studies, preclinical candidates, compounds launched for clinical application, and those withdrawn from use. In the instant case, prediction scores for each compound were determined, molecules were ranked based on their probability of displaying growth inhibition against *E. coli*, and compounds with molecular graphs common between the training dataset and the Drug Repurposing Hub were removed (FIG. 2C). Notably, the molecule prediction ranks from the model were compared to numerous others, including a learned model without RDKit feature augmentation, a model trained exclusively on RDKit features, a feed-forward deep neural network model using Morgan fingerprints as the molecular representation, a random forest classifier using Morgan fingerprints, and a support-vector machine model using Morgan fingerprints (see Example 1).

Figure 2D:
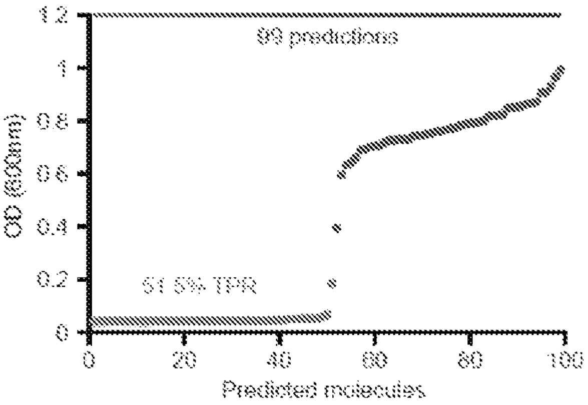
Figure 2E:
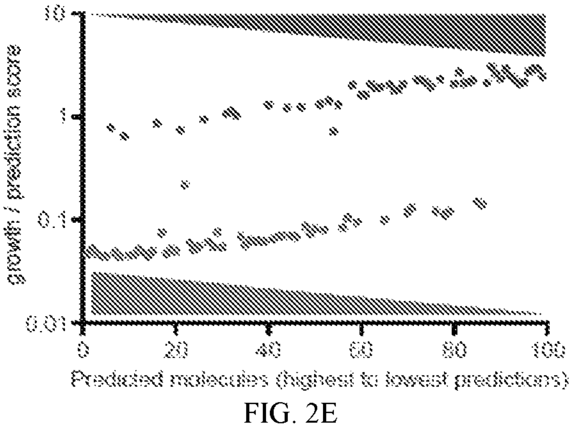
Figure 2F:
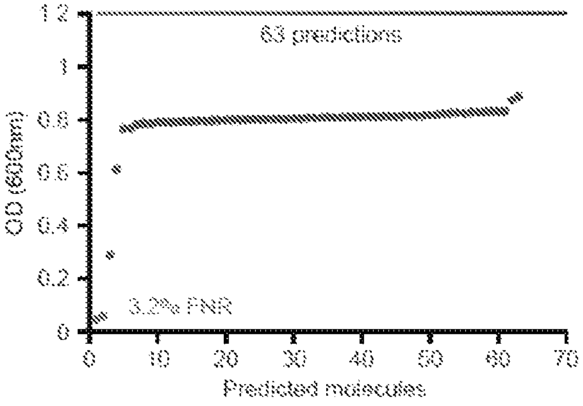
Figure 2G:
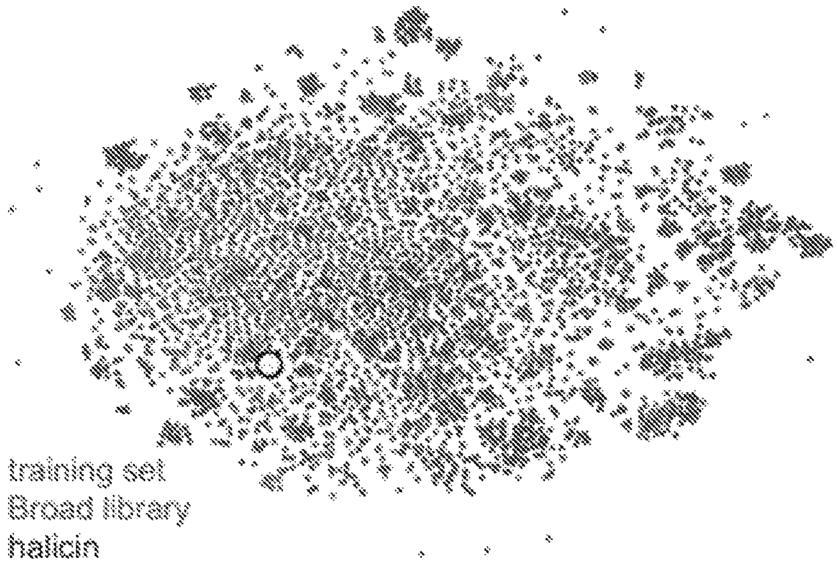
Figure 2H:
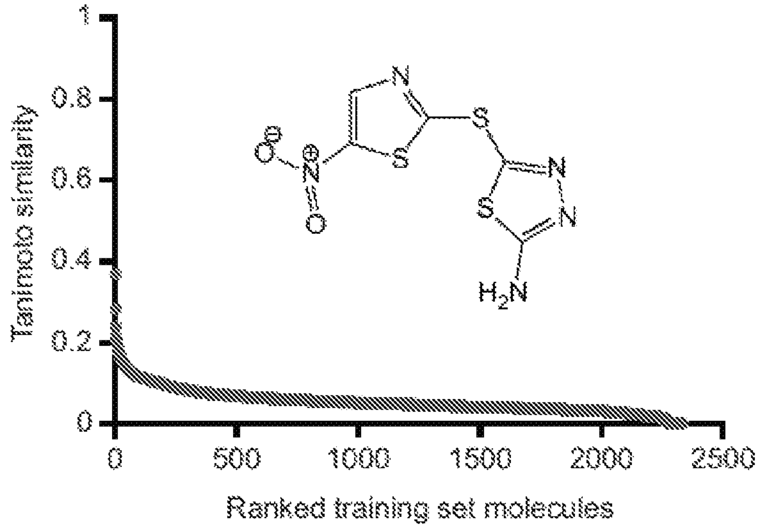
Figure 2I:
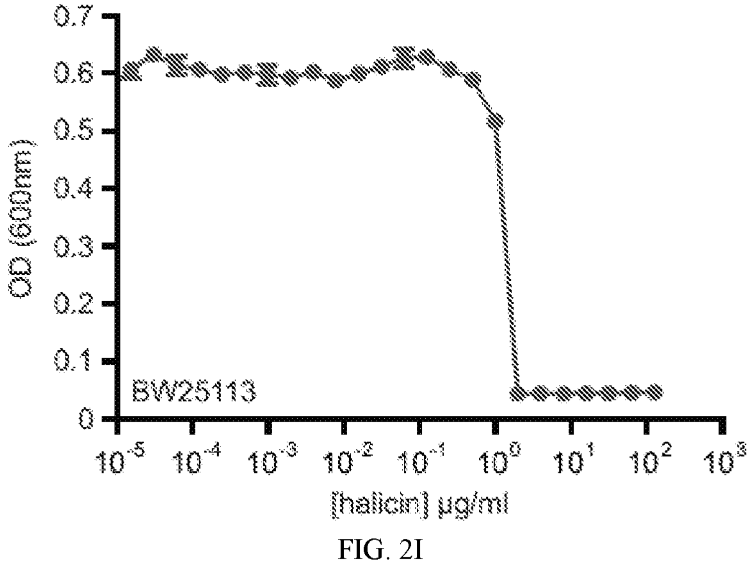

Next, the 99 molecules unique to the Drug Repurposing Hub that were most strongly predicted to display antibacterial properties were curated and empirically tested for growth inhibition. It was observed that 51 of the 99 predicted molecules (51.5% true positive rate) displayed growth inhibition against *E. coli* when empirically assayed based on a cut-off of $OD_{600}<0.2$ (FIG. 2D). Importantly, within this set of 99 molecules, higher prediction scores correlated with a greater probability of growth inhibition (FIG. 2E). Furthermore, empirically testing the lowest predicted 63 molecules that were unique to the Broad Repurposing Hub revealed that only two of these compounds displayed growth inhibitory activity (3.2% false negative rate; FIG. 2F). Collectively, these data highlighted the accuracy of the instant disclosure's model in assigning high prediction scores to compounds more likely to display antibacterial properties, and low prediction scores to non-antibiotic molecules. After identifying the 51 molecules that displayed growth inhibition against *E. coli*, these were then prioritized based on clinical phase of investigation, structural similarity to molecules in the primary training dataset, and predicted toxicity using a deep neural network model trained on the ClinTox database (Gayvert et al., 2016; Wu et al., 2017). Specifically prioritized were: predicted compounds with unconventional biological functions; those in preclinical or phase 1, 2, and 3 studies; those with low structural similarity to training set molecules; and those with low predicted toxicity. The predicted compound that satisfied all of these criteria was the c-Jun N-terminal kinase inhibitor SU3327 (De et al., 2009; Jang et al., 2015) (renamed "halicin" herein), a preclinical nitrothiazole derivative under investigation as a treatment for diabetes. Halicin is structurally most similar to a family of nitro-containing antiparasitic compounds (Tanimoto similarity≈0.37; FIGS. 2G and 2H) (Rogers and Hahn, 2010) and the antibiotic metronidazole (Tanimoto similarity≈0.21). Excitingly, halicin displayed excellent growth inhibitory activity against *E. coli* when tested in dose, achieving a minimum inhibitory concentration (MIC) of 2 μg/ml in rich growth conditions (FIG. 2I).

Notably, it was observed that the prediction rank of halicin in the model was greater than that in four of the other five models tested. Indeed, only the learned model without RDKit augmentation positioned halicin in a higher prediction rank. These data highlighted the importance of using a directed-message passing deep neural network approach in the discovery of halicin, and indicated that this novel antibacterial compound would have been overlooked using more common approaches.

Example 3: Halicin is a Broad-Spectrum Bactericidal Antibiotic

Figure 3A:
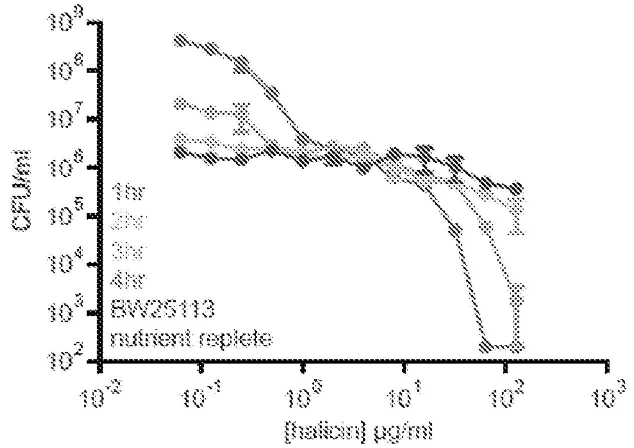
FIGS. 3A-3G provide extensive evidence that halicin is a broad-spectrum bactericidal antibiotic.
Figure 8A:
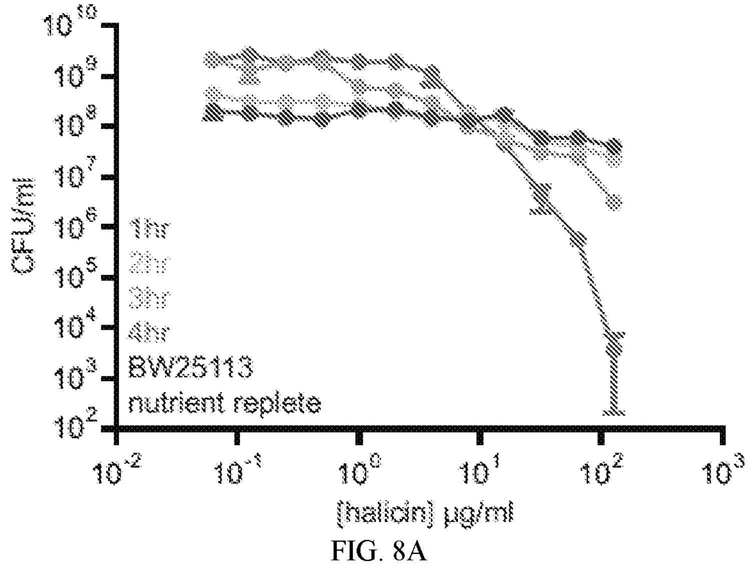
FIGS. 8A-8M show the observed antibacterial activity of halicin (in support of FIGS. 3A-3G above).
Figure 8B:
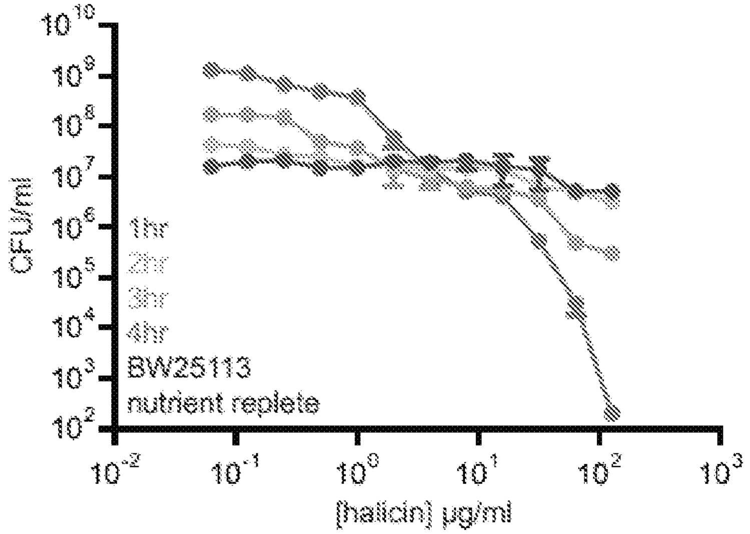

Given that halicin displayed potent growth inhibitory activity against *E. coli*, time and concentration-dependent killing assays were next performed to determine whether this compound inhibited growth through a bactericidal or bacteriostatic mechanism. In rich growth conditions against an initial cell density of ~$10^6$ CFU/ml, bacterial cell killing was observed in the presence of halicin (FIG. 3A). Consistent with observations using conventional antibiotics, the apparent potency of halicin decreased as initial cell density increased (FIGS. 8A and 8B), likely as a result of dilution of the molecule over a greater number of cells. Next, it was considered whether halicin would induce bacterial cell death against *E. coli* in a metabolically repressed, antibiotic-tolerant state (Balaban et al., 2019; Stokes et al., 2019a; 2019b). Indeed, given that metronidazole is bactericidal against non-replicating cells (Tally et al., 1978), it was reasoned that halicin similarly would display this activity.

Figure 3B:
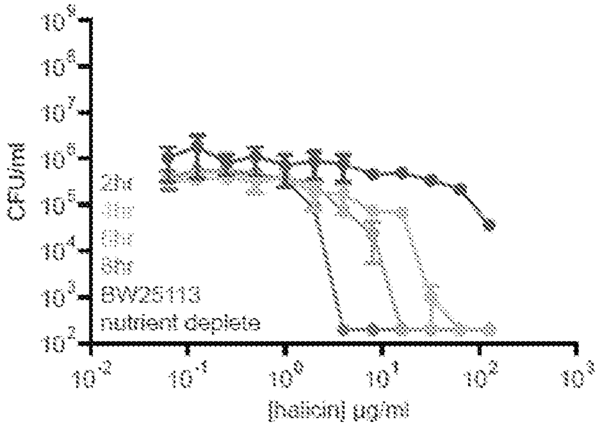
Figure 3C:
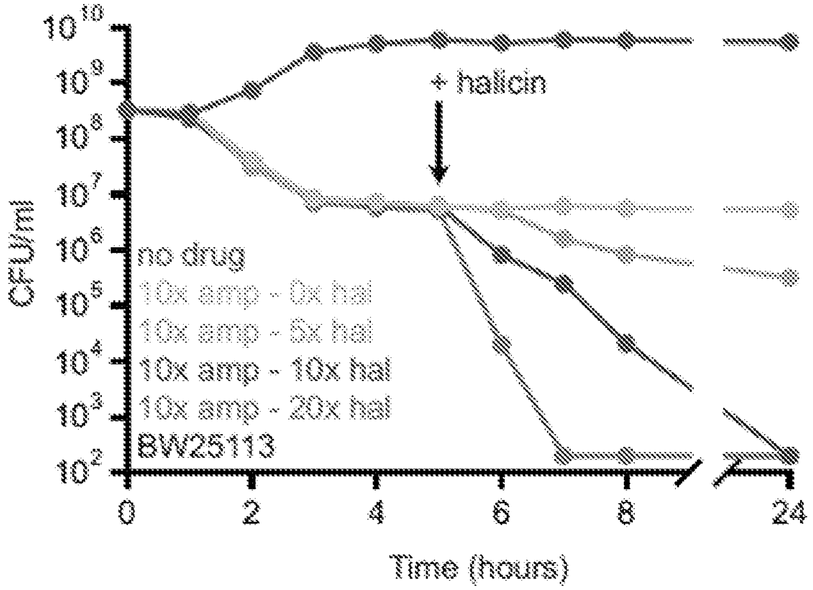
Figure 8C:
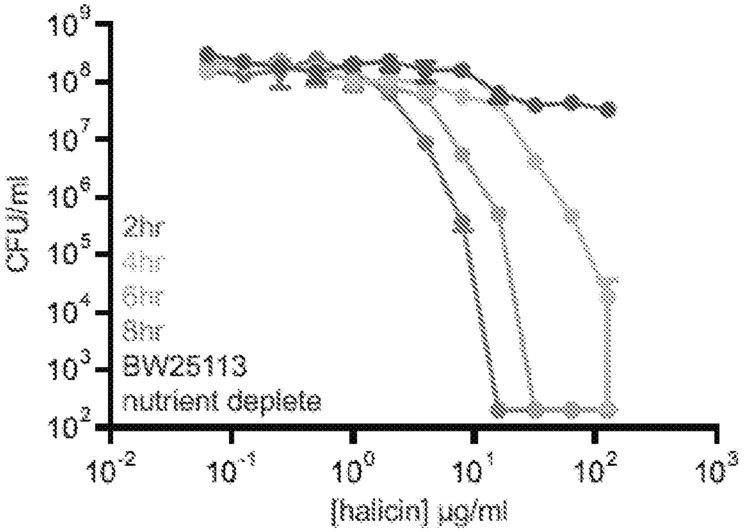
Figure 8D:
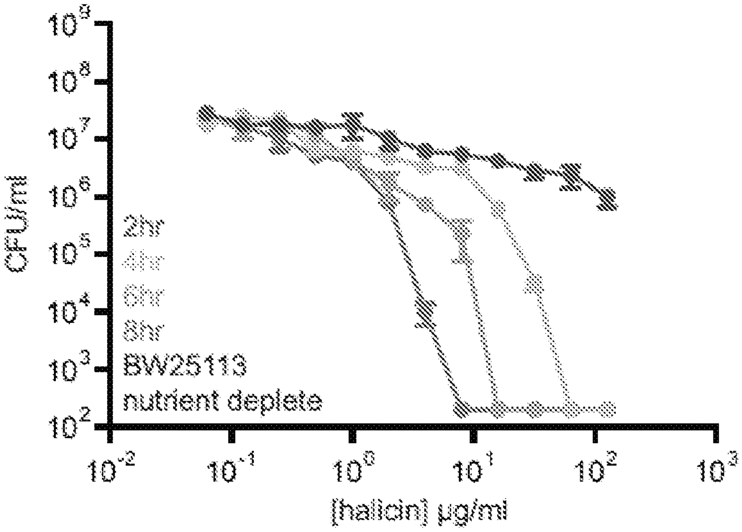
Figure 8E:
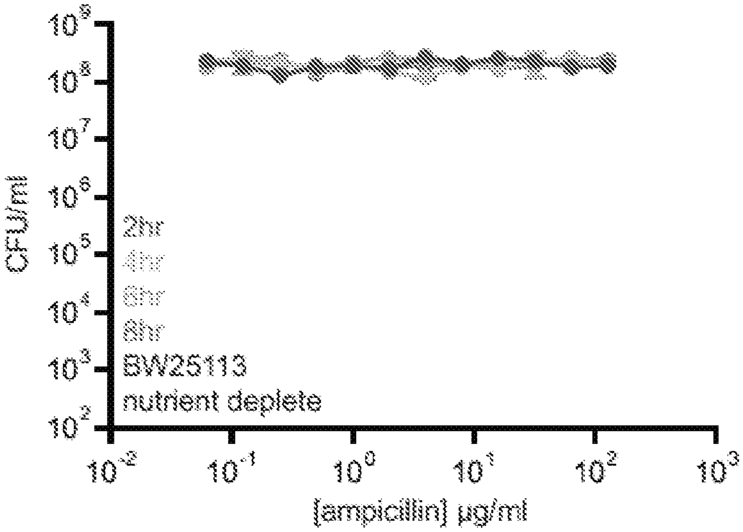
Figure 8F:
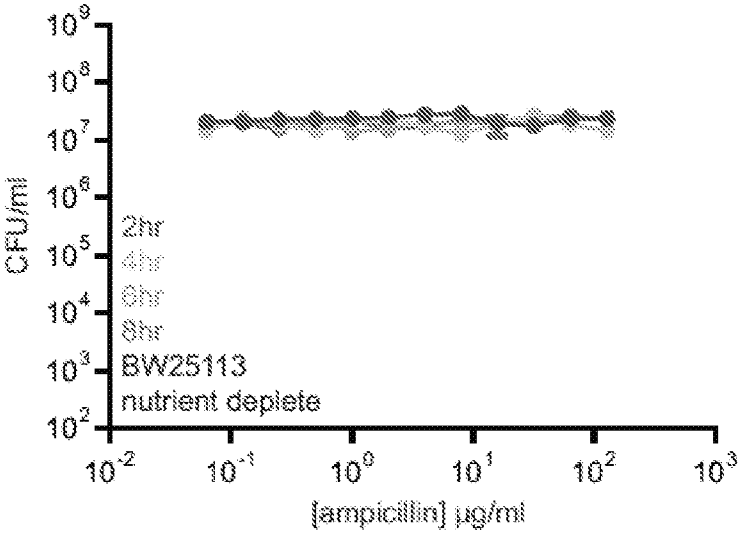
Figure 8G:
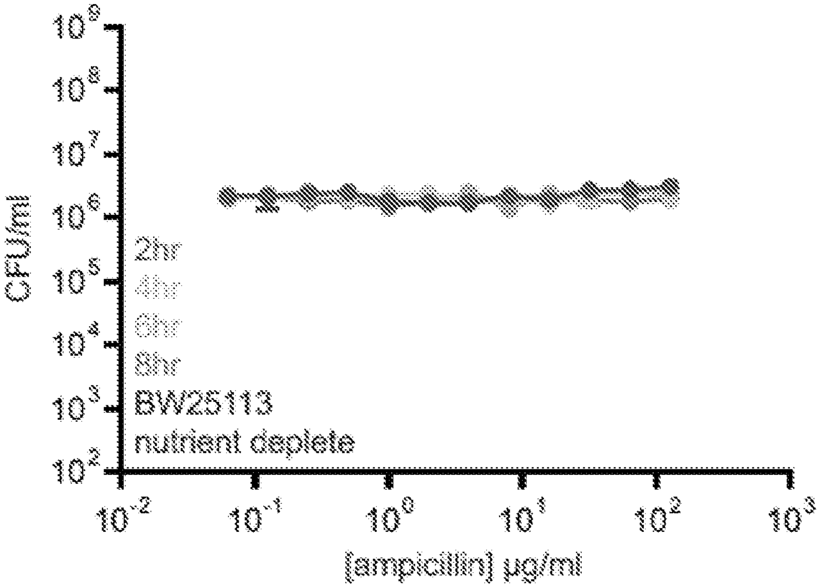
Figure 8H:
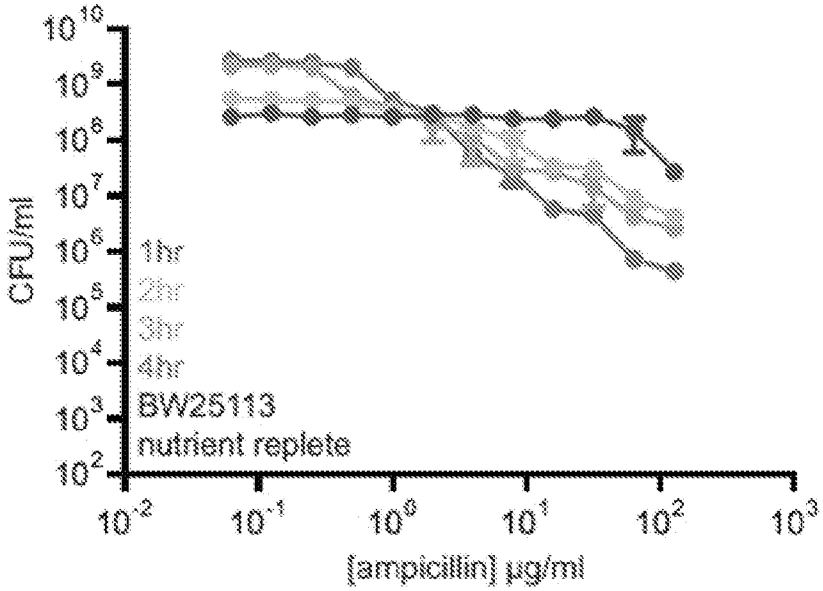
Figure 8I:
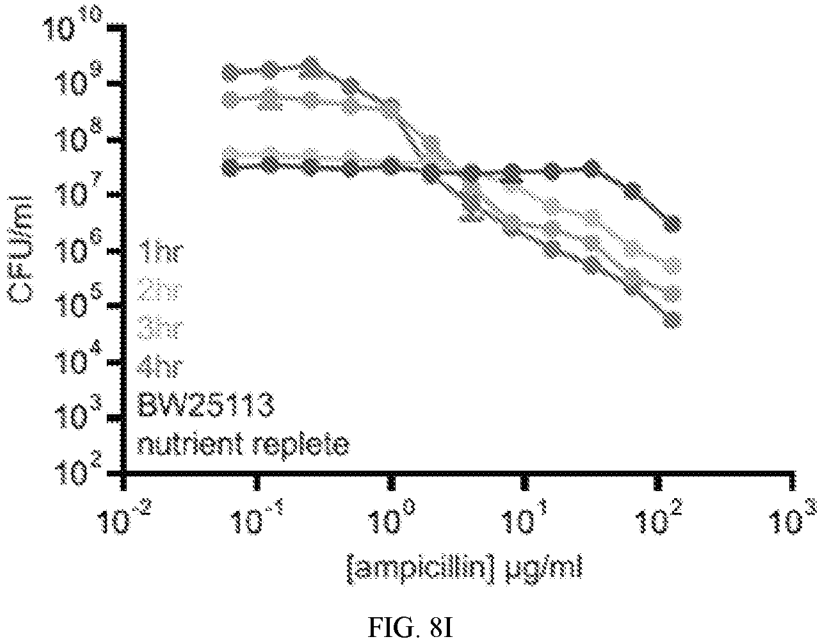
Figure 8J:
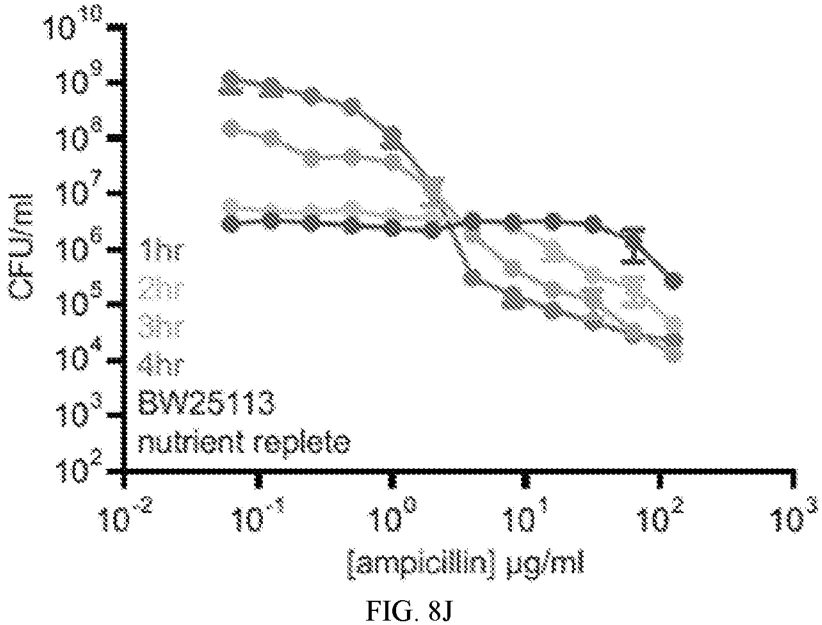

Remarkably, by incubating *E. coli* in nutrient-free buffer supplemented with halicin, it was observed that this molecule retained bactericidal activity against tolerant cells (FIGS. 3B, 8C, and 8D). This was in stark contrast to the conventionally bactericidal antibiotic ampicillin, which was unable to eradicate *E. coli* existing in metabolically repressed states (FIGS. 8E to 8G), despite its efficacy against metabolically active cells (FIGS. 8H to 8J). Moreover, halicin was able to eradicate *E. coli* persister cells that remained after treatment with ampicillin (FIG. 3C), consistent with its retained bactericidal activity against cells in nutrient-free buffer conditions.

Figure 3D:
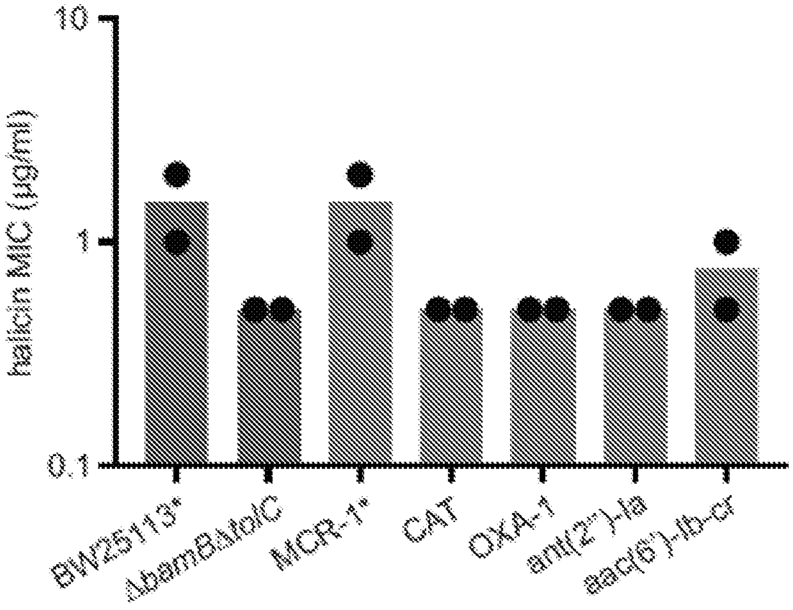
Figure 8K:
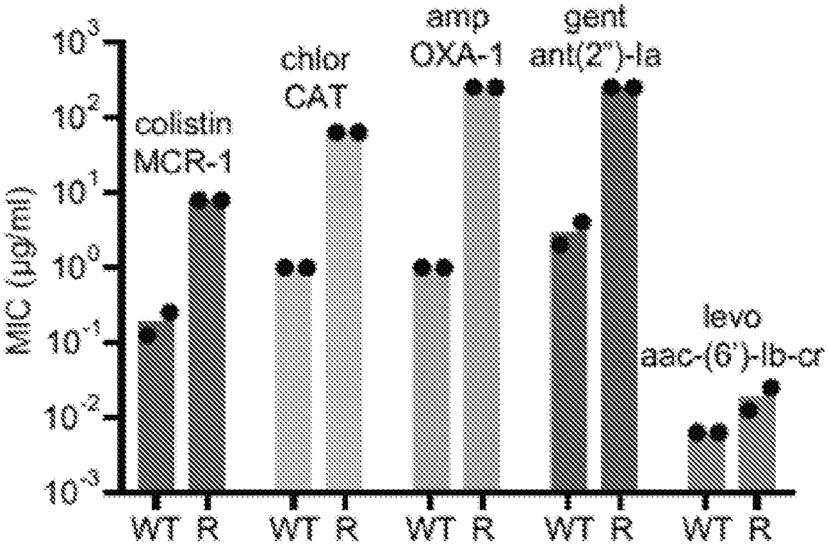
Figure 8L:
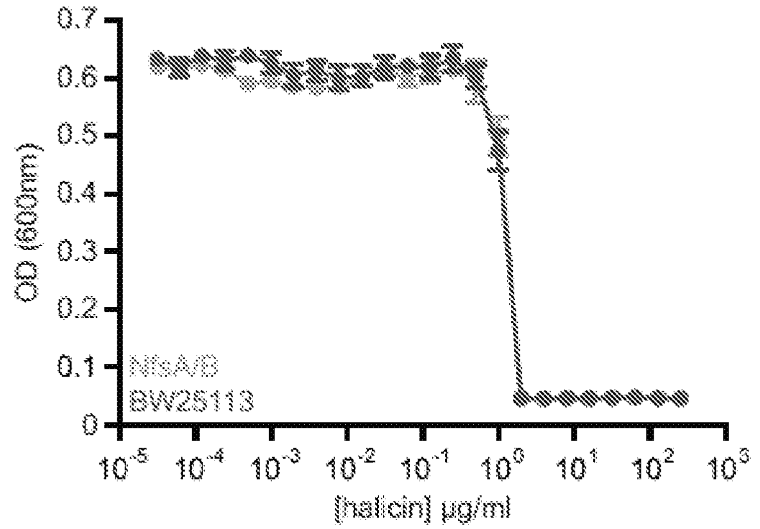
Figure 8M:
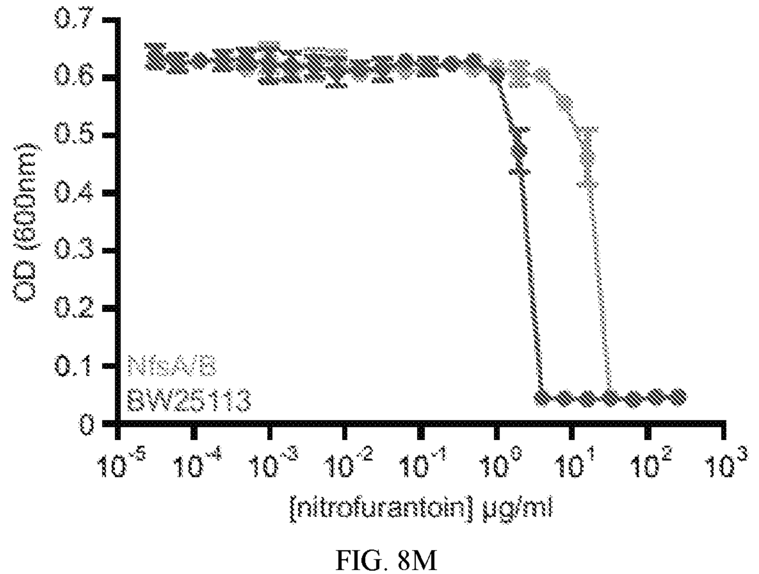

The efficacy of halicin against antibiotic-tolerant cells represented a significant improvement over the majority of conventional bactericidal antibiotics (Lobritz et al., 2015; Stokes et al., 2019b). Without wishing to be bound by theory, this observation indicated that the molecule could function through an uncommon mechanism of action, and therefore overcome many common resistance mechanisms that plague existing clinical antibiotics. Initially, halicin was tested against a modest selection of *E. coli* strains harboring plasmid-borne antibiotic-resistance genes conferring resistance to polymyxins (MCR-1), chloramphenicol (CAT), b-lactams (OXA-1), aminoglycosides[ant(2")-Ia], and fluoroquinolones [aac(6')-Ib-cr]. No change in halicin MIC was observed in the presence of any resistance gene relative to the antibiotic-susceptible parent strains (FIGS. 3D and 8K). Similarly, the MIC of halicin did not change in *E. coli* displaying resistance to the nitrofuran antibiotic nitrofurantoin via deletion of nfsA and nfsB (Sandegren et al., 2008) (FIGS. 8L and 8M), further indicating a unique mechanism of action. To more comprehensively assess the ability of halicin to overcome clinically burdensome, antibiotic-resistance genes, as well as understand Gram-negative phylogenetic spectrum of bioactivity, halicin-dependent growth inhibition was assayed against 36 multidrug-resistant clinical isolates each of Carbapenem-resistant Enterobacteriaceae (CRE), *A. baumannii*, and *Pseudomonas aeruginosa*. These pathogens are regarded by the World Health Organization as the bacteria that most urgently require new clinical treatments. Excitingly, it was observed that halicin was rapidly bactericidal against *M. tuberculosis* (FIGS. 3E and 3F) and had strong growth inhibitory activity against CRE and *A. baumannii* clinical isolates (FIG. 3G). The lack of efficacy against *P. aeruginosa* may be explained by insufficient permeability to the cell membrane, which is a common intrinsic mechanism of resistance displayed by *Pseudomonas* species (Angus et al., 1982; Yoshimura and Nikaido, 1982). Nevertheless, these data showed that halicin eradicated conventionally antibiotic-tolerant cells, and retained activity in the presence of some of the most clinically problematic, antibiotic-resistant Gram-negative pathogens.

Example 4: Halicin Dissipates the ΔpH Component of the Proton Motive Force

Figure 4A:
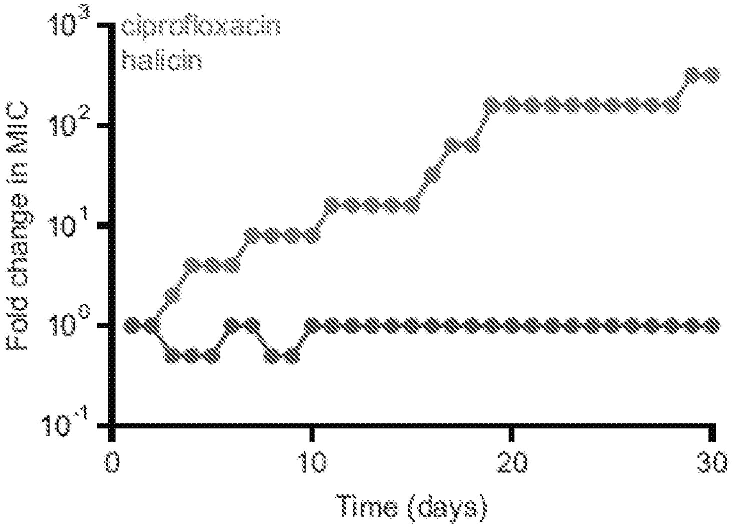
FIGS. 4A-4E demonstrate that halicin dissipates the ΔpH component of the proton motive force.
Figure 4B:
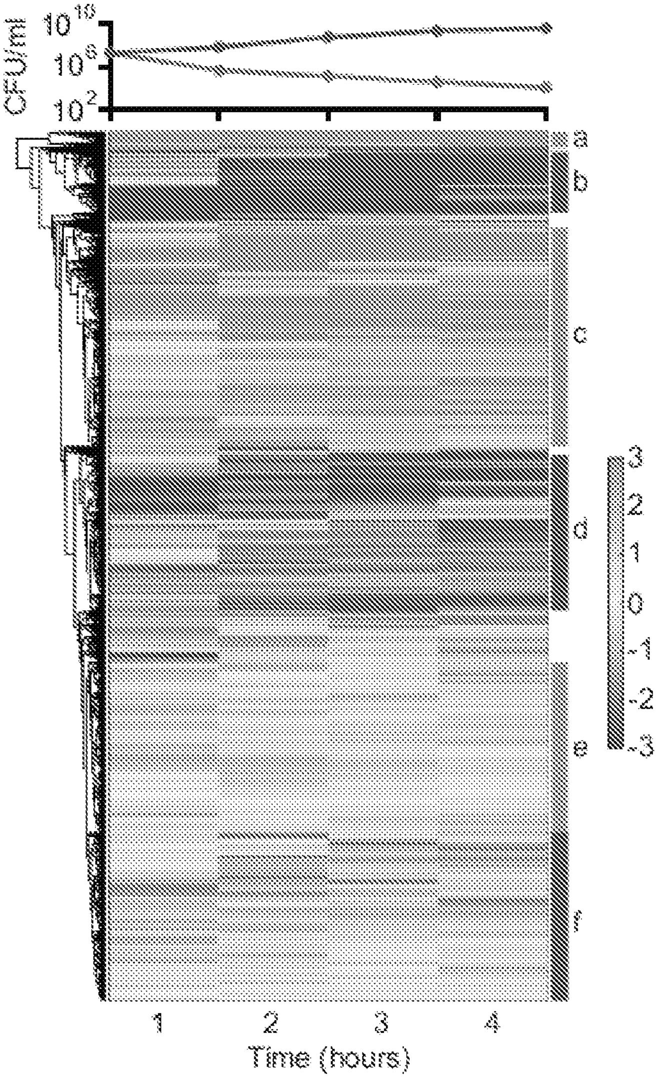
Figure 9A:
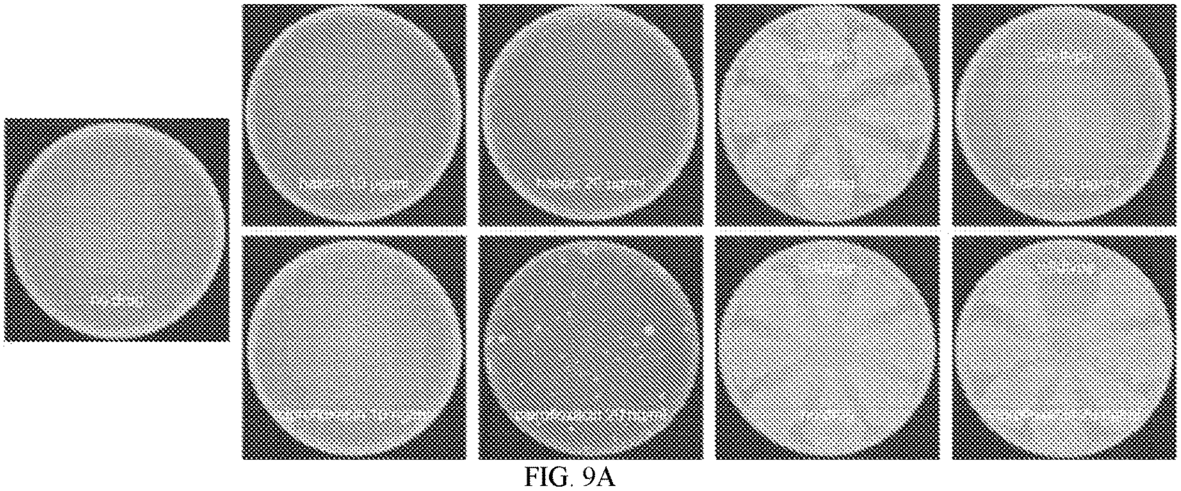
FIGS. 9A-9H demonstrate the investigation performed herein into the antibacterial mechanism of halicin (in support of FIGS. 4A-4E above).
Figure 9B:
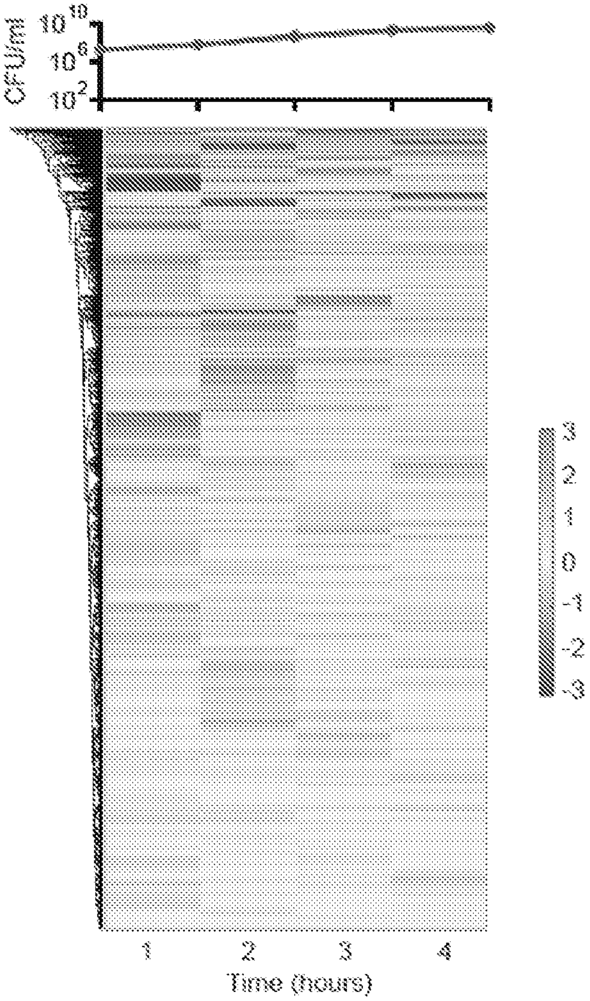
Figure 9C:
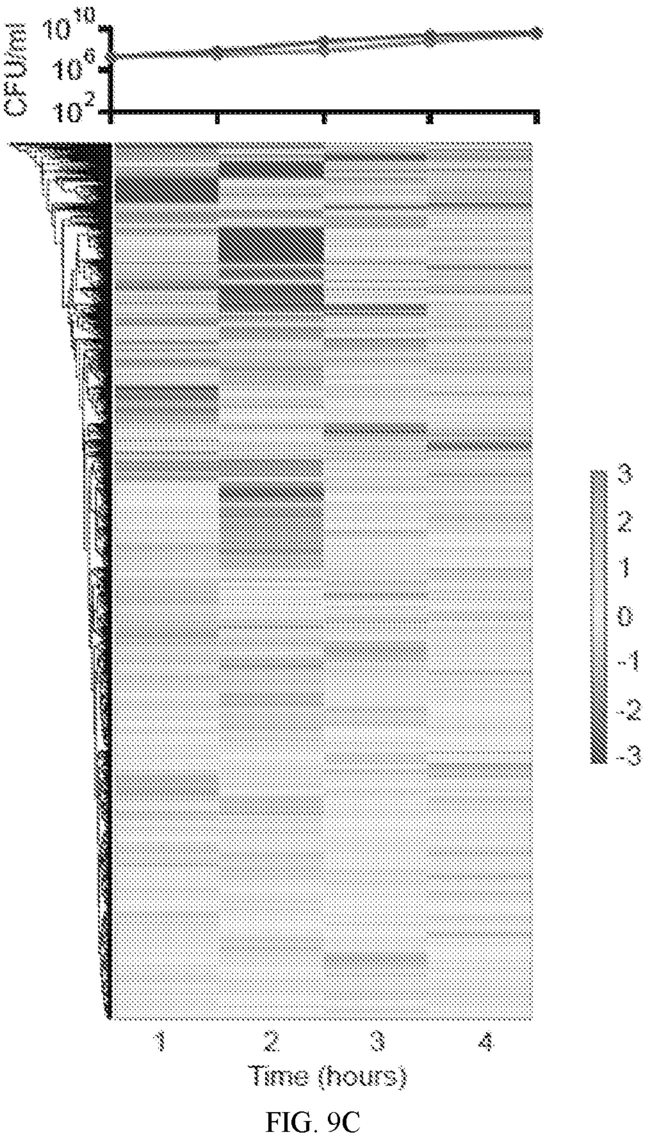

The observations that halicin retained bactericidal activity against metabolically restricted, antibiotic-tolerant *E. coli*, as well as growth inhibitory properties against multidrug-resistant Gram-negative clinical isolates, indicated that this compound was antibacterial through an unconventional mechanism. Since the model of the instant disclosure was agnostic to the mechanism of action underlying growth inhibition, an initial attempt was made to elucidate mechanism of action through the evolution of halicin-resistant mutants. However, it was observed as not possible to isolate spontaneous suppressor mutants after 30 days of serial passaging in liquid media (FIG. 4A) or after seven days of continuous halicin exposure on solid media (FIG. 9A). Therefore, RNA sequencing was applied to understand the physiologic response of *E. coli* to halicin. Here, early-log phase cells were treated with a range of concentrations of compound for varying durations, and whole-transcriptome sequencing was performed. Notably, a rapid downregulation of genes involved in cell motility across all concentrations was observed, as well as the upregulation of genes required for iron homeostasis at sub-lethal concentrations (FIGS. 4B, 9B, and 9C). Previous work has shown that dissipation of the cytoplasmic transmembrane potential resulted in decreased bacterial locomotion and flagellar biosynthesis (Manson et al., 1977; Paul et al., 2008; Shioi et al., 1982), consistent with the transcriptomics data of the instant disclosure. Moreover, given that cells must maintain an electrochemical transmembrane gradient for viability (Hurdle et al., 2011; Coates and Hu, 2008), dissipation of the proton motive force results in the death of tolerant cells.

Figure 4C:
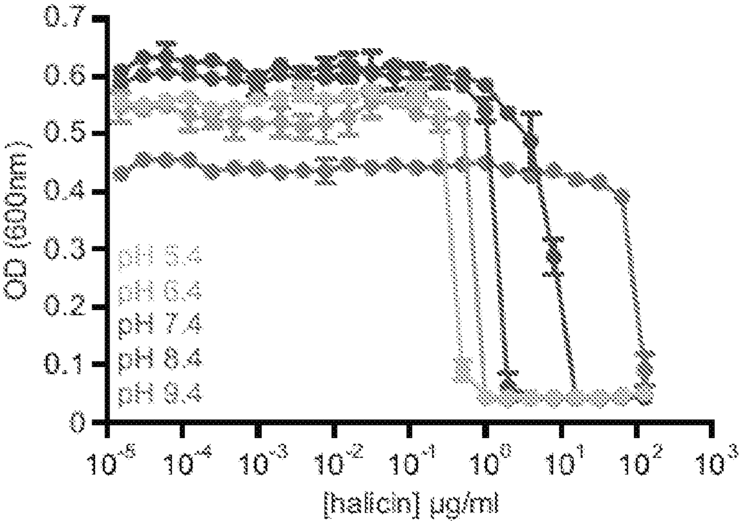
Figure 9D:
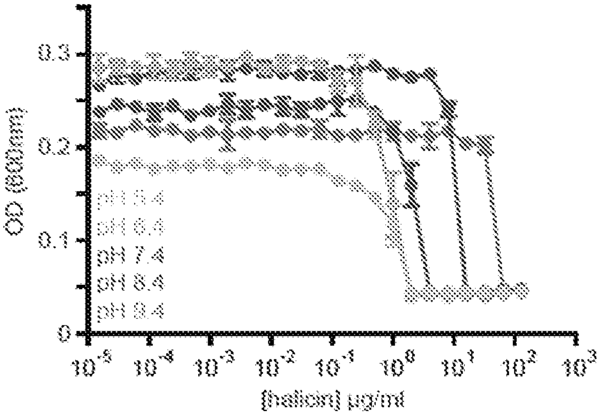
Figure 9E:
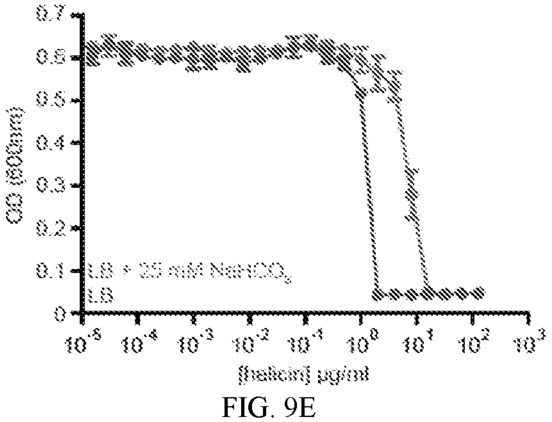

To examine if halicin dissipated the proton motive force, first changes in halicin MIC against *E. coli* as a function of media pH were assayed. Indeed, molecules with pH-dependent growth inhibitory properties can have proton motive force-dissipating functions (Farha et al., 2013). In *E. coli* (FIG. 4C), as well as *Staphylococcus aureus* (FIG. 9D), it was observed that halicin potency decreased as pH increased, providing evidence that this compound was likely dissipating the ΔpH component of the proton motive force, in agreement with previous results (Farha et al., 2013). Consistent with this observation, the addition of 25 mM sodium bicarbonate to the growth medium antagonized the action of halicin against *E. coli* (FIG. 9E).

Figure 4D:
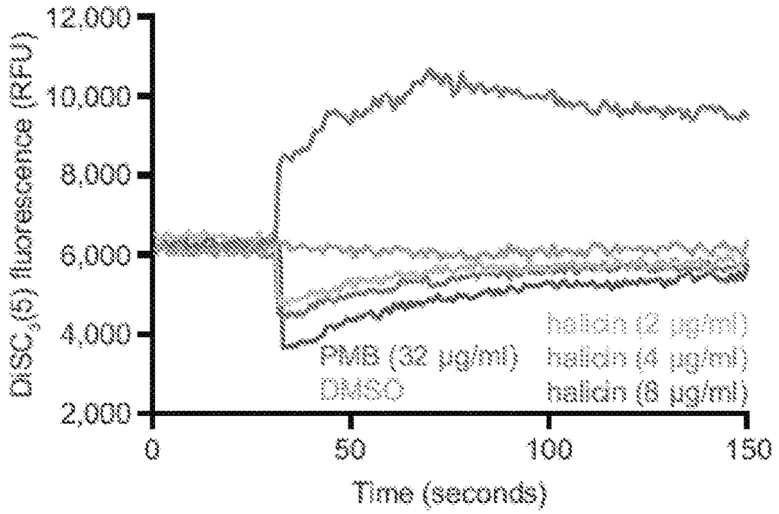
Figure 9F:
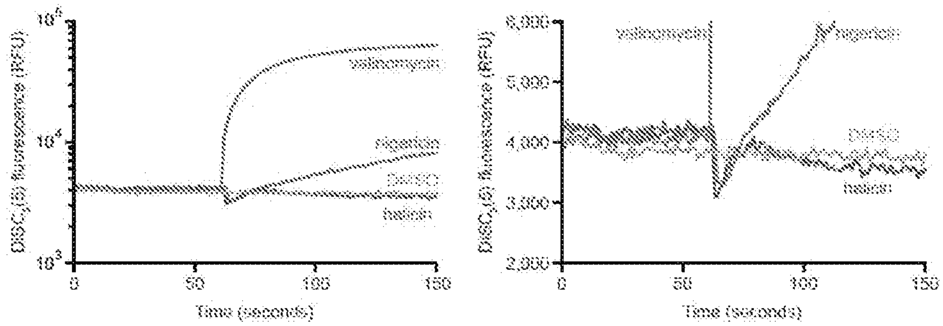
Figure 9G:
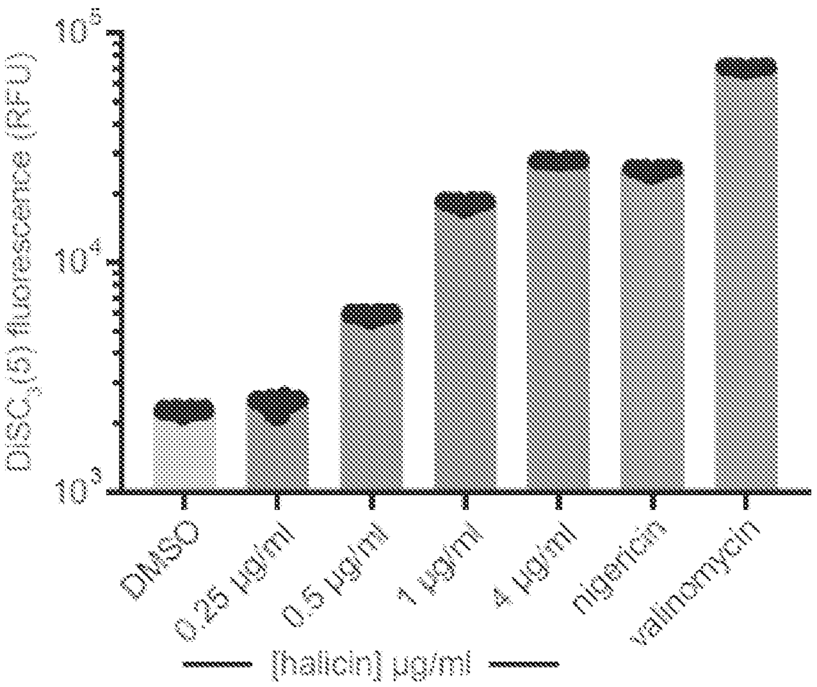

To further assess the effect of halicin on transmembrane ΔpH potential dissipation in bacteria, the potentiometric fluorophore 3,3'-dipropylthiadicarbocyanine iodide [DiSC3 (5)](Wu et al., 1999) was employed. DiSC3(5)accumulates in the cytoplasmic membrane in response to the Δψ component of the proton motive force, and self-quenches its own fluorescence. When Δψ is disrupted or the membrane is permeabilized, the probe is released into the extracellular milieu resulting in increased fluorescence signal. Conversely, when ΔpH is disrupted, cells compensate by increasing Δψ, resulting in enhanced DiSC3(5) uptake into the cytoplasmic membrane and therefore decreased fluorescence. Here, early-log *E. coli* cells were washed in buffer and introduced to $DiSC_3(5)$ to allow fluorescence equilibration. Cells were then introduced to polymyxin B (FIG. 4D), which disrupts the cytoplasmic membrane, causing release of $DiSC_3(5)$ from the membrane and a corresponding increase in fluorescence. Next, cells were introduced to varying concentrations of halicin, and observed an immediate decrease in $DiSC_3(5)$ fluorescence in a dose-dependent manner (FIG. 4D), which indicated that halicin selectively dissipated the ΔpH component of the proton motive force. Similar $DiSC_3(5)$ fluorescence changes were observed in *S. aureus* treated with halicin (FIGS. 9F and 9G). Moreover, halicin displayed antibiotic antagonism and synergy profiles consistent with ΔpH dissipation. Of note, halicin antagonized the activity of tetracycline in *E. coli*, and synergized with kanamycin (FIG. 4E), consistent with previous work showing that the uptake of tetracyclines was dependent upon the ΔpH component of the cytoplasmic membrane (Yamaguchi et al., 1991), whereas aminoglycoside uptake was driven largely by Δψ (Taber et al., 1987).

Figure 4E:
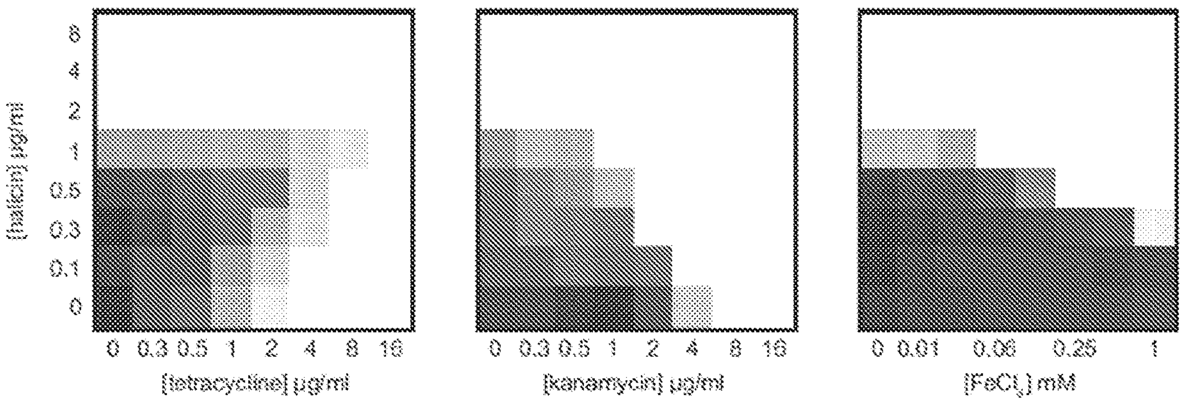
Figure 9H:
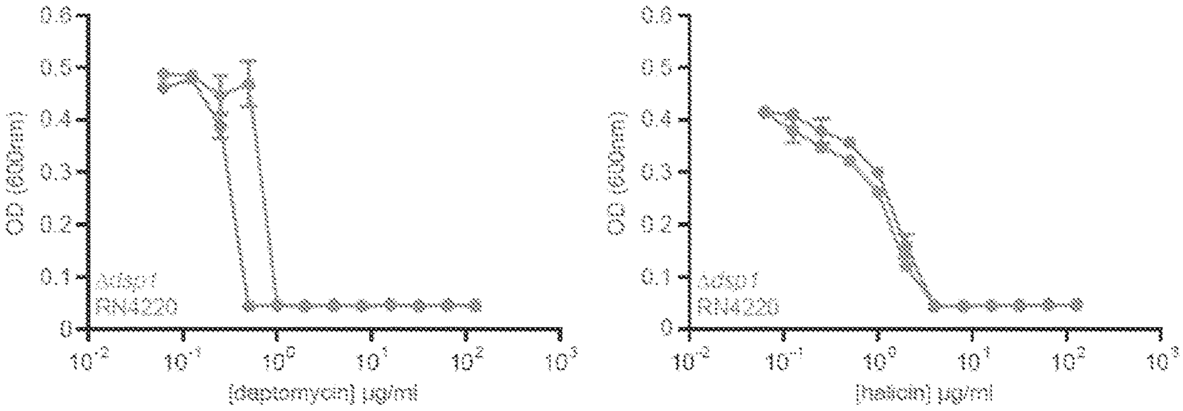

Interestingly, the observations that halicin induced the expression of iron acquisition genes at sub-lethal concentrations (Tables 6 to 8) indicated that this compound complexed with iron in solution, thereby dissipating the bacterial transmembrane ΔpH potential similarly to other antibacterial ionophores (Farha et al., 2013). Notably, daptomycin resistance via deletion of dspl in *S. aureus* did not confer cross-resistance to halicin (FIG. 9H). Indeed, enhanced potency of halicin against *E. coli* was observed with increasing concentrations of environmental $Fe^{3+}$ (FIG. 4E). This was consistent with a mechanism of action wherein halicin binds ironin solution prior to membrane association and ΔpH dissipation. However, further experimentation is contemplated to elucidate the atomic geometry of halicin-$Fe^{3+}$ association and the precise chemistry of interaction at the cytoplasmic membrane.

Example 5: Halicin Displayed Efficacy in Murine Models of Infection

Figure 5A:
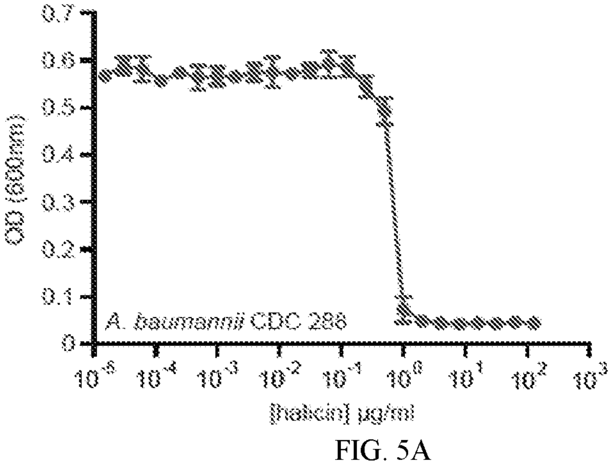
FIGS. 5A-5F demonstrate that halicin displayed efficacy in murine models of infection.
Figure 5B:
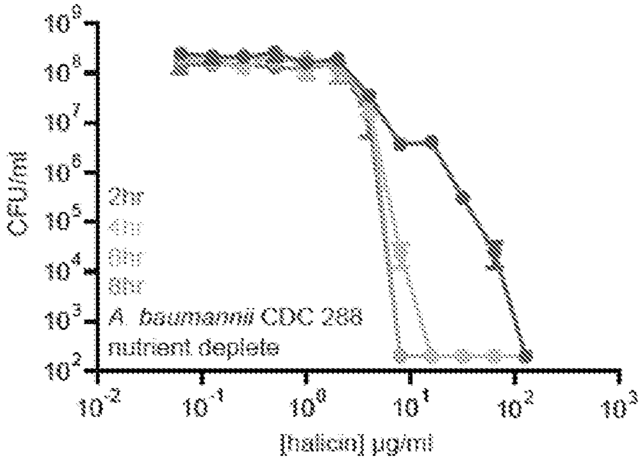
Figure 5C:
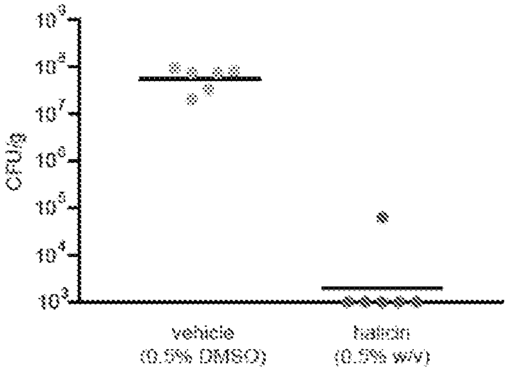
Figure 10A:
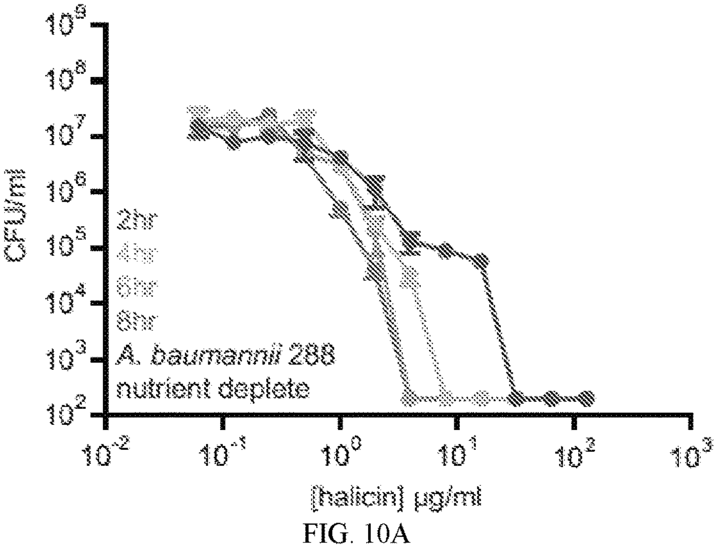
FIGS. 10A and JOB show the activity of halicin against *A. baumannii* CDC 288, in support of FIGS. 5A-5F above.
Figure 10B:
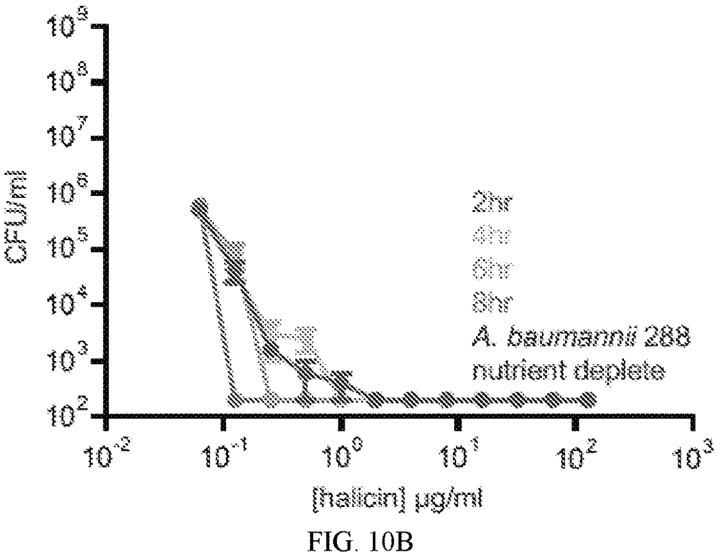

Given that halicin displayed broad-spectrum bactericidal activity and was not highly susceptible to plasmid-borne antibiotic-resistance elements or de novo resistance mutations at high frequency, it was next asked whether this compound had utility as an antibiotic in vivo. To initially understand its potential clinical utility, the efficacy of halicin was tested in a murine wound model of *A. baumannii* infection. On the dorsal surface of neutropenic Balb/c mice, a 2 $cm^2$ wound was established and infected with ≈$2.5\times10^5$ CFU of *A. baumannii* strain 288 acquired from the Centers for Disease Control and Prevention (CDC). This strain is non-sensitive to any clinical antibiotics generally used for treatment of *A. baumannii*, and therefore represented a pan-resistant isolate. Importantly, halicin displayed potent growth inhibition against this strain in vitro (MIC=1 μg/ml; FIG. 5A) and was able to sterilize *A. baumannii* 288 cells residing in metabolically repressed, antibiotic-tolerant conditions (FIGS. 5B, 10A, and 10B). After 1 hour of infection establishment, mice were treated with Glaxal Base Moisturizing Cream supplemented with vehicle (0.5% DMSO) or halicin (0.5% w/v). Mice were then treated after 4 hours, 8 hours, 12 hours, 20 hours, and 24 hours of infection, and mice were sacrificed at 25 hours post-infection. It was observed that wound-carrying capacity had reached ≈$10^8$ CFU/g in the vehicle control group, whereas 5 of the 6 mice treated with halicin contained less than $10^3$ CFU/g (below the limit of detection) and one mouse contained ≈$10^5$ CFU/g.

Figure 5D:
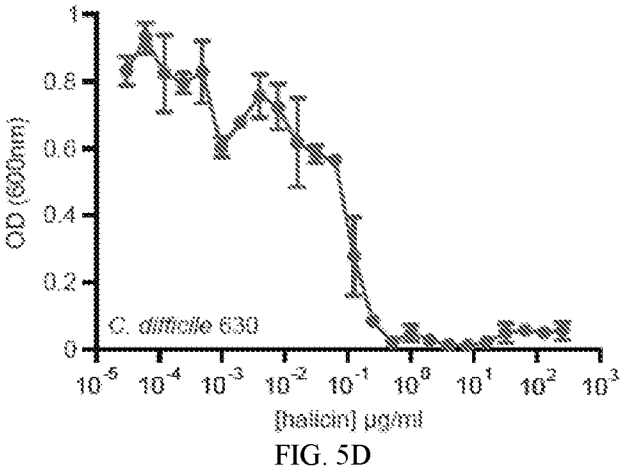
Figure 5E:
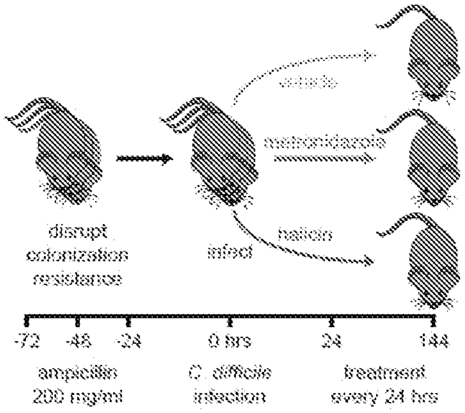
Figure 5F:
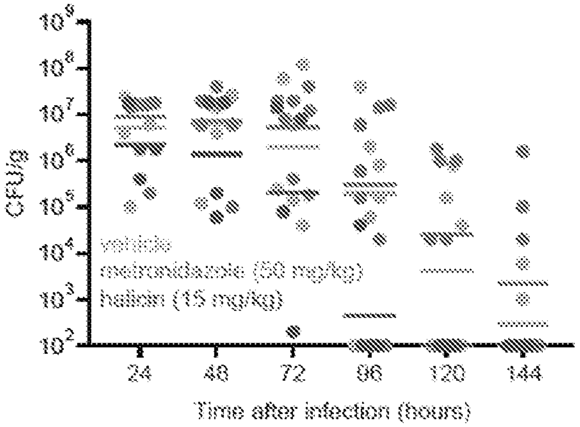

After showing that halicin displayed efficacy against *A. baumannii* in a murine wound model, it was next investigated whether this molecule also would exhibit utility against a phylogenetically divergent pathogen that is increasingly becoming burdensome to healthcare systems—namely, *C. difficile*. This spore-forming anaerobe causes pseudomembranous colitis, often as a result of dysbiosis following systemic antibiotic administration. Metronidazole or vancomycin are first-line treatments, with failure resulting from antibiotic resistance and/or the presence of metabolically dormant cells (Surawicz et al., 2013). In cases of recurrent infection, fecal bacteriotherapy is required to re-establish the normal colonic microbiota to outcompete *C. difficile* cells (Gough et al., 2011), which can be substantially more invasive than antibiotic therapy. Towards understanding the efficacy of halicin against *C. difficile* infections, the ability of this molecule to inhibit the growth of *C. difficile* strain 630 in vitro was assayed and an MIC of 0.5 μg/ml (FIG. 5D) was observed. To establish the murine infection, C57BL/6 mice were administered intraperitoneal injections of ampicillin (200 mg/kg) every 24 hours for 72 hours. Mice were then given 24 hours to recover, and subsequently administered $5\times10^3$ spores of *C. difficile* 630 via oral gavage. Beginning 24 hours after *C. difficile* gavage, mice were gavaged with antibiotics (50 mg/kg metronidazole or 15 mg/kg halicin) or vehicle (10% PEG 300) every 24 hours for five days, and fecal samples were collected to quantify *C. difficile* load (FIG. 5E). Excitingly, it was observed that halicin resulted in *C. difficile* clearance from feces at a greater rate than vehicle or the antibiotic metronidazole (FIG. 5F), which is not only a first-line treatment for *C. difficile* infection, but also the antibiotic most similar to halicin based on Tanimoto score (FIG. 2H). Indeed, halicin resulted in sterilization of 3 out of 4 mice after 72 hours of treatment, and 4 out of 4 mice after 96 hours of treatment, providing strong evidence that this compound represents a new structural class of antibiotics against *C. difficile*, a notoriously difficult pathogen to treat.

Example 6: Predicting New Antibiotic Candidates from Vast Chemical Libraries

Figure 11A:
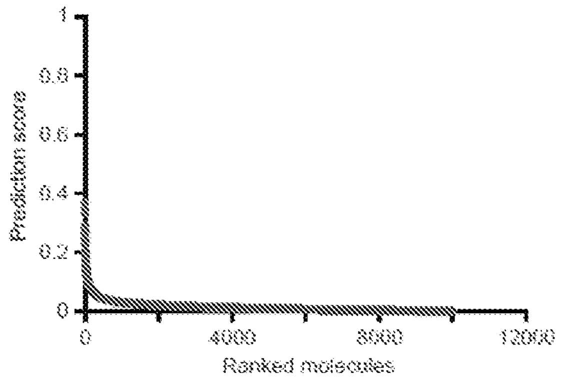
FIGS. 11A-11M show model predictions from the WuXi anti-tuberculosis library and the ZINC15 database, in support of FIGS. 6A-6I above and FIGS. 12A-12W below.
Figure 11B:
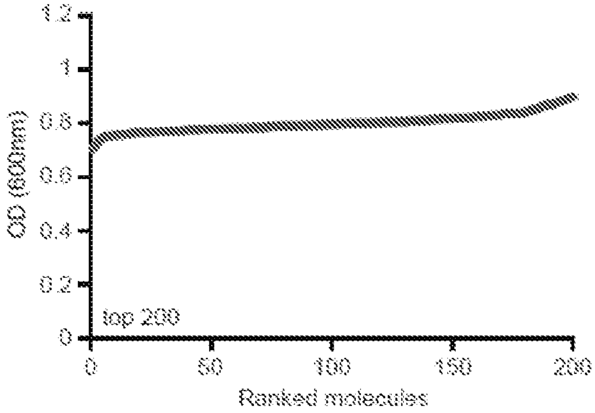
Figure 11C:
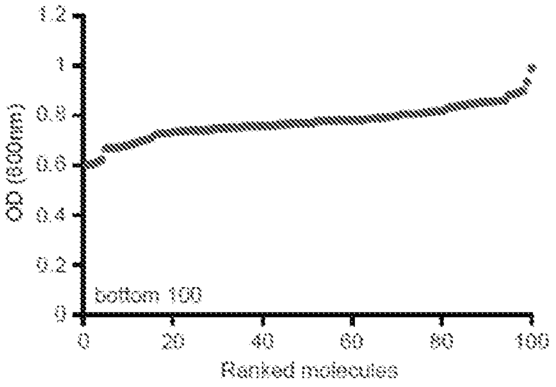
Figure 11D:
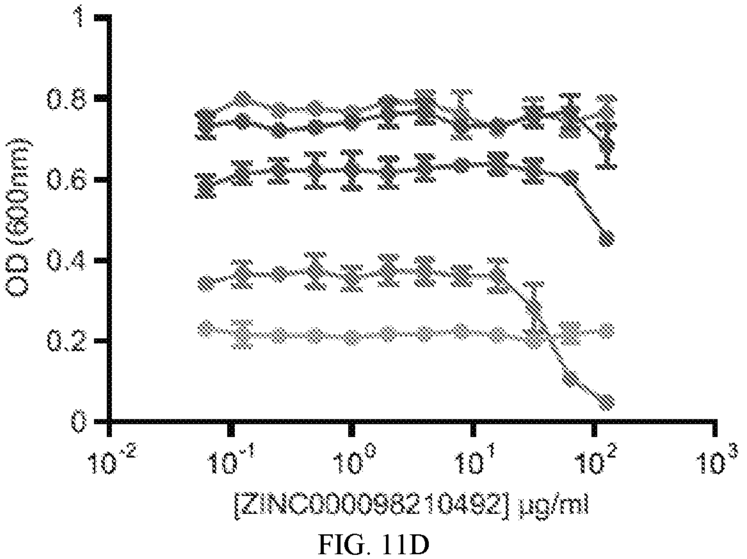
Figure 11E:
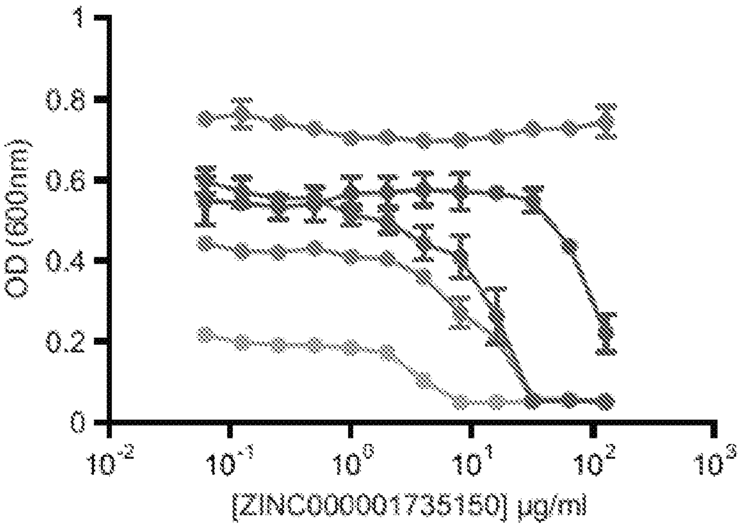
Figure 11F:
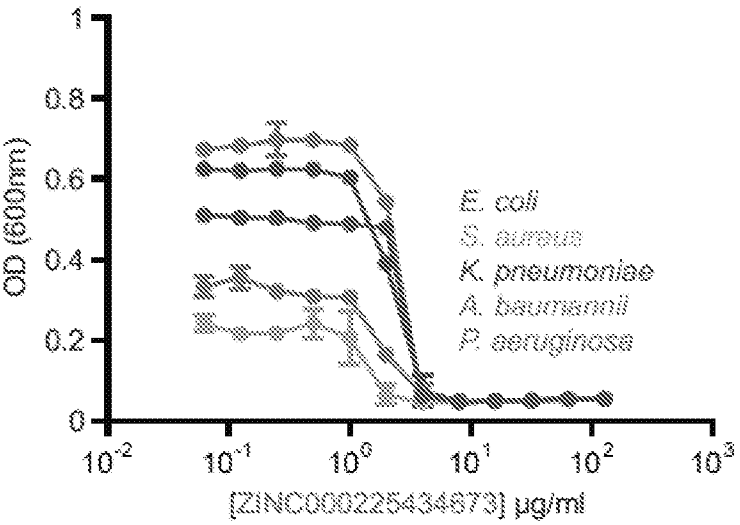
Figure 11G:
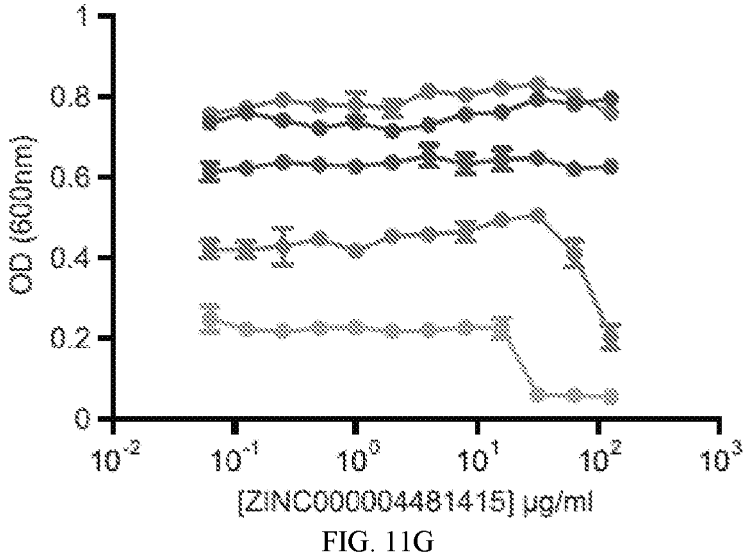
Figure 11H:
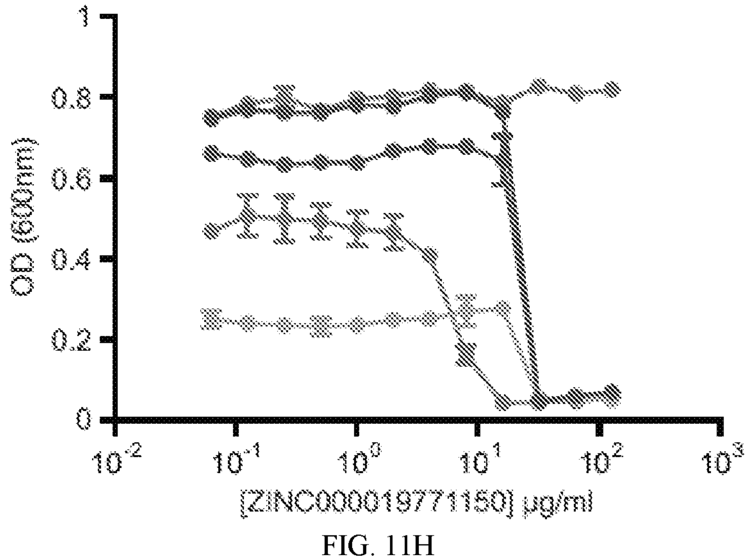
Figure 11I:
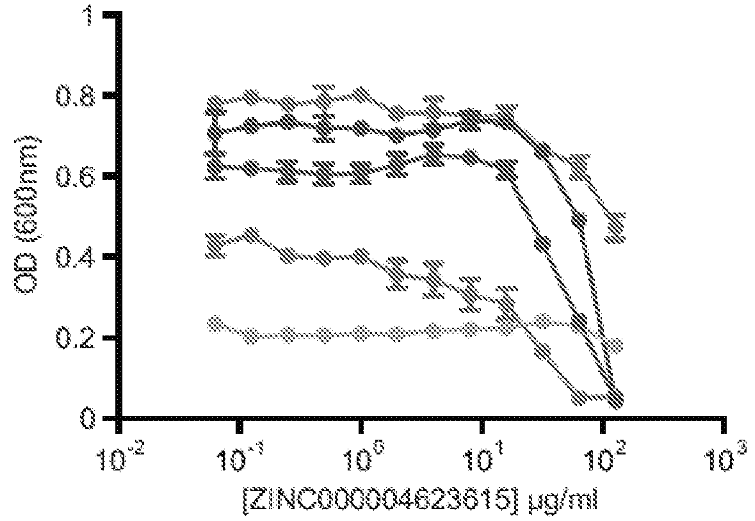
Figure 11J:
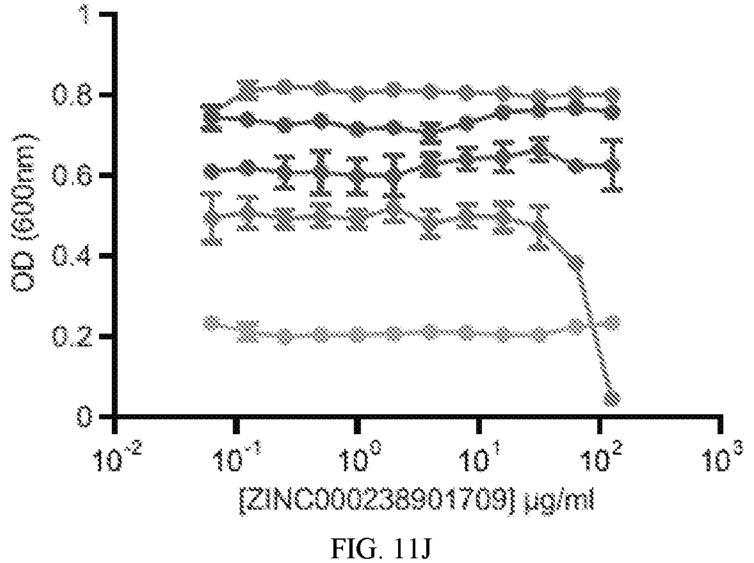
Figure 11K:
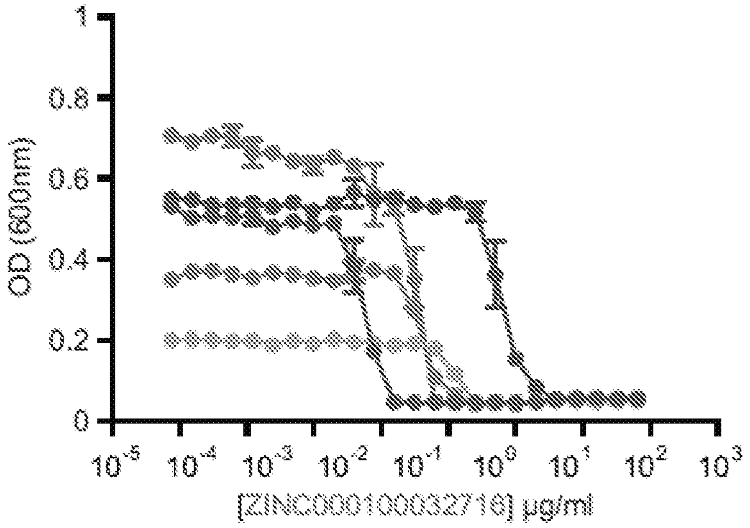

After successfully applying the deep neural network model to identify antibiotic candidates from the Broad Repurposing Hub, two additional chemical libraries were subsequently explored—the WuXi anti-tuberculosis library housed at the Broad Institute that contains 9,997 molecules, and the ZINC15 database, a virtual collection of ≈1.5 billion molecules designed for in silico screening (Sterling and Irwin, 2015). Notably, the WuXi anti-tuberculosis library served to test the model in chemical spaces that were highly divergent from the training dataset, prior to conducting large-scale predictions in the vast ZINC15database. To this end, the empirical data gathered from the Broad Repurposing Hub molecules was applied to re-train the original model and then applied this new model to the WuXi anti-tuberculosis library. Interestingly, an upper limit prediction score of just 0.37 was observed for the WuXi anti-tuberculosis library (FIG. 11A), which was substantially lower than the prediction scores observed for the Broad Repurposing Hub (upper limit 0.97; FIG. 2C). As was done for those molecules predicted from the Drug Repurposing Hub, the 200 WuXi anti-tuberculosis library compounds with the highest prediction scores, as well as the 100 with the lowest, were curated. As expected, based on the low prediction scores, none of the 300 molecules empirically assayed for growth inhibition against *E. coli* displayed antibacterial activity (FIGS. 11B and 11C).

Figure 6A:
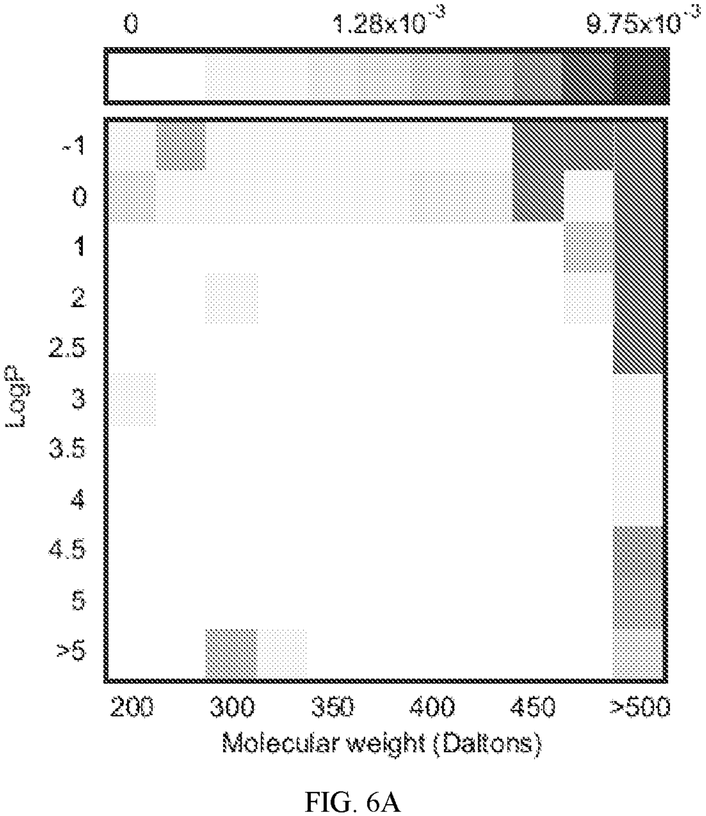

After again re-training the model with the data gathered from these 300 WuXi anti-tuberculosis library molecules, predictions were performed on a subset of the ZINC15 database. Rather than screening the entire ≈1.5 billion-molecule database, specifically those tranches that contained molecules with physicochemical properties that were unique to antibiotic-like compounds (FIG. 6A) were selected. Indeed, molecules with antibacterial activity tend to be higher in molecular weight and more hydrophilic than molecules that engage eukaryotic targets. This more focused approach resulted in the in silico curation of 107,349,233 molecules. Notably, this curated library was two orders of magnitude larger than empirical screening has permitted (D. G. Brown et al., 2014), the in silico screen of the library could be performed in approximately four days, and the screen was negligible in cost.

Figure 6B:
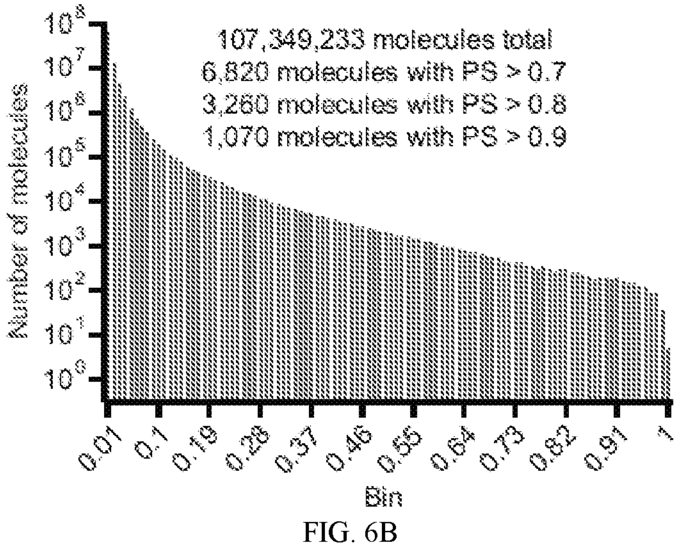

After running predictions on the selected tranches of the ZINC15 database, compounds were binned based on prediction score. This resulted in 6,820 molecules with scores greater than 0.7, 3,260 molecules with scores greater than 0.8, and 1,070 molecules with scores greater than 0.9 (FIG. 6B and FIG. 14). As was done for the Drug Repurposing Hub, the top 6,820 ZINC15 prediction ranks from the model were compared to numerous others, including a learned model without RDKit feature augmentation; a model trained exclusively on RDKit features; a feed-forward deep neural network model using Morgan fingerprints as the molecular representation, a random forest classifier using Morgan fingerprints, and a support-vector machine model using Morgan fingerprints (see Methods). Next, all molecules were rank ordered based on prediction score alone, or on prediction score together with the Tanimoto similarity to all known antibacterial molecules.

To determine molecules with predictions cores alone, prediction scores greater than 0.7 were clustered into 50 groups based on structure, and compounds with the top two prediction scores in each cluster were prioritized for curation. Of these 100 compounds, 15 were chosen for empirical testing due primarily to the difficult of synthesizing many of the antibacterial candidates. However, these 15 molecules displayed a wide range of similarities to their closest clinical antibiotic (Tanimoto scores ranging from ≈0.65 to ≈0.15), thereby providing adequate opportunity to analyze model performance as chemical divergence from the training set was modulated.

Figure 12A:
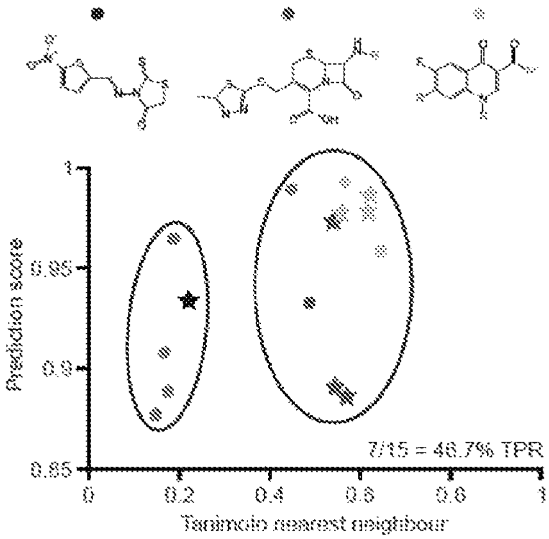
FIGS. 12A-12W show the prediction scores and growth inhibition results of the 15 curated based on prediction score alone (and not curated based on Tanimoto similarity as in FIGS. 6A-6I and FIGS. 11A-11M above).
Figure 12B:
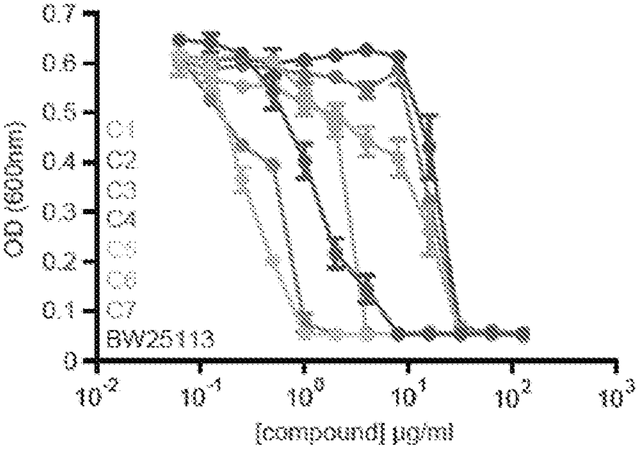
FIG. 12B shows the growth inhibition of *E. coli* by each of the seven active predictions from the ZINC15 database. Shown is the mean of two biological replicates. Bars denote absolute error.
Figure 12C:
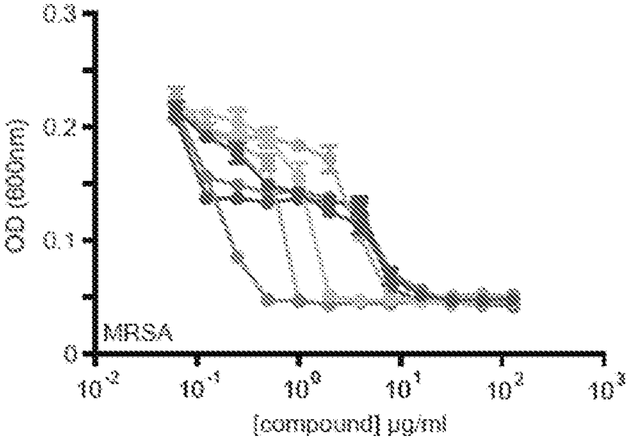
FIG. 12C shows the growth inhibition of MRSA (Methicillin-resistant *Staphylococcus aureus*) by each of the seven active predictions from the ZINC15 database. Shown is the mean of two biological replicates. Bars denote absolute error.
Figure 12D:
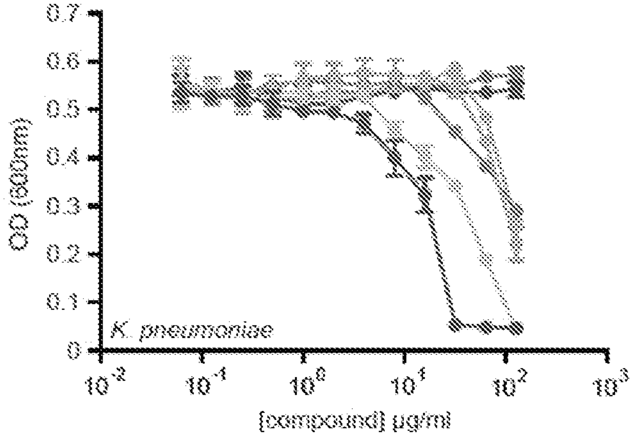
FIG. 12D shows the growth inhibition of *K. pneumoniae* by each of the seven active predictions from the ZINC15 database. Shown is the mean of two biological replicates. Bars denote absolute error.
Figure 12E:
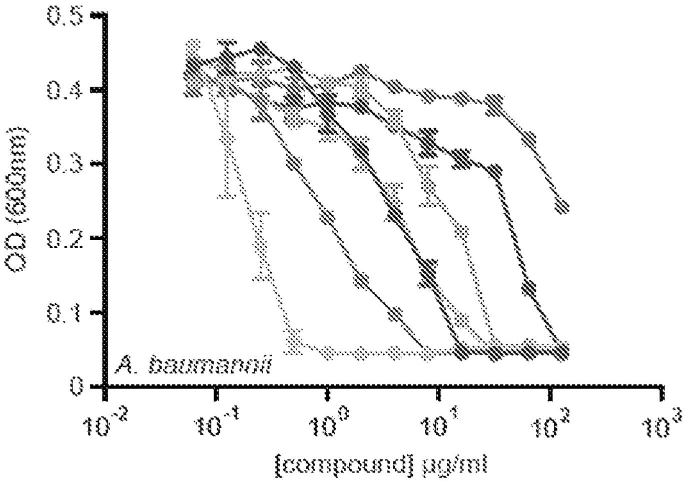
FIG. 12E shows the growth inhibition of *A. baumannii* by each of the seven active predictions from the ZINC15 database. Shown is the mean of two biological replicates. Bars denote absolute error.
Figure 12F:
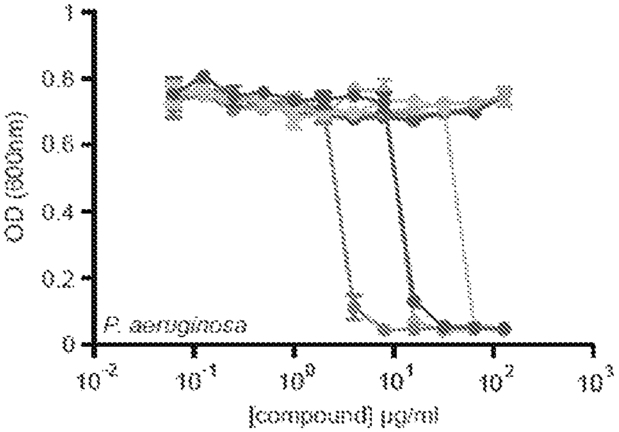
FIG. 12F shows the growth inhibition of *P. aeruginosa* by each of the seven active predictions from the ZINC15 database. Shown is the mean of two biological replicates. Bars denote absolute error.
Figure 12I:
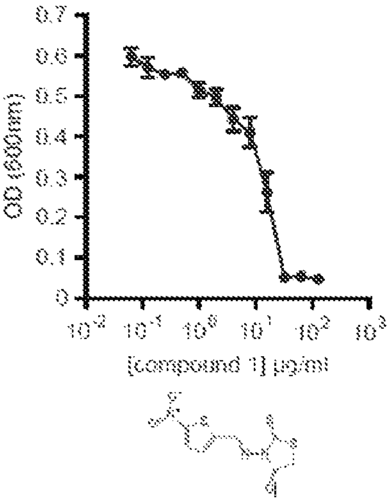
Figure 12J:
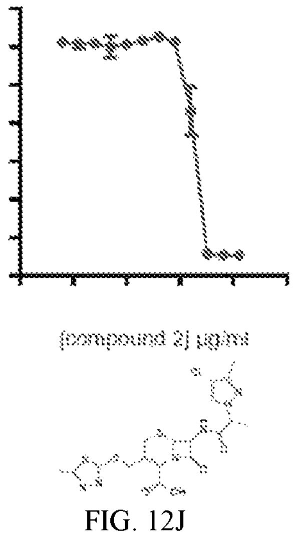
FIG. 12J shows the growth inhibition of *E. coli* with compound 2 of the predicted compounds. Shown is the mean of two biological replicates. Bars denote absolute error. Color denotes structural relationships described in FIG. 6I.
Figure 12K:
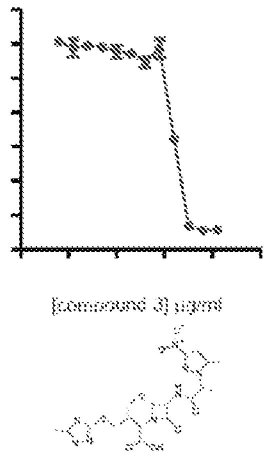
FIG. 12K shows the growth inhibition of *E. coli* with compound 3 of the predicted compounds. Shown is the mean of two biological replicates. Bars denote absolute error. Color denotes structural relationships described in FIG. 6I.
Figure 12L:
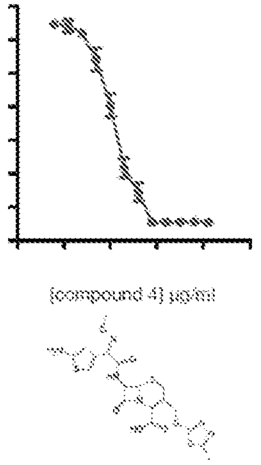
FIG. 12L shows the growth inhibition of *E. coli* with compound 4 of the predicted compounds. Shown is the mean of two biological replicates. Bars denote absolute error. Color denotes structural relationships described in FIG. 6I.
Figure 12M:
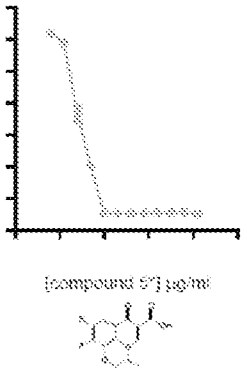
FIG. 12M shows the growth inhibition of *E. coli* with compound 5 of the predicted compounds. Compound 5 (*) is also known as levofloxacin Q-acid and is a precursor to a variety for fluoroquinolones. Shown is the mean of two biological replicates. Bars denote absolute error. Color denotes structural relationships described in FIG. 6I.
Figure 12N:
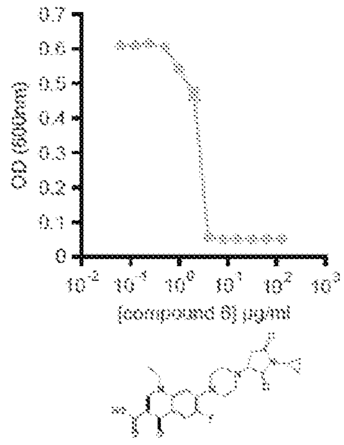
FIG. 12N shows the growth inhibition of *E. coli* with compound 6 of the predicted compounds. Shown is the mean of two biological replicates. Bars denote absolute error. Color denotes structural relationships described in FIG. 6I.
Figure 12O:
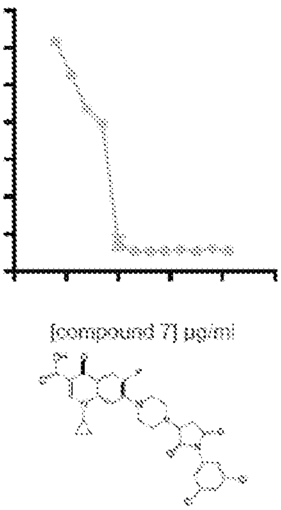
FIG. 12O shows the growth inhibition of *E. coli* with compound 7 of the predicted compounds. Shown is the mean of two biological replicates. Bars denote absolute error. Color denotes structural relationships described in FIG. 6I.
Figure 12P:
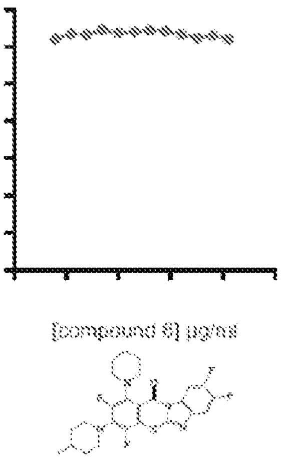
FIG. 12P shows the growth inhibition of *E. coli* with compound 8 of the predicted compounds. Shown is the mean of two biological replicates. Bars denote absolute error. Color denotes structural relationships described in FIG. 6I.
Figure 12Q:
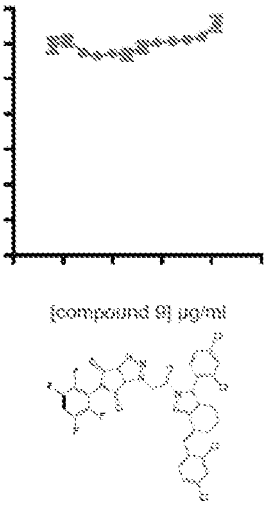
FIG. 12Q shows the growth inhibition of *E. coli* with compound 9 of the predicted compounds. Shown is the mean of two biological replicates. Bars denote absolute error. Color denotes structural relationships described in FIG. 6I.
Figure 12R:
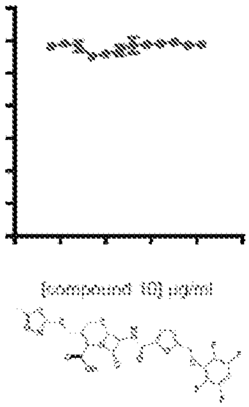
FIG. 12R shows the growth inhibition of *E. coli* with compound 10 of the predicted compounds. Shown is the mean of two biological replicates. Bars denote absolute error. Color denotes structural relationships described in FIG. 6I.
Figure 12S:
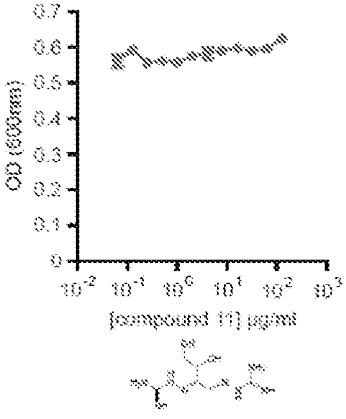
FIG. 12S shows the growth inhibition of *E. coli* with compound 11 of the predicted compounds. Shown is the mean of two biological replicates. Bars denote absolute error. Color denotes structural relationships described in FIG. 6I.
Figure 12T:
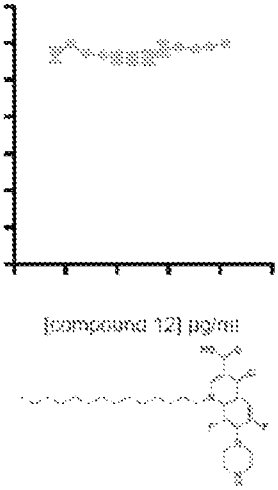
FIG. 12T shows the growth inhibition of *E. coli* with compound 12 of the predicted compounds. Shown is the mean of two biological replicates. Bars denote absolute error. Color denotes structural relationships described in FIG. 6I.
Figure 12U:
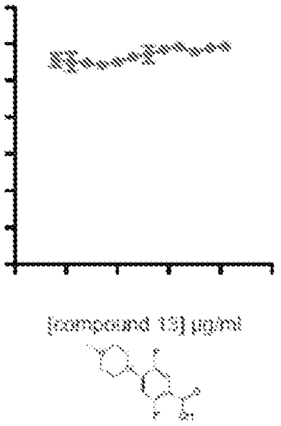
FIG. 12U shows the growth inhibition of *E. coli* with compound 13 of the predicted compounds. Shown is the mean of two biological replicates. Bars denote absolute error. Color denotes structural relationships described in FIG. 6I.
Figure 12V:
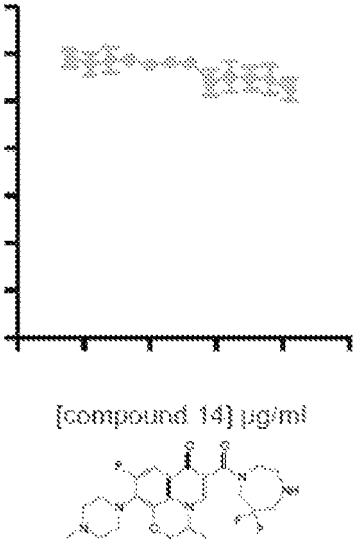
FIG. 12V shows the growth inhibition of *E. coli* with compound 14 of the predicted compounds. Shown is the mean of two biological replicates. Bars denote absolute error. Color denotes structural relationships described in FIG. 6I.
Figure 12W:
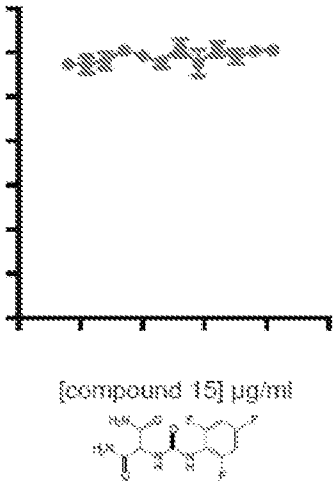

After assaying these 15 compounds for growth inhibition against *E. coli*, it was observed that 7 of the 15 (46.7%) were correct predictions (FIGS. 12A, 12B, and 11D to 11R). This true positive rate was similar to that obtained from the Broad Repurposing Hub molecules (51.5%). Interestingly, upon testing these seven molecules against *S. aureus* (FIG. 12C), *Klebsiella pneumoniae* (FIG. 12D), *A. baumannii* (FIG. 12E), and *P. aeruginosa* (FIG. 12F), it was observed that all compounds displayed growth inhibitory activity against at least one other species (FIG. 12G), providing additional support that the model is not limited to identifying *E. coli*-specific antibiotics despite being trained using *E. coli* as the model organism.

Finally, upon the instant disclosure's determination of the growth inhibitory properties of these 15 predicted molecules, an understanding of the chemistry of the candidate compounds was sought relative to the training data. The structural relationship between the following was investigated: the 15 candidate compounds, the ZINC15 molecules with prediction scores greater than 0.9, the primary training set molecules, the Broad Repurposing Hub molecules, and the WuXi anti-tuberculosis library molecules (FIG. 12H). Intriguingly, the analysis revealed that the WuXi anti-tuberculosis library contained molecules that largely occupied a distinct chemical space relative to compounds with antibacterial activity, consistent with the results showing that even the highest predicted of these were unable to inhibit the growth of *E. coli*. Moreover, this analysis emphasized the fact that molecules occupying highly similar chemical spaces can display significant differences in property cliffs. It is therefore encouraging that 3 of the 5 empirically tested fluoroquinolones and 3 of the 4 predicted 3-lactams were true positives, indicating that the model of the instant disclosure was capable of avoiding chemicals with moieties that were not conducive to bacterial growth inhibition, even though they contained structural features common to efficacious antibiotics. Indeed, given the vast expanse of chemical spaces that are accessible by the derivatization of complex scaffolds such as 3-lactams and fluoroquinolones, the 6 out of 9 (66.7%) true positive rate of identifying novel candidates of these classes emphasizes the utility that deep neural network models, including those specifically disclosed herein, can have on rapidly identifying new antibacterial candidates without the necessity of large derivatization efforts.

Figure 6C:
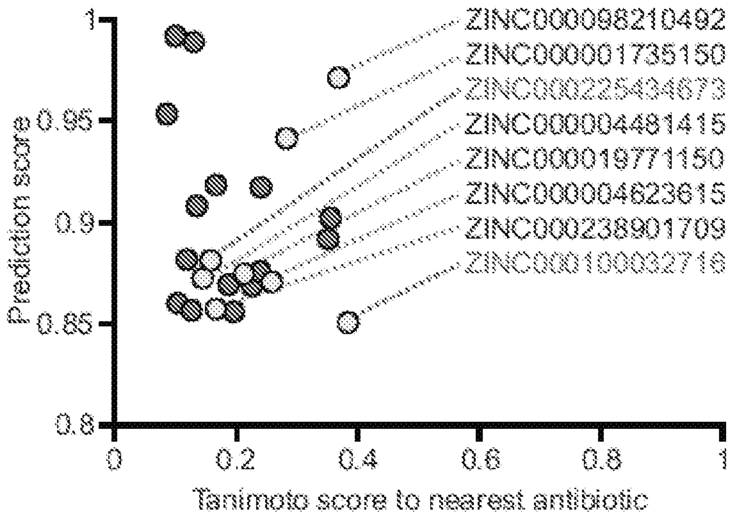

To identify new antibacterial molecules structurally dissimilar from current antibiotics, compounds were prioritized for curation, with thresholds set for prediction scores>0.8 together with Tanimoto similarities to any known antibiotic<0.4. 23 compounds that met the aforementioned criteria were then successfully curated for empirical testing (FIG. 6C, FIGS. 15A and 15B).

Next, these 23 compounds were assayed for growth inhibition against a range of pathogens including *E. coli, S. aureus, Klebsiella pneumoniae, A. baumannii*, and *P. aeruginosa*. Indeed, even though the model was trained on growth inhibition against *E. coli*, because the majority of antibiotics displayed activity against numerous bacterial species, it was proposed that some of these predicted antibiotics would possess bioactivity against diverse clinically relevant pathogens. Importantly, 8 of the 23 molecules displayed detectable growth inhibitory activity against at least one of the tested species (FIGS. 6C, 6D, 11D-11K, 15A, and 15B), which provided additional support that the model was not limited to identifying *E. coli*-specific antibiotics, despite being trained using *E. coli* as the model organism.

Figure 3E:
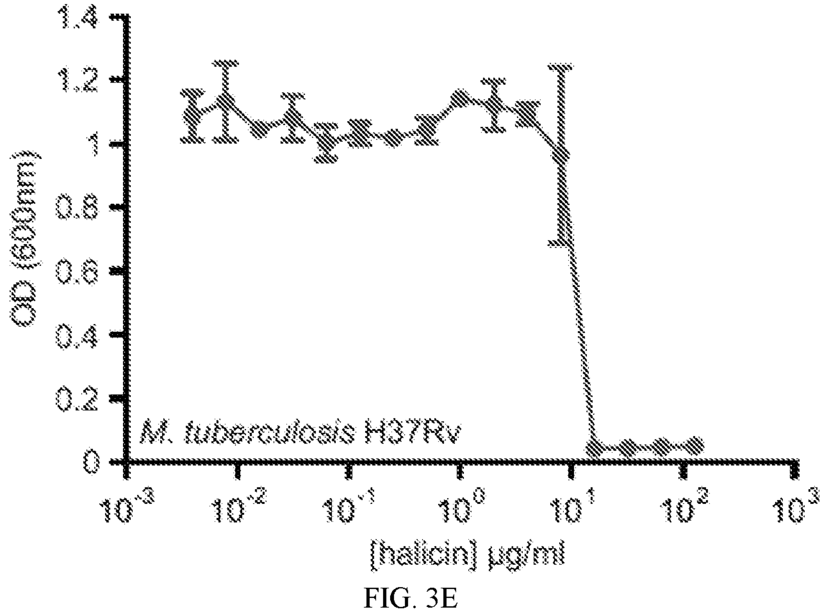
Figure 3F:
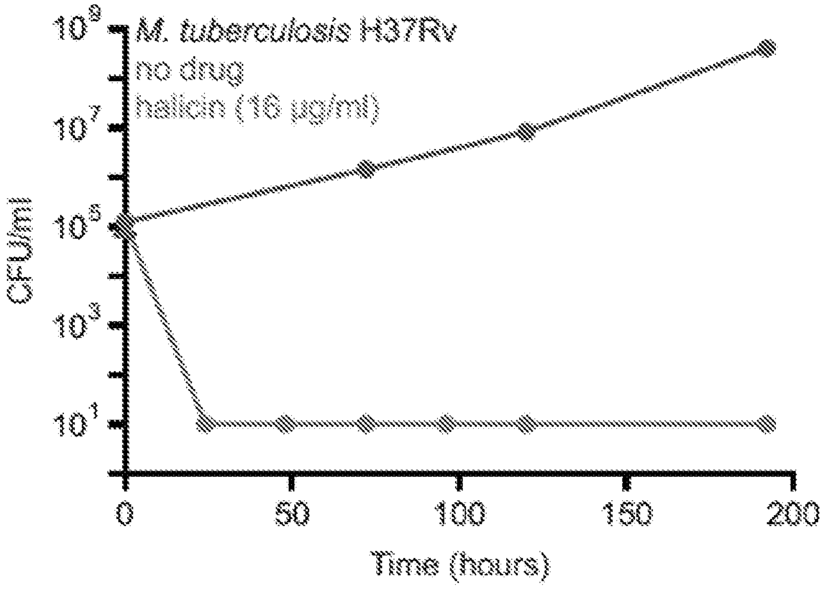
Figure 3G:
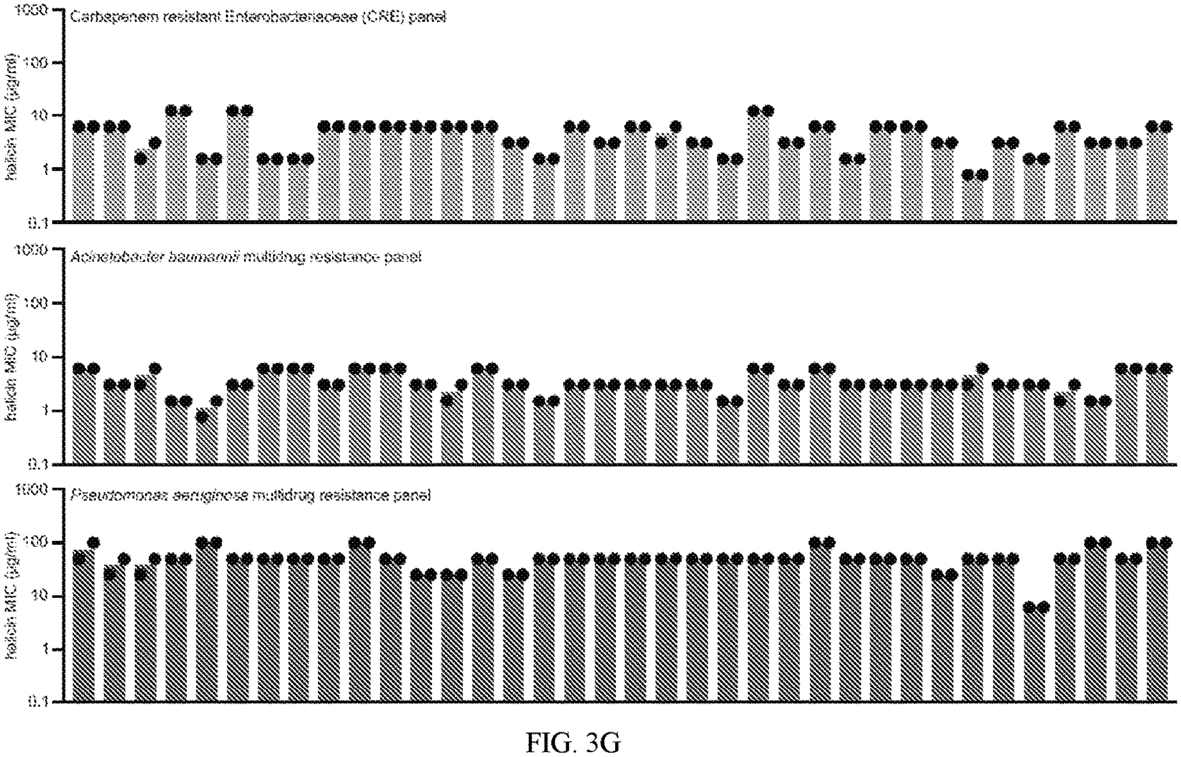
Figure 6E:
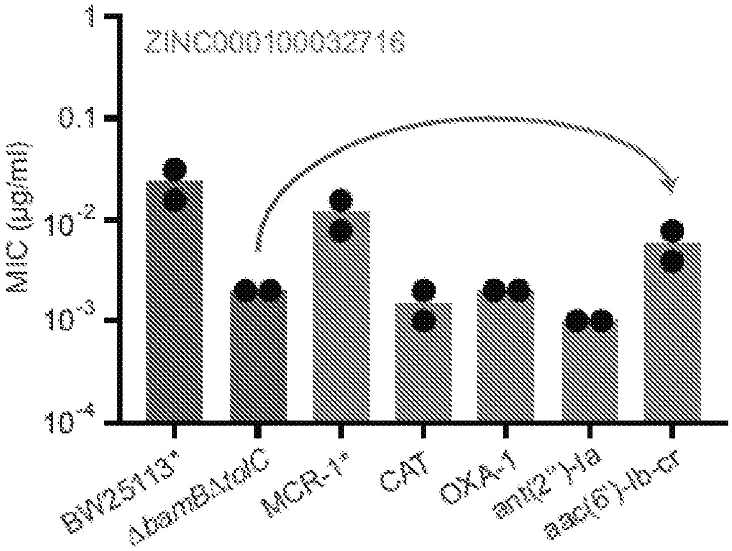
Figure 6F:
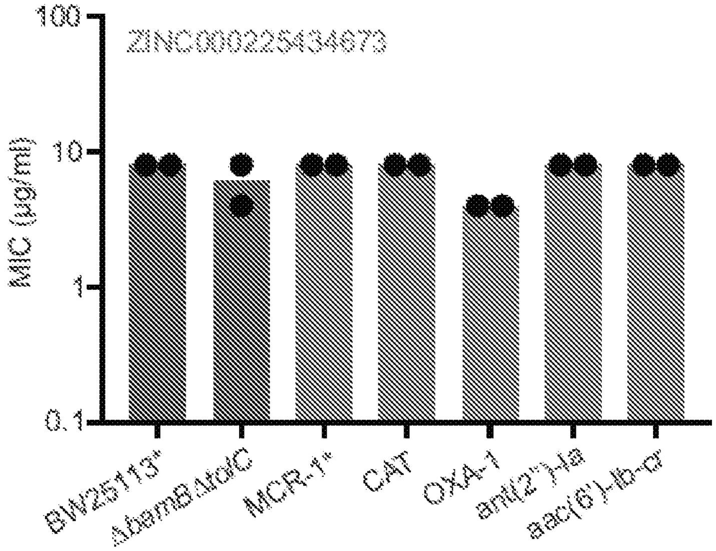
Figure 6G:
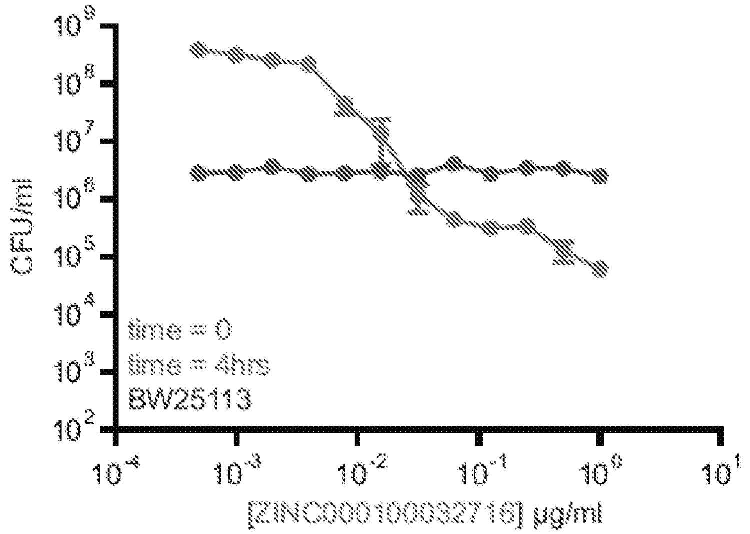
Figure 6H:
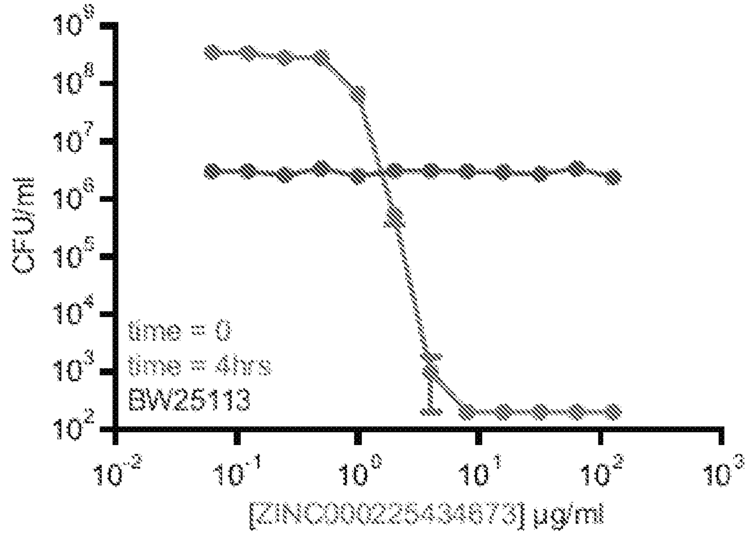
Figure 11L:
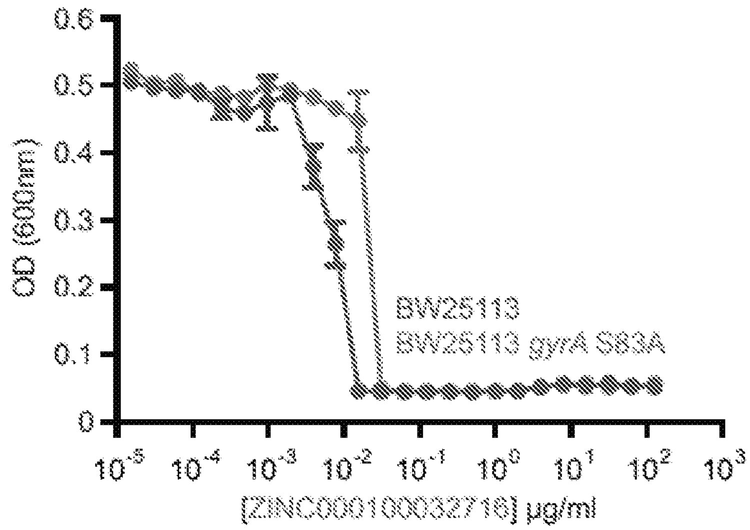
Figure 11M:
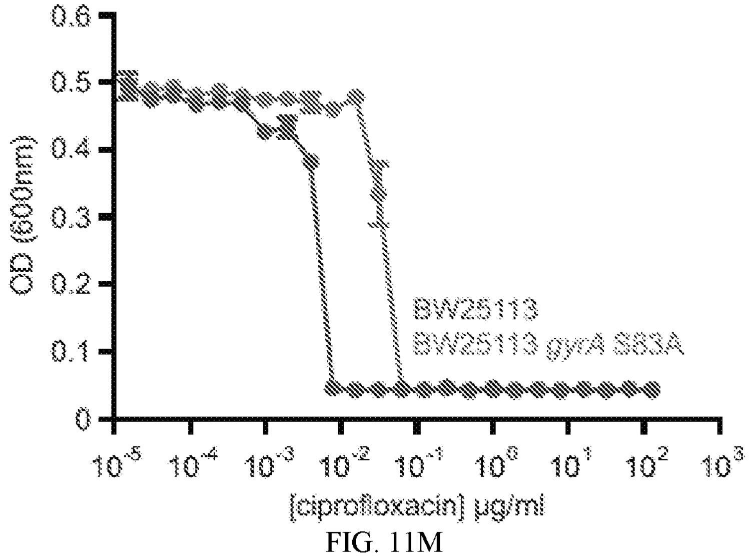

Two compounds were observed to display potent broad-spectrum activity, ZINC000100032716 and ZINC000225434673 (FIG. 6D), and also to overcome an array of common resistance determinants (FIGS. 3E and 3F). Interestingly, ZINC000100032716 possesses structural features found in both quinolones and sulfa drugs, yet remains highly divergent from known antibiotics (enrofloxacin nearest neighbor with Tanimoto similarity ~0.39) and was only weakly impacted by plasmid-borne fluoroquinolone resistance via aac(6')-Ib-cr (FIG. 6E) or chromosomal resistance via mutation of gyrA (FIG. 11L, 11M). Moreover, both ZINC000100032716 and ZINC000225434673 displayed bactericidal activity against *E. coli* in rich medium (FIGS. 6G and 6H), with the latter resulting in complete sterilization after just 4 hours of treatment. Given the novel structure (nitromide is the nearest neighbor with a Tanimoto similarity of 0.16) and low predicted toxicity in humans (FIGS. 15A and 15B), ZINC000225434673 has been predicted herein to be a promising antibiotic.

Figure 6I:
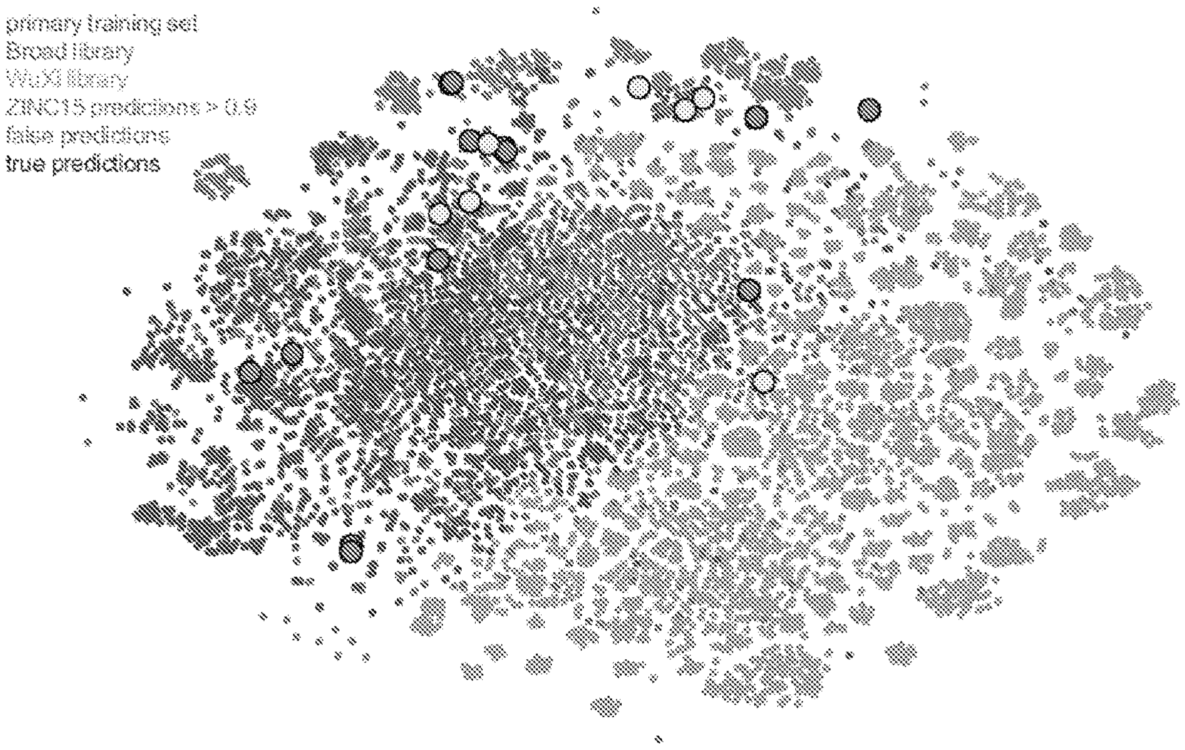

Lastly, upon determining the antibacterial properties of these 23 predicted antibiotic molecules, an understanding of their chemical relationships to the training data was sought. The structural relationships were investigated between these compounds, ZINC15 molecules with prediction scores>0.9, the primary training set, the Drug Repurposing Hub, and the WuXi anti-tuberculosis library (FIG. 6I). Intriguingly, this analysis revealed that the WuXi anti-tuberculosis library contained molecules that largely occupied a distinct chemical space relative to compounds with antibacterial activity, consistent with the results showing that even the highest predicted of these were unable to inhibit the growth of *E. coli*. Moreover, this analysis emphasized the fact that the predicted compounds resided in varied chemical spaces, which indicated that the model was largely unbiased in enriching for specific chemical moieties—at least below the Tanimoto nearest neighbor threshold of 0.4. Furthermore, it was intriguing to observe that molecules occupying highly similar chemical spaces could display significant differences in antibacterial activity, signifying the presence of steep property cliffs. Indeed, additional model training is expected to help improve the understanding of the structural/functional nature of these cliffs, as well as the array of chemical features that can be leveraged to avoid such cliffs, towards the design and optimization of novel antibiotics.

REFERENCES

Abeel, T., Van Parys, T., Saeys, Y., Galagan, J., Van de Peer, Y., 2012. GenomeView: a next-generation genome browser. Nucleic Acids Res. 40, e12.

Angus, B. L., Carey, A. M., Caron, D. A., Kropinski, A. M., Hancock, R. E., 1982. Outer membrane permeabilityin *Pseudomonas aeruginosa*: comparison of a wild-type with an antibiotic-supersusceptible mutant. Antimicrob. Agents Chemother. 21, 299-309.

Balaban, N. Q., Helaine, S., Lewis, K., Ackermann, M., Aldridge, B., Andersson, D. I., Brynildsen, M. P., Bumann, D., Camilli, A., Collins, J. J., Dehio, C., Fortune, S., Ghigo, J. M., Hardt, W. D., Harms, A., Heinemann, M., Hung, D. T., Jenal, U., Levin, B. R., Michiels, J., Storz, G., Tan, M. W., Tenson, T., Van Melderen, L., Zinkernagel, A., 2019. Definitions and guidelines for research on antibiotic persistence. Nat. Rev. Microbiol. 17, 441-448.

Brown, D. G., May-Dracka, T. L., Gagnon, M. M., Tommasi, R., 2014. Trends and exceptions of physical properties on antibacterial activity for Gram-positive and Gram-negative pathogens. J. Med. Chem. 57, 10144-10161.

Brown, E. D., Wright, G. D., 2016. Antibacterial drug discovery in the resistance era. Nature 529, 336-343.

Camacho, D. M., Collins, K. M., Powers, R. K., Costello, J. C., Collins, J. J., 2018. Next-generation machine learning for biological networks. Cell 173, 1581-1592.

Clardy, J., Fischbach, M. A., Walsh, C. T., 2006. New antibiotics from bacterial natural products. Nat. Biotechnol. 24, 1541-1550.

Coley, C. W., Jin, W., Rogers, L., Jamison, T. F., Jaakkola, T. S., Green, W. H., Barzilay, R., Jensen, K. F., 2019. A graph-convolutional neural network model for the prediction of chemical reactivity. Chem. Sci. 10, 370-377.

Corsello, S. M., Bittker, J. A., Liu, Z., Gould, J., McCarren, P., Hirschman, J. E., Johnston, S. E., Vrcic, A., Wong, B., Khan, M., Asiedu, J., Narayan, R., Mader, C. C., Subramanian, A., Golub, T. R., 2017. The Drug Repurposing Hub: a next-generation drug library and information resource. Nat. Med. 23, 405-408.

Cox, G., Sieron, A., King, A. M., De Pascale, G., Pawlowski, A. C., Koteva, K., Wright, G. D., 2017. A common platform for antibiotic dereplication and adjuvant discovery. Cell Chem. Biol. 24, 98-109.

D'haeseleer, P., 2005. How does gene expression clustering work?Nat. Biotechnol. 23, 1499-1501.
Datsenko, K. A., Wanner, B. L., 2000. One-step inactivation of chromosomal genes in *Escherichia coli* K-12 using PCR products. Proc. Natl. Acad. Sci. USA 97, 6640-6645.
De, S. K., Stebbins, J. L., Chen, L. H., Riel-Mehan, M., Machleidt, T., Dahl, R., Yuan, H., Emdadi, A., Barile, E., Chen, V., Murphy, R., Pellecchia, M., 2009. Design, synthesis, and structure-activity relationship of substrate competitive, selective, and in vivo active triazole and thiadiazole inhibitors of the c-Jun N-terminal kinase. J. Med. Chem. 52, 1943-1952.
Dietterich, T. G., 2000. Ensemble Methods in Machine Learning: Multiple Classifier Systems. Springer, Berlin, Heidelberg.
Edwards, A. N., McBride, S. M., 2016. Isolating and purifying *Clostridium difficile* spores. Methods Mol. Biol. 1476, 117-128.
Farha, M. A., Brown, E. D., 2015. Unconventional screening approaches for antibiotic discovery. Ann. N. Y. Acad. Sci. 1354, 54-66.
Farha, M. A., Verschoor, C. P., Bowdish, D., Brown, E. D., 2013. Collapsing the proton motive force to identifysynergistic combinations against *Staphylococcus aureus*. Chem. Biol. 20, 1168-1178.
Gao, H., Struble, T. J., Coley, C. W., Wang, Y., Green, W. H., Jensen, K. F., 2018. Using machine learning to predict suitable conditions for organic reactions. ACS Cent. Sci. 4, 1465-1476.
Gayvert, K. M., Madhukar, N. S., Elemento, O., 2016. A data-driven approach to predicting successes and failures of clinical trials. Cell Chem. Biol. 23, 1294-1301.
Gough, E., Shaikh, H., Manges, A. R., 2011. Systematic review of intestinal microbiota transplantation (fecal bacteriotherapy) for recurrent *Clostridium difficile* infection. Clin. Infect. Dis. 53, 994-1002.
Hurdle, J. G., O'Neill, A. J., Chopra, I., Lee, R. E., 2011. Targeting bacterial membrane function: an underexploited mechanism for treating persistent infections. Nat. Rev. Microbiol. 9, 62-75.
Jang, S., Yu, L. R., Abdelmegeed, M. A., Gao, Y., Banerjee, A., Song, B. J., 2015. Critical role of c-jun N-terminal protein kinase in promoting mitochondrial dysfunction and acute liver injury. Redox Biol. 6, 552-564.
Jaskowiak, P. A., Campello, R. J., Costa, I. G., 2014. On the selection of appropriate distances for gene expression data clustering. BMC Bioinformatics 15, Suppl 2:S2.
Karp, P. D., 2001. Pathway databases: a case study in computational symbolic theories. Science 293, 2040-2044.
Karp, P. D., Latendresse, M., Paley, S. M., Krummenacker, M., Ong, Q. D., Billington, R., Kothari, A., Weaver, D., Lee, T., Subhraveti, P., Spaulding, A., Fulcher, C., Keseler, L. M., Caspi, R., 2016. Pathway Tools version 19,0 update: software for pathway/genome informatics and systems biology. Brief. Bioinform. 17, 877-890.
Keseler, I. M., Mackie, A., Peralta-Gil, M., Santos-Zavaleta, A., Gama-Castro, S., Bonavides-Martinez, C., Fulcher, C., Huerta, A. M., Kothari, A., Krummenacker, M., Latendresse, M., Muñiz-Rascado, L., Ong, Q., Paley, S., Schröder, I., Shearer, A. G., Subhraveti, P., Travers, M., Weerasinghe, D., Weiss, V., Collado-Vides, J., Gunsalus, R. P., Paulsen, I., Karp, P. D., 2013. EcoCyc: fusing model organism databases with systems biology. Nucleic Acids Res. 41, D605-D612.
Kohanski, M. A., Dwyer, D. J., Collins, J. J., 2010. How antibiotics kill bacteria: from targets to networks. Nat. Rev. Microbiol. 8, 423-435.
Landrum, G., 2006. RDKit: Open-source cheminformatics. https://rdkit.org/docs/index.html.
Lee, C. R., Lee, J. H., Park, M., Park, K. S., Bae, I. K., Kim, Y. B., Cha, C. J., Jeong, B. C., Lee, S. H., 2017. Biology of *Acinetobacter baumannii*: pathogenesis, antibiotic resistance mechanisms, and prospective treatment options. Front. Cell Infect. Microbiol. 7:55.
Li, H., Durbin, R., 2009. Fast and accurate short read alignment with Burrows-Wheeler transform. Bioinformatics 25, 1754-1760.
Lobritz, M. A., Belenky, P., Porter, C. B., Gutierrez, A., Yang, J. H., Schwarz, E. G., Dwyer, D. J., Khalil, A. S., Collins, J. J., 2015. Antibiotic efficacy is linked to bacterial cellular respiration. Proc. Natl. Acad. Sci. USA. 112, 8173-8180.
Loewenstein, Y., Portugaly, E., Fromer, M., Linial, M., 2008. Efficient algorithms for accurate hierarchical clustering of huge datasets: tackling the entire protein space. Bioinformatics 24, i41-i49.
Love, M. I., Huber, W., Anders, S., 2014. Moderated estimation of fold change and dispersion for RNA-seq data with DESeq2. Genome Biol. 15:550.
Manson, M. D., Tedesco, P., Berg, H. C., Harold, F. M., Van der Drift, C., 1977. A protonmotive force drives bacterial flagella. Proc. Natl. Acad. Sci. USA. 74, 3060-3064.
Mauri, A., Consonni, V., Pavan, M., Todeschini, R., 2006. Dragon software: an easy approach to molecular descriptor calculations. MATCH Commun. Math. Comput. Chem. 56, 237-248.
Mayr, A., Klambauer, G., Unterthiner, T., Steijaert, M., Wegner, J. K., Ceulemans, H., Clevert, D. A.,
Hochreiter, S., 2018. Large-scale comparison of machine learning methods for drug target prediction on ChEMBL. Chem. Sci. 9, 5441-5451.
Moriwaki, H., Tian, Y. S., Kawashita, N., Takagi, T., 2018. Mordred: a molecular descriptor calculator. J. Cheminform. 10:4.
O'Neill, J., 2014. Antimicrobial resistance: tackling a crisis for the health and wealth of nations. Review on Antimicrobial Resistance.
Ortholand, J. Y., Ganesan, A., 2004. Natural products and combinatorial chemistry: back to the future. Curr. Opin. Chem. Biol. 8, 271-280.
Paul, K., Erhardt, M., Hirano, T., Blair, D. F., Hughes, K. T., 2008. Energy source of flagellar type III secretion. Nature 451, 489-492.
Perez, F., Hujer, A. M., Hujer, K. M., Decker, B. K., Rather, P. N., Bonomo, R. A., 2007. Global challenge of multidrug-resistant *Acinetobacter baumannii*. Antimicrob. Agents Chemother. 51, 3471-3484.
PEW Trusts, 2019. Five-year analysis shows continued deficiencies in antibiotic development. www.pewtrusts.org/en/research-and-analysis/data-visualizations/2019/five-year-analysis-shows-continued-deficiencies-in-antibiotic-development.
Robinson, M. D., McCarthy, D. J., Smyth, G. K., 2010. edgeR: a Bioconductor package for differential expression analysis of digital gene expression data. Bioinformatics 26, 139-140.
Rogers, D., Hahn, M., 2010. Extended-connectivity fingerprints. J. Chem. Inf. Model. 50, 742-754.

Sandegren, L., Lindqvist, A., Kahlmeter, G., Andersson, D. I., 2008. Nitrofurantoin resistance mechanism and fitness cost in *Escherichia coli*. J. Antimicrob. Chemother. 62, 495-503.

Shioi, J. I., Galloway, R. J., Niwano, M., Chinnock, R. E., Taylor, B. L., 1982. Requirement of ATP in bacterial chemotaxis. J. Biol. Chem. 257, 7969-7975.

Shishkin, A. A., Giannoukos, G., Kucukural, A., Ciulla, D., Busby, M., Surka, C., Chen, J., Bhattacharyya, R. P., Rudy, R. F., Patel, M. M., Novod, N., Hung, D. T., Gnirke, A., Garber, M., Guttman, M., Livny, J., 2015. Simultaneous generation of many RNA-seq libraries in a single reaction. Nat. Methods 12, 323-325.

Sterling, T., Irwin, J. J., 2015. ZINC 15-ligand discovery for everyone. J. Chem. Inf. Model. 55, 2324-2337.

Stokes, J. M., Brown, E. D., 2015. Chemical modulators of ribosome biogenesis as biological probes. Nat. Chem. Biol. 11, 924-932.

Stokes, J. M., French, S., Ovchinnikova, O. G., Bouwman, C., Whitfield, C., Brown, E. D., 2016. Cold stress makes *Escherichia coli* susceptible to glycopeptide antibiotics by altering outer membrane integrity. Cell Chem. Biol. 23, 267-277.

Stokes, J. M., Gutierrez, A., Lopatkin, A. J., Andrews, I. W., French, S., Matic, I., Brown, E. D., Collins, J. J., 2019a. A multiplexable assay for screening antibiotic lethality against drug-tolerant bacteria. Nat. Meth. 16, 303-306.

Stokes, J. M., Lopatkin, A. J., Lobritz, M. A., Collins, J. J., 2019b. Bacterial Metabolism and Antibiotic Efficacy. Cell Metab. 30, 251-259.

Stokes, J. M., MacNair, C. R., Ilyas, B., French, S., Cote, J. P., Bouwman, C., Farha, M. A., Sieron, A. O., Whitfield, C., Coombes, B. K., Brown, E. D., 2017. Pentamidine sensitizes Gram-negative pathogens to antibiotics and overcomes acquired colistin resistance. Nat. Microbiol. 2:17028.

Surawicz, C. M., Brandt, L. J., Binion, D. G., Ananthakrishnan, A. N., Curry, S. R., Gilligan, P. H., McFarland, L. V., Mellow, M., Zuckerbraun, B. S., 2013. Guidelines for diagnosis, treatment, and prevention of *Clostridium difficile* infections. Am. J. Gasteroenterol. 108, 478-498.

Taber, H. W., Mueller, J. P., Miller, P. F., Arrow, A. S., 1987. Bacterial uptake of aminoglycoside antibiotics. Microbiol. Rev. 51, 439-457.

Tally, F. P., Goldin, B. R., Sullivan, N., Johnston, J., Gorbach, S. L., 1978. Antimicrobial activity of metronidazole in anaerobic bacteria. Antimicrob. Agents Chemother. 13, 460-465.

Coates, A. R., Hu, Y., 2008. Targeting non-multiplying organisms as a way to develop novel antimicrobials. Trends Pharmacol. Sci. 29, 143-150.

Tommasi, R., Brown, D. G., Walkup, G. K., Manchester, J. I., Miller, A. A., 2015. ESKAPEing the labyrinth of antibacterial discovery. Nat. Rev. Drug. Discov. 14, 529-542.

Wang, Y., Bryant, S. H., Cheng, T., Wang, J., Gindulyte, A., Shoemaker, B. A., Thiessen, P. A., He, S., Zhang, J., 2017. PubChem BioAssay: 2017 update. Nucleic Acids Res. 45, D955-D963.

Winston, J. A., Thanissery, R., Montgomery, S. A., Theriot, C. M., 2016. Cefoperazone-treated mouse model of clinically-relevant *Clostridium difficile* strain R20291. J. Vis. Exp. e54850.

Wright, G. D., 2017. Opportunities for natural products in 21st century antibiotic discovery. Nat. Prod. Rep. 34, 694-701.

Wu, M., Maier, E., Benz, R., Hancock, R. E., 1999. Mechanism of interaction of different classes of cationic antimicrobial peptides with planar bilayers and with the cytoplasmic membrane of *Escherichia coli*. Biochemistry 38, 7235-7242.

Wu, Z., Ramsundar, B., Feinberg, E. N., Gomes, J., Geniesse, C., Pappu, A. S., Leswing, K., Pande, V., 2017. MoleculeNet: a benchmark for molecular machine learning. Chem. Sci. 9, 513-530.

Yamaguchi, A., Ohmori, H., Kaneko-Ohdera, M., Nomura, T., Sawai, T., 1991. Delta pH-dependent accumulation of tetracycline in *Escherichia coli*. Antimicrob. Agents Chemother. 35, 53-56.

Yang, J. H., Wright, S. N., Hamblin, M., McCloskey, D., Alcantar, M. A., Schrubbers, L., Lopatkin, A. J., Satish, S., *Nili*, A., Palsson, B. O., Walker, G. C., Collins, J. J., 2019. A white-box machine learning approach for revealing antibiotic mechanisms of action. Cell 177, 1649-1661.

Yang, K., Swanson, K., Jin, W., Coley, C., Eiden, P., Gao, H., Guzman-Perez, A., Hopper, T., Kelley, B., Mathea, M., Palmer, A., Settels, V., Jaakkola, T., Jensen, K., Barzilay, R., 2019. Analyzing learned molecular representations for property prediction. J. Chem. Inf. Model. 13:10.1021/acs/jcim.9b00237.

Yoshimura, F., Nikaido, H., 1982. Permeability of *Pseudomonas aeruginosa* outer membrane to hydrophilic solutes. J. Bacteriol. 152, 636-642.

Zhu, Y. Y., Machleder, E. M., Chenchik, A., Li, R., Siebert, P. D., 2018. Reverse transcriptase template switching: a SMART approach for full-length cDNA library construction. Biotechniques 30, 892-897.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A pharmaceutical composition for treating a microbial infection in a subject comprising a therapeutically effective amount of:

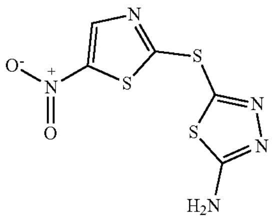

5-[(5-nitro-1,3-thiazol-2-yl)sulfanyl]-1,3,4-thiadiazol-2-amine, or a pharmaceutically acceptable salt or stereoisomer thereof, and a pharmaceutically acceptable carrier.

2. The pharmaceutical composition of claim 1, wherein the microbial infection is resistant to or tolerant to one or more antimicrobial agents.

3. The pharmaceutical composition of claim 1, wherein the microbial infection is a bacterial infection.

4. The pharmaceutical composition of claim 1, wherein the microbial infection is caused by:

an *Acinetobacter* spp., *Acinetobacter baumannii, Escherichia* spp., *Escherichia coli, Campylobacter, Neisseria gonorrhoeae, Providencia* spp., *Enterobacter* spp., *Enterobacter cloacae, Enterobacter aerogenes*, carbapenem-resistant Enterobacteriaceae, *Klebsiella* spp. *Klebsiella pneumoniae, Salmonella, Pasteurella* spp., *Proteus* spp., *Proteus mirabilis, Serratia* spp., *Serratia marcescens, Citrobacter* spp., *Acinetobacter, Morganella morganii, Pseudomonas aeruginosa, Burkholderia pseudomallei, Burkholderia cenocepacia, Helicobacter pylori, Treponema pallidum, Hemophilus influenza, Clostridium difficile, Enterococcus, E. faecalis, E. faecium, E. casseliflavus, E. gallinarum, E. raffinosus*, vanomycin-resistant *Enteroccocus* (VRE), *Mycobacterium tuberculosis, Mycobacterium avium* complex, *Mycobacterium intracellulare*, and *Mycobacterium avium, Mycobacterium smegmatis, Mycoplasms genitalium, Staphylococcus aureus*, methicillin-resistant *Staphylococcus aureus* (MRSA), *Streptococcus pyogenes, Streptococcus pneumoniae, Mycobaterium leprae, Listeria* spp., and/or *Listeria monocytogenes* bacteria; or an *Aspergillus, Blastomyces, Candida, Candida auris, Coccidioides, Candida neoformans, Candida gattii, Histoplasma, Mucormycetes, Mycetoma, Pneumocytsis jirovencii, Trichophyton, Microsporum, Epidermophyton, Sporothrix, Paracoccidioidomycosis, Talaromycosis*, and/or *Cryptococcus* fungus.

5. A method of treating a microbial infection comprising administering to a subject in need thereof a therapeutically effective amount of the pharmaceutical composition of claim 1

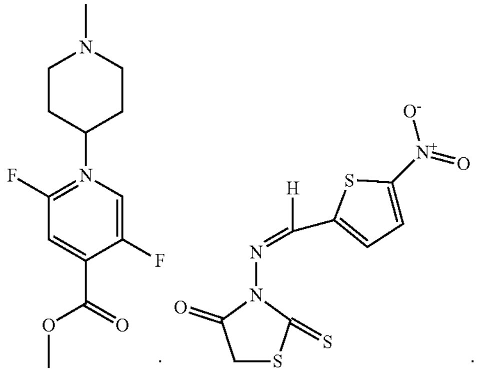

.

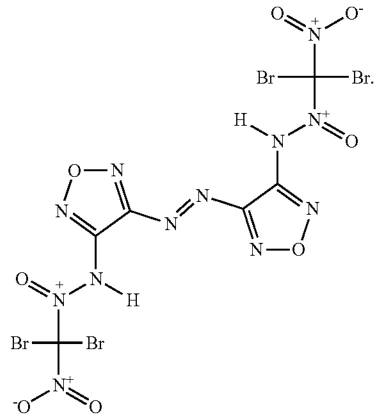

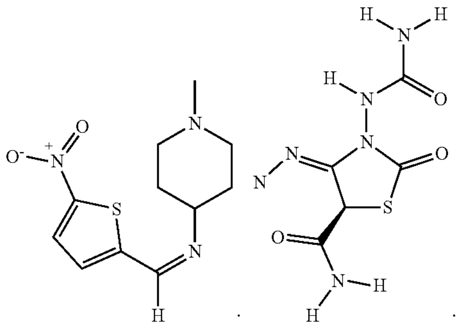

.

-continued

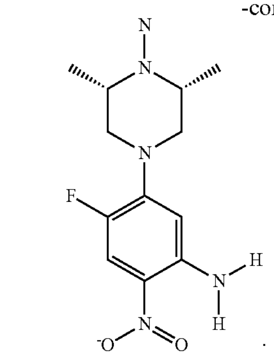

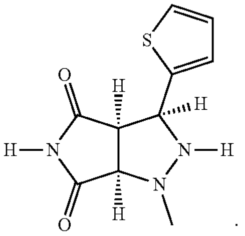

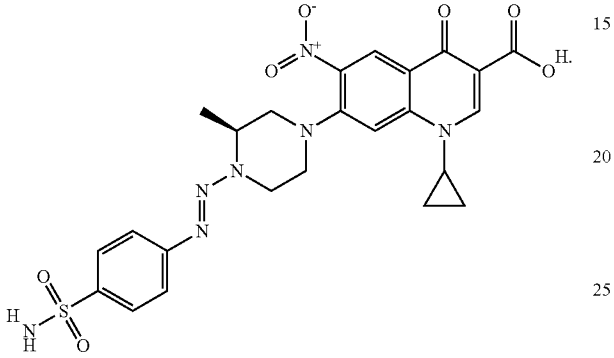

6. The method of claim 5, wherein the microbial infection is resistant to or tolerant to one or more antimicrobial agents.

7. The method of claim 5, wherein the microbial infection is a bacterial infection.

8. The method of claim 5, wherein the microbial infection is caused by:

an *Acinetobacter* spp., *Acinetobacter baumannii, Escherichia* spp., *Escherichia coli, Campylobacter, Neisseria gonorrhoeae, Providencia* spp., *Enterobacter* spp., *Enterobacter cloacae, Enterobacter aerogenes*, carbpanem-resistant Enterobacteriaceae, *Klebsiella* spp. *Klebsiella pneumoniae, Salmonella, Pasteurella* spp., *Proteus* spp., *Proteus mirabilis, Serratia* spp. *Serratia marcescens, Citrobacter* spp., *Acinetobacter, Morganella morganii, Pseudomonas aeruginosa, Burkholderia pseudomallei, Burkholderia cenocepacia, Helicobacter pylori, Treponema pallidum Hemophilus influenza, Clostridium difficile, Enterococcus, E. faecalis, E. faecium, E. casseliflavus, E. gallinarum, E. raffinosus*, vanomycin-resistant *Enteroccocus* (VRE), *Mycobacterium tuberculosis, Mycobacterium avium* complex *Mycobacterium intracellulare*, and *Mycobacterium avium, Mycobacterium smegmatis, Mycoplasms genitalium, Staphylococcus aureus*, methicillin-resistant *Staphylococcus aureus* (MRSA), *Streptococcus pyogenes, Streptococcus pneumoniae, Mycobaterium leprae, Listeria* spp., and/or *Listeria monocytogenes* bacteria; or an *Aspergillus, Blastomyces, Candida, Candida auris, Coccidioides, Candida neoformans, Candida gattii, Histoplasma, Mucormycetes, Mycetoma, Pneumocytsis jirovencii, Trichophyton, Microsporum, Epidermophyton, Sporothrix, Paracoccidioidomycosis, Talaromycosis*, and/or *Cryptococcus* fungus.

9. The pharmaceutical composition of claim 1, wherein the microbial infection is an antibiotic-resistant bacterial infection or an antibiotic-tolerant bacterial infection.

10. The pharmaceutical composition of claim 1, wherein the microbial infection is caused by a bacteria selected from the group consisting of Clostridioides *difficile*, pan-resistant *Acinetobacter baumannii*, carbapenem-resistant Enterobacteriaceae (CRE) species, *Mycobacterium tuberculosis*, and Methicillin-resistant *Staphylococcus aureus* (MRSA).

11. The pharmaceutical composition of claim 1, formulated for oral administration, intravenous administration, intramuscular administration, intraperitoneal administration, intracerobrospinal administration, intracranial administration, intraspinal administration, subcutaneous administration, intraarticular administration, intrasynovial administration, intrathecal administration, topical administration, or administration via inhalation.

12. The pharmaceutical composition of claim 1, wherein the pharmaceutically acceptable carrier comprises a liquid filler, a solid filler, a diluent, an excipient, a solvent, or an encapsulating material.

13. The pharmaceutical composition of claim 1 in the form of a pharmaceutically acceptable salt.

14. The pharmaceutical composition of claim 1 comprising a therapeutically effective amount of 5-[(5-nitro-1,3-thiazol-2-yl)sulfanyl]-1,3,4-thiadiazol-2-amine and a pharmaceutically acceptable carrier.

15. A pharmaceutical composition for treating a bacterial infection in a subject comprising a therapeutically effective amount of:

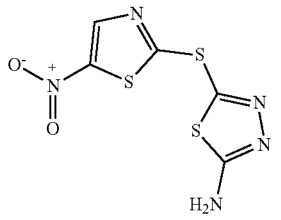

5-[(5-nitro-1,3-thiazol-2-yl)sulfanyl]-1,3,4-thiadiazol-2-amine, or a pharmaceutically acceptable salt or stereoisomer thereof, and a pharmaceutically acceptable carrier.

16. The pharmaceutical composition of claim 15, wherein the bacterial infection is resistant to one or more antibiotic agents.

17. The pharmaceutical composition of claim 15, wherein the bacterial infection is caused by an *Acinetobacter* spp., *Acinetobacter baumannii, Escherichia* spp., *Escherichia coli, Campylobacter, Neisseria gonorrhoeae, Providencia* spp., *Enterobacter* spp., *Enterobacter cloacae, Enterobacter aerogenes*, carbpanem-resistant Enterobacteriaceae, *Klebsiella* spp., *Klebsiella pneumoniae, Salmonella, Pasteurella* spp., *Proteus* spp., *Proteus mirabilis, Serratia* spp., *Serratia marcescens, Citrobacter* spp., *Acinetobacter, Morganella morganii, Pseudomonas aeruginosa, Burkholderia pseudomallei, Burkholderia cenocepacia, Helicobacter pylori, Treponema pallidum, Hemophilus influenza, Clostridium difficile, Enterococcus, E. faecalis, E. faecium, E. casseliflavus, E. gallinarum, E. raffinosus*, vanomycin-resistant *Enteroccocus* (VRE), *Mycobacterium tuberculosis, Mycobacterium avium* complex, *Mycobacterium intracellulare, Mycobacterium avium, Mycobacterium smegmatis, Mycoplasms genitalium, Staphylococcus aureus*, methicillin-resistant *Staphylococcus aureus* (MRSA), *Streptococcus pyogenes, Streptococcus pneumoniae, Mycobaterium leprae, Listeria* spp., and/or *Listeria monocytogenes* bacteria.

18. A pharmaceutical composition for treating a fungal infection in a subject comprising a therapeutically effective amount of:

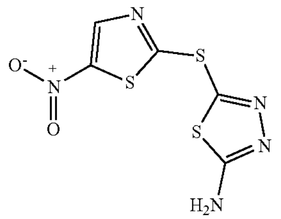

5-[(5-nitro-1,3-thiazol-2-yl)sulfanyl]-1,3,4-thiadiazol-2-amine, or a pharmaceutically acceptable salt or stereoisomer thereof, and a pharmaceutically acceptable carrier.

19. The pharmaceutical composition of claim 18, wherein the fungal infection is resistant to one or more antifungal agents.

20. The pharmaceutical composition of claim 18, wherein the fungal infection is caused by an *Aspergillus, Blastomyces, Candida, Candida auris, Coccidioides, Candida neoformans, Candida gattii, Histoplasma, Mucormycetes, Mycetoma, Pneumocytsis jirovencii, Trichophyton, Microsporum, Epidermophyton, Sporothrix, Paracoccidioidomycosis, Talaromycosis*, and/or *Cryptococcus* fungus.

* * * * *